US011939574B2

(12) United States Patent
Shapiro et al.

(10) Patent No.: US 11,939,574 B2
(45) Date of Patent: Mar. 26, 2024

(54) RIBOSOMAL RNA ORIGAMI AND METHODS PREPARING THEREOF

(71) Applicant: AUGMANITY NANO LTD, Rehovot (IL)

(72) Inventors: Anastasia Shapiro, Rishon Lezion (IL); Ido Bachelet, Tel-Aviv (IL); Yaniv Amir, Yehud (IL); Erez Lavi, Bat Yam (IL); Danielle Karo-Atar, Ramla (IL)

(73) Assignee: AUGMANITY NANO LTD, Rehovot (IL)

( * ) Notice: Subject to any disclaimer, the term of this patent is extended or adjusted under 35 U.S.C. 154(b) by 1100 days.

(21) Appl. No.: 16/479,000

(22) PCT Filed: Jan. 18, 2018

(86) PCT No.: PCT/IL2018/050072
§ 371 (c)(1),
(2) Date: Jul. 18, 2019

(87) PCT Pub. No.: WO2018/134825
PCT Pub. Date: Jul. 26, 2018

(65) Prior Publication Data

US 2019/0352640 A1 Nov. 21, 2019

(30) Foreign Application Priority Data

Jan. 19, 2017 (IL) .......................................... 250207

(51) Int. Cl.
*C12N 15/11* (2006.01)
*C12N 15/10* (2006.01)
*C12N 15/115* (2010.01)

(52) U.S. Cl.
CPC .............. *C12N 15/11* (2013.01); *C12N 15/10* (2013.01); *C12N 15/115* (2013.01); *C12N 2310/16* (2013.01); *C12N 2310/3513* (2013.01); *C12N 2310/3519* (2013.01); *C12N 2310/50* (2013.01); *C12N 2310/53* (2013.01)

(58) Field of Classification Search
CPC ...... C12N 15/11; C12N 15/10; C12N 15/115; C12N 2310/50
See application file for complete search history.

(56) References Cited

U.S. PATENT DOCUMENTS

| | | | | |
|---|---|---|---|---|
| 5,582,981 | A | 12/1996 | Toole | |
| 5,756,291 | A | 5/1998 | Griffin | |
| 5,840,867 | A | 11/1998 | Toole | |
| 7,745,607 | B2 | 6/2010 | Li | |
| 2007/0117109 | A1 | 5/2007 | Rothemund | |
| 2010/0279302 | A1* | 11/2010 | Segal | C12Q 1/6809 435/6.14 |
| 2012/0251583 | A1* | 10/2012 | Rothemund | C12P 19/34 530/358 |

FOREIGN PATENT DOCUMENTS

WO 2012061719 A2 5/2012

OTHER PUBLICATIONS

Endo, Masayuki, et al. "Preparation of chemically modified RNA origami nanostructures." Chemistry—A European Journal 20.47 (2014): 15330-15333. (Year: 2014).*
Wang, Pengfei, et al. "RNA-DNA hybrid origami: folding of a long RNA single strand into complex nanostructures using short DNA helper strands." Chemical Communications 49.48 (2013): 5462-5464. (Year: 2013).*
Gerasimova, Yulia V., and Dmitry M. Kolpashchikov. "Folding of 16S rRNA in a Signal-Producing Structure for the Detection of Bacteria." Angewandte Chemie International Edition 52.40 (2013): 10586-10588. (Year: 2013).*
Tanaka et al. ("A'-form RNA double helix in the single crystal structure of r (UGAGCUUCGGCUC)." Nucleic acids research 27.4 (1999): 949-955) (Year: 1999).*
Endo et al., (2014) Preparation of chemically modified RNA origami nanostructures. Chemistry 20(47): 15330-15333 with Supporting Information.
Geary et al., (2014) RNA nanostructures. A single-stranded architecture for cotranscriptional folding of RNA nanostructures. Science 345(6198): 799-804.
Gerasimova and Kolpashchikov (2013) Folding of 16S rRNA in a signal-producing structure for the detection of bacteria. Angew Chem Int Ed Engl. Sep. 27, 2013; 52(40): doi:10.1002/anie.201303919. 7 pages.
Noon et al., (1998) Posttranscriptional modifications in 16S and 23S rRNAs of the archaeal hyperthermophile Sulfolobus solfataricus. J Bacteriol 180(11): 2883-2888.
Rothemund (2006) Folding DNA to create nanoscale shapes and patterns. Nature 440(7082): 297-302.
Tang et al., (2007) Selection of aptamers for molecular recognition and characterization of cancer cells. Anal Chem 79(13): 4900-4907.
Todd M. Lowe; Ribosomal RNA Modifications; Mar. 31, 2000 (Mar. 31, 2000). Retrieved from: https://users.soe.ucsc.edu/~lowe/thesis/node15.html on Jan. 15, 2020. 2 pages.
Wang et al., (2013) RNA-DNA hybrid origami: folding of a long RNA single strand into complex nanostructures using short DNA helper strands. Chem Commun (Camb) 49(48): 5462-5464.
Afonin et al., (2013) Engineered RNA Nanodesigns for Applications in RNA Nanotechnology. DNA and RNA Nanotechnology 1(1): 1-15.
Geary et al., (2014) RNA nanostructures. A single-stranded architecture for cotranscriptional folding of RNA nanostructures. Science 345(6198): 799-804 with supplementary materials.

(Continued)

*Primary Examiner* — Sahana S Kaup
(74) *Attorney, Agent, or Firm* — Dorsey & Whitney LLP

(57) ABSTRACT

The present invention provides ribosomal RNA origami nanostructures and in particular nanostructures comprising RNA staples, composition comprising such origami nanostructures as well as methods for manufacturing such origami structures.

17 Claims, 21 Drawing Sheets

Specification includes a Sequence Listing.

(56) References Cited

OTHER PUBLICATIONS

James et al., (1997) A phylogenetic analysis of the genus *Saccharomyces* based on 18S rRNA gene sequences: description of *Saccharomyces kunashirensis* sp. nov. and *Saccharomyces martiniae* sp. nov. Int J Syst Bacteriol 47(2): 453-460.

Kim et al., (2016) Generation of siRNA Nanosheets for Efficient RNA Interference. Sci Rep 6: 25146; 7 pages.

Nemoto et al., (2010) Yeast 18 S rRNA is directly involved in the ribosomal response to stringent AUG selection during translation initiation. J Biol Chem 285(42): 32200-32212.

Yu et al., (2015) De novo design of an RNA tile that self-assembles into a homo-octameric nanoprism. Nat Commun 6:5724; 6 pages.

* cited by examiner

FIG. 38
1 2 3 4 5 6 7 8 9 10 11 12 13 14 15 16 17 18 19 20 21
ivt product
306b scaffold
FIG. 39
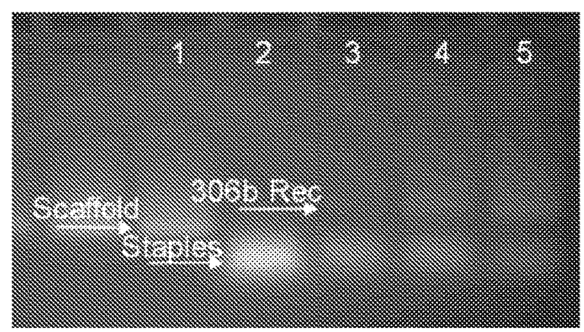
FIG. 40A
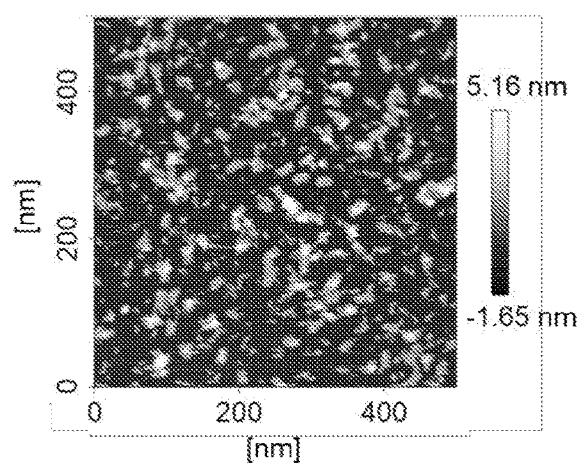
FIG 40B
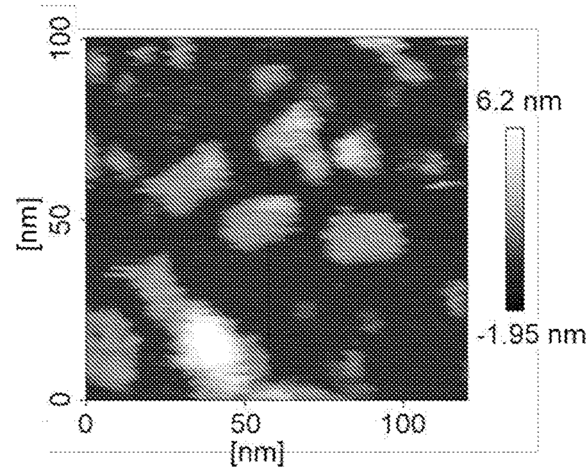

RIBOSOMAL RNA ORIGAMI AND METHODS PREPARING THEREOF

FIELD OF THE INVENTION

The present invention relates to ribosomal RNA origami nanostructures and methods for the producing same. The structures may have a complex 2D and 3D structure designed to the required function.

BACKGROUND OF THE INVENTION

DNA have been used for the rational design and construction of nanoscale Objects for nearly 30 years. Recently, 'scaffolded DNA origami' has emerged as one of the most promising assembly techniques in DNA nanotechnology with a broad range of applications (Rothemund, 2006, Nature, 440, 297-301). Since the creation of this method, software was developed to assist the process using computer-aided design (CAD) software allowing pre-calculating and determining the sequences of scaffolds and staples needed to form a certain shape.

Despite the big promise, DNA origami did not penetrate strongly to the industry. One of the main obstacles is the high price of the raw material, i.e., the single stranded DNA. While only small quantities are needed for regular laboratory experiments, when commercialization is considered, the cost is too high.

Although it is a well-known fact that RNA is much more abundant than DNA, RNA was not considered a potential "raw material" for production of origami structures. Endo et al., (*Chem. Eur. J.* 2014, 20, 15330-15333) and Wang et al., (*Chem. Commun.,* 2013, 49, 5462-5464) describe preparation of nucleic acid origami using relatively short strands of artificially transcribed RNA with limited yield. Gerasimova and Kolpashchikov (Angew. Chem. Int. Ed. Engl. 2013 52(40) doi:10.1002anie.201303919 described an assay that analyzes bacterial RNA exploiting deoxyribozyme sensors—two DNA stands containing fragments complementary to a target analyte and fragments complementary to a fluorophore and quiencher-labeled fluorogenic reporter substrate. Gerasimova and Kolpashchikov showed that hybridization of the staples to the RNA unwinds its secondary structure to form "deoxyribozymes-on-a-string" complex. However, there is no example for real tools allowing mass-production of cheap and readily available origami nanostructures. There is an unmet need for methods utilizing a cheap source of genetic material that may be used for industrial scale manufacture of biological nanostructures.

SUMMARY OF THE INVENTION

Approximately 80 percent of the total RNA in rapidly growing mammalian cells (e.g., cultured HeLa cells) is a ribosomal RNA (rRNA) making it one of the most available and cheapest sources of genetic material. Until now, rRNA was not considered as a potential material for developing rationally designed biological structures. The present invention shows for the first time that rRNA may be used for manufacturing 2D and 3D rRNA origami nanostructures. Methods for processing rRNA and its folding to rRNA origami structures are provided as well.

In one aspect, the present invention provides an RNA origami nanostructure comprising one or more scaffold nucleic acid strands and a plurality of staple nucleic acid strands, wherein said one or more scaffold nucleic acid strand(s) comprises a ribosomal RNA (rRNA) nucleic acid strand, fragment or analog thereof. According to some embodiment, the scaffold strand comprises about 1100 nucleotides or more, from about 1100 to about 5000 or from, about 1300 to about 4000 nucleotides. According to some embodiments, the staples nucleic acids are RNA nucleic acids. According to some embodiments, the staples nucleic acid consist of 5 to 300, 10 to 200 to 30-100 nucleotides. According to one embodiment, the scaffold nucleic acid strand and the RNA staple nucleic acid strands form an A-conformation double helix. In one embodiment, the A-conformation double helix has 12 base-pairs per turn. According to some embodiments, the staples nucleic acids are DNA nucleic acid. According to one embodiment, the scaffold nucleic acid strand and the DNA staple nucleic acid strands form an A-conformation double helix. According to some embodiments, the rRNA nanostructure comprises an active moiety, and/or a targeting domain.

According to another aspect the present invention provides a method for preparation of the RNA origami nanostructure of the present invention, said method comprises: incubating an initial mixture comprising rRNA scaffold nucleic acid, fragment or analog thereof, and staple nucleic acids at about 57° C. to about 65° C. for about 0.5 to about 5 min:

(b) incubating the mixture of (a) at about 53° C. to about 58° C. for about 3 to about 10 min;

(c) incubating the mixture of (b) at about 48° C. to about 53° C. for about 3 to about 15 min;

(d) incubating the mixture of (c) at about 32° C. to about 48° C. for about 5 to about 20 min; and (e) incubating the mixture of (d) at about 20° C. to about 32° C. for about 5 to about 20 minutes; or cooling down the mixture of (d) to the temperature in the range of from about 20° C. to 4° C., at the rate of about −0.05° C./1 min to about −2° C./min.

According to a further aspect, the present invention provides a method for preparation of the RNA origami nanostructure of the present invention, said method comprises:

(a) incubating an initial mixture comprising rRNA scaffold nucleic acid, fragment or analog thereof, and staple nucleic acids at about 57° C. to about 65° C. for about 0.5 to about 2 min:

(b) cooling down the mixture of (a) to the temperature in the range of about 58 to about 52° C., at the rate of about −0.5° C./1 min to about −2° C./min; and (c1) cooling down the mixture of (b) to the temperature in the range of about 15 to about 30, at the rate of about −0.3° C./1 min to about −3° C./min; or (c2.i) incubating the mixture of (b) at about 53° C. to about 58° C. for about 3 to about 10 min;

(c2.ii) cooling down the mixture of (c2.i) to the temperature in the range of about 52° C. to about 48° C. at the rate of about −0.3° C./1 min to about −3° C./min;

(c2.iii) incubating the mixture of (c2.ii) at about 48° C. to about 52° C. for about 5 to about 15 min;

(c2.iv) cooling down the mixture of (c2.iii) to the temperature in the range of 40° C. to about 35 at the rate of about −0.3° C./1 min to about −3° C./min;

(c2.v) incubating the mixture of (c2.iv) at about 35° C. to about 40° C. for about 5 to about 15 min;

(c2.vi) cooling down the mixture of (c2.v) to the temperature in the range of about 30° C. to about 15° C. at the rate of about −0.3° C./1 min to about −3° C./min; and (c2.vii) incubating the mixture of (c2.vi) at about 20° C. to about 30° C. for about 5 to about 15 min.

According to yet another aspect, the present invention provides a method for preparation of the RNA origami nanostructure of the present invention, said method comprises incubating initial mixture comprising scaffold nucleic acid, fragment or analog thereof, and staples nucleic acids at a constant temperature of about 40° C. to about 60° C. for about 0.2 to about 5 days.

According to certain aspects, the present invention provides a method for preparation of the RNA origami nanostructure of the present invention, said method comprising:
(a) separately heating (i) the staple nucleic acid strands at 65° C. for 10 minutes and (ii) scaffold nucleic acid strand at 60° C. for 1 minute;
(b) mixing the heated staple nucleic acids and the pre-heated scaffold nucleic acid strand of step (a); and
(c) cooling of the obtained mixture from 60° C. to 15° C. at the rate of −1° C./min.

According to some aspects, the present invention provides a nucleic acid molecule comprising the sequences set forth in (i) SEQ ID NOs: 1-55, (ii) SEQ ID NOs: 1-67, (iii) SEQ ID NOs: 1 and 508-561, (iv) SEQ ID NOs: 1 and 562-573, (v) SEQ ID NOs: 68-170; (vi) SEQ ID NOs: 68-186, (vii) SEQ ID NOs: 68 and in SEQ ID NOs: 360-437, or (vii) SEQ ID NOs: 68 and in SEQ ID NOs: 438-500; or (viii) in SEQ ID NOs: 1, 68 and 187-359.

According to another aspect, the present invention provides an RNA origami nanostructure comprising one or more scaffold nucleic acid strands and a plurality of staple nucleic acid strands, wherein said scaffold nucleic acid strand comprises a ribosomal RNA (rRNA) nucleic acid strand, fragment or analog thereof and said RNA origami nanostructure is prepared by any one of the methods of the present invention.

According to one aspect, the present invention provides a nucleic acid construct comprising at least one nucleic acid molecule of the present invention.

According to a further aspect, the present invention provides a vector comprising the nucleic acid construct of the present invention.

According to another aspect, the present invention provides a cell comprising the nucleic acid construct or nucleic acid molecule of the present invention.

According to some aspects, the present invention provides a pharmaceutical composition comprising the RNA origami nanostructure of the present invention.

BRIEF DESCRIPTION OF THE FIGURES

FIG. 1A: lanes 2-6: 5 min in 65° C., 61.6° C., 57.6° C., 52.7° C. and 45, respectively; lanes 7-11: 10 min in 65° C., 61.6° C., 57.6° C., 52.7° C. and 45, respectively; lanes 12-16: 20 min in 65° C., 61.6° C., 57.6° C., 52.7° C. and 45, respectively;

FIG. 11 shows AFM images of 18S rRNA-DNA structures folded from a total RNA or purified 18S rRNA and kept at 37° C. for 2.5 or 9.5 days.

FIG. 22 shows agarose gel of the 25S RNA-DNA structures folded using 4 different protocols, while the resulted structure were further incubated at 37° C. for different periods of time.

FIG. 23 shows AFM images of the 25S rRNA-DNA structures folded using protocols 1-4 and further incubated at 37° C. for different period of time.

FIG. 24 shows agarose gel of the 25S RNA-DNA structures folded using protocol 5 at 45° C.

FIG. 29 shows AFM images of simultaneous folding of 25S and 18S rRNA-DNA structures from total RNA at 16 mM $MgCl_2$ after 6.5 days at 37° C.

FIG. 35 shows AFM images of 2D rRNA-DNA cuboctahedron.

FIG. 37 shows AFM images of 3D rRNA-DNA cuboctahedron.

FIG. 38 shows an agarose gel of 306 bases ssRNA tested for stability at different temperatures: lanes 2-6: 65° C., 5, 10, 20, 40, and 60 minutes, respectively; lanes 7-11: ~60° C., 5, 10, 20, 40, and 60 minutes, respectively; lanes 12-16: ~55° C., 5, 10, 20, 40, and 60 minutes, respectively; lanes 17-21: 50° C., 5, 10, 20, 40, and 60 minutes, respectively.

FIG. 39 shows an agarose gel of 306b-RNA-RNA folded structure: lane 1: scaffold; lane 2: staples; lanes 3-5: folding using 25 (scaffold:staples—1:10), 50 (scaffold:staples—1:5) or 100 nM (scaffold:staples—1:2.5) of scaffold keeping the staple concentration constant at 250 nM. The folding was done in folding buffer 1×TAE, 11 mM $MgCl_2$.

FIG. 40 shows AFM images of 306b-RNA-RNA folded structure using 100 nM scaffold (two different resolutions).

DETAILED DESCRIPTION OF THE INVENTION

Figure 1A:
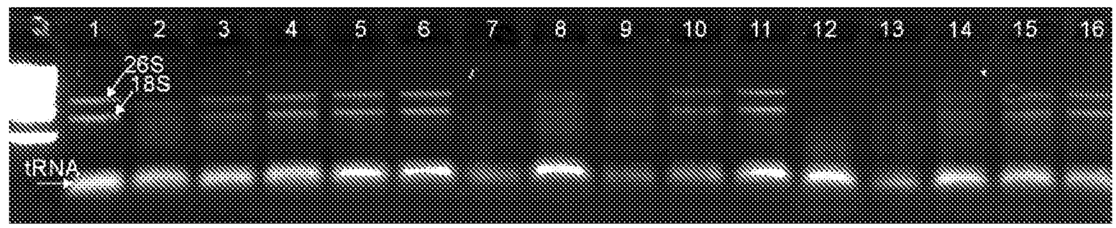
FIG. 1A shows stability of *S. cerevisiae* ribosomal RNA (rRNA) at different temperatures for up to 1 hour (agarose gel).

It is well know that long strands of RNA are not stable at high temperatures. As shown in Example 1, at 65° C. ribosomal RNA from *S. cerevisiae* was not stable, and degraded almost completely after 5 minutes. Short RNA strands were shown to be more stable; RNA oligonucleotides (staples) were stable for up to 2 hours at 65° C. As follows from these observations, methods used for generation of DNA origami structures are not applicable for preparation of RNA origami from long polynucleotide strands, thus development of new techniques was required. It has been surprisingly found that applying relatively high temperature for short period of time with subsequent cooling and incubating at more moderated temperature allowed successfully folding rRNA-DNA and rRNA-RNA origami nanostructures. Moreover, it was surprisingly found that incubating of the resulted nanostructures at a temperature close to 37° C. improved the quality and yield of folding.

This invention describes a novel way to use RNA nucleic acids strands and in particular rRNA nucleic acids to construct nucleic acid origami nanostructures, either hybrid RNA-DNA or pure RNA-RNA structures, such that the cost of production is reduced by a factor of 100 to 1000 in comparison to the known methods for folding nucleic acid origami nanostructures. This cost reduction follows from a fact that has been overlooked so far, which is that RNA nucleic acid strands (i.e. number of copies of specific sequences of RNA nucleic acids) are several orders of magnitude more abundant, on a per-cell basis, than DNA: in any given native bacterial cell there is only 1 copy of a DNA molecules; in a mammalian cell there are 2 copies (one per chromosome); there are, however, thousands of copies of specific RNA sequences/molecules (or ~110 ng/cell). In particular, ribosomal RNA (rRNA) constitute 80-90% of the total RNA of any cell (bacterial, yeast, mammalian etc.). Since the production of total RNA is straightforward and inexpensive, large quantities of rRNA (on the order of grams) can be readily obtained for a relatively low price. Such quantities of ssDNA would cost 3-4 orders of magnitude more.

Thus, the present invention provides an RNA origami nanostructure comprising one or more scaffold nucleic acids strands and a plurality of staple nucleic acid strands, wherein said one or more scaffold nucleic acids comprise RNA nucleic acid strands, fragment or analog thereof. According to some embodiments, the plurality of the staple nucleic acids define a set of staples. The terms "set of staples" and "set of staple nucleic acids" are used herein interchangeably and refer to a set of staple nucleic acid strands used for folding one RNA origami nanostructure based on a specific scaffold or on a combination of scaffolds. According to one embodiment, the scaffold is an RNA nucleic acid.

According to some embodiments, the RNA is a cell derived RNA. The term "cell derived RNA" as used herein refers to RNA obtained from or produced by cells. Examples for such RNA are ribosomal RNA, tRNA, mRNA and other non-coding RNA. This term excludes, however, any RNA produces synthetically or artificially in vitro by any known transcription technique. As well known, the structure of cell derived RNA is significantly different from that obtained in vitro. In part this difference may be explained by post-transcription modifications. Any design of a certain shape and folding have to take into account differences arising from the native configuration of the scaffold strand upon its synthesis and derivation from natural, "dirty" sources. Native rRNA or other native RNA molecules are different from RNA made by in-vitro transcription (IVT) or synthetically since they undergo internal modifications besides cleavage, further trimming and/or splicing and 5' capping. Pre-rRNA undergo internal modifications either simultaneous or immediately following its synthesis. The three basic modification found in rRNA are base methylation, ribose methylation, and pseudouridylation. These rRNA and pre-rRNA modifications found both in eukaryotic and prokaryotic cells. For example: *S. cerevisiae*'s rRNA have 10 base methyls, 55 2'- O-ribose Methyls and 44 Pseudouridines, total 112 modified bases (e.g. in Bachellerie & Cavaille, 1998, H. Grosjean & R. Benne (Eds.), *Modification and Editing of RNA* (pp. 255-272); Ofengand & Fournier, 1998, H. Grosjean & R. Benne (Eds.), *Modification and Editing of RNA* (pp. 229-254)). These modifications play an important role in guiding rRNA structure, function and rRNA folding.

According to one embodiment, the RNA nucleic acid strand is a ribosomal RNA nucleic acid (rRNA) thus the present invention provides in one aspect an RNA origami nanostructure comprising one or more scaffold nucleic acid strands and a plurality of staple nucleic acid strands, wherein said one or more scaffold nucleic acid strands comprises a ribosomal RNA (rRNA) nucleic acid strand(s), fragment or analog thereof. According to some embodiments, the RNA nucleic acid is a polynucleotide and/or the staple nucleic acid strands are oligonucleotides. According to one embodiment, the present invention provides an RNA origami nanostructure comprising one or more scaffold polynucleotide strands and a plurality of staple oligonucleotides strands, wherein said one or more scaffold polynucleotide strands comprises or being a ribosomal RNA (rRNA) polynucleotide strand(s), fragment or analog thereof.

The terms "nucleic acid origami nanostructure", "origami nanostructure", "nanostructure" and "RNA origami nanostructure" are used herein interchangeably and refer to a 2 dimensional or 3 dimensional custom shaped nanostructure comprising RNA polynucleotide strand(s) as a scaffold(s), such as rRNA scaffold nucleic acid (e.g. a polynucleotide), and a plurality of staple nucleic acids (e.g. oligonucleotides), wherein the scaffold is folded by the staples to the desired 2D or 3D structure.

In general, the nucleic acid origami nanostructures are obtained by folding of one or more long nucleic acid referred as a "scaffold" into a particular shape using a plurality of rationally designed nucleic acids referred to as "staples". The sequences of the staple nucleic acids are designed to hybridize with at least two non-contiguous sequences of the scaffold nucleic acid and therefore to force its folding into a particular shape.

The term "nucleic acid" refers to a sequence (polymer) of deoxyribonucleotides or ribonucleotides. In addition, the polynucleotide includes analogues of natural polynucleotides, unless specifically mentioned. The nucleic acid may be selected from deoxyribonucleic acid (DNA), ribonucleic acid (RNA), peptide nucleic acid (PNA), locked nucleic acid (IAA), and analogues thereof, but is not limited thereto. The term encompasses DNA and RNA, either single stranded or double stranded and chemical modifications thereof.

The term "polynucleotide" as used herein refers to a long nucleic acid comprising more than 200 nucleotides. In some embodiments, the terms polynucleotide and "scaffold" are used interchangeably.

The term "oligonucleotide" as used herein refers to a short sequence of nucleic acid such as ribonucleic acid (RNA), deoxyribonucleic acid (DNA) or mimetics thereof, said nucleic acid has typically less than or equal to 200 nucleotides.

The terms "nucleotide base" and "nucleotide" and "nucleic acid base" are used herein interchangeably and refer to a DNA or RNA base and any modification thereof.

The terms "scaffold", "scaffold strand", "scaffold nucleic acid strand" and "scaffold nucleic acid" are used herein interchangeably and refer to a long single stranded RNA nucleic acid. Non-limiting examples of RNA scaffolds are rRNA nucleic acid, e.g. *C. elegans* 26S or 18S rRNA nucleic acid strands. The RNA polynucleotide may, in some embodiments, comprise 1000 nucleotides or more. According to some embodiments, scaffold polynucleotide comprises about 1100 to about 20000 RNA bases. According to some embodiment, the scaffold nucleic acid is a polynucleotide.

The terms "staple", "staple strand", "staple nucleic acid", and "staple nucleic acid strand" are used herein interchangeably and refer to single stranded nucleic acid designed to hybridize with a scaffold nucleic acid strand, in particular to hybridize with at least two non-contiguous sequences within the scaffold nucleic acid. According to some embodiments, the staples are synthetic nucleic acids. Hybridization of the staples nucleic acids with two or more non-contiguous fragments forces juxtaposing these fragments and therefore forcing the scaffold to fold to a particular 2D or 3D structure.

According to some embodiments, the staple nucleic acids are oligonucleotides. Thus in some embodiments, the terms "staple nucleic acids" and "staple oligonucleotides" may be used interchangeably According to some embodiments, the staples are RNA nucleic acids. According to other embodiments, the staples are DNA nucleic acids. According to some embodiments, the staples are RNA oligonucleotides. According to other embodiments, the staples are DNA oligonucleotides. In a further embodiment, the staple oligonucleotides are both, DNA and RNA oligonucleotides. In some embodiments, the terms "oligonucleotide" and "staple" are used interchangeably. According to some embodiments, the staple oligonucleotide simultaneously hybridizes or binds specifically to two or more non-contiguous sequences within the scaffold polynucleotide. Thus, in one embodiment, the staple nucleic acids comprise two or more regions each comprising a sequence complementary to scaffold sequence. According to one embodiment, the staple nucleic acids has at least 99%, 98%, 97%, 96% or 95% sequence complementarity to each fragment of the scaffold nucleic acid to which it binds. According to other embodiment, the staple nucleic acids has at least 50%, 55%, 60%, 65%, 70%, 75%, 80%, 85%, or 90% sequence complementarity to each fragment of the scaffold nucleic acid to which it binds. According to some embodiments, the staple oligonucleotide has a non-binding region between the two binding regions. As referred to herein, the term "complementary" is directed to base pairing between strands of nucleic acids. As known in the art, each strand of a nucleic acid may be complementary to another strand in that the base pairs between the strands are non-covalently connected via two or three hydrogen bonds. For example, "100% complementarity" indicates that all the nucleotides in each strand form base pairs with the complement strand. For example, "95% complementarity" indicates that 95% of the nucleotides in each strand form base pair with the complement strand. The term sufficient complementarity may include any percentage of complementarity from about 30% to about 100%.

According to any aspect and embodiments of the present invention a plurality of staple nucleic acids that used for folding one RNA origami nanostructure based on a specific scaffold or a combination of specific scaffolds is a set of staples. According to some embodiments, the set of staples further comprise nucleic acids complementary to a fragment of a scaffold. In some embodiments, the present invention provides an RNA origami nanostructure comprising one or more scaffold nucleic acids strands and a set of staple nucleic acid strands, wherein said one or more scaffold nucleic acids comprise RNA nucleic acid strands, fragment or analog thereof. According to one embodiment, the RNA is an rRNA. The term "fragment" as used herein refers to a part or a fragment of the scaffold nucleic acid such as a fragment of a native rRNA nucleic acid. According to some embodiments, the term fragment corresponds to a nucleic acid comprising about 50% to about 99%, about 60% to about 98%, about 70% to about 97%, about 75% to about 96%, about 80% to about 95%, about 85% to about 92% or about 87 to about 90% of the native rRNA nucleic acid. According to other embodiment, the fragment comprises from 10% to 60%, from 20% to 50%, from 30% to 40% of the native rRNA nucleic acid. According to some embodiments, the fragment comprises more than 200, more than 300, more than 500, more than 700, or more than 750 bases. According to one embodiment, the fragment comprises more than 800, more than 900, more than 1000, more than 1100, more than 1200, more than 1300, more than 1500, more than 1700, more than 2000, more than 2500, more than 2800, more than 3000, more than 3500 or more than 4000 bases. According to another embodiment, the fragment of scaffold nucleic acid strand comprises about 700 to about 20000, about 750 to about 15000, about 800 to about 13000, about 850 to about 12000, about 900 to about 11000, about 1000 to about 10000, about 1100 to about 8000, about 1200 to about 5000, or about 1300 to about 4000 nucleotides. According to additional embodiments, the fragment comprises about 1500 to about 3500, about 1800 to about 3000, about 2000 to about 3800, or about 2500 to about 3500 nucleotides. According to yet another embodiment, the fragment comprises about 2800 to about 3200 or about 3000 bases. According to more specific embodiment, the scaffold nucleic acid strand comprises about 1600 to about 3500 nucleotides. According other embodiment, the fragment comprises from about 200 to about 5000, about 300 to about 4000, about 400 to about 3000, about 500 to about 2000 or about 600 to about 1800 nucleotide bases. According to such embodiments, the scaffold nucleic acid is a polynucleotide.

The term "analog" and "variant" are used herein interchangeably and refer to an RNA nucleic acid with one or more modified or substituted nucleotides. Such substituted RNA may comprise nucleotide(s) which confer resistance to nucleases. Examples for such substituted nucleic acids include substituted pyrimidines, such as 2'-fluoro-pyrimidines including 2'-fluoro-2'deoxycytidine or 2'-fluoro-2'-deoxyuridine residues. The substituted pyrimidines may also comprise 2'-amino-pyrimidine such as 2'-amino-2'-deoxycytidine or 2'-amino-2'-deoxyuridine residues. The nucleotides may also comprise substituted purines such as 2'-fluoro-purine including 2'-fluoro-2'-deoxyadenine or 2'-fluoro-2'-deoxyguanidine residues. Also included are substituted purines comprising 2'-amino-purine and including 2'-amino-2'deoxyadenine or 2'-amino-2'-deoxyguanidine residues. Other contemplated modifications are biotin binding, methylation, phosphorylation, SS, NH, attachment of fluorophores. The term analog refers both to the native rRNA and to a fragment thereof. This term also refers to modification of the staples, either DNA or RNA staples. In one particular embodiment, the RNA staples are modified.

According to some embodiments, the scaffold nucleic acid strand is an isolated RNA nucleic acid. According to one embodiment, the isolated RNA is an isolated rRNA nucleic acid strand. It is well known that rRNA is present in cells in complex with proteins and additional rRNAs as a part of a ribosome. As such, the isolated rRNA strand has a completely different structure and function than the native rRNA. According to some embodiments, the scaffold nucleic acid is an isolated fragment of rRNA or an isolated analog of rRNA or of the fragment of the rRNA nucleic acid. According to such embodiments, the scaffold nucleic acid is a polynucleotide.

As defined hereinabove, the scaffold nucleic acid strand is a long rRNA nucleic acid. According to some embodiments, the scaffold nucleic acid is a polynucleotide. According to one embodiment, the scaffold polynucleotide comprises at least 800 nucleotides. According to another embodiment, the scaffold strand comprises about 1000 nucleotide bases or more. According to a further embodiment, the scaffold polynucleotide comprises more than 200, more than 300, more than 500, more than 700, or more than 750 bases. According to a further embodiment, the scaffold polynucleotide comprises more than 800, more than 900, more than 1000, more than 1100, more than 1200, more than 1300, more than 1500, more than 1700, more than 2000, more than 2500, more than 2800, more than 3000, more than 3500 or more than 4000 bases. According to another embodiment, the scaffold polynucleotide strand comprises about from about 700 to about 20000, about 750 to about 15000, about 800 to about 13000, about 850 to about 12000, about 900 to about 11000, about 1000 to about 10000, about 1100 to about 8000, about 1200 to about 5000, or about 1300 to about 4000 nucleotides. According to an additional embodiment, the scaffold polynucleotide comprises about 1500 to about 3500, about 1800 to about 3000, about 2000 to about 3800, or about 2500 to about 3500 nucleotides. According to yet another embodiment, the scaffold polynucleotide comprises about 2800 to about 3200 or about 3000 bases. According to more specific embodiment, the scaffold polynucleotide comprises about 1600 to about 3500 nucleotide bases. According other embodiment, the polynucleotide, fragment or analog thereof comprises about 200 to about 5000, about 300 to about 4000, about 400 to about 3000, about 500 to about 2000 or about 600 to about 1800 nucleotide bases.

According to any one of the above embodiment, the rRNA nucleic acid strand is selected from a prokaryotic and eukaryotic rRNA nucleic acid. According to one embodiment, the rRNA nucleic acid is a prokaryotic rRNA nucleic acid. According to another embodiment, the rRNA nucleic acid is a eukaryotic rRNA nucleic acid. According to some embodiments, the rRNA is a precursor rRNA (pre-rRNA) such as 45S, 47S, 40S, 37S and 35S pre-rRNA. According to one embodiment, the prokaryotic rRNA is a bacterial rRNA. According to another embodiment, the prokaryotic rRNA is an archaeal rRNA. According to such embodiments, the scaffold nucleic acid is a polynucleotide.

According to some embodiments the prokaryotic rRNA is an rRNA of non pathogenic bacteria. According to some embodiments the rRNA is selected from rRNA of *Bifidobacterium* spp. (e.g., *bifidum, longum, infantis*), *Lactobacillus* spp. (e.g., *bulgaricus, acidophilus, lactis, helveticus, casei, plantarum, reuteri, delbrueckii, chamnosus, johnsonii, paracasei*), *Streptococcus* spp. (e.g., *thermophilus, diacetilactis, cremoris, durans, faecalis*), *Saccharomyces* spp. (e.g., *pombe, boulardii*), *Leuconostoc* spp. (e.g., citrovorum, dextranicum) and *Bacillus* sp. (e.g., *pasteurii*), *Lactococcus, Streptomyces*, and *Thermotoga*. Non-limiting examples of prokaryotic rRNA strands are *E. coli, Staphylococcus epidermidis, Lactobacillus Acidophilus*, and *Bifidobacteria* rRNA strand. In more particular embodiments, the prokaryotic rRNA is a prokaryotic 16S, 23S (analogous to plant or fungi 25S-26S rRNA, or to eukaryotic 28S rRNA), or 5S rRNA nucleic acid. In one more particular embodiment, the rRNA nucleic acid strand is *E. coli, Staphylococcus epidermidis, Lactobacillus Acidophilus*, or *Bifidobacteria* 16S or 23S rRNA nucleic acid strand.

According to some embodiments, the rRNA is eukaryotic rRNA. According to one embodiment, the eukaryote is selected from yeast, a fungus, a plant, an invertebrate animal and a vertebrate animal. In certain embodiments, the yeast is *Phaffia rhodozyma, Saccharomyces cerevisiae, Schizosaccharomyces pombe, Pichia pastoris, Pichia stipitis, Candida utilis, Candida albicans, Candida guilliermondii* or *Cryptococcus albidus*. In certain other embodiments, the fungus is *Metarhizium flavivoride, Beauvueria bassiana, Paecilomyces fumosoreus* or *Gladiocladium fimbriatum*. In certain other embodiments the plant is *Taxus brevifolia*. In other embodiments the invertebrate animal is a nematode (e.g., *C. elegans*) or an insect (e.g., *Trichoplusia ni*). In other embodiments the vertebrate animal is a reptile, an amphibian, a bird, a fish or a mammal. In certain further embodiments, the mammal is a human, a non-human primate, a rodent, a bovine, an equine, an ovine and a porcine. In another embodiment, the archaebacterium is *Marinococcus* or *Sulfolobus shibatae*. According to one embodiment, the eukaryotic rRNA nucleic acid strand is selected from *S. cerevisiae*, yeast, human, plant and bovine rRNA nucleic acid. According to a particular embodiment, the eukaryotic rRNA nucleic acid is selected from eukaryotic 26S, 5S, 5.8S, 28S, 18S, 25S, 45S and 35S rRNA nucleic acid. According to a more particular embodiment, the rRNA nucleic acid is selected from human or bovine 28S or 18S rRNA polynucleotide. According to one embodiment, the rRNA is an rRNA polynucleotide of 25S or 18S of *Saccharomyces cerevisiae*. There is some discrepancy in the field regarding the names of rRNA. For example 25S and 26S rRNA may refer to same rRNA and being analogous to 28S rRNA, therefore, the terms "25S rRNA", "26S rRNA" and "28S rRNA" may be used in some embodiments interchangeably. According to such embodiments, the scaffold nucleic acid may be a polynucleotide.

According to other embodiments, the rRNA nucleic acid strand is archaeal rRNA nucleic acid such as rRNA nucleic acid of *Sulfolobus*.

As discussed above, generation of RNA origami structures involves folding a single stranded scaffold nucleic acid strand(s) into a particular shape using a plurality of rationally designed staple nucleic acids. The scaffold and the staples form a double stranded nucleic acid or polynucleotide. According to any one of the above embodiments, the scaffold and the staples of the present invention form a double helix having A-conformation, e.g. A-RNA:RNA or A-RNA:DNA conformation which is similar to A-DNA double helix geometry and have similar structural properties of A-DNA double helix.

According to one embodiment, the staple nucleic acids according to the present invention are DNA nucleic acids. According to another embodiment, the staple nucleic acids are RNA nucleic acids. According to a further embodiment, the staple nucleic acids are a combination of RNA and DNA nucleic acids. According to one embodiment, the staple consists of 10 to 300 nucleotides, 15 to 280, 20 to 250, 25 to 220, 30 to 200, 35 to 180, 40 to 150, 50 to 120, or 70 to 100 nucleotides. According to some embodiments, the staple nucleic acids are staple oligonucleotides. According to some embodiments, the staple oligonucleotides consist of 5 to 120 or 10 to 100 nucleotides. According to one embodiment, the staple oligonucleotides consist of 5 to 80 nucleotides. According to another embodiment, the staple oligonucleotides consist of 6 to 60, 7 to 50 or 8 to 45 nucleotides. According to a further embodiment, the staple oligonucleotides consist of 10 to 45 or 15 to 40 nucleotides. According to certain embodiment, the staple oligonucleotides consist of 7 to 75 nucleotides.

According to some embodiments, the staples are RNA nucleic acid staples. According to one embodiment, the scaffold and the RNA nucleic acid staples form A-conformation double helix. The term "A-conformation" as used herein refers to a polynucleotide double helix having the characteristics similar to that of A-DNA double helix. Therefore, the terms "A-RNA:RNA", "A-RNA" are used herein interchangeably and refers to RNA-RNA double helix having A-conformational geometry (A-type helix), and the terms "A-RNA:DNA" and "A-DNA", are used herein interchangeably and refer to RNA-DNA double helix having A-conformational geometry. According to one particular embodiment, the scaffold and the RNA staples form A-RNA:RNA double helix having periodicity of 12 base-pairs per turn. The terms "base-pairs per turn" and "nucleotides per turn" are used interchangeably. The term "nucleotides per turn" refers to number of nucleotides of a single stranded scaffold nucleic acid in the double stranded structure found in one turn of the helix. According to one embodiment, the RNA nucleic acid staples are designed to form A-RNA:RNA double helix with a scaffold. In a more particular embodiment, the RNA nucleic acid staples are designed to form A-RNA:RNA double helix with a scaffold forming helical periodicity of 12 base-pairs per turn. Thus in one embodiment, the present invention provides an RNA origami nanostructure comprising one or more scaffold rRNA nucleic acid strands and a plurality of staple RNA nucleic acid strands, wherein the scaffold and the staples form an RNA-RNA double helix having 12 base-pairs per turn. Optionally, the RNA-RNA double helix has A-conformational geometry. As shown in the Examples, e.g. Examples 22-24, using rRNA staples forming A-conformation geometry with 12 base-pairs per turn results in high yield of rRNA-RNA origami nanostructures. According to such embodiment, the scaffold is selected from 28S, 25S, 26S, 18S rRNA or any combination thereof. According other such embodiment, the scaffold is selected from 5S and 5.8S, 28S, 25S, 26S, 18S rRNA or any combination thereof. According to one embodiment, the scaffold is a polynucleotide and/or the staples are oligonucleotides.

According to one embodiment, the staples are DNA staples. According to one embodiment, the scaffold and the DNA staples form RNA:DNA A-conformation double helix. According to some embodiments, the RNA origami nanostructure comprises both RNA and DNA staples. According to some embodiments, the RNA:DNA A-conformation double helix has 11 base-pairs per turn.

According to any one of the above embodiments, the RNA origami nanostructure comprises a plurality of scaffold nucleic acid strands. The scaffold nucleic acids are as defined above. According to one embodiment, the RNA origami nanostructure comprises 2 to 10, 3 to 9, 4 to 8 or 5 to 7 scaffold nucleic acids. According to another embodiment, the RNA origami nanostructure comprises 2, 3, 4, 5, 6, 7, 8, 9 or 10 nucleic acid or polynucleotide strands. According to some embodiments, all scaffold nucleic acids have the same sequence, i.e. multiple copies of one nucleic acid. According to other embodiment, the scaffold nucleic acids are different nucleic acids, i.e. having different sequences. According to one embodiment, RNA origami nanostructure comprises 2, 3 or 4 scaffold nucleic acids, all having different sequences. According to some embodiments, the scaffold nucleic acids are eukaryotic and/or bacterial rRNA nucleic acids. According to one particular embodiment, the RNA origami nanostructure comprises a plurality of eukaryotic 18S rRNA nucleic acids, a plurality of eukaryotic 25S rRNA nucleic acid strands or a combination of 18S rRNA and 25S rRNA nucleic acid strands. According to such embodiments, the scaffold nucleic acid may be a polynucleotide.

According to any one of the above embodiments, the molar ratio between the scaffold(s) and a set of staples required for folding one rRNA origami nanostructure based on that scaffold(s) (scaffold:staples set molar ratio) is about 1:1 to about 1:30. According to some embodiments, the ratio is about 1:2 to 1:20, 1:3 to about 1:15, about 1:4 to about 1:12, or about 1:6 to about 1:8. According to another embodiment, the ratio is about 1:5 to about 1:10. According to some embodiments, the staple nucleic acids are staple oligonucleotides.

According to any one of the embodiments of the present invention the term "comprises" encompasses also the meaning of consisting of and may be substituted by it. Thus, in the embodiments, defining that scaffold nucleic acid comprises a ribosomal RNA (rRNA) nucleic acid the embodiments encompasses that the scaffold nucleic acid consists of rRNA or being an rRNA.

According to any one of the above embodiments, the RNA origami nanostructure further comprises an active moiety. According to some embodiments, the active moiety is selected from a protein, nucleic acid, lipid, glycoprotein, glycolipid, rRNA origami, DNA origami and small molecule. According to some embodiments, the active moiety is bound to the inner surface of the nanostructure. According to another embodiment, the active moiety is bound to the outer surface of the nanostructure. According to a further embodiment the active moiety is enclosed or entrapped within the RNA origami nanostructure. The term “active agent” and “active moiety” are used herein interchangeable and refer to any molecule, drug, compound, composition of matter or mixture thereof which provides some pharmacologic effects.

According to some embodiments, the active moiety is covalently bound to the inner or to the outer surface of the RNA origami nanostructure. According to one embodiment, the active moiety is directly bound to one of the surfaces, i.e. to the inner or to the outer surface. According to other embodiments, the active moiety is bound via a handle. According to another embodiment, the active moiety is bound to the surface or to the handle via a linker. The term “handle” as used herein refers to a staple capable of binding an active moiety or to other entity bound to the active moiety. The term “linker” as used herein refers to any non-staple molecule connecting the active moiety to the RNA origami nanostructure or to handle. This term comprises, an oligonucleotide which is not a staple, peptides, polypeptides, organic and inorganic molecules.

According to any one of the above embodiments, the RNA origami nanostructure comprises a targeting domain. According to one embodiment, the targeting domain is located on the outer surface of the nanostructure. According to other embodiments, the targeting domain is located on the inner surface, or both on the outer an on the inner surface. The term “targeting domain” as used herein refers to any molecule, e.g. a nucleic acid molecule such as a staple, which is capable of specifically binding a target molecule.

The targeting domain can be designed to target essentially any target molecule of interest using methods known in the art. For example, methods of designing aptamers specific for a target of interest can be found in U.S. Pat. Nos. 5,582,981, 5,756,291, 5,840,867 and 7,745,607, and in Tang et al, Anal. Chem. 79:4900-4907 (2007), each of which are incorporated by reference in their entirety. According to one embodiment, the targeting domain is an aptamer. According to other embodiments the targeting domain is a poly-PNA.

According to one embodiment, the target molecule is selected from a tumor associated molecule, cell-membrane receptor, growth factor, or pathogenic antigen.

The RNA origami nanostructure of the present invention is able to undergo a transition from one conformation (e.g. close conformation) to another conformation (e.g. open conformation) in response to e.g. an environmental stimulus. The term “close conformation” as used herein refers to a steric conformation in which a portion of the RNA origami nanostructure’s surface is sterically separated or hidden from the environment. The term “open conformation” as used herein refers to a conformation in which all available RNA origami nanostructure’s surface is exposed to the environment. The term “inner surface” as used herein refers to any surface area of the RNA origami nanostructure which is not exposed to and does not contact with the immediate environment of the RNA origami nanostructure. The term “outer surface” as used herein refers to any surface area of the RNA origami nanostructure which is exposed to the immediate environment RNA origami nanostructure.

According to some embodiments, the RNA origami nanostructure of the present invention can present in open or close conformation. According to one embodiment, the RNA origami nanostructure of the present invention comprising a latch domain. According to one embodiment the latch domain and the targeting domain are capable of hybridizing and thus maintaining the RNA origami nanostructure in the close conformation. According to another embodiment, the latch domain and the targeting domain are capable of detaching upon binding of the targeting domain to a target molecule thereby transiting the nanostructure from a close to an open conformation. According to other embodiments, the latch domain hybridizes with targeting domain upon environmental stimulus, therefore changing from open conformation to close conformation. The term “latch domain” as used herein refers to a nucleic acid domain capable of hybridizing to a targeting domain, e.g. an aptamer, and thereby holds the nucleic acid origami nanostructure in a closed configuration.

According to some embodiments upon converting from a close to open conformation the active moiety transports from the inner to the outer surface. According to another embodiment, upon converting from an open to close conformation the active moiety transports from the outer surface to the inner surface.

Thus according to one embodiments, the RNA origami nanostructure comprises a latch domain hybridized to the targeting domain, wherein said targeting domain and said latch domain are capable of detaching upon binding of the targeting domain to a target molecule thereby transiting the nanostructure from a closed to an open conformation.

According to any one of the above embodiments, the scaffold polynucleotide comprises the nucleic acid sequence SEQ ID NO:1. According to a particular embodiment, the scaffold polynucleotide comprises the sequence being a fragment of sequence SEQ ID NO:1, e.g. comprising the sequence being about 50% to about 99%, about 60% to about 90%, about 70% to about 80%, about 80% to about 99%, about 85% to about 98%, about 90% to about 97%, about 92% to about 95%, or about 95% to about 99% in length of SEQ ID NO:1. According to a further embodiment, the scaffold polynucleotide comprises the sequence being an analog of the SEQ ID NO:1 or a fragment thereof. According some embodiments, the scaffold polynucleotide consists of the nucleic acid sequence SEQ ID NO:1.

According to any one of the aspects and embodiments of the invention, the terms “nucleic acid comprising the nucleic acid sequence as set forth in SEQ ID NO: X”, “nucleic acid comprising the sequence set forth in SEQ ID NO: X”, “nucleic acid comprising SEQ ID NO: X” and “nucleic acid having SEQ ID NO: X” are used herein interchangeably. The terms “nucleic acid consisting of the nucleic acid sequence set forth in SEQ ID NO: X”, “nucleic acid consisting of sequence set forth in SEQ ID NO: X” “nucleic acid consisting of SEQ ID NO: X” and “nucleic acid of SEQ ID NO: X” are used herein interchangeably. In any one of the aspects and embodiments of the invention the term comprise encompasses also the term consists therefore in any one of the aspects and embodiments of the invention the term “nucleic acid comprising the sequence SEQ ID NO: X” encompasses the term “nucleic acid consisting of sequence SEQ ID NO: X" and may be replaced by it. These statements are true for polynucleotides and oligonucleotides as well.

According to such embodiments, the RNA origami nanostructure comprises a scaffold polynucleotide comprising the nucleic acid sequence SEQ ID NO:1 and staple nucleic acids being DNA nucleic acids, i.e. DNA staple oligonucleotides. According to one embodiment, the staple oligonucleotides have the sequences as set forth in SEQ ID NOs: 2-55. According to another embodiment, such RNA origami nanostructure further comprises DNA staples oligonucleotides having the sequences set forth in SEQ ID NOs: 56-67. Thus, staple oligonucleotides having the sequences set forth in SEQ ID NOs: 2-55 define a set of staples. However, such RNA origami nanostructure may lack some staple oligonucleotides of that set. Thus, according to one embodiment, the RNA origami nanostructure comprises about 50% to about 99%, about 60 to about 95%, about 70% to about 90%, or about 80% to 85% of the set of staples oligonucleotides having the sequences set forth in SEQ ID NOs: 2-55.

According to another such embodiment, the RNA origami nanostructure comprises staple nucleic acids being RNA nucleic acids, i.e. RNA staple oligonucleotides. According to one embodiment, the staple oligonucleotides have the sequences set forth in SEQ ID NOs: 508-561. According to another embodiment, the RNA origami nanostructure further comprises RNA staples oligonucleotides having the sequences set forth in SEQ ID NOs 562-573. According to one embodiment, the RNA origami nanostructure comprises from about 50% to about 99%, about 60 to about 95%, about 70% to about 90%, or about 80% to 85% of the set of staple oligonucleotides having the sequences as set forth in SEQ ID NOs: 508-561 or SEQ ID NOs: 562-573. Similarly, the staples oligonucleotides having the sequences SEQ ID NOs: 2-67 define a set of staples.

According to another embodiment, the RNA origami nanostructure comprises a scaffold polynucleotide comprising the nucleic acid sequence SEQ ID NO:1 and staple oligonucleotides having the sequences set forth in SEQ ID NOs: 655-695. According to one embodiment, the RNA origami nanostructure comprises about 50% to about 99%, about 60 to about 95%, about 70% to about 90%, or about 80% to 85% of the set of staple oligonucleotides having the sequences as set forth in SEQ ID NOs: 655-695.

According to another embodiment, the RNA origami nanostructure comprises staple nucleic acids being a combination of RNA and DNA staple nucleic acids. According to one embodiment, the staples are a combination of staples having the sequences set forth in SEQ ID NOs: 2-55 and in 508-561. According to another embodiment, the RNA origami nanostructure further comprises a combination of staples having the sequences SEQ ID NOs: 56-67 and of staples having the sequences 562-573.

According to one embodiment, the RNA origami comprises polynucleotide scaffold comprising or consisting of SEQ ID NO: 1 and a set of staples comprising oligonucleotides having SEQ ID NOs 2-55. According to another embodiment, the RNA origami comprises polynucleotide scaffold comprising or consisting of SEQ ID NO: 1 and a set of staples comprising oligonucleotides having SEQ ID NOs 508-561. According to certain embodiments, the RNA origami comprises polynucleotide scaffold comprising or consisting of SEQ ID NO: 1 and a set of staples comprising oligonucleotides having SEQ ID NOs: 2-67. According to yet another embodiment, the RNA origami comprises polynucleotide scaffold comprising or consisting of SEQ ID NO: 1 and a set of staples comprising oligonucleotides having SEQ ID NOs 508-573. According to one embodiment, the set of staples comprises from about 50% to about 99%, about 60 to about 95%, about 70% to about 90%, or about 80% to 85% of the original set of staples.

According to a further embodiment, such RNA origami nanostructures further comprises an active moiety.

According to some embodiments, the scaffold polynucleotide comprises the sequence set forth in SEQ ID NO:68. According to a particular embodiment, the scaffold polynucleotide strand comprises the sequence being a fragment of sequence SEQ ID NO:68, e.g. comprising the sequence being about 50% to about 99%, about 60% to about 90%, about 70% to about 80%, about 80% to about 99%, about 85% to about 98%, about 90% to about 97%, about 92% to about 95%, or about 95% to about 99% in length of SEQ ID NO:68. According to a further embodiment, the scaffold polynucleotide strand comprises the sequence being an analog of the SEQ ID NO:68 or a fragment thereof. According to some embodiments, the scaffold polynucleotide consists of the sequence SEQ ID NO:68.

According to such embodiments, the RNA origami nanostructure comprises DNA staple nucleic acids. According to one embodiment, the set of staples comprises staple oligonucleotides having the sequences SEQ ID NOs: 69-170. According to another embodiment, the set of staples further comprises staple oligonucleotides having the sequences SEQ ID NOs: 171-186. According to yet another embodiment, the staple oligonucleotides have the sequences set forth in SEQ ID NOs: 360-437. According to a further embodiment, the set of staples comprises staple oligonucleotides having the sequences SEQ ID NOs: 438-500, and wherein the nanostructure is in a form of a 3D cuboctahedron.

According to other such embodiments, the RNA origami nanostructure comprises RNA staple nucleic acids. According to one embodiment, the RNA staples have the sequence SEQ ID NOs: 69-170 with T-nucleotides substituted with U-nucleotides. According to another embodiment, the set of staples further comprises staple oligonucleotides having the sequences SEQ ID NOs: 171-186 with T-nucleotides substituted with U-nucleotides. According to certain embodiments, the RNA staples have the sequence SEQ ID NOs: 360-437 with T-nucleotides substituted with U-nucleotides. According to another embodiment, the RNA staples have the sequence SEQ ID NOs: 438-500 with T-nucleotides substituted with U-nucleotides, and the nanostructure is in a form of a 3D cuboctahedron.

According to one embodiment, the RNA origami nanostructure comprises the scaffold polynucleotide comprising or consisting of SEQ ID NO:68 and a set of staples selected from a set comprising sequences SEQ ID NOs: 69-170, SEQ ID NOs: 69-186, SEQ ID NOs: 360-437 and SEQ ID NOs: 438-500. According to another embodiment, the RNA origami nanostructure comprises the scaffold polynucleotide comprising or consisting of SEQ ID NO:68 and a set of staples being RNA oligonucleotides, wherein said of staples is selected from a set comprising sequences SEQ ID NOs: 69-170, SEQ ID NOs: 69-186, SEQ ID NOs: 360-437 and SEQ ID NOs: 438-500, in which T-nucleotides substituted with U-nucleotides.

According to some embodiments, the RNA origami nanostructure of the present invention comprises a plurality of scaffold nucleic acids. According to one embodiment, such RNA origami nanostructure comprises at least one scaffold polynucleotide having the sequence set forth in SEQ ID NO:1. According to another embodiment, such RNA origami nanostructure comprises at least one scaffold polynucleotide having the sequence set forth in SEQ ID NO:68.

According to a further embodiment, RNA origami nanostructure comprises at least one scaffold polynucleotide having the sequence set forth in SEQ ID NO:1 and at least one scaffold polynucleotide having the sequence set forth in SEQ ID NO:68. According to a one embodiment, RNA origami nanostructure comprises one scaffold polynucleotide consisting of sequence set forth in SEQ ID NO:1 and one scaffold polynucleotide consisting of sequence set forth in SEQ ID NO:68. According to another embodiment, the RNA origami nanostructure comprises the DNA staple oligonucleotides having the sequences set forth in SEQ ID NOs: 187-359 or RNA staples having the sequences set forth in SEQ ID NOs: 187-359 with T-nucleotides substituted with U-nucleotides.

According to any one of the above embodiments, the molar ratio between the scaffold(s) and a set of staples required for folding one rRNA origami nanostructure based on that scaffold(s) (scaffold:staples set molar ratio) is about 1:1 to about 1:30. According to some embodiments, the ratio is about 1:2 to 1:20, 1:3 to about 1:15, about 1:4 to about 1:12, or about 1:6 to about 1:8. According to some embodiments, the ratio is about 1:3 to about 1:15. According to another embodiment, the ratio is about 1:5 to about 1:10.

According to any one of the above embodiments, the RNA origami nanostructure of the present invention further comprises an active moiety. According to one embodiment, the RNA origami nanostructure comprising an active moiety comprises a scaffold polynucleotide strand having the sequence SEQ ID NO:1 or SEQ ID NO:68, or a plurality of scaffolds, e.g. a plurality of scaffold polynucleotide strands having the sequence set forth in SEQ ID NO:1 or in SEQ ID NO:68 or wherein at least one scaffold polynucleotide has the sequence as set forth SEQ ID NO:1 and at least one scaffold polynucleotide strand has the sequence set forth SEQ ID NO:68.

According to another embodiment, such RNA origami nanostructure further comprises one or more targeting domain on the surface of the nanostructure. According to yet another embodiment, the RNA origami nanostructure further comprising a latch domain hybridized to said targeting domain, wherein said targeting domain and said latch domain are capable of detaching upon binding of the targeting domain to a target molecule thereby transiting the nanostructure from a closed to an open conformation.

As described above, folding long and vulnerable RNA molecules to form a complex 3D structures by nucleic acid origami technology required development of unique methods and protocols, thus in another aspect, the present invention provides a method for preparation of RNA origami nanostructure of any one of the above embodiments.

According to some embodiments the present invention provides a method for preparation of RNA origami nanostructure according to any one of the above embodiments, said method comprising the following steps:

(a) incubating an initial mixture comprising rRNA scaffold nucleic acid(s), fragment or analog thereof, and staples nucleic acids at about 57° C. to about 65° C. for about 0.5 min to about 5 min, or for about 1 min to about 2 min:

(b) incubating the mixture of (a) at about 53° C. to about 58° C. for about 3 to about 10 min;

(c) incubating the mixture of (b) at about 48° C. to about 53° C. for about 3 to about 15 min;

(d) incubating the mixture of (c) at about 32° C. to about 48° C. for about 5 to about 20 min; and (e) incubating the mixture of (d) at about 20° C. to about 32° C. for about 5 to about 20 minutes or cooling down the mixture of (d) to the temperature in the range of from about 20° C. to 4° C. or from about 15 to about 10° C., at the rate of about 0.05° C./min to about −2° C./min or at the rate of about 0.1° C./1 min to about 1° C./1 min or about 0.15° C./min to about 0.5° C./min.

The term "incubating" as used herein refers to holding, keeping or maintaining the mixture, composition or preparation at a constant defined temperature for a defined period of time. When the term is used with respect to a range of temperatures, e.g. incubating at about 30° C. to about 40° C., the term refers to holding, keeping or maintaining the mixture, composition or preparation at one constant temperature within the defined range for a defined period of time.

According to one embodiment, the method comprises:

(a) incubating an initial mixture comprising rRNA scaffold nucleic acid(s), fragment or analog thereof, and staples nucleic acids at about 60° C. for about 0.5 to about 2 min:

(b) incubating the mixture of (a) at about 55° C. for about 3 to about 10 min;

(c) incubating the mixture of (b) at about 50° C. for about 3 to about 15 min;

(d) incubating the mixture of (c) at about 37° C. for about 5 to about 20 min; and (e) incubating the mixture of (d) at about 25° C. for about 5 to about 20 minutes.

According to another embodiment, the method comprises:

(a) incubating an initial mixture comprising rRNA scaffold nucleic acid(s), fragment or analog thereof, and staples nucleic acids at about 57° C. to about 65° C. for about 1 min:

(b) incubating the mixture of (a) at about 53° C. to about 58° C. for about 2 min;

(c) incubating the mixture of (b) at about 48° C. to about 52° C. for about 10 min;

(d) incubating the mixture of (c) at about 32° C. to about 47° C. for about 10 min; and (e) incubating the mixture of (d) at about 20° C. to about 30° C. for about 10 min.

According to a further embodiment, the method comprises:

(a) incubating an initial mixture comprising rRNA scaffold nucleic acid(s), fragment or analog thereof, and staples nucleic acids at about 60° C. for about 0.5 to about 2 min:

(b) incubating the mixture of (a) at about 55° C. for about 3 to about 10 min;

(c) incubating rRNA scaffold and staples at about 50° C. for about 3 to about 15 min;

(d) incubating the mixture of (c) at about 45° C. for about 5 to about 20 min; and (e) cooling down mixture of (d) from about 45° C. to about 15° C., at the rate of about −0.05° C./1 min to about 0.15° C./min.

According to yet another embodiment, the method comprises:

(a) incubating an initial mixture comprising rRNA scaffold nucleic acid(s), fragment or analog thereof, and staples nucleic acids at about 57° C. to about 65° C. for about 1 min:

(b) incubating the mixture of (a) at about 53° C. to about 58° C. for about 5 min;

(c) incubating the mixture of (b) at about 48° C. to about 52° C. for about 5 min;

(d) incubating the mixture of (c) at about 32° C. to about 47° C. for about 10 min; and (e) cooling down mixture of (d) to the temperature in the range of from about 20° C. to 10° C. about 15° C., at the rate of about −0.01° C./1 min.

According to one embodiment, the cooling in step (e) is from 40° C. to about 15° C., at the rate of about −0.01° C./min.

According to any one of the above and below embodiments, the cooling may be performed at the rate between 0.01° C./min to 5° C./min, 0.015° C./min to 4° C./min, 0.02° C./min to 3° C./min, 0.2° C./min to 2° C./min, 0.5° C./min to 1° C./min, 0.6° C./min to 0.8° C./min.

According to any one of the above embodiments, the method further comprises incubating the obtained RNA origami nanostructures at about 33° C. to about 42° C. for about 1 to about 10 days, about 2 to about 8 or about 3 to about 6 days. According to another embodiment, the method comprises incubating the obtained RNA origami nanostructures at about 35° C. to about 40° C. for about 2 to about 8, about 3 to about 6 days or about 4 to about 5 days. According to a further particular embodiment, the method comprises incubating the RNA origami nanostructures at about 37° C. for about 1 to about 10 days, about 2 to about 8, about 3 to about 6, or about 4 to about 5 days.

According to some embodiments the present invention provides a method for preparation of RNA origami nanostructure according to any one of the above embodiments, said method comprises the following steps:

(a) incubating an initial mixture comprising rRNA nucleic acid scaffold(s), fragment or analog thereof and staples nucleic acids at about 57° C. to about 65° C. for about 0.5 to about 5 min or for about 1 to about 2 min:

(b) cooling down the mixture of (a)) to the temperature in the range of about 58° C. to about 52° C., at the rate of about −0.5° C./1 min to about −2° C./min; and (c) cooling down the mixture of (b)) to the temperature in the range of about 15° C. to about 30, at the rate of about −0.3° C./1 min to about −3° C./min;

According to another embodiment, the method comprises (a) incubating an initial mixture comprising rRNA nucleic acid scaffold(s), fragment or analog thereof and staples nucleic acids at about 60° C. for about 0.5 to about 2 min:

(b) cooling down the mixture of (a) from about 59° C. to about 56° C., at the rate of about −0.5° C./1 min to about −2° C./min; and (c) cooling down the mixture of (b) from about 55° C. to about 25, at the rate of about −0.5° C./1 min to about −2° C./min.

According to another embodiment, the method comprises the following steps:

(a) incubating an initial mixture comprising rRNA nucleic acid scaffold(s), fragment or analog thereof and staples nucleic acids at about 57° C. to about 65° C. for about 0.5 to about 2 min:

(b) cooling down the mixture of (a)) to the temperature in the range of 58 to about 52° C., at the rate of about −0.5° C./1 min to about −2° C./min;

(c) incubating the mixture of (b) at about 53° C. to about 58° C. for about 3 to about 10 min;

(d) cooling down the mixture of (c)) to the temperature in the range of about 52° C. to about 48° C. at the rate of about −0.3° C./1 min to about −3° C./min;

(e) incubating the mixture of (d) at about 48° C. to about 52° C. for about 5 to about 15 min;

(f) cooling down the mixture of (e) to the temperature in the range of about 40° C. to about 35 at the rate of about −0.3° C./1 min to about −3° C./min;

(g) incubating the mixture of (f) at about 35° C. to about 40° C. for about 5 to about 15 min;

(h) cooling down the mixture of (g) to the temperature in the range of about 30° C. to about 15° C. at the rate of about −0.3° C./1 min to about −3° C./min; and (i) incubating the mixture of (h) at about 20° C. to about 30° C. for about 5 to about 15 min.

In a further embodiment, the method comprises the following steps:

(a) incubating an initial mixture comprising rRNA nucleic acid scaffold(s), fragment or analog thereof and staples nucleic acids at about 60° C. for about 0.5 to about 2 min:

(b) cooling down the mixture of (a) from about 59° C. to about 56° C., at the rate of about −0.5° C./1 min to about −2° C./min;

(c) incubating the mixture of (b) at about 55° C. for about 3 to about 10 min;

(d) cooling down the mixture of (c) from about 54° C. to about 51° C. at the rate of about −0.5° C./1 min to about −2° C./min;

(e) incubating the mixture of (d) at about 50° C. for about 5 to about 15 min;

(f) cooling down the mixture of (e) from about 49° C. to about 38° C. at the rate of about −0.5° C./1 min to about −2° C./min;

(g) incubating the mixture of (f) at about 37° for about 5 to about 15 min;

(h) cooling down the mixture of (g) from about 36° C. to about 26° C. at the rate of about −0.5° C./min to about −2° C./min; and (i) incubating the mixture of (h) at about 25° C. for about 5 to about 15 min.

According to any one of the above embodiments, the staples are RNA nucleic acids. According to other embodiments, the staples are DNA nucleic acids.

According to any one of the above embodiments, the scaffold:staples set molar ratio is about 1:1 to about 1:30. According to some embodiments, the ratio is about 1:2 to 1:20, 1:3 to about 1:15, about 1:4 to about 1:12, or about 1:6 to about 1:8. According to some embodiments, the ratio is about 1:3 to about 1:15. According to another embodiment, the ratio is about 1:5 to about 1:10.

According to any one of the above embodiments, the method further comprising incubating the obtained RNA origami nanostructures at about 33° C. to about 42° C. for about 1 to about 10 days, about 2 to about 8 or about 3 to about 6 days. According to another embodiment, the method comprises incubating the obtained RNA origami nanostructures at about 35° C. to about 40° C. for about 2 to about 8, about 3 to about 6 days or about 4 to about 5 days. According to a further particular embodiment, the method comprises incubating the RNA origami nanostructures at about 37° C. for about 1 to about 10 days, about 2 to about 8, about 3 to about 6, or about 4 to about 5 days.

According to yet further embodiments, the present invention provides a method for preparation of RNA origami nanostructure according to any one of the above embodiments comprising incubating rRNA nucleic acid scaffold(s), fragment or analog thereof, and staples at a constant temperature of about 40° C. to about 60° C. for about 0.2 to about 6 days. According to another embodiment, the incubation is at a constant temperature of about 45° C. to about 55° C. According to some embodiments, the method comprises incubating rRNA scaffold, fragment or analog thereof, and staples at a constant temperature of about 50° C. to about 55° C. for about 5 to about 72 hours or about 7 to about 60 hour or about 12 to about 48 hours or about 18 to about 36 hour.

According to yet another embodiment, the method for preparing a RNA origami nanostructure according to any one of the above embodiments comprises the steps of:

(a) separately heating (i) the staple nucleic acid strands at 65° C. for 10 minutes and (ii) the scaffold nucleic acid strand(s) at 60° C. for 1 minute; and (b) mixing the heated staple nucleic acid strands and the pre-heated scaffold nucleic acid strand(s) of step (a); and (c) stepwise cooling of the mixture of (b) from 60° C. to 15° C. at the rate of −1° C./min.

According to any one of the above embodiments and methods, the scaffold nucleic acid and the staples nucleic acid strands are as defined in any one of the above aspects and embodiments. According to one embodiment, the scaffold nucleic acid strand, fragment or analog thereof is an isolated RNA nucleic acid, fragment or analog thereof. According to some embodiments, the RNA is a cell derived RNA such as ribosomal RNA or non-coding RNA. According to one embodiment, the RNA is a ribosomal RNA. According to one embodiment, the scaffold nucleic acid, fragment or analog thereof is an isolated rRNA nucleic acid, fragment or analog thereof. According to certain embodiment, the isolated RNA and in particular isolated rRNA comprises RNA isolated from cells, i.e. cell derived RNA, such as cell derived rRNA. Thus, according to any one of above embodiments, the above described methods comprise isolation of the RNA and in particular rRNA from the cells such as from bacteria or *S. cerevisiae*. Thus according to one embodiment, the method for preparation of the RNA origami nanostructure according to any one of the above embodiments comprises mixing an isolated rRNA nucleic acid and staples to obtain a mixture. According to another embodiment, the method for preparation of RNA origami nanostructure comprises mixing a total cell RNA with staples to obtain an initial mixture.

According to any one of the above embodiments, the method for preparation of RNA origami nanostructure according to the present invention comprises incubating an initial mixture comprising scaffold nucleic acid strand, fragment or analog thereof and staples, wherein the scaffold nucleic acid comprises more than 200, more than 300, more than 500, more than 700, more than 750, more than 800, more than 900, more than 1000, more than 1100, more than 1200, more than 1300, more than 1500, more than 1700, more than 2000, more than 2500, more than 2800, more than 3000, more than 3500 or more that 4000 bases. According to another embodiment, the scaffold polynucleotide comprises about 700 to 20000, about 750 to about 15000, about 800 to about 13000, about 850 to about 12000, about 900 to about 11000, about 1000 to about 10000, about 1100 to about 8000, about 1200 to about 5000, or about 1300 to about 4000 nucleotides. According to additional embodiment, the scaffold polynucleotide comprises about 1500 to about 3500, about 1800 to about 3000, about 2000 to about 3800, or about 2500 to about 3500 nucleotides. According to yet another embodiment, the scaffold polynucleotide comprises about 2800 to about 3200 or about 3000 bases. According to more specific embodiment, the scaffold polynucleotide comprises about 1600 to about 3500 nucleotide bases. According other embodiment, the polynucleotide, fragment or analog thereof comprises about 200 to about 5000, about 300 to about 4000, about 400 to about 3000, about 500 to about 2000 or about 600 to about 1800 nucleotide bases.

According to some embodiments, the staples are RNA nucleic acids. According to other embodiments, the staples are DNA nucleic acids.

According to some embodiment, the scaffold nucleic acid used for preparing RNA origami nanostructure according to the present invention is a scaffold having the sequence selected from SEQ ID NO:1 and SEQ ID NO: 68, or a fragment or analog thereof.

According to another embodiment, RNA origami nanostructure comprises the scaffold polynucleotide comprising the sequence SEQ ID NO:1 and a set of staples comprising staple oligonucleotide having the sequences (i) SEQ ID NOs: 2-55, (ii) SEQ ID NOs: 508-561 or (iii) any combination of sequences of (i) and (ii). According to some embodiments, the RNA origami nanostructure, obtained by a method of the present invention, further comprise staples having the sequences set forth in (a) SEQ ID NOs: 56-67, (b) SEQ ID NOs: 561-573, or (c) any combination thereof.

According to another embodiment, the RNA origami nanostructure comprises a scaffold polynucleotide comprising the nucleic acid sequence SEQ ID NO:1 and staple oligonucleotides having the sequences set forth in SEQ ID NOs: 655-695. According to one embodiment, the RNA origami nanostructure comprises about 50% to about 99%, about 60 to about 95%, about 70% to about 90%, or about 80% to 85% of the set of staple oligonucleotides having the sequences as set forth in SEQ ID NOs: 655-695.

According to another embodiment, the scaffold polynucleotide comprises the sequence set forth in SEQ ID NO:68 and the staple oligonucleotide strands having the sequences set forth in (i) SEQ ID NOs: 69-170, and optionally 171-186 (ii) SEQ ID NOs: 360-437, or (iii) SEQ ID NOs: 438-500 and wherein the obtained nanostructure is a cuboctahedron.

According to some embodiments, the method is selected from Protocol 1, Protocol 2, protocol 3, protocol 4, Protocol 5, Protocol 6, and protocol 7 as described below.

Protocol 1—incubating an initial mixture comprising rRNA scaffold nucleic acid, fragment or analog thereof, and staples nucleic acids as follows:

a. incubating at 60° C. for 1 min
b. incubating at 55° C. for 5 min
c. incubating at 50° C. for 10 min
d. incubating at 37° C. for 10 min; and
e. incubating at 25° C. for 10 min.

Protocol 2—incubating an initial mixture comprising rRNA scaffold nucleic acid, fragment or analog thereof, and staples nucleic acids as follows:

(a) incubating at 60° C. for 1.5 min;
(b) incubating at 55° C. for 7.5 min;
(c) incubating at 50° C. for 15 min;
(d) incubating at 37° C. for 15 min; and
(e) incubating at 25° C. for 15 min.

Folding protocol 3—incubating an initial mixture comprising rRNA scaffold nucleic acid, fragment or analog thereof, and staples nucleic acids as follows:

(a) incubating at 60° C. for 1 min;
(b) cooling from 59° C. to 56° C. at a rate of −1° C./0.5 min;
(c) incubating at 55° C. for 5 min;
(d) cooling from 54° C. to 51° C. at a rate of −1° C./0.5 min;
(e) incubating at 50° C. for 10 min;
(f) cooling from 49° C. to 38° C. at a rate of −1° C./0.5 min;
(g) incubating at 37° C. for 10 min;
(h) cooling from 36° C. to 26° C. at a rate of −1° C./0.5 min;
(i) incubating at 25° C. for 10 min.

Folding protocol 4—incubating an initial mixture comprising rRNA scaffold nucleic acid, fragment or analog thereof, and staples nucleic acids as follows:

(a) incubating at 60° C., 1.5 min;
(b) cooling from 59° C. to 56° C. at a rate of −1° C./0.5 min;

(c) cooling from 55° C. to 25° C. at a rate of −1° C./1 min;

Folding protocol 6—incubating an initial mixture comprising rRNA scaffold nucleic acid, fragment or analog thereof, and staples nucleic acids as follows:

(a) incubating at 60° C. for 1 min;

(b) incubating at 55° C. for 5 min;

(c) incubating at 50° C. for 5 min;

(d) incubating at 45° C. for 10 min; and (e) cooling from 40° C. to 15° C. at a rate of −1° C./10 min.

Folding protocol 7: cooling the initial mixture comprising rRNA scaffold nucleic acid, fragment or analog thereof, and staples nucleic acids as follows from 65° C. to 15° C. at a rate −1° C./min.

According to some embodiments, the method is Protocol 5 as described in the Examples.

According to any one of the above embodiments, the present invention provides an RNA origami nanostructure of the present intention prepared by any one of the methods of the present invention. Thus in one embodiment, the present invention provides an RNA origami nanostructure comprising one or more scaffold nucleic acid strands and a plurality of staple oligonucleotide strands, wherein said one or more scaffold polynucleotide strand comprises a ribosomal RNA (rRNA) polynucleotide strand, fragment or an analog thereof and wherein the RNA origami nanostructure is prepared by any one of the methods of the present invention. According to one embodiment, the RNA origami nanostructure further comprises an active moiety.

According to another aspect, the present invention provides a nucleic acid molecule comprising the rRNA scaffold and the staple nucleic acids of the present invention. In one embodiment, the present invention provides a nucleic acid molecule comprising the sequences set forth in SEQ ID NO: 1-55. According to one embodiment, a nucleic acid molecule comprises the sequences set forth in SEQ ID NO: 1-67.

According to another embodiment, the present invention provides a nucleic acid molecule comprising the sequences set forth in SEQ ID NO: 1 and 508-561. According to a further embodiment, the nucleic acid molecule further comprises the sequences set forth in SEQ ID NOs: 562-573.

According to another embodiment, the present invention provides a nucleic acid molecule comprising the sequences set forth in SEQ ID NO: 1 and 655-695.

According to some embodiments, the present invention provides a nucleic acid molecule comprising the sequences set forth in SEQ ID NO: 68-170. According to one embodiment, the present invention provides a nucleic acid molecule comprising the sequences set forth in SEQ ID NOs: 68-186. According to another embodiment, the present invention provides a nucleic acid molecule comprising the sequences set forth in SEQ ID NOs: 68 and 360-437. According to yet another embodiment, the present invention provides a nucleic acid molecule comprising the sequences set forth in SEQ ID NOs: 68 and 438-500.

According to other embodiments, the present invention provides a nucleic acid molecule comprising the sequences set forth in SEQ ID NO: 1, 68 and 187-359.

According to some embodiments, the nucleic acid molecule comprises about 50% to about 99%, about 60 to about 95%, about 70% to about 90%, or about 80% to 85% of the set of staples defined hereinabove.

According to another aspect, the present invention provides a nucleic acid construct comprising at least one nucleic acid molecule of any one of the above embodiments operably linked to a promoter.

The term "promoter" as used herein is a regulator sequence that initiates transcription of a downstream nucleic acid.

The term "operably linked" as used herein refers to an arrangement of elements that allows them to be functionally related. For example, a promoter is operably linked to a sequence if it controls the sequence's transcription to RNA or translation to a protein.

According to a further embodiment, the present invention provides a vector comprising the nucleic acid construct of the present invention.

The terms "vector" and "expression vector" are used herein interchangeably and refer to any viral or non-viral vector such as plasmid, virus, retrovirus, bacteriophage, cosmid, artificial chromosome (bacterial or yeast), phage, phagemid, binary vector in double or single stranded linear or circular form, or nucleic acid, sequence which is able to transform host cells and optionally capable of replicating in a host cell. The vector may be integrated into the cellular genome or may exist extrachromosomally (e.g., autonomous replicating plasmid with an origin of replication). The vector may contain an optional marker suitable for use in the identification of transformed cells, e.g., tetracycline resistance, kanamycin resistance or ampicillin resistance. A cloning vector may or may not possess the features necessary for it to operate as an expression vector.

According to still another aspect, the present invention provides a host cell comprising the nucleic acid molecule, the nucleic acid construct or the vector according to any one of the above embodiments. According to some embodiments, the cell is a prokaryotic or eukaryotic cell. As such, the present invention encompasses an RNA origami nanostructure comprising one or more scaffold nucleic acid strands and a plurality of staple nucleic acid strands, wherein said one or more RNA scaffold nucleic acid comprises a ribosomal RNA (rRNA) nucleic acid, fragment or an analog thereof, wherein said RNA origami nanostructure is formed within a cell.

According to yet another aspect the present invention provides a pharmaceutical composition comprising a plurality of RNA origami nanostructures of the present invention.

The term "pharmaceutical composition" as used herein refers to a composition comprising at least one RNA origami nanostructure as disclosed herein optionally formulated together with one or more pharmaceutically acceptable carriers.

Formulation of the pharmaceutical composition may be adjusted according to applications. In particular, the pharmaceutical composition may be formulated using a method known in the art so as to provide rapid, continuous or delayed release of the active ingredient after administration to mammals.

According to any one of the above embodiments, the pharmaceutical composition is in a form selected from the group consisting of tablets, pills, capsules, pellets, granules, powders, lozenges, sachets, cachets, elixirs, suspensions, dispersions, emulsions, solutions, infusions, syrups, aerosols, ophthalmic ointments, ointments, soft and hard gelatin capsules, suppositories, sterile injectable solutions, and sterile packaged powders.

According to any one of the above embodiments, the pharmaceutical composition is suitable for administration via a route selected from the group consisting of oral, rectal, intramuscular, subcutaneous, intravenous, inrtaperitoneal, intranasal, intraarterial, intravesicle, intraocular, transdermal and topical.

The composition for oral administration may be in a form of tablets, troches, lozenges, aqueous, or oily suspensions, dispersible powders or granules, emulsions, hard or soft capsules, or syrups or elixirs. Pharmaceutical compositions intended for oral use may be prepared according to any method known to the art for the manufacture of pharmaceutical compositions and may further comprise one or more agents selected from sweetening agents, flavoring agents, coloring agents and preserving agents in order to provide pharmaceutically elegant and palatable preparations. Tablets contain the active agent in admixture with non-toxic pharmaceutically acceptable excipients, which are suitable for the manufacture of tablets. These excipients may be, e.g., inert diluents such as calcium carbonate, sodium carbonate, lactose, calcium phosphate, or sodium phosphate; granulating and disintegrating agents, e.g., corn starch or alginic acid; binders; and lubricating agents. The tablets are preferably coated utilizing known techniques to delay disintegration and absorption in the gastrointestinal tract and thereby provide an extended release of the drug over a longer period.

The term “pharmaceutically acceptable carrier” or “pharmaceutically acceptable excipient” as used herein refers to any and all solvents, dispersion media, preservatives, antioxidants, coatings, isotonic and absorption delaying agents, surfactants, fillers, disintegrants, binders, diluents, lubricants, glidants, pH adjusting agents, buffering agents, enhancers, wetting agents, solubilizing agents, surfactants, antioxidants the like, that are compatible with pharmaceutical administration. The use of such media and agents for pharmaceutically active substances is well known in the art. The compositions may contain other active compounds providing supplemental, additional, or enhanced therapeutic functions. Solid carriers or excipients are, for example, lactose, starch or talcum or liquid carriers such as, for example, water, fatty oils or liquid paraffins.

Other carriers or excipients which may be used include, but are not limited to, materials derived from animal or vegetable proteins, such as the gelatins, dextrins and soy, wheat and psyllium seed proteins; gums such as acacia, guar, agar, and xanthan; polysaccharides; alginates; carboxymethylcelluloses; carrageenans; dextrans; pectins; synthetic polymers such as polyvinylpyrrolidone; polypeptide/protein or polysaccharide complexes such as gelatin-acacia complexes; sugars such as mannitol, dextrose, galactose and trehalose; cyclic sugars such as cyclodextrin; inorganic salts such as sodium phosphate, sodium chloride and aluminium silicates; and amino acids having from 2 to 12 carbon atoms and derivatives thereof such as, but not limited to, glycine, L-alanine, L-aspartic acid, L-glutamic acid, L-hydroxyproline, L-isoleucine, L-leucine and L-phenylalanine. Each possibility represents a separate embodiment of the present invention.

Solutions or suspensions used for parenteral, intradermal, or subcutaneous application typically include the following components: a sterile diluent such as water for injection, saline solution, fixed oils, polyethylene glycols, glycerine, propylene glycol (or other synthetic solvents), antibacterial agents (e.g., benzyl alcohol, methyl parabens), antioxidants (e.g., ascorbic acid, sodium bisulfite), chelating agents (e.g., ethylenediaminetetraacetic acid), buffers (e.g., acetates, citrates, phosphates), and agents that adjust tonicity (e.g., sodium chloride, dextrose). The pH can be adjusted with acids or bases, such as hydrochloric acid or sodium hydroxide, for example. The parenteral preparation can be enclosed in ampules, disposable syringes or multiple dose glass or plastic vials.

Pharmaceutical compositions adapted for parenteral administration include, but are not limited to, aqueous and non-aqueous sterile injectable solutions or suspensions, which can contain antioxidants, buffers, bacteriostats and solutes that render the compositions substantially isotonic with the blood of an intended recipient. Such compositions can also comprise water, alcohols, polyols, glycerine and vegetable oils, for example. Extemporaneous injection solutions and suspensions can be prepared from sterile powders, granules and tablets. Such compositions preferably comprise a therapeutically effective amount of a compound of the invention and/or other therapeutic agent(s), together with a suitable amount of carrier so as to provide the form for proper administration to the subject.

The terms “pharmaceutically acceptable” and “pharmacologically acceptable” include molecular entities and compositions that do not produce an adverse, allergic, or other untoward reactions when administered to an animal, or human, as appropriate. For human administration, preparations should meet sterility, pyrogenicity, general safety, and purity standards as required by a government drug regulatory agency, e.g., the United States Food and Drug Administration (FDA) Office of Biologics standards.

The pharmaceutical composition of the present invention may be administered by any known method. For example, a compound or an agent can be administered, intravenously, arterially, intradermally, intramuscularly, intraperitonealy, intravenously, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods. In some aspects, the administration includes both direct administration, including self-administration, and indirect administration, including the act of prescribing a drug. For example, as used herein, a physician who instructs a patient to self-administer a drug, or to have the drug administered by another and/or who provides a patient with a prescription for a drug is administering the drug to the patient.

According to one embodiment, pharmaceutical composition comprises a plurality of the RNA origami nanostructures comprising one or more scaffold nucleic acid strands and a plurality of staple nucleic acid strands, wherein said scaffold nucleic acid comprises a cell derived RNA. According to another embodiment, the cell derived RNA is a ribosomal RNA (rRNA), thus in some embodiments, pharmaceutical composition comprises the RNA origami nanostructure comprising one or more scaffold nucleic acid strands and a plurality of staple nucleic acids, wherein said scaffold nucleic acid(s) comprises an rRNA nucleic acid, fragment or analog thereof.

According to one embodiment, the scaffold nucleic acid strand is an isolated rRNA polynucleotide. According to one embodiment, the scaffold polynucleotide comprises at least 800 nucleotides. According to another embodiment, the scaffold polynucleotide strand comprises about 1000 nucleotides or more. According to a further embodiment, the scaffold polynucleotide comprises more than 700, more than 750, more than 800, more than 900, more than 1000, more than 1100, more than 1200, more than 1300, more than 1500, more than 1700, more than 2000, more than 2500, more than 2800, more than 3000, more than 3500 or more than 4000 nucleotides. According to another embodiment, the scaffold polynucleotide comprises about 700 to about 20000, about 750 to about 15000, about 800 to about 13000, about 850 to about 12000, about 900 to about 11000, about 1000 to about 10000, about 1100 to about 8000, about 1200 to about 5000, or about 1300 to about 4000 nucleotides. According to additional embodiment, the scaffold polynucleotide comprises about 1500 to about 3500, about 1800 to about 3000, about 2000 to about 3800, or about 2500 to about 3500 nucleotides. According to yet another embodiment, the scaffold polynucleotide comprises about 2800 to about 3200 or about 3000 bases. According to more specific embodiment, the scaffold polynucleotide comprises about 1600 to about 3500 nucleotide bases. According other embodiment, the scaffold polynucleotide strand, fragment or analog thereof comprises about 200 to about 5000, about 300 to about 4000, about 400 to about 3000, about 500 to about 2000 or about 600 to about 1800 nucleotides.

According to any one of the above embodiment, the rRNA nucleic acid is selected from prokaryotic and eukaryotic rRNA nucleic acid. According to one embodiment, the rRNA is a bacterial rRNA. According to one embodiment, the rRNA is an eukaryotic rRNA nucleic acid such as rRNA from *S. cerevisiae*. According to some embodiment, the staple according to the present invention are RNA staples, DNA staples or a combination of RNA and DNA staples. According to some embodiments, the staples are RNA staples forming an A-conformation double helix with a scaffold(s). According to one particular embodiment, the scaffold and the RNA staples form A-conformation RNA: RNA double helix having 12 base-pairs per turn. According to another embodiment, the scaffold and the staples form RNA:DNA A-conformation double helix. According to any one of the above embodiments, the RNA origami nanostructure comprises a plurality of scaffold nucleic acids. According some embodiments, the RNA origami nanostructure further comprises an active moiety. According to some embodiments, the active moiety is selected from a protein, nucleic acid, lipid, glycoprotein, glycolipid, and small molecule. According to any one of the above embodiments, the RNA origami nanostructure comprises a targeting domain. According to one embodiment, the RNA origami nanostructure comprises a latch domain hybridized to the targeting domain, wherein said targeting domain and said latch domain are capable of detaching upon binding of the targeting domain to a target molecule thereby transiting the nanostructure from a closed to an open conformation.

According to other embodiments the pharmaceutical composition according to the present invention comprises an RNA origami nanostructure comprising the scaffold polynucleotide having the sequence SEQ ID NO:1, a fragment or analog thereof. According to such embodiment, the RNA origami nanostructure comprises staple oligonucleotides having the sequences set forth in SEQ ID NOs: 2-55 or 508-561 and optionally further comprising staples having the sequences set forth in SEQ ID NOs. 56-67 or 561-573. According to another embodiment, the pharmaceutical composition comprises an RNA origami nanostructure comprising the scaffold polynucleotide having the sequence SEQ ID NO:1, a fragment or analog thereof and staple oligonucleotides having the sequences set forth in SEQ ID NOs: 655-695.

According to other embodiments the pharmaceutical composition according to the present invention comprises an RNA origami nanostructure comprising the scaffold polynucleotide having the sequence SEQ ID NO:68, fragment or analog thereof. According to such embodiment, the RNA origami nanostructure comprises staple oligonucleotides having the sequences set forth in (i) SEQ ID NOs: 69-170 and optionally oligonucleotides having sequences SEQ ID NOs: 171-186 (ii) SEQ ID NOs: 360-437, or (iii) in SEQ ID NOs: 438-500. According to some embodiments, the pharmaceutical composition according to the present invention comprises the RNA origami nanostructure comprising a plurality of scaffold polynucleotide(s) e.g. plurality of scaffold polynucleotides having the sequence set forth in SEQ ID NO:1 or in SEQ ID NO:68. Such RNA origami nanostructure, according to another embodiment, comprises the staple oligonucleotides having the sequences set forth in SEQ ID NOs: 187-359. According to some embodiments, the RNA origami nanostructure comprises about 50% to about 99%, about 60 to about 95%, about 70% to about 90%, or about 80% to 85% of the set of staples defined hereinabove.

The rRNA origami structures according to the present invention as well as pharmaceutical composition comprising same may be used as well known in the art, e.g. for delivering an active moiety to a particular target.

A Set of Antibacterial Nucleic Acids

The present invention is based in part on the observation that administering to bacteria a set of staple nucleic acids capable of forming a nucleic acid origami nanostructure together with bacterial ribosomal RNA provides a bactericidal effect.

The present invention provides in a further aspect a set of antibacterial nucleic acids, wherein the set comprises a plurality of different staple nucleic acids, wherein said staple nucleic acids bind specifically to a bacterial ribosomal RNA (rRNA) to form a nucleic acid origami nanostructure.

In some embodiments, the terms "staples nucleic acid" and "staple" are used interchangeably and refer to a staple nucleic acid that hybridize with at least two non-contiguous sequences within the bacterial rRNA.

According to one embodiment, the term "scaffold" refers to a long single stranded bacterial rRNA nucleic acid.

According to one embodiment, the terms "set of staples" and "set of staple nucleic acids" are used herein interchangeably and refer to a set of staple nucleic acids used for folding one nucleic acid origami nanostructure based on one or more a particular bacterial rRNA(s). The term "antibacterial nucleic acids" as used herein means that the nucleic acids bind to a bacterial rRNA.

According to one embodiment, the bacterial rRNA, is selected from 16S, 23S, 5S rRNA and pre-rRNA. The term "pre-rRNA", also known as a primary transcript, refers to a bacterial ribosomal RNA precursor which typically containing up to 3 copies of each one of 16S, 23S, and 5S rRNA.

According to one embodiment, the staple nucleic acids are DNA nucleic acids. According to another embodiment, the staple nucleic acids are RNA nucleic acids. According to some embodiment, the staple nucleic acids are oligonucleotides.

According to some embodiments, the staple nucleic acids, such as staple oligonucleotides, consist of 5 to 120 or 10 to 100 nucleotides. According to one embodiment, the staple oligonucleotides consist of 5 to 80 nucleotides. According to another embodiment, the staple oligonucleotides consist of 6 to 60, 7 to 50 or 8 to 45 nucleotides. According to a further embodiment, the staple oligonucleotides consist of 10 to 45 or 15 to 40 nucleotides. According to certain embodiment, the staple oligonucleotides consist of 7 to 75 nucleotides. According to another embodiment, the staple consists of 10 to 300 nucleotides, 15 to 280, 20 to 250, 25 to 220, 30 to 200, 35 to 180, 40 to 150, 50 to 120, or 70 to 100 nucleotides. In some embodiments, the staples consist of 100 to 600, 120 to 560, from 150 to 520 from 200 to 480, from 250 to 420, from 300 to 380 or from 320 to 360 nucleotides. In other embodiment, the staple consists of up to 60% of the number of nucleotides in the target scaffold.

According to some embodiments, the set of staple nucleic acids comprises from 2 to 400 different staple nucleic acids. According to some embodiments, the set comprises from 5 to 250, from 10 to 200, from 15 to 180, from 20 to 150, from 25 to 120, from 30 to 100, from 35 to 80, from 40 to 60 staple nucleic acids. The term "different" means that the staples have different sequences.

According to one embodiment, the set comprises staple nucleic acids having the sequences as set forth is SEQ ID NO: 575-627. According to another embodiment, the set comprises staple nucleic acids having the sequences as set forth is SEQ ID NO: 628-654. According to one embodiment, the set comprises from about 10% to about 99%, about 20% to about 95%, about 30% to about 90%, about 40% to about 85%, about 50% to about 80% or about 60% to about 70% of the set of staples nucleic acids having the sequences SEQ ID NO: 575-627 or SEQ ID NO: 628-654.

According to some embodiments, the present invention provides a nucleic acid construct comprising the sequences of the staple nucleic acids of the set of antibacterial nucleic acids as described above. According to some embodiment, the nucleic acid construct comprises the sequences of 10% to 90% of the staple nucleic acids of the set.

According to some embodiments, the nucleic acid construct comprises reverse sequences of the staple nucleic acids of the set of antibacterial nucleic acids as described above. According to some embodiment, the nucleic acid construct comprises the reverse sequences of 10% to 90% of the staple nucleic acids of the set.

According to a further embodiment, the nucleic acid construct is conjugated to a permeability-enhancing moiety.

The term "permeability-enhancing moiety" refers to any moiety known in the art to facilitate actively or passively or enhance permeability of the compound into the cells. According to one embodiment, the permeability-enhancing moiety is a polysaccharide.

According to a further embodiment, the present invention provides a vector comprising the nucleic acid construct of the present invention.

According to one embodiment, the vector comprises a nucleic acid construct comprising the sequences of the staple nucleic acids of the set of antibacterial nucleic acids according to the present invention as described above. According to one embodiment, each one of the sequences of the staple nucleic acids is operably linked to an origin of replication and to a termination site.

In one embodiment, each one of the staple oligonucleotides is operably linked to an origin of replication and to a termination site such that each staple oligonucleotide is separately replicated by the bacterial DNA replication machinery.

According to another embodiment, the vector comprises a nucleic acid construct comprising the sequences of the staple nucleic acids of the set of antibacterial nucleic acids according to the present invention as described above, wherein the nucleic acid construct is operably linked to an origin of replication and to a termination site, and wherein the nucleic acid construct comprises a cleavable sequence between every pair of nucleic acids' sequences. According to one embodiment, the cleavable sequence is a hairpin-forming sequence. According to some embodiments, the hairpin is an enzymatically cleavable hairpin. According to such embodiments, the nucleic acid comprising the sequences of the staple oligonucleotides is replicated by the bacterial DNA replication machinery and consequently spliced or parsed either via self-splicing or via enzymatic splicing to produce DNA staple oligonucleotides. According to some embodiment, the cleavable sequence is cleavable by or consists of ribozyme.

According to one embodiment, the vector comprises a nucleic acid construct comprising the reverse sequences of the staple nucleic acids of the set of antibacterial nucleic acids according to the present invention as described above. According to one embodiment, the each one of the reverse sequences of the staple nucleic acids is operably linked to a promoter. According to such embodiments, each reverse sequences of staple nucleic acids is separately transcribed by the bacterial transcription machinery to produce RNA staple nucleic acids.

According to another embodiment, the vector comprises a nucleic acid construct comprising the reverse sequences of the staple oligonucleotides of the set of antibacterial oligonucleotides according to the present invention as described above, wherein the nucleic acid construct is operably linked to a promoter, and wherein the nucleic acid construct encodes for a cleavable sequence between every pair of nucleic acids sequences. According to one embodiment, the cleavable sequence is a hairpin-forming sequence. According to some embodiments, the hairpin is an enzymatically cleavable hairpin. According to such embodiments, the nucleic acid comprising the sequences of the staple oligonucleotides is transcribed by the bacterial transcription machinery and consequently spliced or parsed either via self-splicing or via enzymatic splicing to obtain RNA staple oligonucleotides. According to some embodiment, the cleavable sequence is cleavable by or consists of ribozyme.

According to one embodiment, the vector is a plasmid. According to another embodiment, the vector is a phage.

According to any one of the embodiment, staple oligonucleotides are obtained upon replication or transcription of the vector.

According to a further embodiment, the vector is conjugated to a permeability-enhancing moiety.

According to one embodiment, the vector of the present invention is formulated in a delivery system vehicle. According to one embodiment, the delivery system is selected from liposomes, micelles, nanoparticle, viral nanoperticals, carbonano tubes, aptamer, polymer drug conjugates, dendrimers, gelatin capsules, proliposomes, microspheres, gels, cyclodextrins, microspheres, nanostructures, virosomes, polymeric micelles, and chitosan.

According to a further aspect, the present invention provides a method for treating bacteria comprising contacting the bacteria with the set of antibacterial nucleic acids, with a nucleic acid construct comprising the set of antibacterial nucleic acids or with the vector of comprising such a nucleic acid construct.

According to one embodiment, the term "treating bacteria" as used herein refers to killing bacteria as well as preventing bacteria growth and replication. According to one embodiment, the present invention provides a method for treating bacteria comprising contacting the bacteria with the set of antibacterial oligonucleotides, with the nucleic acid construct or with the vector of the present invention.

According to some embodiments, the bacteria are gram positive bacteria. According to one embodiment, the gram positive bacteria are selected from *Streptococcus, Staphylococcus, Enterococcus*, Gram positive cocci, and *Peptostreptococcus*. Further optionally, the gram-positive bacteria is selected from beta-hemolytic *Streptococcus*, coagulase negative *Staphylococcus, Enterococcus faecalis* (VSE), *Staphylococcus aureus*, and *Streptococcus pyogenes*. Still further optionally, the gram-positive bacteria is selected from methicillin-sensitive *Staphylococcus aureus* (MSSA), and methicillin-resistant *Staphylococcus aureus* (MRSA), *Staphylococcus aureus, Staphylococcus epidermis* and other coagulase-negative staphylococci, *Streptococcus pyogenes, Streptococcus pneumoniae, Streptococcus agalactiae*, and *Enterococcus*.

According to other embodiments, the bacteria are gram negative bacteria. According to one embodiment, the gram negative bacteria are selected from the group consisting of: *Actinobacillus, Aeromonas, Anaplasma, Arcobacter, Avibacterium, Bacteroides, Bartonella, Bordetella, Borrelia, Brachyspira, Brucella, Campylobacter, Capnocytophaga, Chlamydia, Chlamydophila, Chryseobacterium, Coxiella, Cytophaga, Dichelobacter, Edwardsiella, Ehrlichia, Escherichia, Flavobacterium, Francisella, Fusobacterium, Gallibacterium, Haemophilus, Histophilus, Klebsiella, Lawsonia, Leptospira, Mannheimia, Megasphaera, Moraxella, Neorickettsia, Nicoletella, Ornithobacterium, Pasteurella, Photobacterium, Piscichlamydia, Piscirickettsia, Porphyromonas, Prevotella, Proteus, Pseudomonas, Rickettsia, Riemerella, Salmonella, Streptobacillus, Tenacibaculum, Vibrio* and *Yersinia*.

Further optionally, the gram-positive bacteria are selected from *Staphylococcus* spp, *Streptococci, Enterococcus* spp, *Leuconostoc* spp, *Corynebacterium* spp, *Arcanobacteria* spp, *Trueperella* spp, *Rhodococcus* spp, *Bacillus* spp, Anaerobic Cocci, Anaerobic Gram-Positive Nonsporulating Bacilli, *Actinomyces* spp, *Clostridium* spp, *Nocardia* spp, *Erysipelothrix* spp, *Listeria* spp, *Kytococcus* spp, *Mycoplasma* spp, *Ureaplasma* spp, and *Mycobacterium* spp.

According to another aspect the present invention provides a pharmaceutical composition comprising at least one of (i) at least one set of antibacterial nucleic acids of the present invention; (ii) at least one nucleic acid construct comprising the sequences or reverse sequences of the set of antibacterial nucleic acids; or (iii) at least one vector comprising the nucleic acid construct of (ii), and a pharmaceutically acceptable excipient.

Formulation of the pharmaceutical composition may be adjusted according to applications. In particular, the pharmaceutical composition may be formulated using a method known in the art so as to provide rapid, continuous or delayed release of the active ingredient after administration to mammals.

According to any one of the above embodiments, the pharmaceutical composition is in a form selected from the group consisting of tablets, pills, capsules, pellets, granules, powders, lozenges, sachets, cachets, elixirs, suspensions, dispersions, emulsions, solutions, infusions, syrups, aerosols, ophthalmic ointments, ointments, soft and hard gelatin capsules, suppositories, sterile injectable solutions, and sterile packaged powders.

According to any one of the above embodiments, the pharmaceutical composition is suitable for administration via a route selected from the group consisting of oral, rectal, intramuscular, subcutaneous, intravenous, inrtaperitoneal, intranasal, intraarterial, intravesicle, intraocular, transdermal and topical.

The pharmaceutical composition may be administered by any know method. The term "administering" or "administration of" a substance, a compound or an agent to a subject can be carried out using one of a variety of methods known to those skilled in the art. For example, a compound or an agent can be administered, intravenously, arterially, intradermally, intramuscularly, intraperitonealy, intravenously, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods. In some aspects, the administration includes both direct administration, including self-administration, and indirect administration, including the act of prescribing a drug. For example, as used herein, a physician who instructs a patient to self-administer a drug, or to have the drug administered by another and/or who provides a patient with a prescription for a drug is administering the drug to the patient.

According to one embodiment, the present invention provides a pharmaceutical composition comprising at least one set of antibacterial nucleic acids, wherein the set comprises a plurality of different staple nucleic acids, wherein said staple nucleic acids bind specifically to a bacterial ribosomal RNA (rRNA) to form a nucleic acid origami nanostructure. According to one embodiment, the bacterial rRNA is selected from 16S, 23 S, 5S rRNA and pre-rRNA. According to another embodiment, the staple nucleic acids are selected from DNA and RNA nucleic acids. According to a further embodiment, the set comprises from 2 to 400 different staple nucleic acids. According to a certain embodiment, the set comprises staple nucleic acids having the sequences as set forth in SEQ ID NOs: 575-627 or in SEQ ID NOs: 628-654.

According to one embodiment, the present invention provides a pharmaceutical composition comprising at least one nucleic acid construct comprising the sequences of a set of antibacterial nucleic acids wherein said staple nucleic acids bind specifically to a bacterial ribosomal RNA (rRNA) to form a nucleic acid origami nanostructure.

According to one embodiment, the present invention provides a pharmaceutical composition comprising the at least one nucleic acid construct comprising the reverse sequences of a set of antibacterial nucleic acids, wherein said staple nucleic acids bind specifically to a bacterial ribosomal RNA (rRNA) to form a nucleic acid origami nanostructure.

According to a further embodiment, the present invention provides a pharmaceutical composition comprising the at least one vector comprising the nucleic acid construct comprising the sequences or the reverse sequences of a set of antibacterial nucleic acids, wherein said staple nucleic acids bind specifically to a bacterial ribosomal RNA (rRNA) to form a nucleic acid origami nanostructure. According to one embodiment, the vector is a plasmid. According to another embodiment, the vector is a phage.

According to any one of the above embodiments, the pharmaceutical composition is formulated to enhance the permeability of the vector, e.g. plasmid, into bacterial cell.

According to any one of the above embodiments, the pharmaceutical composition is for use in treating a bacterial infection. According to some embodiment, the pharmaceutical composition is for use in treating a bacterial infection caused by gram positive or gram negative bacteria. According to some embodiment, the gram positive bacteria are selected from *Streptococcus, Staphylococcus, Enterococcus*, gram positive cocci, and *Peptostreptococcus*. According to other embodiments, the gram negative bacteria are selected *Actinobacillus, Aeromonas, Anaplasma, Arcobacter, Avibacterium, Bacteroides, Bartonella, Bordetella, Borrelia, Brachyspira, Brucella, Campylobacter, Capnocytophaga, Chlamydia, Chlamydophila, Chryseobacterium, Coxiella, Cytophaga, Dichelobacter, Edwardsiella, Ehrlichia, Escherichia, Flavobacterium, Francisella, Fusobacterium, Gallibacterium, Haemophilus, Histophilus, Klebsiella, Lawsonia, Leptospira, Mannheimia, Megasphaera, Moraxella, Neorickettsia, Nicoletella, Ornithobacterium, Pasteurella, Photobacterium, Piscichlamydia, Piscirickettsia, Porphyromonas, Prevotella, Proteus, Pseudomonas, Rickettsia, Riemerella, Salmonella, Streptobacillus, Tenacibaculum, Vibrio* and *Yersinia*.

According to another embodiment, the present invention provides a method of treating a bacterial infection in a subject in a need thereof comprising administering to said subject the pharmaceutical composition comprising at least one of (i) at least one set of antibacterial nucleic acids of the present invention; (ii) at least one nucleic acid construct comprising the sequences or reverse sequence of the set of antibacterial nucleic acids; or (iii) at least one vector comprising the nucleic acid construct of (ii); and a pharmaceutically acceptable excipient.

According to some embodiments, the method comprises administering the pharmaceutical composition via a route selected from the group consisting of oral, rectal, intramuscular, subcutaneous, intravenous, inrtaperitoneal, intranasal, intraarterial, intravesicle, intraocular, transdermal and topical.

The terms "comprising", "comprise(s)", "include(s)", "having", "has" and "contain(s)," are used herein interchangeably and have the meaning of "consisting at least in part of". When interpreting each statement in this specification that includes the term "comprising", features other than that or those prefaced by the term may also be present. Related terms such as "comprise" and "comprises" are to be interpreted in the same manner. The terms "have", "has", "having" and "comprising" may also encompass the meaning of "consisting of" and "consisting essentially of", and may be substituted by these terms. The term "consisting of" excludes any component, step or procedure not specifically delineated or listed.

As used herein, the term "about" means within ±10% of the value that follows it. In some embodiments term about "about" means within ±5% or about ±1% of the value that follows it.

This invention is further illustrated by the following examples, which should not be construed as limiting. Those skilled in the art will recognize, or be able to ascertain, using no more than routine experimentation, numerous equivalents to the specific substances and procedures described herein. Such equivalents are intended to be encompassed in the scope of the claims that follow the examples below.

EXAMPLES

Figure 1B:
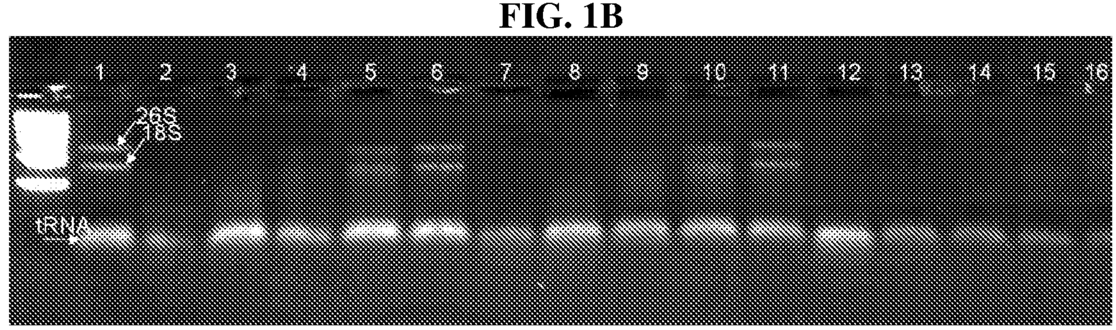
FIG. 1B, lanes 2-6: 30 min in 65° C., 61.6° C., 57.6° C., 52.7° C. and 45, respectively; lanes 7-11: 40 min in 65° C., 61.6° C., 57.6° C., 52.7° C. and 45, respectively; lanes 12-16: 60 min in 65° C., 61.6° C., 57.6° C., 52.7° C. and 45, respectively (agarose gel).

Example 1. Stability of rRNA Polynucleotide Strands at Different Temperature A stability of *S. cerevisiae* ribosomal RNA was tested at different temperatures, i.e. at 45° C., 52.7° C., 57.6° C., 61.6° C. and 65° C., for up to 1 hour in 1×TAE buffer supplemented with 10 mM $MgCl_2$. As can be seen from FIG. 1, at 65° C. rRNA is not stable, and degrades almost completely after 5 minutes. At lower temperatures (61.6° C., 57.6° C., 52.7° C. and 45° C.), rRNA is more stable, for example rRNA is completely stable at 52.7° C. for 20 minutes, but starts degrading between 20 and 30 minutes. After 40 minutes, only the sample kept at 45° C. is stable under these conditions.

Figure 2:
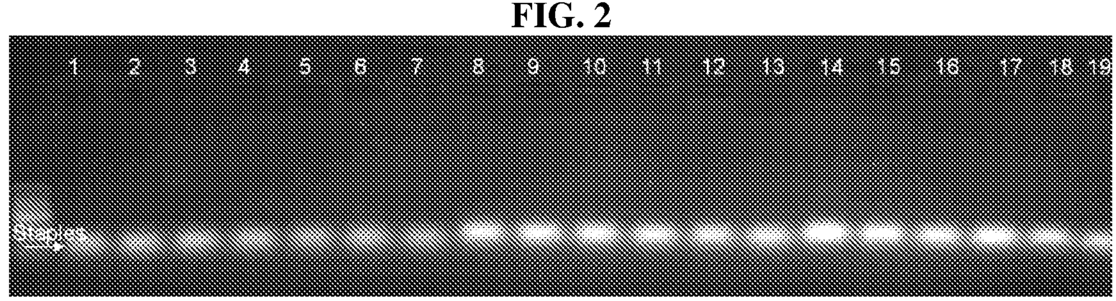
FIG. 2 shows a stability of RNA staples at 3 different temperatures, i.e. 65° C. (lanes 2-7), 61° C. (lanes 8-13) and 57.5° C. (lanes 14-19) tested over 2 hour. The tested time points were: 10, 20, 40, 60, 90 and 120 minutes at each temperature. Lane 1, used as a control—the sample was not subjected to high temperature (agarose gel).

Example 2. Stability of Short RNA Oligonucleotide Strands at Different Temperature Nucleic acid nanostructures, formed as an RNA double helix, can be built using RNA staples made ex-cellulo by in-vitro transcription The stability of such short RNA staples (SEQ ID NOs 508-573) at different temperatures was tested. As shown in FIG. 2, short RNA oligonucleotide strands were stable for up to 2 hours at 65° C. At this temperature rRNA degraded within several minutes.

Example 3. rRNA Extraction Protocol

Yeast cells (*S. cerevisiae*) were grown in 1500 ml of the appropriate medium to a density of approximately 1-2×$10^7$ cell s/ml (log phase) and pelleted by centrifugation. The pellet was resuspended in 30 ml of sterile saline (0.9% W/V, NaCl) and centrifuged at high speed. The pellet was resuspended in 3 ml of STE (0.32 M Sucrose, 20 mM Tris.Cl-pH 7.5, 10 mM EDTA-pH 8.0) and briefly vortexed in the presence of acid washed beads (Sigma #G8772).

18 ml of NTES (100 mM NaCl, 5 mM EDTA, 50 mM Tris.Cl-pH 7.5, 1% SDS) was added and the mixture briefly vortexed again. 15 ml of hot acidic phenol (Sigma #P4682, 65° C.) was added and the mixture was immediately vortexed and further incubated at 65° C. for 5 minutes with frequent vortexing. The aqueous phase of the mixture was removed and washed twice by centrifuging the mixture at high speed for 5 minute, and the removing the aqueous phase and protein interface into about 15 ml aliquot of hot phenol and incubating at 65° C. for 2 minutes with frequent vortexing.

The aqueous phase only was then removed into 12 ml of phenol/chloroform (1:1 phenol Sigma #P4682 and chloroform:isoamyl alcohol 24:1 Sigma #C0549) at room temperature, vortexed and spinned down. The aqueous phase was re-extracted with 9 ml of chloroform (Sigma #C0549), vortexed and spinned down. The aqueous phase was precipitated by the addition of 1/10 volume of 3M sodium acetate (pH 5.2) (Ambion #AM9740), followed by 2.5 volumes of absolute ethanol, vortexed and incubated overnight at −80° C. Following precipitation, the mixture was centrifuged at high speed for 40 minutes. The pellet was washed in 30 ml 70% cold ethanol in DEPC, centrifuged at 4500 rpm for 10 minutes and briefly dried. RNA pellet was resuspended in 5 ml DEPC and left to be dissolved at 55° C. for 10 minutes. RNA is than stored at −20 to −80° C. Concentration and quality were estimated by spectrophotometry (O.D and 260/280 ratio).

18S rRNA-DNA Structures

Series of experiment aimed at development and improving a protocol for folding 18S rRNA-DNA structures and assessing their stability were performed. In these experiments, unless stated otherwise, the concentration of the scaffold was 10 or 50 nM and the scaffold:staples set ratio was 1:10 or 1:5.

Example 4. Folding: Purified Vs. Not Purified Scaffold

In this experiment the folding rRNA-DNA structures according to folding protocol 1, using 18S *S. cerevisiae* rRNA (SEQ ID NO: 1) as scaffold and staples (SEQ ID NOs: 2-55) at 12 mM $MgCl_2$ was tested. The folding was perfumed using total RNA from *S. cerevisiae* or purified scaffold 18S rRNA.

Protocol 1:

f. incubating at 60° C. for 1 min
g. incubating at 55° C. for 5 min
h. incubating at 50° C. for 10 min
i. incubating at 37° C. for 10 min; and
j. incubating at 25° C. for 10 min.

Figure 3:
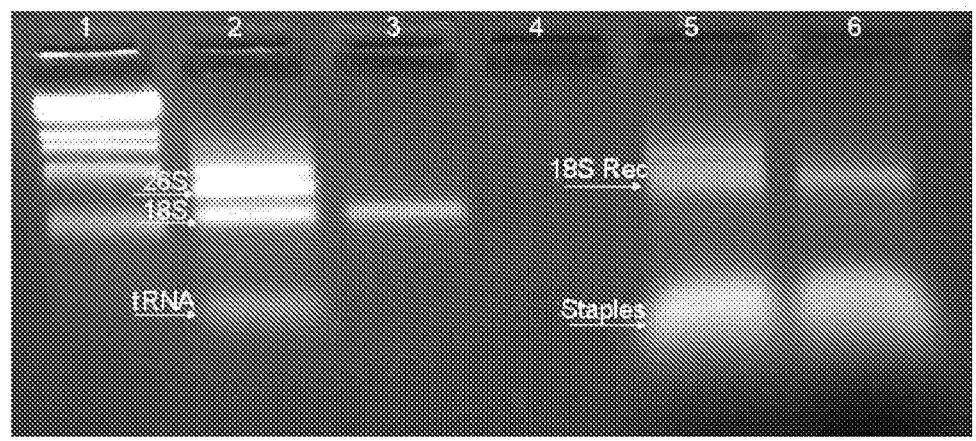
FIG. 3 shows an agarose gel of a comparison between folding using "not purified" scaffold (lane 2—total RNA extracted from *S. cerevisiae*), and purified scaffold (lane 3—18S rRNA purified on agarose gel); lanes 5 and 6 are folded "not purified" and purified 18S rRNA, respectively; lane 1: 1 kb DNA ladder. The folding was carried out in 1×TAE at 12 mM $MgCl_2$.
Figure 4:
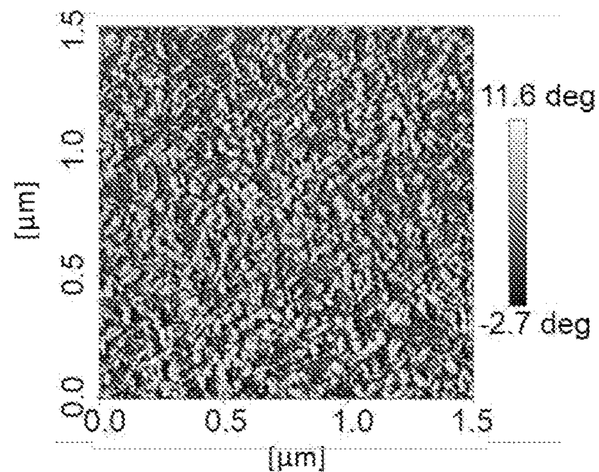
FIG. 4 shows an atomic force microscopy (AFM) scan of folded purified 18S rRNA-DNA structure of Example 4.

As can be seen from the gel (FIG. 3) the folding succeeded in both case (lanes 5-6), however folding with total RNA as scaffold results in smeary bands (lane 5) and dirtier sample than with purified 18S subunit (lane 6). On FIG. 4, showing an AFM image of the folded rRNA-DNA obtained from purified 18S rRNA it can be seen a defined rectangle structures of 18S rRNA-DNA. The sample wasn't cleaned from staple excess before the scan.

Example 5. Folding *S. cerevisiae* 18S rRNA-DNA Structure with or without Edge Staples at Different Concentration of $MgCl_2$ Folding 18S rRNA-DNA structures using 18S *S. cerevisiae* rRNA (SEQ ID NO: 1) as scaffold, and staples (SEQ ID NO: 2-55 and SEQ ID NO: 56-67: edges staples) at different $MgCl_2$ concentrations (from 10 mM to 20 mM at +2 mM steps) using the folding protocol 1 was performed.

Figure 5A:
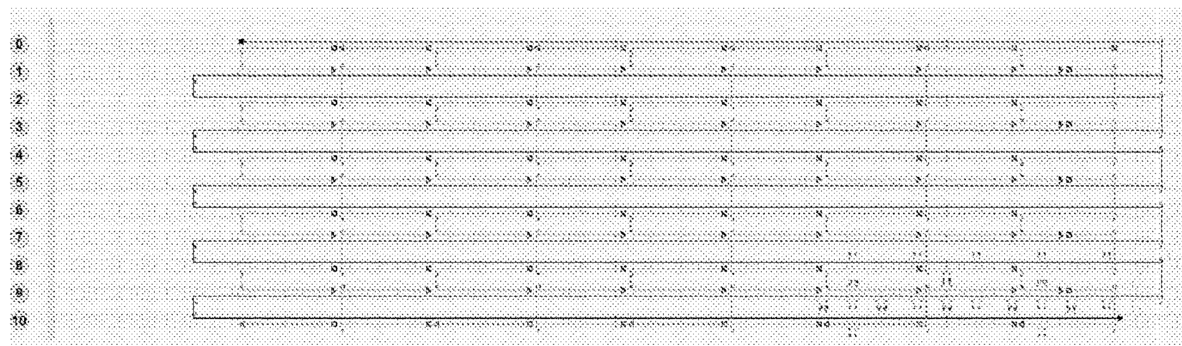
FIG. 5 shows a schematic presentation of 18S rRNA-DNA structure without (FIG. 5A) or with (FIG. 5B) edge staples (staples are colored in gray; scaffold colored in black. Edges staples are the staples that are found at the left and right sides of the shape).
Figure 5B:
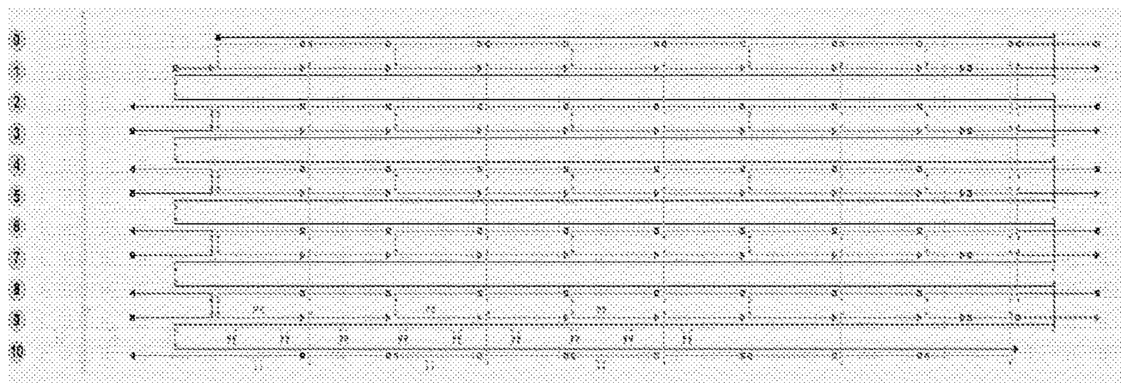

A schematic representation of the 18S rRNA-DNA structures comprising the scaffold and scaffold staples (FIG. 5A) and further comprising edge staples (SEQ ID NOs: 56-67, FIG. 5B) are presented.

Figure 6:
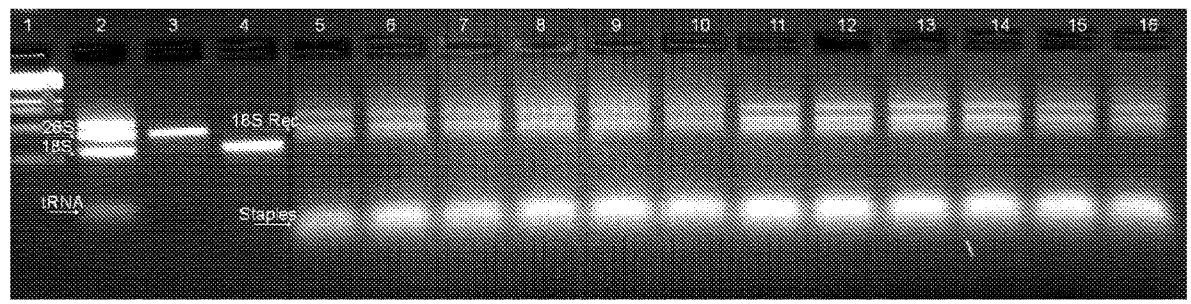
FIG. 6 shows an agarose gel of 18S rRNA-DNA structures folded in 1×TAE at different concentrations of $MgCl_2$ with (lanes 5-10) or without (lanes 11-16) edge staples. Lane 1: 1 kb DNA ladder; lane 2: total RNA extracted from *S. cerevisiae*; lane 3 and 4: purified 25S and 18S rRNA subunits, respectively. The experiment was carried out using total RNA. Each lane represent increasing $MgCl_2$ concentration staring from 10 mM in lanes 5 and 11, and up to 20 mM at lanes 10 and 16, in steps of +2 mM.

As can be seen from FIG. 6, there was no significant difference in folding 18S rRNA-DNA structures with (lanes 5-10) or without (lanes 11-16) edges. According to the gel, folding occurred in all $MgCl_2$ concentrations: 10 mM, 12 mM, 14 mM, 16 mM, 18 mM and 20 mM.

Example 6. Stability of Folded 18S rRNA-DNA Structures in Different Cations Conditions Stability of 18S RNA-DNA structures, folded according to folding protocol 1 using purified 18S rRNA as scaffold in different buffers (1×TAE, 12 mM $MgCl_2$; 1×TAE+2 mM $MgCl_2$; and DEPC), at 37° C. over 0, 1, 3 hours and over night was assessed. The results are presented in FIG. 7.

In addition, stability of folded (protocol 1) and cleaned 18S rRNA-DNA structures at 37° C. in different osmolarity conditions was tested for several time intervals. The tested conditions were 1×TAE, 12 mM $MgCl_2$ and 1.5 mM MgCl2, 140 mM NaCl, 4.2 mM KCl and 1.93 mM $CaCl_2$ (conditions resembling human blood). The tested time points were: 0, 30, 60, 120, 240 and 360 minutes. The results are presented in FIG. 8.

Figure 7:
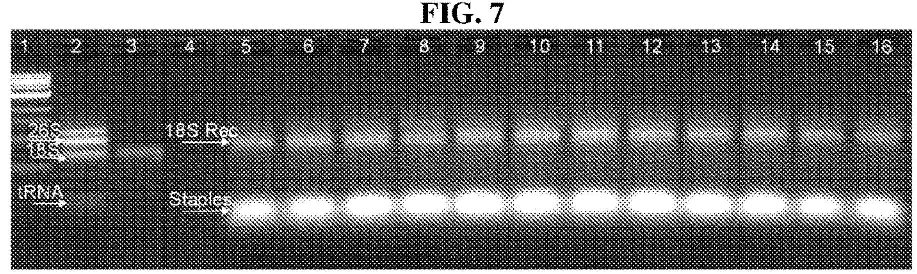
FIG. 7 shows an agarose gel of the folded 18S rRNA-DNA structures further incubated at 37° C. in 1×TAE 12 mM $MgCl_2$ (control—lanes 5-8), 1×TAE+2 mM $MgCl_2$ (lanes 9-12) and DEPC (lanes 13-16) over 0, 1, 3 hours and over night.

As can be seen from FIG. 7, there was a slight smear in the bands after 3 hours and O.N. when the folding condition are 1×TAE+2 mM $MgCl_2$ or DEPC, meaning that that the shapes start to fall apart when decreasing the $MgCl_2$ concentration. In addition, the 18S rRNA-DNA structures band slightly shifts down in lanes 15-16, indicating that DEPC is less suitable for DNA-RNA origami stability.

Figure 8:
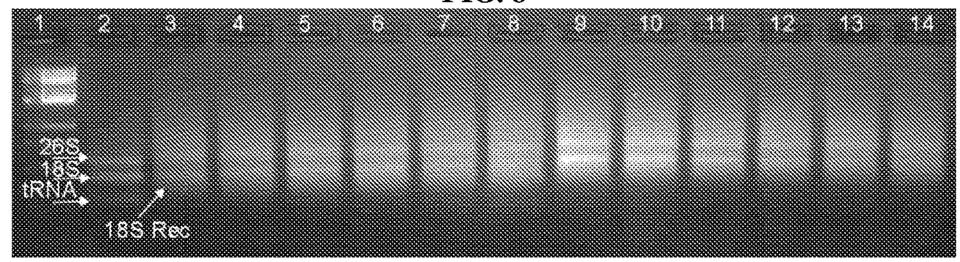
FIG. 8 shows the agarose gel of the folded 18S rRNA-DNA structures further incubated at 37° C. in 1×TAE at 125 mM $MgCl_2$ (lanes 9-14) or in condition mimicking human blood osmolarity (1.5 mM $MgCl_2$, 140 mM NaCl, 4.2 mM KCl and 1.93 mM $CaCl_2$)—lanes 3-8, for 0 (lanes 3 and 9), 30, 60, 120, 240 and 360 minutes (lanes 8 and 14, respectively).

As can be seen from FIG. 8, the rRNA structures were stable in both conditions over 6 hours. The bands become smearer probably because of a slight degradation of other RNA molecules that present in the total RNA extraction and weren't removed by centrifugation in centrifugal filter with 100 kDa cut off (100k amicon), e.g. 25S subunit. There is also an indication that after 3 hours and O.N the shapes (i.e. the folded structures) created dimmers. It was concluded that other cations present in the mixture, mimicking human blood, compensate for the decrease in the $MgCl_2$ concentration from 12 mM to 1.5 mM.

Example 7. Modifications of Protocol 1: Stability of 18S rRNA-DNA Structures at 37° C.

Figure 9:
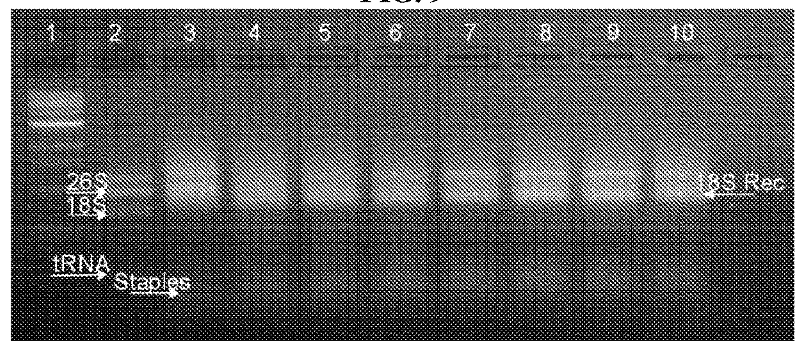
FIG. 9 shows an agarose gel of 18S rRNA-DNA structures folded from total RNA using protocol 1 and further incubated at 37° C. over 9 days. Lane 1: 1 kb DNA ladder; lane 2: total RNA; lane 3—18S rRNA-DNA folded structures that were not held at 37° C.; and lanes: 4-10: 18S rRNA-DNA structures incubated at 37° C. over 9 days at 37° C. The folding reactions were carried out in 1×TAE at 12 mM $MgCl_2$.

18S rRNA-DNA structures were folded from total RNA according to folding protocol 1 and then incubated in 1×TAE buffer (12 mM $MgCl_2$) at 37° C. for up to 9 days in order to test stability in human body temperature. The results presented in FIG. 9 show that the bands on the gel became stronger as the structures/shapes were incubated longer at 37° C. This indicated that not only that the shapes were stable at 37° C., but that keeping the 18S rRNA-DNA structures at 37° C. improved the folding quality and yield. The upper band appearing sharper in lanes 7-10 (the band above the 25S Rec. bands) may indicate that the shapes might form dimmers.

Figure 10:
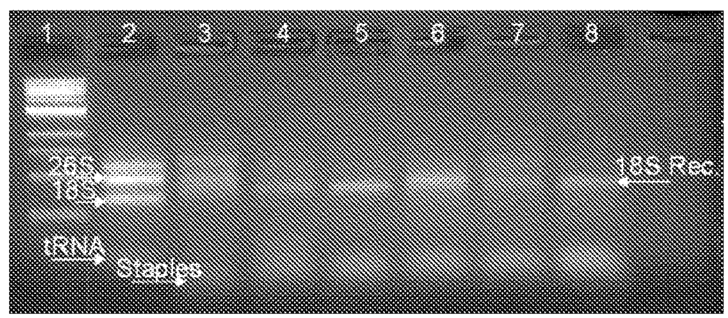
FIG. 10 shows an agarose gel of 18S rRNA-DNA structures folded according to folding protocol 1 (Example 4) and then incubated at 37° C. for different periods of time. Lane 1: 1 kb DNA ladder; lane 2: total RNA; 18S RNA-DNA structures folded from total RNA (lanes 3-5) or from purified 18S (lanes 6-8) and kept for 0 hour (lanes 3 and 6), 2.5 hours (lanes 4 and 7) or 9.5 hours (lanes 5 and 8) at 37° C. The folding was carried out in 1×TAE at 12 mM $MgCl_2$.
Figure 11A:
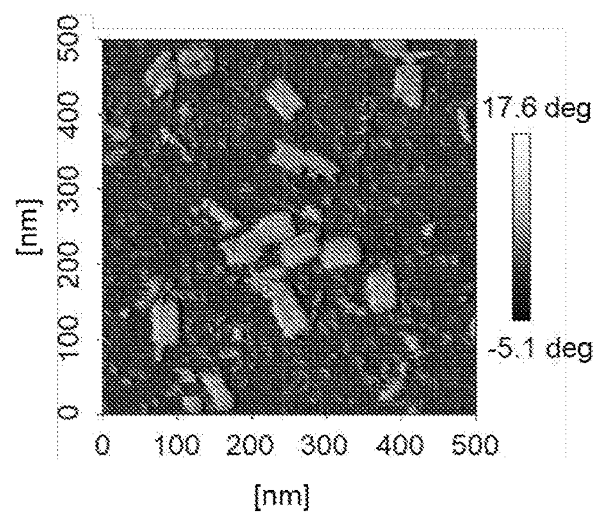
FIGS. 11A and 11B: not-purified, 2.5 days (different magnifications)
Figure 11B:
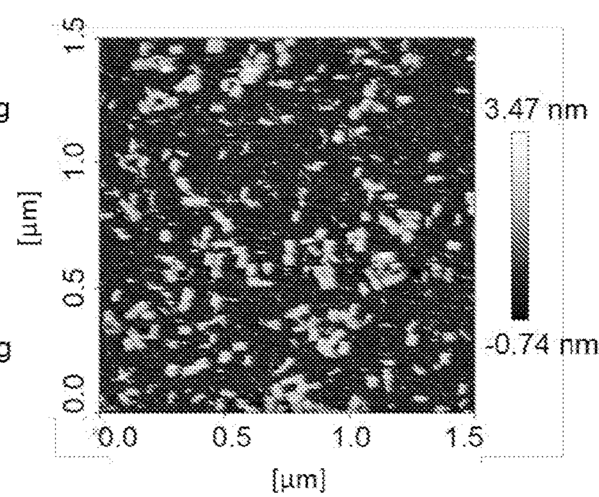
Figure 11C:
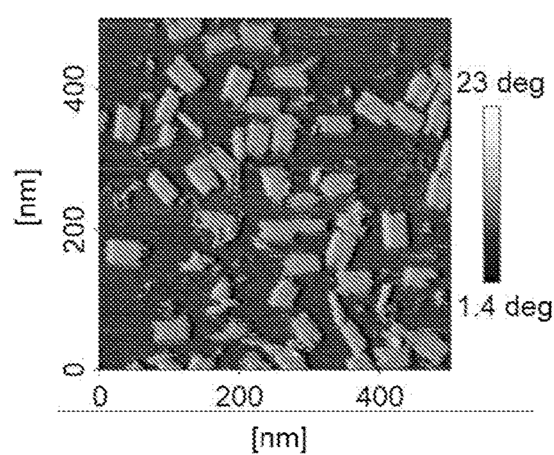
FIGS. 11C and 11D: purified, 2.5 days (different magnifications)
Figure 11D:
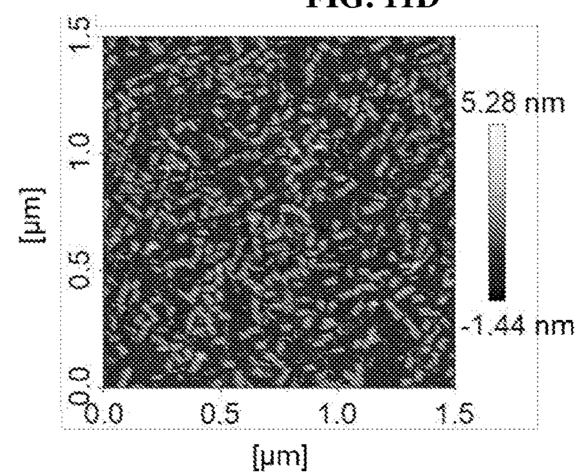
Figure 11E:
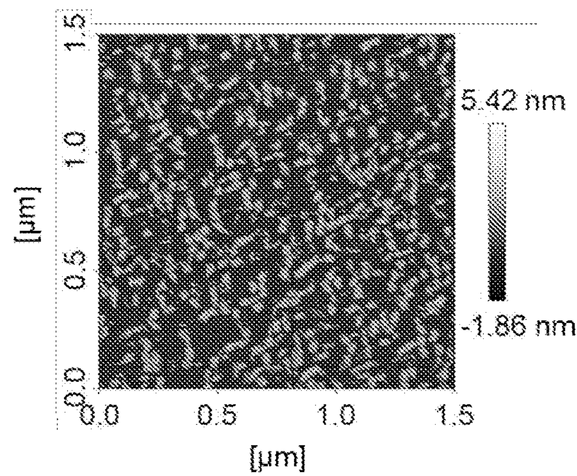
FIG. 11E: not-purified, 9.5 days.
Figure 11F:
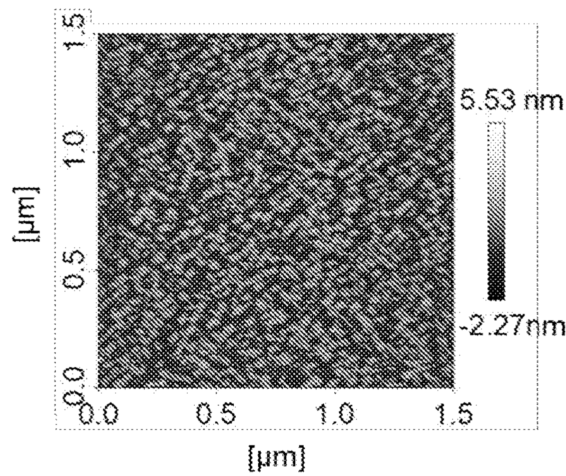
FIG. 11F: purified, 9.5 days.

Example 8. Modifications of Protocol 1: Stability of 18S rRNA-DNAs Structures at 37° C.—Purified Vs. Not-Purified Further to Example 7, we have tested the effect of purification of 18S rRNA on the efficacy of folding, performed in similar conditions as in Example 7. Structures from folded from a purified or not-purified RNA and were incubated for 2.5 and 9.5 days at 37° C. The gel and the AFM scans are presented in FIGS. 10 and 11, respectively.

It can be seen from these results that the folding succeeded in both experiments, however folding with total RNA usually results in smeary bands, when running in agarose gel, as well as in dirtier sample as shown on AFM, what affects the scan quality. In the higher resolution images it can be seen that the background of FIG. 11A image (not-purified) is much dirtier than the background of FIG. 11C (folded from purified 18S rRNA).

Moreover, the bands became more intense and sharp after 9.5 days, meaning that incubating the folded structure at 37° C. (after competing folding protocol 1) improves the folding quality and yield.

Example 9. Protocol 1—Optimization

Figure 12:
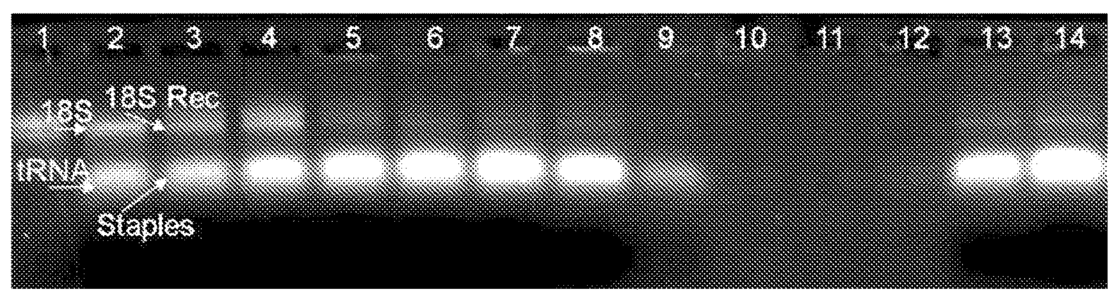
FIG. 12 shows agarose gel of 18S rRNA-DNA folded according to folding protocol 1, in folding buffer (1×TAE, 12 mM $MgCl_2$) and maintained at 37° C. over different periods. Lanes 3-5: stability of 18S rRNA-DNA structures folded using purified 18S rRNA, at 37° C. over 0, 2 and 9 days, respectively; lanes 6-9 and 13-14: stability of 18S rRNA-DNA structures folded using total RNA, at 37° C. over 0, 1, 2, 5, 6 and 9 days, respectively.

We further tested the stability of 18S rRNA-DNA structures (folded according to folding protocol 1 in folding buffer (1×TAE, 12 mM $MgCl_2$)) at 37° C. over different periods of time (0, 1, 2, 5, 6 and 9 days). The results presented on FIG. 12 show that the longer the structures are kept at 37° C., the stronger the bends are, indicating that maintaining the structures at 37° C. improved folding and its yield.

Figure 13:
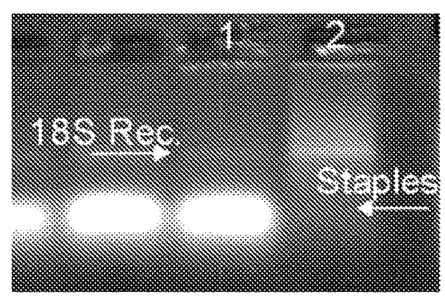
FIG. 13 shows 18S rRNA-DNA structures before and after centrifugation in centrifugal filter with 100 kDa cut off (Amicon 100K).

We than further showed that the excess of staples, and other components of the total RNA below the size of 100 kDa may be eliminated by centrifugation the 18S rRNA-DNA structures in centrifugal filter with 100 kDa cut off (see FIG. 13). The 18S rRNA-DNA structures were not damaged by this procedure. This procedure may also use for concentration of the structures.

Example 10. Generation of 18S rRNA-DNA Structures with Biotin

Figure 14:
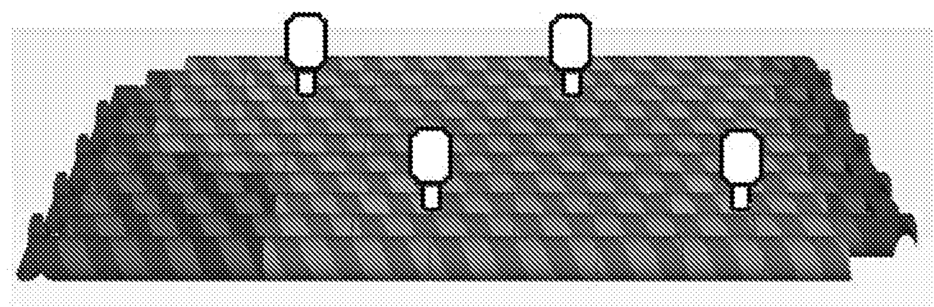
FIG. 14 shows 18S rRNA-DNA structures folded from purified 18S rRNA according to folding protocol 1, the structures comprise four biotin sites represented by white structures.
Figure 15:
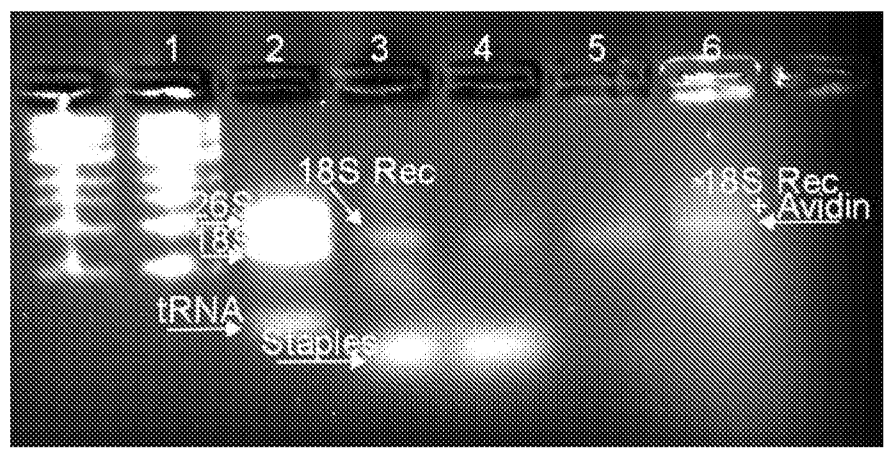
FIG. 15 shows an agarose gel of the folded 18S rRNA-DNA structures having biotin sites with or without avidin. Lanes 3-4: folded 18S rRNA-DNA structures before cleaning; lane 5: folded 18S rRNA-DNA structures after cleaning (using amicon 100K); lane 6: cleaned 18S rRNA-DNA structures bound to avidin.

18S RNA-DNA structures having four biotin sites were folded from purified 18S rRNA according to folding protocol 1, in folding buffer (1×TAE, 12 mM $MgCl_2$). Schematic presentations of the structure are shown in FIG. 14. The binding sites are four original staples (SEQ ID NOs: 4, 28, 48 and 49) that contained biotin at their 5'. These biotin sites may serve as loading sites to a desired payload via biotin-avidin-biotin interaction or in order to execute chemical or biological reaction. In fact any one of the staples can have any modification on its 5' and/or 3', for example: biotin, fluorophore, NH2 etc. As can be seen from FIG. 15, avidin was successfully bound to the structures, as demonstrated by a shift of the corresponding band.

Figure 16:
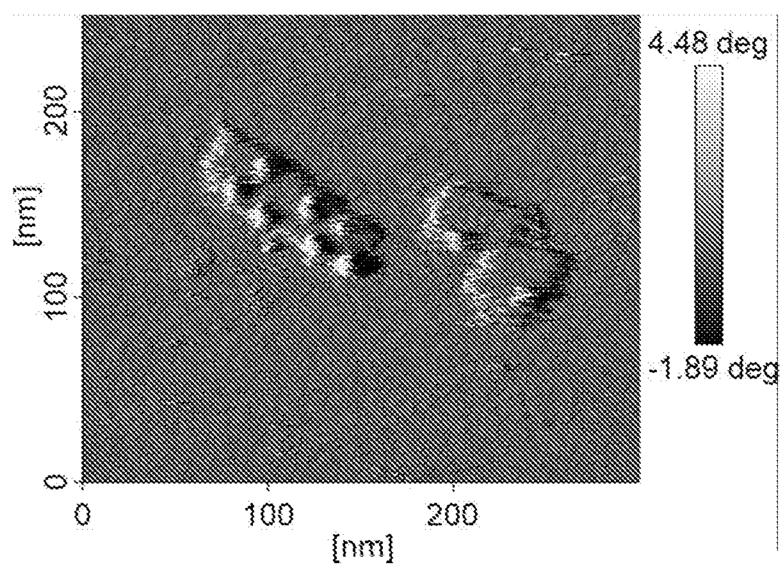
FIG. 16 shows an AFM image of 18S rRNA-DNA structures carrying biotin sites and bound to avidin molecules.

Binding of avidin to the biotin sites within the 18S rRNA-DNA structures was also demonstrated by AFM scan (see FIG. 16). The bright portions on the structures are avidin molecules, meaning the binding was successful. It can be seen that biotin modification on four staples did not effected the folding quality, and the shapes folded well. The percentage of the bound avidin depends, on the loading sites:avidin ratio, and on the incubation time of the avidin with structures.

Example 11. Folding 25S rRNA-DNA Structure

Figure 17:
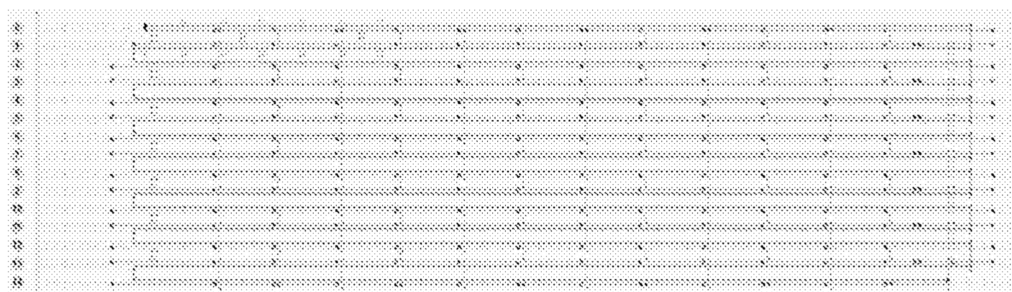
FIG. 17 shows a schematic presentation of 25S rRNA-DNA complex (staples are presented in gray and the scaffold in black).

In this experiment the folding rRNA-DNA structures according to folding protocol 1, using 25S *S. cerevisiae* rRNA (SEQ ID NO: 68) as scaffold and staples (SEQ ID NOs: 69-178) 12 mM $MgCl_2$ was tested. Schematic representation of the structure is shown on FIG. 17.

Figure 18:
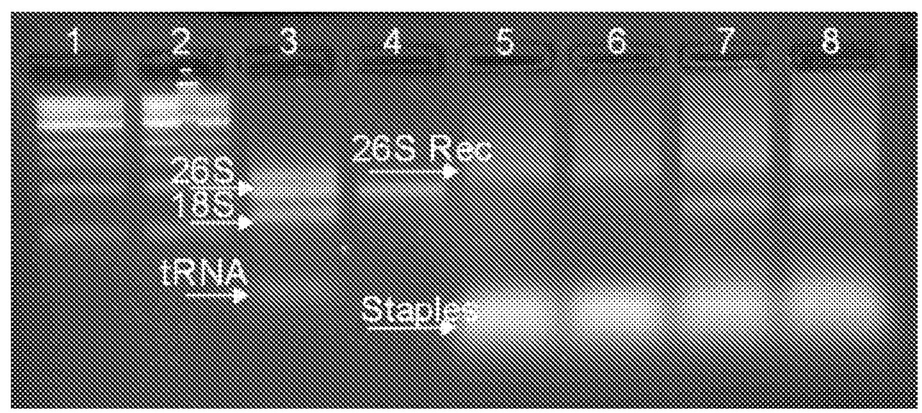
FIG. 18 shows an agarose gel of 25S rRNA-DNA structures folded from total RNA or purified 25S rRNA unit using protocol 1 in 1×TAE at 12.5 mM and 16 mM $MgCl_2$. Lane 3: total RNA from *S. cerevisiae*; lane 4: purified 25S rRNA; lanes 5-6: folding from purified 25S at 12.5 mM and 16 mM $MgCl_2$, respectively; lanes 7-8: folding from total RNA at 12.5 mM and 16 mM $MgCl_2$, respectively.

The structure was folded according to protocol 1 in 1×TAE with 12.5 mM or 16 mM $MgCl_2$ from total RNA of from a purified scaffold. As can be seen from FIG. 18, the folding succeeded regardless whether total RNA or purified 25 S rRNA subunit was used. However, folding with total RNA resulted in smeary bands and dirtier sample.

Figure 19:
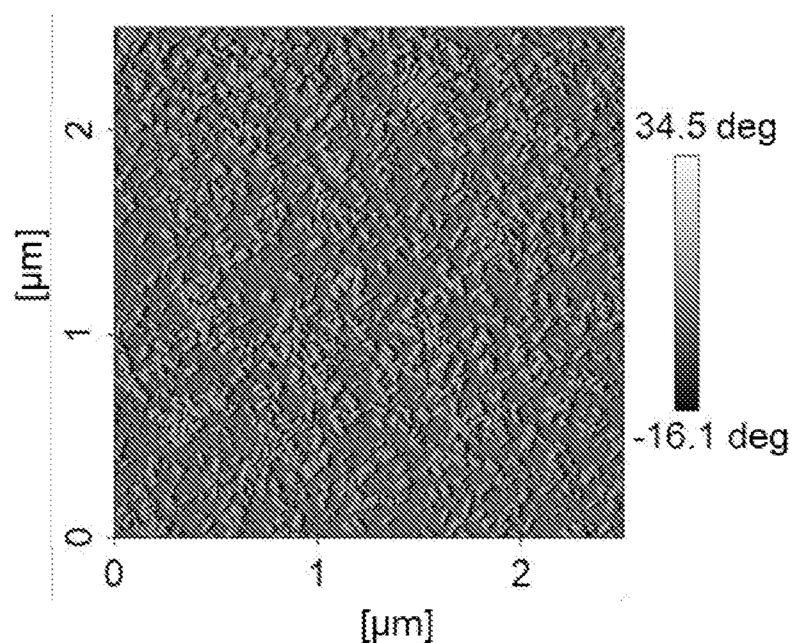
FIG. 19 shows an AFM image of the 25S rRNA-DNA structure folded from purified 26S rRNA at 16 mM $MgCl_2$ following folding protocol 1.

The AFM scan (FIG. 19) indicated that although 25S rRNA-DNA fold to a particular structure, rectangle, the yield and quality are not high enough and the folding protocol and condition have to be optimized.

Example 12. Optimization of the Folding Protocol for Folding 25S rRNA-DNA Structures—I Three different protocols were developed based on protocol 1 as following:

Folding protocol 2:

(a) incubating at 60° C. for 1.5 min;
(b) incubating at 55° C. for 7.5 min;
(c) incubating at 50° C. for 15 min;
(d) incubating at 37° C. for 15 min; and
(e) incubating at 25° C. for 15 min.

Folding protocol 3:

(j) incubating at 60° C. for 1 min;
(k) cooling from 59° C. to 56° C. at a rate of −1° C./0.5 min;
(1) incubating at 55° C. for 5 min;
(m) cooling from 54° C. to 51° C. at a rate of −1° C./0.5 min;
(n) incubating at 50° C. for 10 min;
(o) cooling from 49° C. to 38° C. at a rate of −1° C./0.5 min;
(p) incubating at 37° C. for 10 min;
(q) cooling from 36° C. to 26° C. at a rate of −1° C./0.5 min;
(r) incubating at 25° C. for 10 min.

Folding protocol 4

Figure 20:
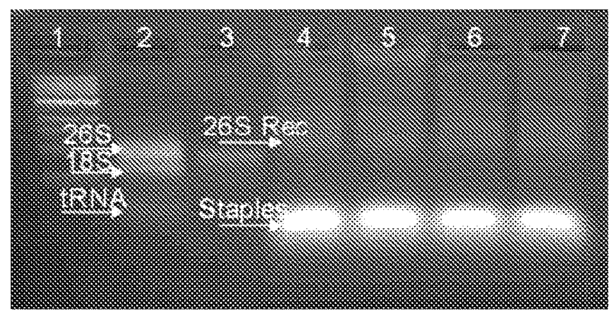
FIG. 20 shows an agarose gel of the 25S RNA-DNA structures folded using 4 different protocols. Lane 1: contains 1 kb DNA ladder; lane 2 and 3: total RNA and purified 26S, respectively; lanes 4-7: folding using protocols 1-4, respectively. The folding buffer was 1×TAE, 16 mM $MgCl_2$.
Figure 21A:
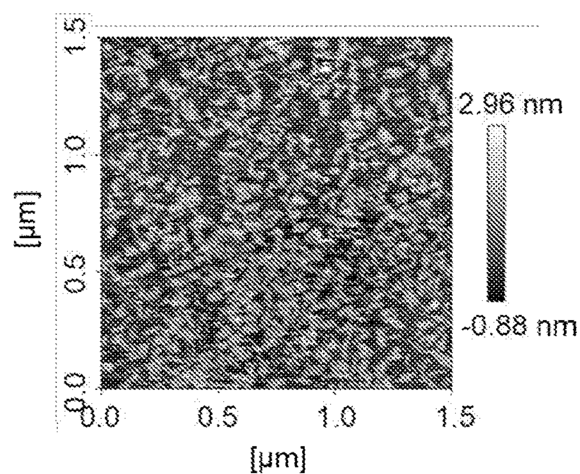
FIG. 21 shows AFM images of the 25S rRNA-DNA structures folded using protocol 2 (FIG. 21A), protocol 3 (FIG. 21B) or protocol 4 (FIG. 21C).
Figure 21B:
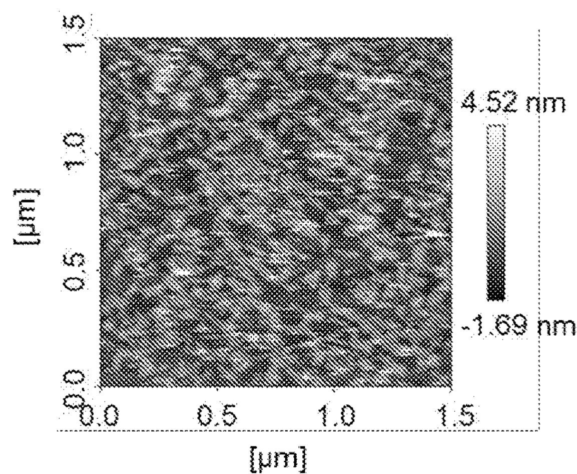
Figure 21C:
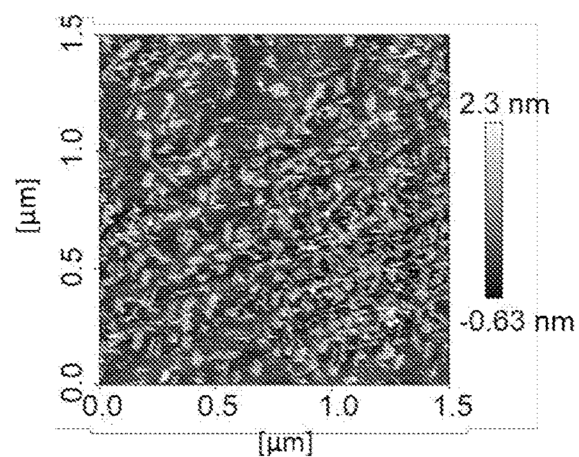

(a) incubating at 60° C., 1.5 min;
(b) cooling from 59° C. to 56° C. at a rate of −1° C./0.5 min;
(c) cooling from 55° C. to 25° C. at a rate of −1° C./1 min;

The results of the folding using different protocols are presented in FIG. 20 (agarose gel) and FIG. 21 showing the AFM images of the folded structures. As follows from these results, the bands indicating the folded 25S rRNA-DNA structures are smeary and not strong and sharp. In the AFM images besides 25S structures, in all four folding protocols partially folded shapes were observed.

Example 13. Optimization of the Folding Protocol for Folding 25S rRNA-DNA Structures—II In a further experiment, the folding was performed as in Example 11, with further incubation of the resulted structures at 37° C. for different periods of time. The folding was performed from total RNA in folding buffer (1×TAE, 16 mM $MgCl_2$). Following the folding, the samples were incubated at 37° C. for 2.5, 4, 5 and 6 day. The results are presented in FIG. 22 (agarose gel) and FIG. 23 (AFM images).

Figure 22A:
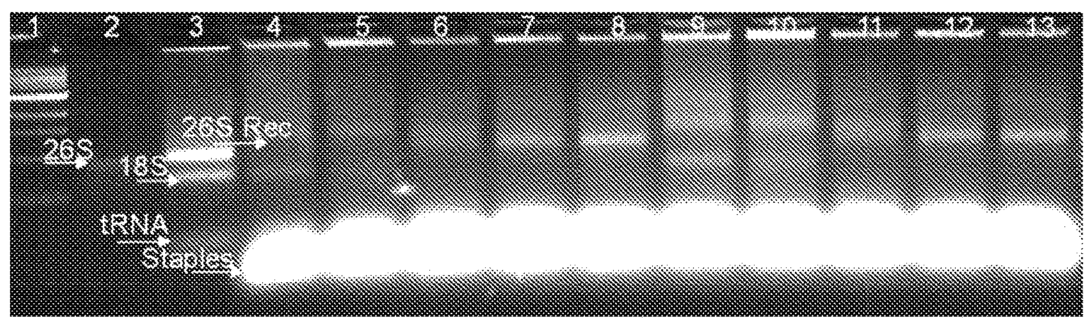
FIG. 22A: lane 1: 1 kb DNA ladder; lane 2: purified 25S rRNA; lane 3: total RNA; lanes 4-8: protocol 1+incubation for 0, 2.5, 4, 5 and 6 days, respectively; lanes 9-13: protocol 2+incubation for 0, 2.5, 4, 5 and 6 days, respectively.
Figure 22B:
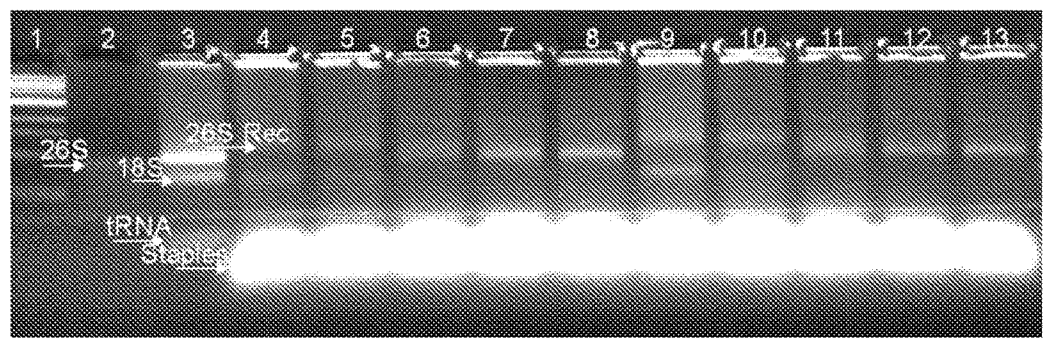
FIG. 22B: lanes 4-8: protocol 3+incubation for 0, 2.5, 4, 5 and 6 days, respectively; lanes 9-13: protocol 4+incubation for 0, 2.5, 4, 5 and 6 days, respectively. The folding buffer was 1×TAE, 16 mM $MgCl_2$.
Figure 23A:
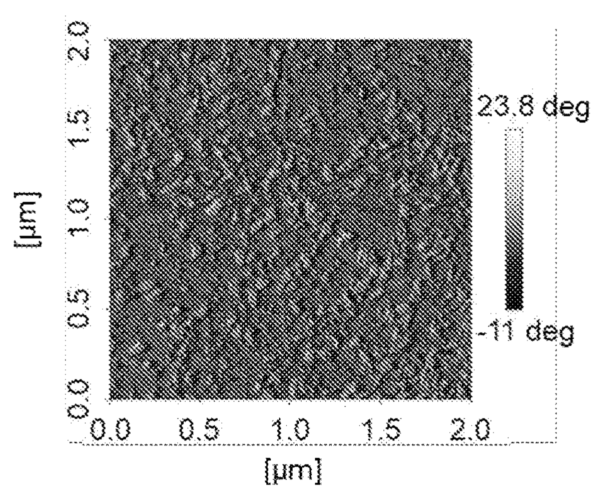
FIGS. 23A and 23B: protocol 1+incubation for 0 or 5 days, respectively.
Figure 23B:
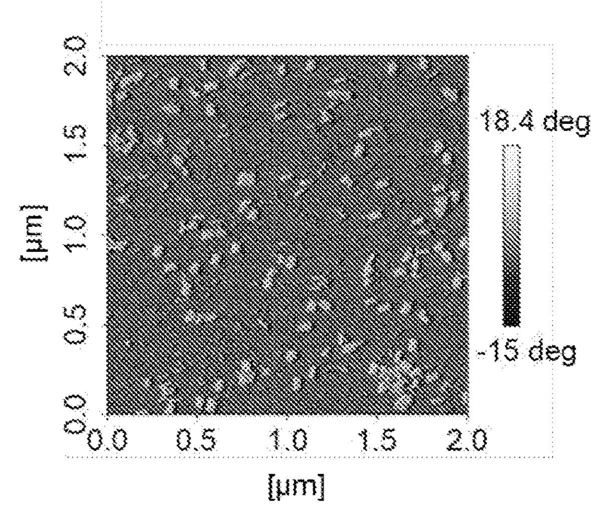
Figure 23C:
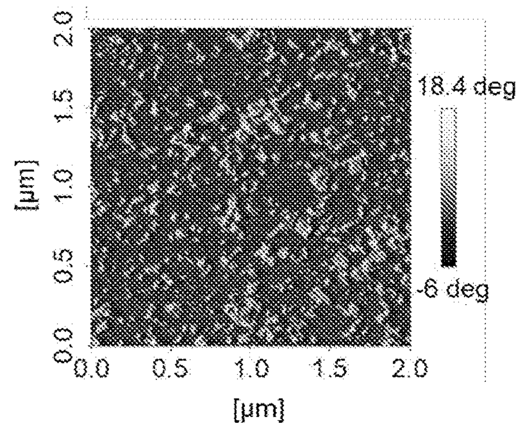
FIGS. 23C and 23D: protocol 2+incubation for 0 or 5 days, respectively.
Figure 23D:
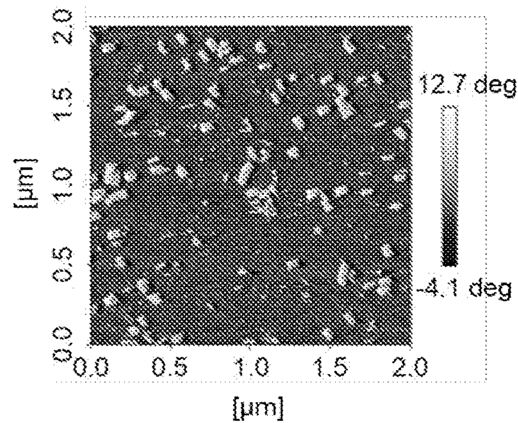
Figure 23E:
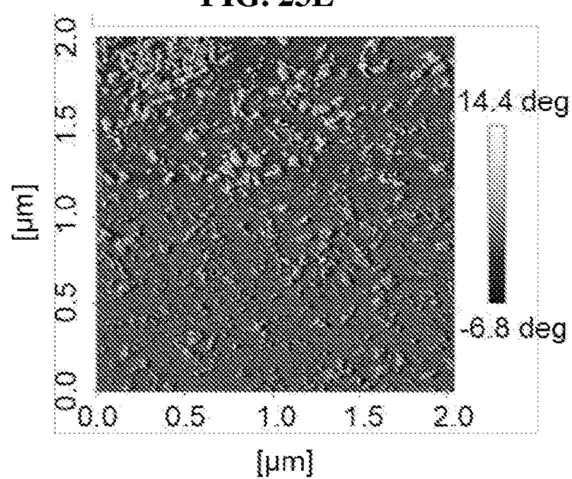
FIGS. 23E and 23F: protocol 3+incubation for 0 or 5 days, respectively.
Figure 23F:
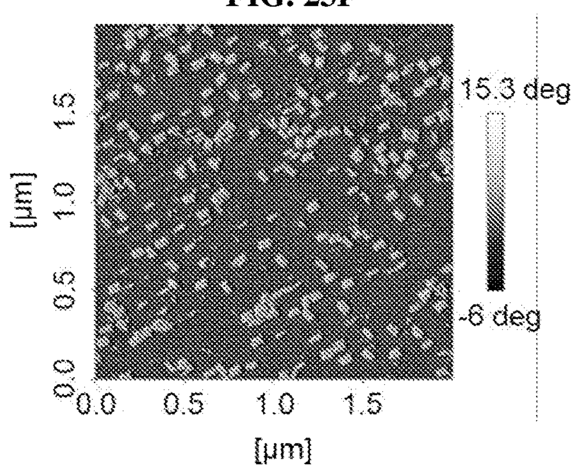
Figure 23G:
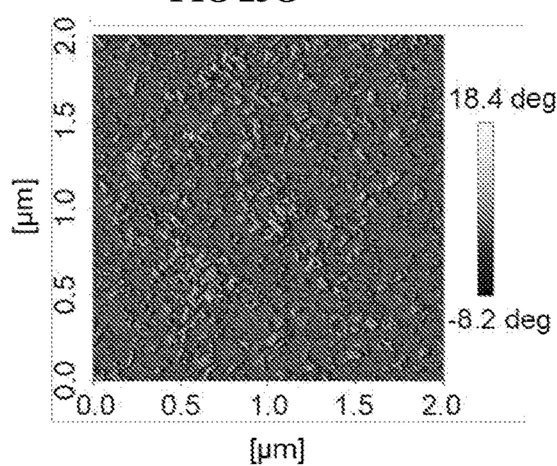
FIG. 23G-23K: protocol 3+incubation for 0, 2.5, 4, 5 and 6 days, respectively.
Figure 23H:
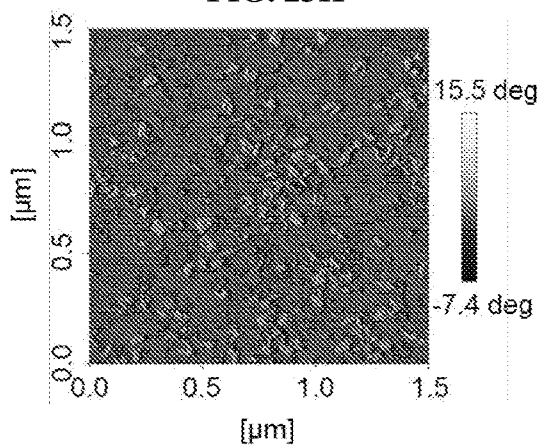
Figure 23I:
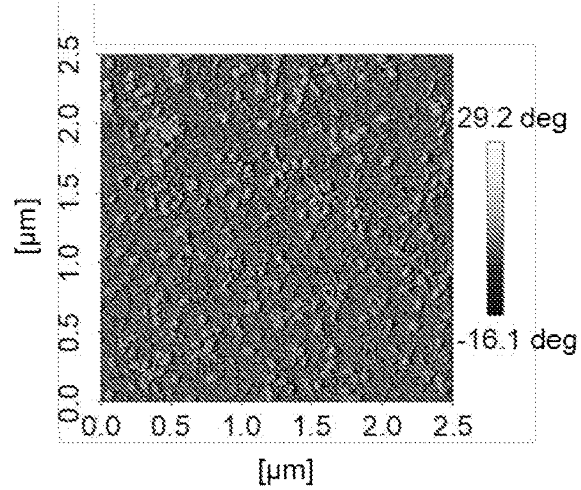
Figure 23J:
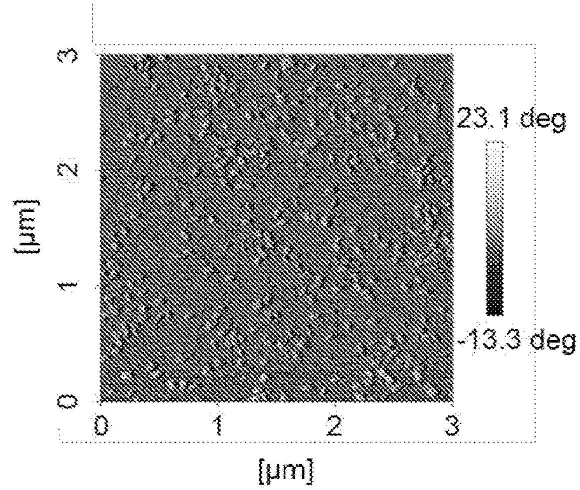
Figure 23K:
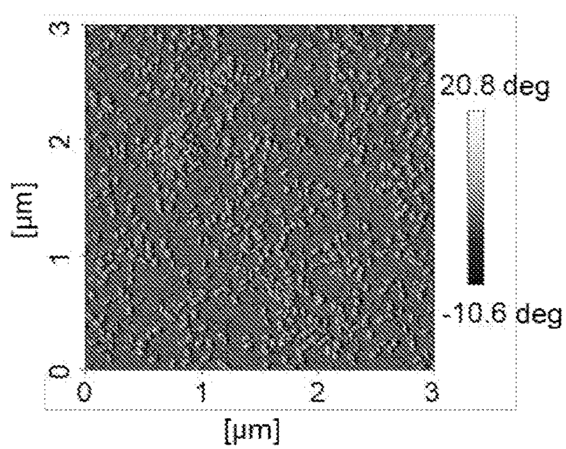

As can be seen on FIG. 22, the bands, indicating the successful folded 25S rRNA-DNA structures, became stronger as the samples were incubated longer at 37° C., indicating that the folding quality and yield were improved. Worth to mention, that the 18S rRNA degrades in these protocols, since after 2.5 days the bands representing 18S rRNA disappeared.

AFM images (FIG. 23) supported the above statement. Moreover, in the based on the images sampling all the 5 time points if incubation at 37° C. of the structures folded using folding protocol 4, it can be seen that at least 4 days at 37° C. are required in order to receive well formed 25S structures in high yield. Shorter time, results in partial structures.

Example 14. Folding 25S rRNA-DNA Structure at Constant Temperature

Figure 24A:
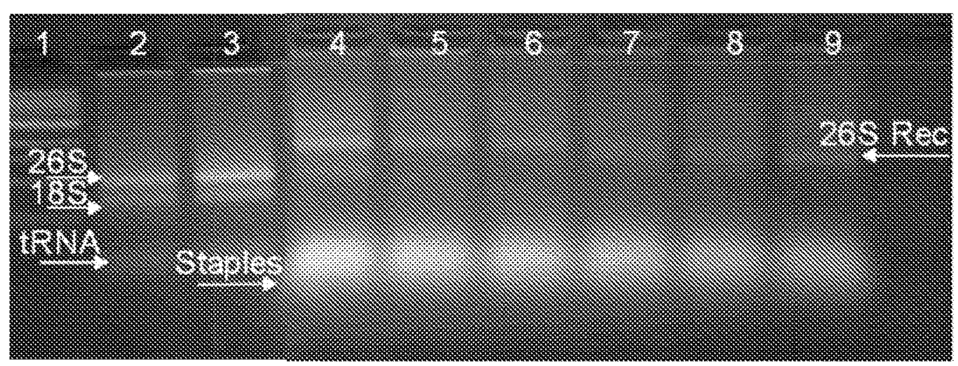
(FIG. 24A) or 50° C.
Figure 24B:
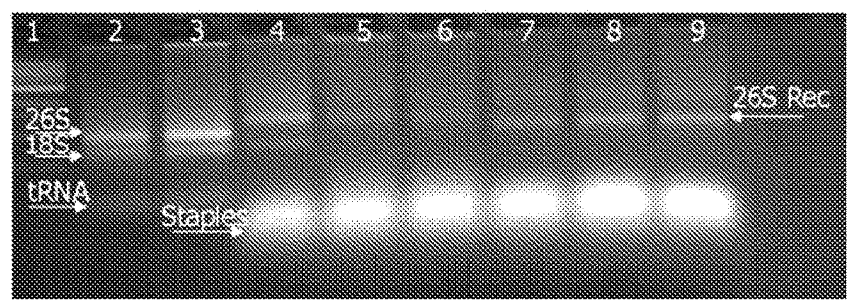
(FIG. 24B) and were tested at after 0, 4, 7 hours, 1, 1.5, and 2 days (lanes 4-9 in both figures). The folding buffer was 1×TAE, 16 mM $MgCl_2$.

A new folding protocol 5 for folding 25S rRNA-DNA structure was developed. The folding was carried out in constant temperatures: 45° C. (see FIG. 24A, lanes 11-16) or 50° C. (FIG. 24B, lanes 4-9) over 2 days. The folding temperature might be lower or higher, and the protocol duration might vary as a function of the complexity of the shape.

Figure 25A:
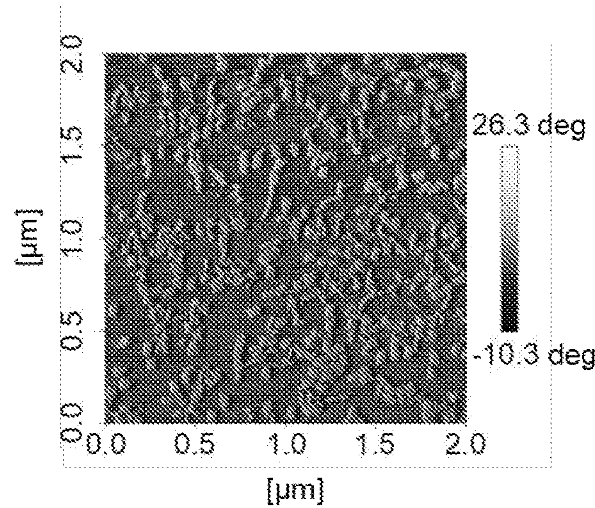
FIG. 25 shows AFM images of the 25S rRNA-DNA structures folded using protocol 5 at 50° C. after 7 hour (FIG. 25A), 1 or 2 days (FIG. 25B and FIG. 25C, respectively).
Figure 25B:
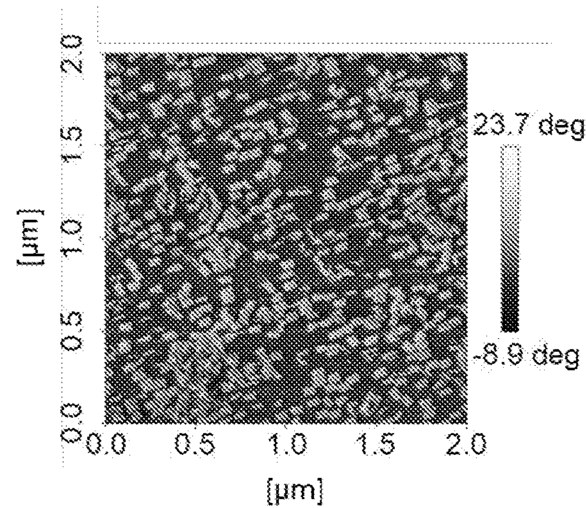
Figure 25C:
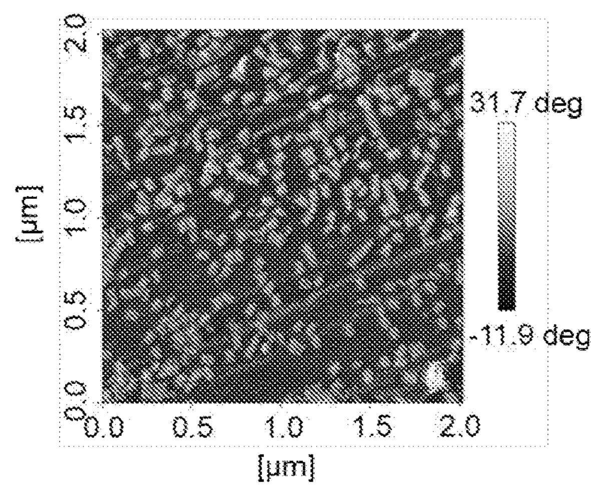

As can be seen from FIG. 24, the folding succeeded both in 45° C. and 50° C. By comparing the band height and intensity it seems that the folding occurs faster and more efficient at 50° C. than at 45° C. FIG. 25 shows that the structures were successfully formed in both temperatures. It can be seen that incubating for 7 hour is enough to obtain the folding in high quality and yield; however as can be seen from the gel (if comparing the bands height at 7 hours and 1.5-2 days) and AFM images, that the folding is optimal at 1-2 days.

Figure 26:
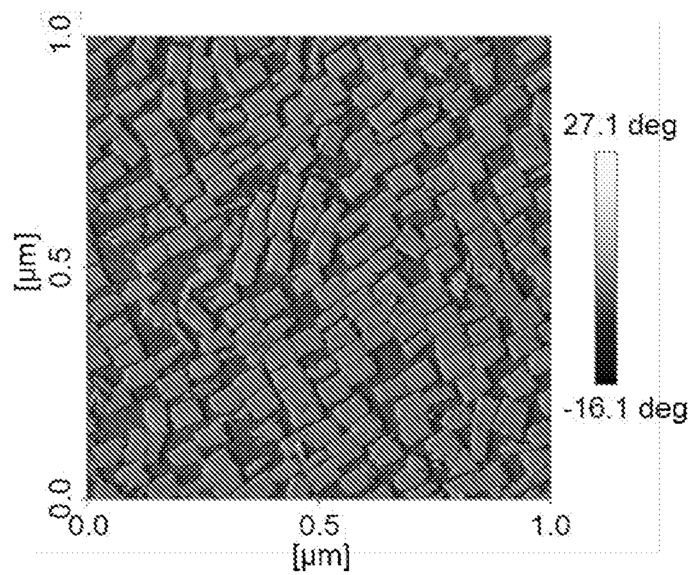
FIG. 26 shows AFM images of the 25S rRNA-DNA structures folded using protocol 5 with $MgCl_2$ and 50° C. after 2 days.

In further experiments it was shown that the folding may be carried out with lower concentration of $MgCl_2$ (e.g. 12 mM) and/or at higher temperature such as 55° C. (FIG. 26). It was observed that the folding is slightly faster at 55° C., since already after 7 hours the band representing 25S rRNA-DNA structures appeared and became more intense over the following days, while at 50° C. the band was more smeary and higher at that time, meaning most of the shapes were still folding. After 1 day the bands looked similar in both temperatures, indicating that folding can carried out in both temperatures and $MgCl_2$ concentrations.

Example 15. Folding 25S and 18S rRNA-DNA Structures from One Mixture: Protocol 1

Figure 27:
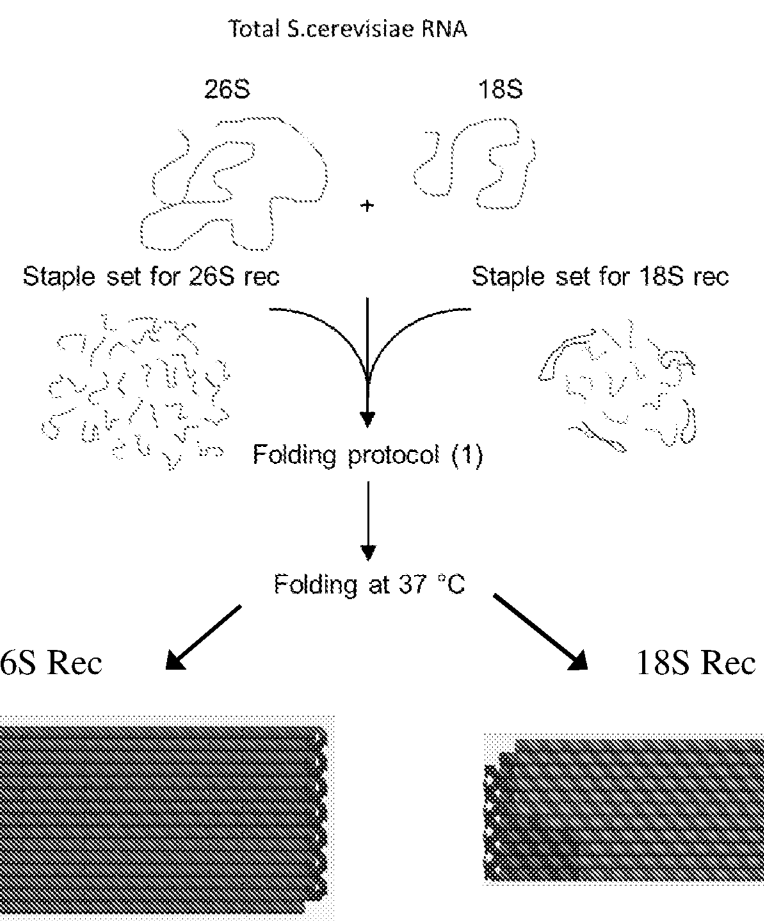
FIG. 27 shows a schematic representation of simultaneous folding of 25S and 18S rRNA-DNA structures from total RNA.

We have calibrated the folding conditions ($MgCl_2$) and folding protocol for folding two different separate rRNA-DNA structures from one reaction referred to as "Mix reaction"; one rectangle is small and is formed having 18S as a scaffold, while the other is bigger and has 25S rRNA as a scaffold (schematic representation of the experiment is presented in FIG. 27). The folding was carried out using total RNA from *S. cerevisiae* in two $MgCl_2$ concentrations: 12 mM and 16 mM in 1×TAE. The folding protocol used was folding protocol 1 which followed by incubation of the structures at 37° C. over 7 days. As a control, 18S rRNA-DNA and 25S rRNA-DNA structures were formed in separate reaction to test folding at these conditions.

Figure 28A:
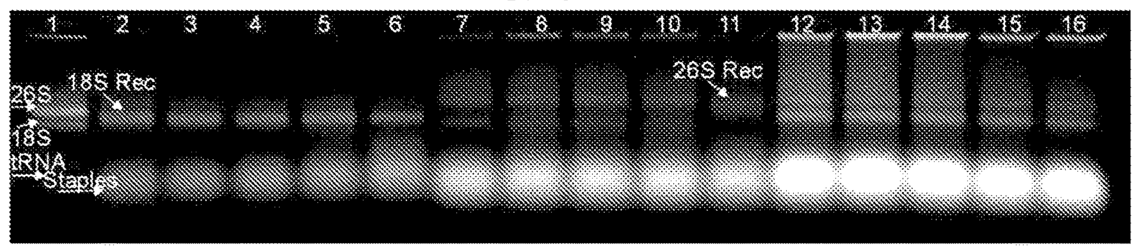
FIG. 28 show agarose gel of simultaneous folding of 25S and 18S rRNA-DNA structures from total rRNA in 1×TAE at 12 mM $MgCl_2$ (FIG. 28A) or 16 mM $MgCl_2$ (FIG. 28B). The 25S and 18S rRNA-DNA structures were folded separately as a control. The structures were tested after 0, 1, 2, 3, 6.5 days incubation at 37° C. For both gels: lane 1: contain total RNA extracted from *S. cerevisiae*; lanes 2-6: control. 5 point times for separate folding 18S rRNA-DNA structure; lanes 7-11: control—5 point times for separate folding of 25S rRNA-DNA structures; and Lanes 12-16: 5 point times for simultaneous folding from total rRNA.
Figure 28B:
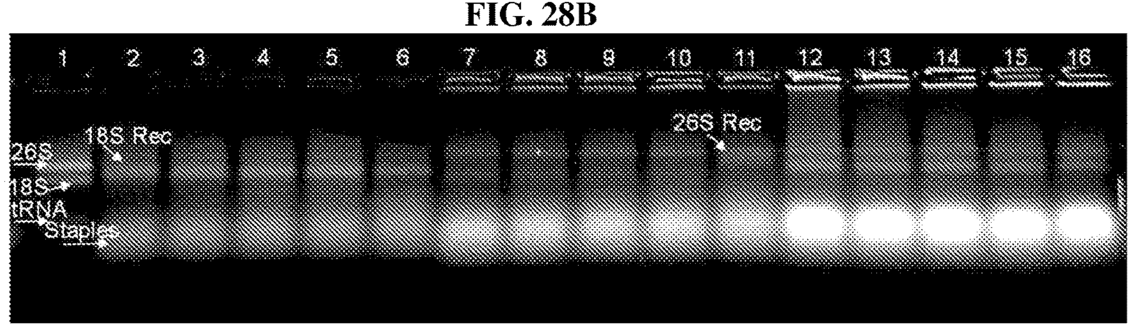
Figure 29A:
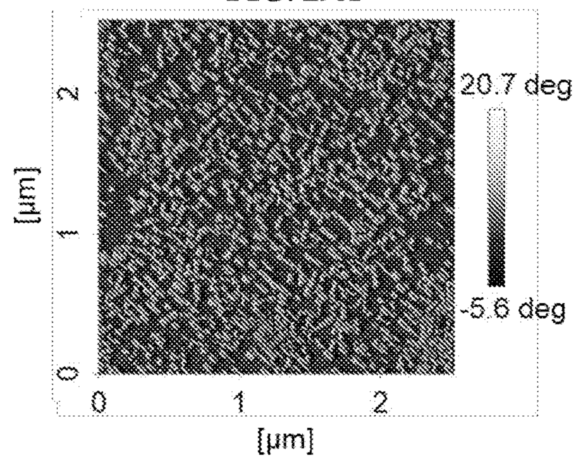
(FIG. 29A and FIG. 29B represent different resolutions).
Figure 29B:
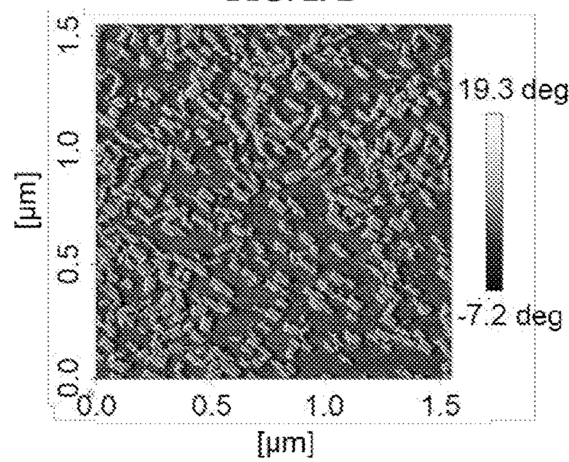

The folding succeeded both $MgCl_2$ concentrations, i.e. 12 mM and 16 Mm (see FIGS. 28 and 29), however as seen in previous examples, incubation at 37° C. for at least 4-5 days after finishing folding protocol 1 is required for well folding and high yield of 25S rRNA-DNA structures.

Example 16. Folding 25S and 18S rRNA-DNA Structures from One Mixture: Protocol 5

Figure 30:
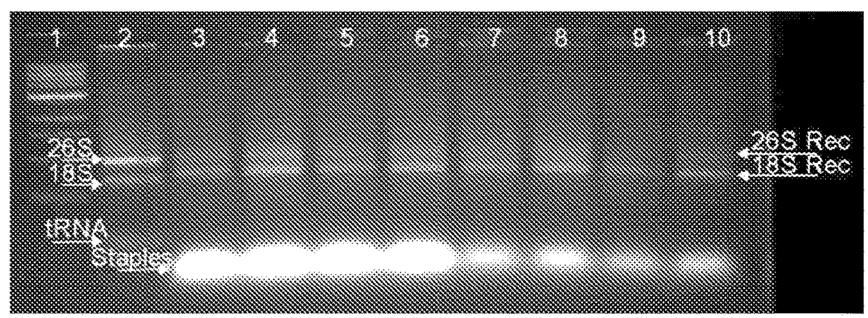
FIG. 30 shows agarose gel of simultaneous folding of 25S and 18S rRNA-DNA structures using protocol 5 at 50° C. in 1×TAE. Lanes 3, 4: 12 mM $MgCl_2$, tested after 2.5 and 5 days, respectively; lanes 5, 6: 16 mM $MgCl_2$, tested after 2.5 and 5 days, respectively; lanes 7, 8: 12 mM $MgCl_2$, tested after 2 and 4 days, respectively; lanes 9, 10: 16 mM $MgCl_2$, tested after 2 and 4 days, respectively. The scaffold:staples ratio was 1:10 in lanes 3-6 and 1:5 in lanes 7-10.
Figure 31A:
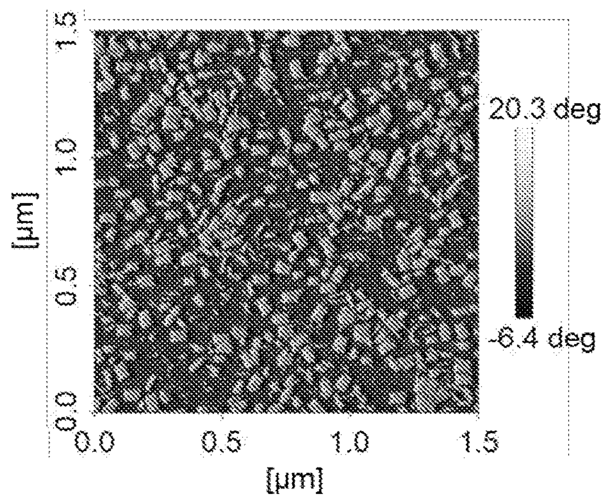
FIG. 31 shows AFM image of simultaneous folding of 25S and 18S rRNA-DNA structures using protocol 5 in 1×TAE at 50° C. over 2 days at 12 mM (FIG. 31A) or 16 mM (FIG. 31B) $MgCl_2$, when the scaffold:staples ratio was 1:5.
FIG. 31C shows folding of 25S and 18S rRNA-DNA structures using protocol 5 at 50° C. over 2 days at 12 mM from total RNA with scaffold concentration of 50 nM, scaffold:staples ratio of 1:5 in high volume of the reaction.
Figure 31B:
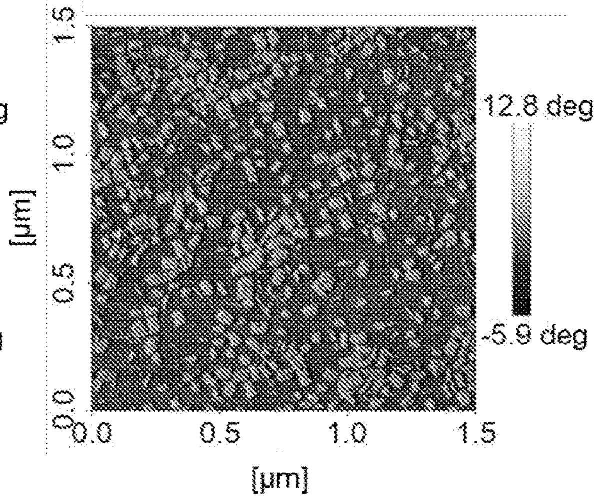
Figure 31C:
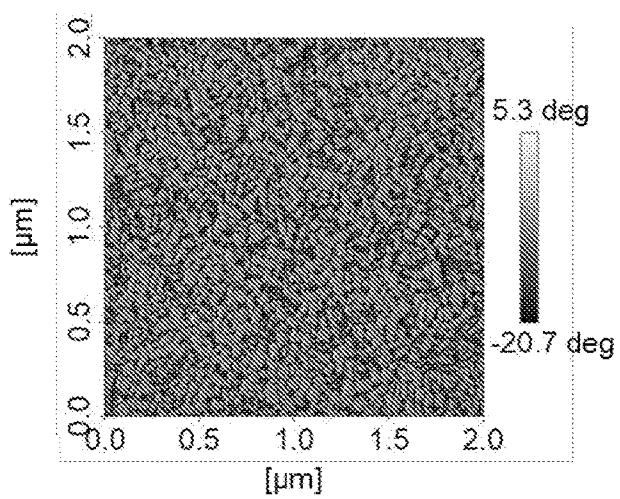

In a further experiment the efficacy of preparation of the structures from a mix reaction in large scale using protocol 5 at 50° C. when lowering the scaffold:staple ratio from 1:10 to 1:5 was assessed. The $MgCl_2$ concentration was varied as well. As following from the results (see FIGS. 30 and 31) the folding was successful already after 2-2.5 days in both experiments, meaning that lowering the $MgCl_2$ concentration to 12 mM, and/or decreasing the scaffold:staples ratio to 1:5 did not affect the folding quality.

In further experiments we showed that it is possible to increase the concentration of scaffolds (and staple, consequently) and thus increasing the yield of the folding. Furthermore we have showed that it is possible to increase the volume of the reaction. The yield and the folding quality were high. The ratio between 18S and 25S structures depended on the ratio of 18S rRNA to 25S rRNA in the total RNA extraction. We managed to increase the volume of the folding reaction, what is critical for large scale production, e.g. fold with devices other than PCR (standard device used for folding DNA origami), when maintaining the quality of the resulted structures (see FIG. 31C).

Example 17. Folding a Combined 25S-18S rRNA-DNA Structure

Figure 32A:
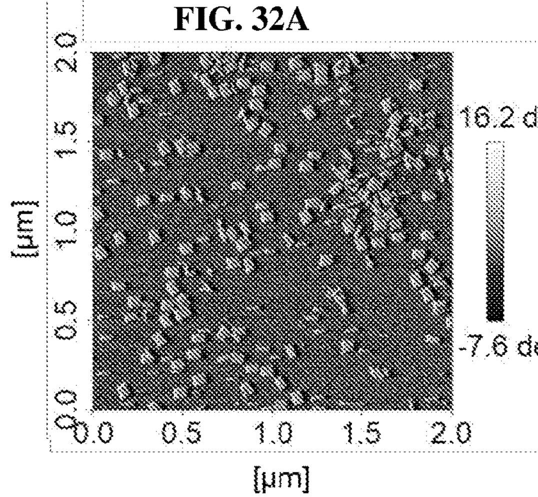
FIG. 32 shows AFM images of folding of 25S-18S rRNA-DNA structure after 2 days at 50° C. without (FIG. 32A) or with (FIG. 32B) pre-incubation with connecting staples. The folding was carried out in folding buffer 1×TAE, 16 mM $MgCl_2$.
Figure 32B:
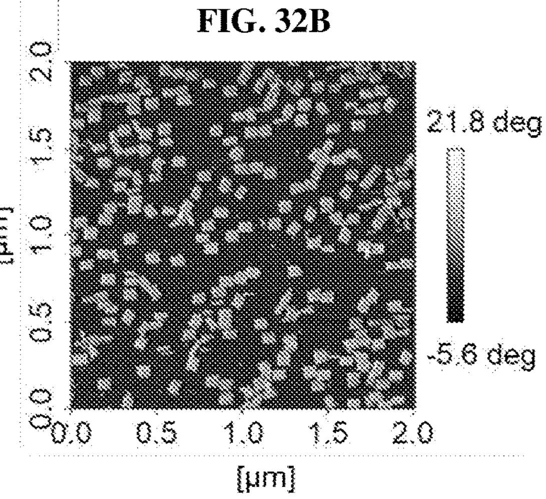

A combined 25S-18S rRNA-DNA structure was formed by folding two different scaffold at 50° C. over 3 days (folding protocol 5) in folding buffer 1×TAE with 16 mM $MgCl_2$. Both 18S rRNA (SEQ ID NO: 1) and 25S rRNA (SEQ ID NO: 68) from *S. cerevisiae* rRNA were used as a scaffold to build one combined shape, (contrary to two structures obtained in Examples 14 or 15). The staples used are SEQ ID NOs: 187-359. In these experiments, one shape from two scaffolds was folded. The experiment was performed in two ways: in $1^{st}$ experiment the 18S and 25S rRNAs used as scaffold were incubated before applying folding protocol with connector staples SEQ ID NOs:333 at room temperature over 2 hours; in $2^{nd}$ experiment the scaffolds were not incubated with connector staples before the folding. It could be seen on the gel (not shown) that bands on days 1-3 were more intense indicating that in both reactions the folding succeeded, as opposed to lanes of 4 hours were the bands were smeary and not sharp. There was no significant difference in folding between $1^{st}$ and $2^{nd}$ experiments, i.e. incubation of S18 rRNA and S25 rRNA scaffold with connecting staple does not improve the results (FIG. 32). These results indicate that the folding can carried out even in higher volumes since PCR is no longer required.

Example 18. Summary of S18, S25 and S18-S25 RNA-DNA Structures

Different parameters were measured for S18, S25 and S18-S25 RNA-DNA structures and are presented in Table 1.

TABLE 1

Parameters of S18, S25 and S18-S25 RNA-DNA structures

| Structure | No. of helices | No. of bases per helix | Average size of the structure |
|---|---|---|---|
| S18 | 11 | 149 + 17 | 32 × 47 $nm^2$ |
| S25 | 15 | 215 + 12 | 44 × 66 $nm^2$ |
| S18-S25 | 20 | 248 + 12 | 60 × 77 $nm^2$ |

Example 19. rRNA-DNA Origami Cuboctahedron (Cub.)—2D

Figure 33A:
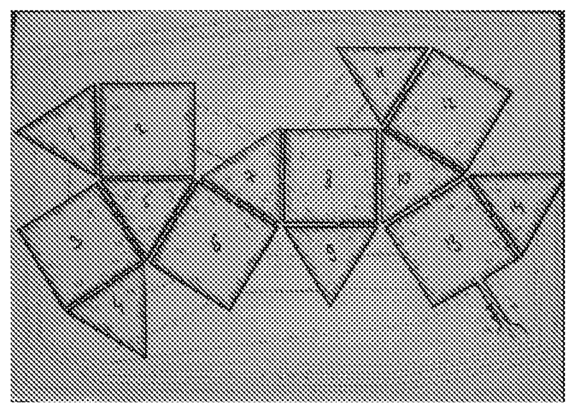
FIG. 33 shows 2D (FIG. 33A) and 3D (FIG. 33B and FIG. 33C) schematic designs for rRNA-DNA cuboctahedron, using *S. cerevisiae* 25S rRNA as a scaffold.
Figure 33B:
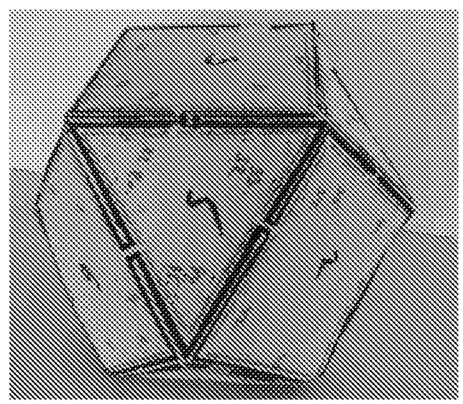
Figure 33C:
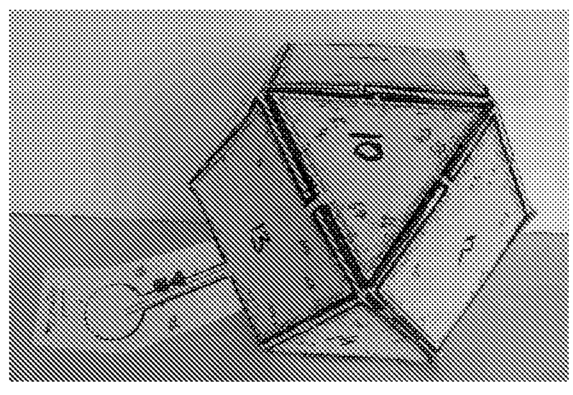

The folding protocols were used to fold both 2D (as shown) and 3D rRNA-DNA origami nanostructures, based on the design principles and the developed folding protocols. FIG. 33 shows 2D (FIG. 33A) and 3D (FIGS. 33B and 33C) schematic designs of rRNA-DNA cuboctahedron (Cub.) using *S. cerevisiae* 25S rRNA as a scaffold.

The design of 2D-Cub. was manual (didn't base on caDNAno software) and based on 11-fold DNA:RNA helical geometry and parameters. Folding of rRNA-DNA cuboctahedron was executed using 25S *S. cerevisiae* rRNA as scaffold and staples of SEQ ID NOs:360-437 according to four different folding protocols. The folding was done in folding buffer 1×TAE, 12.5 mM $MgCl_2$, with total RNA that was cleaned from tRNA and other small molecules by gel filtration chromatography (FIG. 34, lane 3, the tRNA band disappeared after the cleaning), as opposed to total RNA (lane 2)).

The folding protocols were:

Folding protocol 1;

Folding protocol 1 followed by incubation at 37° C. for up to 4.5 days;

Folding protocol 6;

(a) incubating at 60° C. for 1 min;
(b) incubating at 55° C. for 5 min;
(c) incubating at 50° C. for 5 min;
(d) incubating at 45° C. for 10 min; and
(e) cooling from 40° C. to 15° C. at a rate of −1° C./10 min.

Folding protocol 5 incubating at 40° C., for over 2.5 and 4.5 days (lanes: 13-14).

Figure 34:
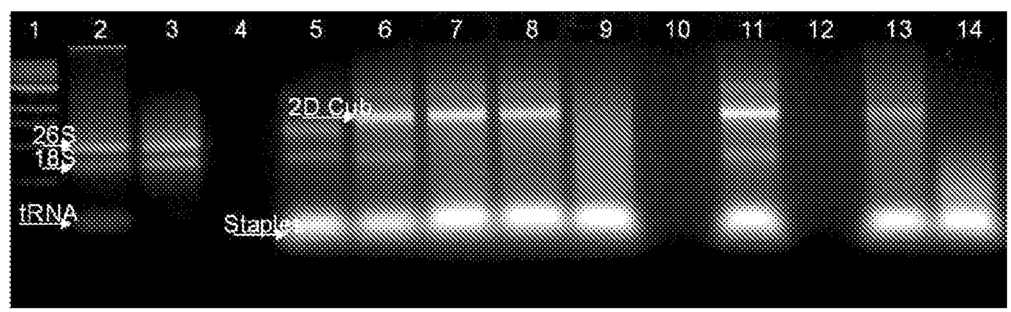
FIG. 34 shows agarose gel of 2D cuboctahedron folded using four different folding protocols in folding buffer 1×TAE, at 12.5 mM $MgCl_2$: lane 1: 1 kb DNA ladder; lane 2: total RNA; lane 3: cleaned total RNA: lane 5: folding mixture that was not subjected to any folding protocol—negative control; lane 6: folding protocol 1; lanes: 7-9: protocol 2+incubation for 2.5, 3.5 and 4.5 days, respectively; lane 11: protocol 6; lanes 13-14: protocol 5 at 40° C. over 2.5 and 4.5 days, respectively. A technical problem occurred in lanes 9 and 14.
Figure 35A:
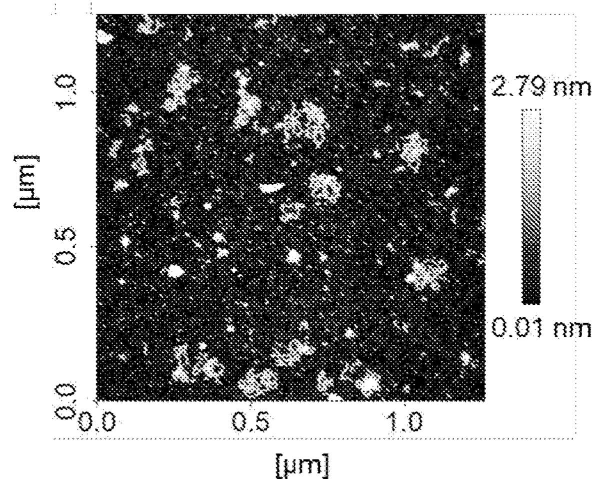
FIGS. 35A and 35B: protocol 1, different resolution.
Figure 35B:
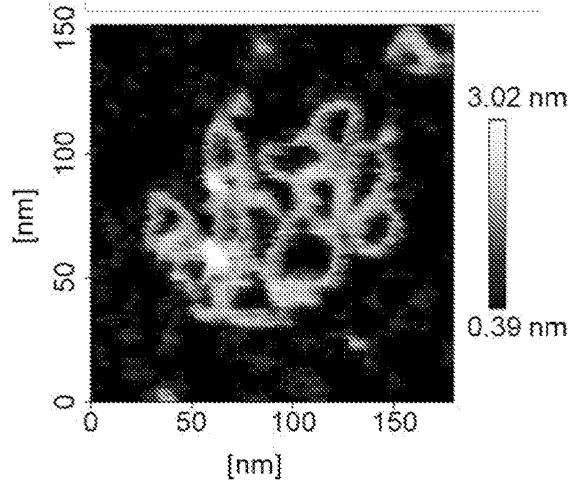
Figure 35C:
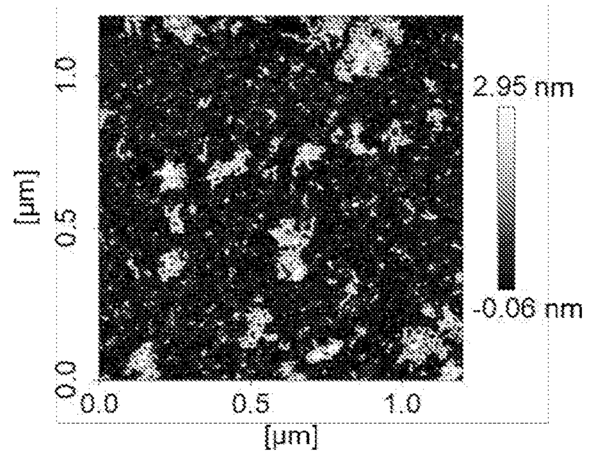
FIG. 35C: protocol 1+incubation for 2.5 days at 37° C.
Figure 35D:
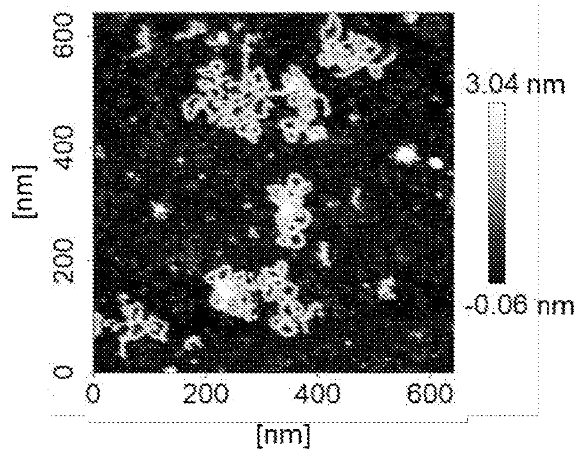
FIG. 35D: protocol 6.

As follows from the result presented on FIGS. 34 and 35, the folding succeeded in all protocols. The bands above 2D Cub. bands indicates that these shapes created dimmers.

On certain the AFM scans, shapes looked a little different from the design, this depends on how the samples deposited and glued to the mica surface as well as on the sample preparation procedure required for the scan.

Example 20. rRNA-DNA Origami Folded Cuboctahedron (Cub.)—3D

The 3D Cub (see FIGS. 33B and C) was designed manually according to 11-FOLD DNA:RNA helical geometry and parameters using 25S *S. cerevisiae* rRNA (SEQ ID NO:68) as scaffold and DNA staples SEQ ID NOs: 438-500.

Figure 36:
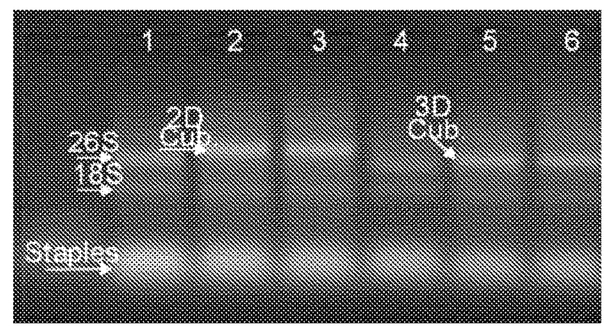
FIG. 36 shows an agarose gel of 3D rRNA-DNA cuboctahedron folded with protocol 1 or protocol 6: lanes 3, 4: 2D folding—protocol 1 and 6, respectively; lanes 5, 6: 3D folding protocols 1 and 6, respectively; lane 1 and 4: negative control for "no folding", by containing mixture with all the components for 2D and 3D folding, respectively, that was not subjected to any folding protocol. The folding was done in folding buffer 1×TAE, 12.5 mM $MgCl_2$.
Figure 37A:
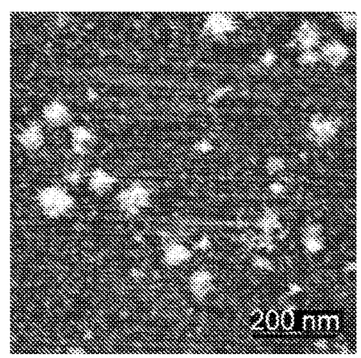
FIG. 37A-C: protocol 1, different resolutions.
Figure 37B:
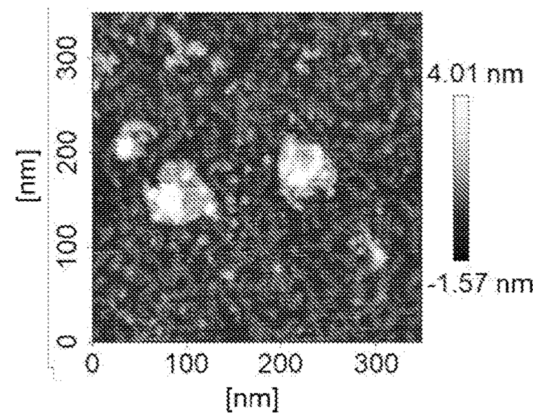
Figure 37C:
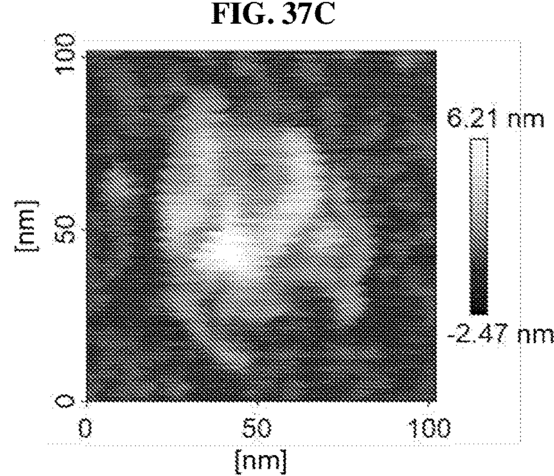
Figure 37D:
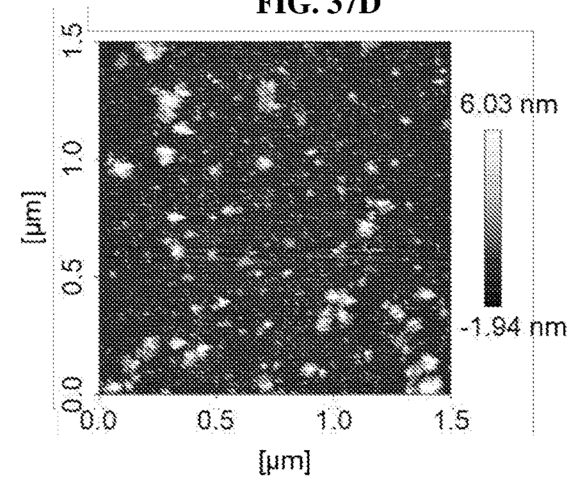
FIG. 37D-F—protocol 1, different resolutions.
Figure 37E:
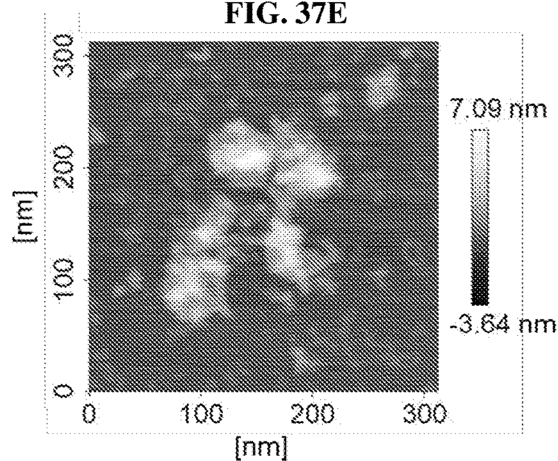
Figure 37F:
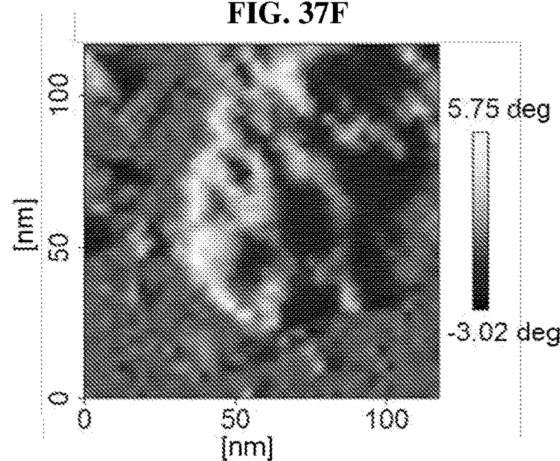

The cuboctahedron was prepared using two folding protocols, i.e. Protocol 1 and 6. The folding was done in folding buffer 1×TAE, 12.5 mM $MgCl_2$, with total RNA that was cleaned from tRNA and other small molecules as in Example 18. We have also compared folding of 2D cuboctahedron (see FIG. 36 lanes 3, 4—folding protocol 1 and 6, respectively), to folding 3D cuboctahedron.

The folding succeeded in both for 2D and 3D cuboctahedron using both protocols. The bands representing the folded shapes are sharp and intense, indicating the high quality of folding. It can be seen (FIG. 36) that the 3D Cub. bands are slightly lower than 2D Cub. bands since the shapes are folded to a globular structure. Such structures migrate faster through the agarose matrix than the open structure of 2D Cub. The AFM images support the gel results and a cuboctahedron structure can be clearly seen (FIG. 37).

Example 21. Stability of 306b ssRNA Scaffold

The stability of 306 bases ssRNA (306b) scaffold (SEQ ID NO:501) in different temperature values (65° C., ~60° C., ~55° C. and 50° C.) incubated for several time periods was assessed. 306b was produced by in-vitro transcription (IVT) reaction based on DNA template. Additional by-product was created in the reaction, which indicated as "IVT Product". All samples were maintained in 1×TAE buffer supplemented with 10 mM $MgCl_2$. The tested time points were: 5, 10, 20, 40, and 60 minutes for each of the temperatures. From the results presented in FIG. 38, it can be seen that at 65° C. 306b started to degrade after 20 minutes. At lower temperatures (55° C. and 50° C.) the 306b ssRNA was more stable; however the degradation was observed after 40 minutes. Only the samples kept at 50° C. were stable after 40 minutes.

It worth to mention, that the longer the ssRNA the less it is stable in higher temperatures; for examples, the IVT by-product (which is a least twice in size that 306b scaffold) degraded faster at 65° C., 60° C. and 55° C. than the shorter. Also 18S and 26S rRNA, which are 1800b and 3396b length, respectively, do not survive at 65° C. for longer than a few minutes. This is important, since DNA is more stable and can be subjected to even 95° C. Considering the different stability of DNA and RNA, different folding protocols should be used when folding RNA:DNA or RNA:RNA origami structures.

In additional experiment, it was shown that 306b scaffold (SEQ ID NO:501) and RNA staples for its folding (SEQ ID NOs: 502-507 and 696-697) were intact over the folding protocol 1 conditions.

Example 22. Folding 306b-RNA-RNA Structure

Folding RNA-RNA structures using 306b scaffold and RNA staples was performed in 1×TAE buffer at 11 mM $MgCl_2$ following folding protocol 1 (see FIG. 39) The folding was carried out in three scaffold estimated concentrations 25 nM (scaffold:staples—1:10), 50 nM (scaffold: staples—1:5) or 100 nM (scaffold:staples—1:2.5), while the sample concentration remained 250 nM. As can be seen from FIG. 39, bands, corresponding to the folded structures, appear in lanes 4 and 5 and indicate for a successful folding of 306b-RNA-RNA structures; the band in lane 3 is hardly seen, due to an inaccurate scaffold concentration, what led to a low folded structures concentration undetectable by gel electrophoresis analysis. The AMF images (FIG. 40) support the gel results of successful folding. The imaged sample is quite dirty because of the high staples concentration (250 nM). These results proved that (a) RNA-RNA origami structures are feasible and that (b) RNA-RNA double helix structure is different from RNA-DNA double helix even though both form an A-conformation double helix structure. These results demonstrated that the helical turn in RNA-RNA structure is 12 base-pairs per turn and not 11 as previously thought.

Example 23. Folding 18S-rRNA-RNA Structures

Figure 41:
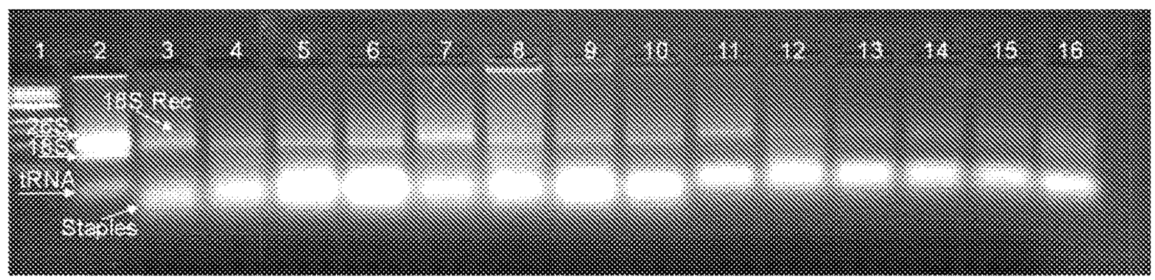
FIG. 41 shows an agarose gel of 18S RNA-RNA structures folded according to folding protocol 1 and incubated at 37° C. for different periods of time. The folding was carried out in folding buffer (1×TAE, 12.5 mM $MgCl_2$) with total rRNA. Lane 1: 1 kb DNA ladder; lane 2: total RNA extracted from *S. cerevisiae*; lanes 3, 7 and 11: folded but not incubated structures, lanes 3-10: control, folded 18S RNA-DNA structures with (3-6) or without (7-10) edges staples and incubated for 0, 1, 4 and 7 days at 37° C., respectively; lanes 11-16: 18S rRNA-RNA (without edges) folded structure incubated for 0, 1, 4, 5, 6, and 7 days at 37° C., respectively.
Figure 42A:
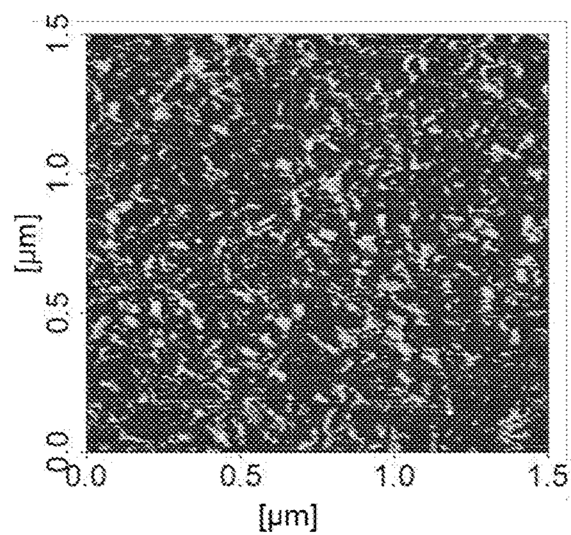
FIG. 42 shows AFM images of 18S-rRNA-RNA (FIG. 42A) or 18S rRNA-DNA (FIG. 42B) folded using protocol 1 without edge staples and incubated for 5 days at 37° C.
Figure 42B:
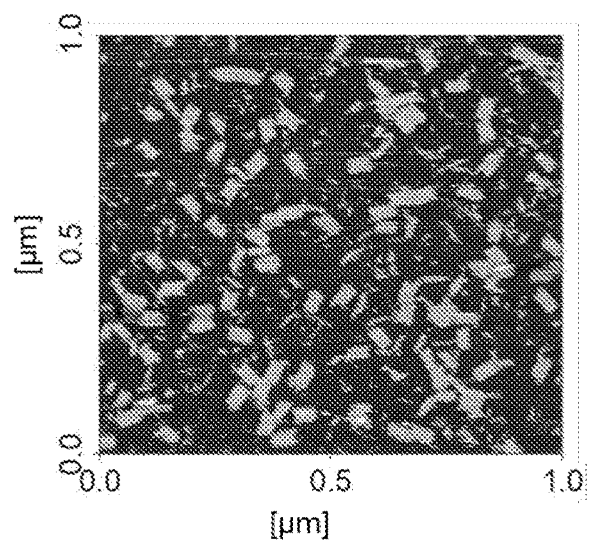

The 18S rRNA-RNA structures using 18S-rRNA (SEQ ID NO:1) as a scaffold and RNA staples having the sequence as SEQ ID NOs 2-67 with T nucleotide substituted with U nucleotide (SEQ ID NOs: 508-573) were folded according to folding protocol 1 and then held at 37° C. over 7 days. The folding reaction was carried out in folding buffer (1×TAE, 12.5 mM $MgCl_2$) from total RNA and tested after 0, 1, 4, 5, 6, and 7 days at 37° C. (see FIG. 41 lanes 11-16 respectively). At time point 0 the shapes were folded only according to folding protocol 1, without being held after at 37° C. The AFM images of 18S-rRNA-RNA structures vs 18S rRNA-DNA structures are present in FIGS. 42A and 42B, respectively.

As follows from the results, the 18S rRNA-RNA structures were obtained; however the yield for folding 18S RNA-RNA was lower than for 18S rRNA-DNA.

Additional protocols were tested to increase the yield of folding, e.g. protocol 7: cooling from 65° C. to 15° C. at a rate −1° C./min in folding buffer 2 (6 mM $Mg(OAc)_2$, 40 mM Na—OAc, 40 mM KCl, 50 mM Tris-OAc (pH 7.8)). This experiment resulted in relatively low yield of folding. Other previously published protocols were tested and resulted in low yield as well.

Example 24. Folding 18S-rRNA-RNA Structures

The 18S rRNA-RNA structures using 18S-rRNA (SEQ ID NO:1) as a scaffold and RNA staples having the sequence SEQ ID NOs: 655-695 are folded according to folding protocol 1 and then held at 37° C. over 7 days. The folding reaction was carried out in folding buffer (1×TAE, 12.5 mM $MgCl_2$) from total RNA and tested after 0, 1, 4, 5, 6, and 7 days at 37° C. At time point 0 the shapes are folded only according to folding protocol 1, without being held after at 37° C. In parallel experiments, the 18S-rRNA and the RNA staples having the sequence SEQ ID NOs: 655-695 are folded according to folding protocols 2-4 and 7.

The design of staples providing an A-RNA:RNA structure with 12 base-pairs per turn allows obtaining much higher yield than in previous experiments.

Example 25. Folding Bacterial 16S rRNA Using Two Different Sets of DNA Staples

In this experiment the folding of rRNA-DNA structures according to folding protocol 1, using total RNA from *E. coli* DH5α comprising 16S rRNA was tested. The 16S rRNA (SEQ ID NO: 574) was used as a scaffold implementing 2 different set of staples: Set 1 (SEQ ID NOs: 575-627) and Set 2 (SEQ ID NOs 628-654) for folding. The folding was performed at 12.5 mM $MgCl_2$, using scaffold:set of staples ratio of 1:10 (20 nM:200 nM).

Protocol 1:

incubating at 60° C. for 1 min
incubating at 55° C. for 5 min
incubating at 50° C. for 10 min
incubating at 37° C. for 10 min; and
incubating at 25° C. for 10 min.

Figure 43:
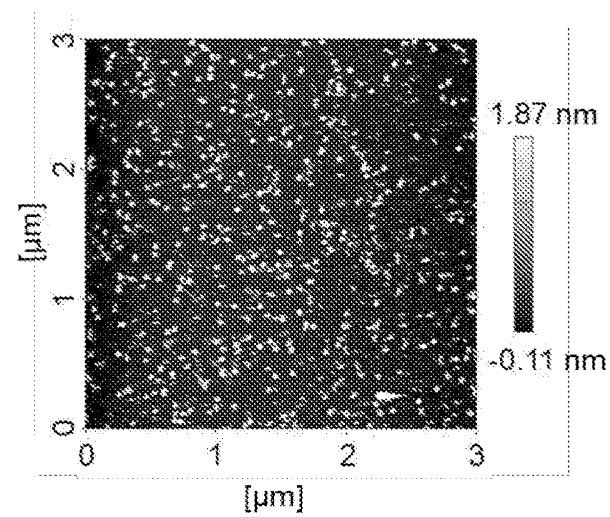
FIG. 43 shows AFM images of the 16S rRNA-DNA structures obtained using *E. coli* 16S rRNA as a scaffold, staples having SEQ ID NOs: 2-54, folded using protocol 1 and further incubated at 37° C. for 5.5 days.
Figure 44:
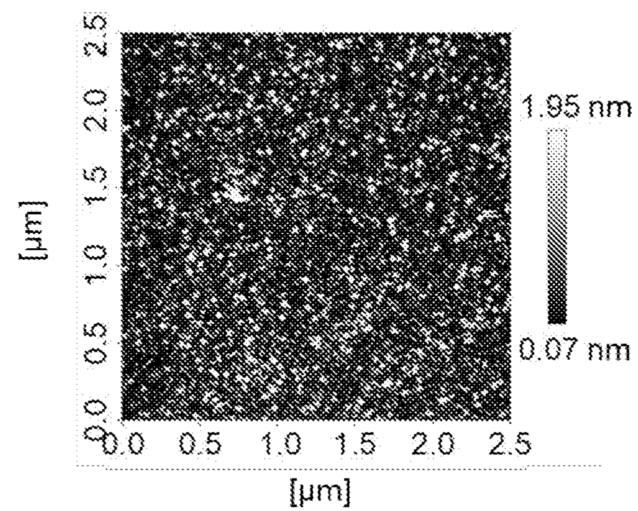
FIG. 44 shows AFM images of the 16S rRNA-DNA structures obtained using *E. coli* 16S rRNA as a scaffold, staples having SEQ ID NOs: 55-81, folded using protocol 1 and further incubated at 37° C. for 5.5 days.

Following the folding, the resulted structures were incubated at 37° C. for 1-6 days. As can be seen from FIGS. 43 and 44 showing the resulted origami structures obtained after incubation for 5.5 days at 37° C., both sets of staples were effective in folding bacterial 16S rRNA.

Example 26. Antibacterial Effect of Staples Nucleic Acids

Figure 45:
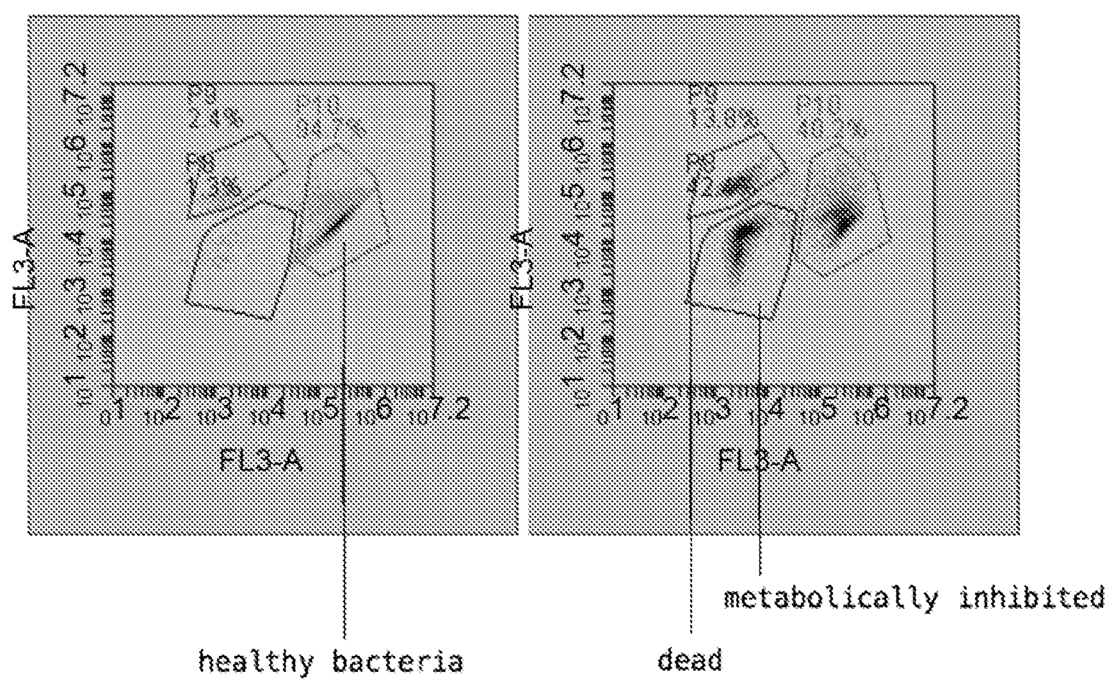
FIG. 45 shows the effect of incubation of *E. coli* K12 in the presence of DNA staple nucleic acids having the sequences SEQ ID NOs: 55-81 targeting the 16s rRNA (right panel) or without it (left panel).

In this experiment we added 1 μM of "Set 2" DNA staples (SEQ ID NOs: 628-654) targeting 16S to *E. coli* K12. Prior to incubation RedoxGreen was added to the bacteria (final concentration of 1 μM). The *E. Coli* were left in incubator for 1 hr. After one hour the cells were taken for analysis in flow cytometry. The results are presented in FIG. 45.

RedoxGreen is an indicator of bacterial metabolic activity and therefore indicates the viability of the *E. Coli*. Live bacteria will have much higher green signal than metabolically inhibited bacteria and dead bacteria. As can be seen from FIG. 45 (right panel), following incubation for only 1 hour, about 14% of bacteria were dead and about 42% were metabolically inhibited indicating for bactericide and bacteriostatic effect of the administered staple nucleic acids.

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

The invention claimed is:

1. An RNA origami nanostructure comprising one or more scaffold nucleic acid strands and a plurality of staple nucleic acid strands, wherein each one of the plurality of staple nucleic acid strands hybridizes with at least two non-contiguous sequences within said one or more scaffold nucleic acid strands, and wherein said one or more scaffold nucleic acid strands comprise a ribosomal RNA (rRNA) nucleic acid, a fragment thereof, or an analog thereof.

2. The RNA origami nanostructure of claim 1, wherein said one or more scaffold nucleic acid strands is an isolated rRNA nucleic acid strand, a fragment thereof, or an analog thereof.

3. The RNA origami nanostructure of claim 1, wherein the one or more scaffold nucleic acids comprise about 1100 nucleotides or more, about 1100 to about 5000 nucleotides, or about 1300 to about 4000 nucleotides.

4. The RNA origami nanostructure of claim 1, wherein said rRNA nucleic acid is selected from a prokaryotic rRNA nucleic acid and an eukaryotic rRNA nucleic acid, optionally wherein said rRNA is selected from a prokaryotic 16S, prokaryotic 23S, prokaryotic 5S, eukaryotic 25S eukaryotic 26S, eukaryotic 5S, eukaryotic 5.8S, eukaryotic 28S and eukaryotic 18S rRNA.

5. The RNA origami nanostructures of claim 1, wherein the one or more scaffold nucleic acid strands and one or more of the plurality of staple nucleic acid strands form an A-conformation double helix.

6. The RNA origami nanostructure of claim 1, wherein the one or more of the plurality of staple nucleic acid strands are RNA nucleic acids and/or DNA nucleic acids.

7. The RNA origami nanostructure of claim 1, wherein the plurality of staple nucleic acid strands are RNA nucleic acids that form a double helix with a scaffold nucleic acid strand, wherein the double helix has 12 base-pairs per turn.

8. The RNA origami nanostructure of claim 1 further comprising an active moiety, optionally wherein the active moiety is selected from the group consisting of a protein, nucleic acid, lipid, glycoprotein, glycolipid, and small molecule.

9. The RNA origami nanostructure of claims 1, further comprising one or more targeting domains on the surface of the nanostructure, optionally wherein the one or more targeting domains is an aptamer, optionally further comprising a latch domain hybridized to said targeting domain, wherein said targeting domain and said latch domain are capable of detaching upon binding of the targeting domain to a target molecule, thereby transiting the nanostructure from a closed to an open conformation.

10. The RNA origami nanostructure of claim 1, wherein the one or more scaffold nucleic acid strands comprise the sequence as set forth in the sequences selected from the group consisting of SEQ ID NO:1, SEQ ID NO:68, a combination of SEQ ID NO:1 and SEQ ID NO:68, a fragment thereof, and an analog thereof.

11. The RNA origami nanostructure of claim 10, wherein: (I) the scaffold nucleic acid strands comprise the sequence as set forth in SEQ ID NO:1, a fragment thereof or an analog thereof, and the origami nanostructure comprises staple nucleic acid strands comprise the sequences set forth in (i) SEQ ID Nos: 2-55, (ii) SEQ ID Nos: 508-561, (iii) SEQ ID Nos: 655-695 or (iv) any combination of the sequences of (i) - (iii), and optionally further comprising staple oligonucleotides having the sequences set forth in (i) SEQ ID Nos 56-67, (ii) SEQ ID Nos: 562-573, or (iii) any combination of the sequences of (i) and (ii); (II) the scaffold nucleotide strands comprise the sequence set forth in SEQ ID NO:68, a fragment thereof, or an analog thereof, and the origami nanostructure comprises staple nucleotide sequences selected from the sequences as set forth in (i) SEQ ID NOs: 69-170 and optionally in SEQ ID NOs: 171-186, (ii) SEQ ID NOs: 360-437, or (iii) SEQ ID NOs: 438-500, wherein said RNA origami nanostructure is a cuboctahedron; or (III) the one or more scaffold nucleic acid strands comprise the sequence as set forth in SEQ ID NO:1 and/or at least one of said scaffold nucleic acids strands has the sequence as set forth in SEQ ID NO:68.

12. The RNA origami nanostructure of claim 10, further comprising an active moiety.

13. A pharmaceutical composition comprising the RNA origami nanostructure of claim 1.

14. The RNA origami nanostructure of claim 4, wherein: the prokaryotic rRNA nucleic acid is selected from bacterial rRNA and archaeal rRNA, optionally wherein the bacterial rRNA is *Escherichia coli* rRNA, *Staphylococcus epidermidis* rRNA, *Lactobacillus acidophilus* rRNA, or *Bifidobacterium* rRNA; and the eukaryotic rRNA nucleic acid is selected from yeast, mammalian, plant, and fungal rRNA, optionally wherein the yeast rRNA is *S. cerevisiae* rRNA.

15. The RNA origami nanostructure of claim 14, wherein the mammalian rRNA nucleic acid is selected from human rRNA and bovine rRNA.

16. The RNA origami nanostructure of claim 9, wherein the target molecule is selected from a tumor associated molecule, a cell-membrane receptor, a growth factor, or a pathogenic antigen.

17. The RNA origami nanostructure of claim 11 (III), wherein one or more of the plurality of staple nucleotide strands comprise the sequences as set forth in SEQ ID NOs: 187-359.

* * * * *

SEQUENCE LISTING

<160> NUMBER OF SEQ ID NOS: 697

<210> SEQ ID NO 1
<211> LENGTH: 1800
<212> TYPE: RNA
<213> ORGANISM: Saccharomyces cerevisiae

<400> SEQUENCE: 1
uaucugguug auccugccag uagucauaug cuugucucaa agauuaagcc augcaugucu 60
aaguauaagc aauuuauaca gugaaacugc gaauggcuca uuaaaucagu uaucguuuau 120
uugauaguuc cuuuacuaca ugguauaacu gugguaauuc uagagcuaau acaugcuuaa 180
aaucucgacc cuuuggaaga gauguauuua uuagauaaaa aaucaauguc uucggacucu 240
uugaugauuc auaauaacuu uucgaaucgc auggccuugu gcuggcgaug guucauucaa 300
auuucugccc uaucaacuuu cgaugguagg auaguggccu accaugguuu caacggguaa 360
cggggaauaa ggguucgauu ccggagaggg agccugagaa acggcuacca cauccaagga 420
aggcagcagg cgcgcaaauu acccaauccu aauucaggga gguagugaca auaaauaacg 480
auacagggcc cauucgggguc uuguaauugg aaugaguaca auguaaauac cuuaacgagg 540
aacaauugga gggcaagucu ggugccagca gccgcgguaa uuccagcucc aauagcguau 600
auuaaaguug uugcaguuaa aaagcucgua guugaacuuu gggcccgguu ggccgguccg 660
auuuuuucgu guacuggauu uccaacgggg ccuuuccuuc uggcuaaccu ugaguccuug 720
uggcucuugg cgaaccagga cuuuuacuuu gaaaaaauua gaguguucaa agcaggcgua 780
uugcucgaau auauuagcau ggaauaauag aauaggacgu uugguucuau uuuguugguu 840
ucuaggacca ucguaaugau uaauagggac ggucgggggc aucaguauuc aauugucaga 900
ggugaaauuc uuggauuuau ugaagacuaa cuacugcgaa agcauuugcc aaggacguuu 960
ucauuaauca agaacgaaag uuaggggauc gaagaugauc agauaccguc guagucuuaa 1020
ccauaaacua ugccgacuag ggaucgggug guguuuuuuu aaugacccac ucggcaccuu 1080
acgagaaauc aaagucuuug gguucugggg ggaguauggu cgcaaggcug aaacuuaaag 1140
gaauugacgg aagggcacca ccaggagugg agccugcggc uuaauuugac ucaacacggg 1200
gaaacucacc agguccagac acaauaagga uugacagauu gagagcucuu ucuugauuuu 1260 gugggguggug gugcauggcc guucuuaguu gguggaguga uuugucugcu uaauugcgau 1320
aacgaacgag accuuaaccu acuaaauagu ggugcuagca uuugcugguu auccacuucu 1380
uagagggacu aucgguuuca agccgaugga aguuugaggc aauaacaggu cugugaugcc 1440

```
cuuagacguu cugggccgca cgcgcgcuac acugacggag ccagcgaguc uaaccuuggc   1500

cgagaggucu ugguaaucuu gugaaacucc gucgugcugg ggauagagca uuguaauuau   1560

ugcucuucaa cgaggaauuc cuaguaagcg caagucauca gcuugcguug auuacguccc   1620

ugcccuuugu acacaccgcc cgucgcuagu accgauugaa uggcuuagug aggccucagg   1680

aucugcuuag agaagggggc aacuccaucu cagagcggag aauuuggaca aacuugguca   1740

uuuagaggaa cuaaaagucg uaacaagguu uccguaggug aaccugcgga aggaucauua   1800


<210> SEQ ID NO 2
<211> LENGTH: 17
<212> TYPE: DNA
<213> ORGANISM: Artificial Sequence
<220> FEATURE:
<223> OTHER INFORMATION: Synthetic sequence

<400> SEQUENCE: 2

gtttgtccaa attctcc                                                    17


<210> SEQ ID NO 3
<211> LENGTH: 34
<212> TYPE: DNA
<213> ORGANISM: Artificial Sequence
<220> FEATURE:
<223> OTHER INFORMATION: Synthetic sequence

<400> SEQUENCE: 3

gcttgaaacc gatagtcgaa gagcaataat taca                                 34


<210> SEQ ID NO 4
<211> LENGTH: 32
<212> TYPE: DNA
<213> ORGANISM: Artificial Sequence
<220> FEATURE:
<223> OTHER INFORMATION: Synthetic sequence

<400> SEQUENCE: 4

ccgttacccg ttgaaaaatg aaccatcgcc ag                                   32


<210> SEQ ID NO 5
<211> LENGTH: 32
<212> TYPE: DNA
<213> ORGANISM: Artificial Sequence
<220> FEATURE:
<223> OTHER INFORMATION: Synthetic sequence

<400> SEQUENCE: 5

gagccacaag gactcatatt ggagctggaa tt                                   32


<210> SEQ ID NO 6
<211> LENGTH: 16
<212> TYPE: DNA
<213> ORGANISM: Artificial Sequence
<220> FEATURE:
<223> OTHER INFORMATION: Synthetic sequence

<400> SEQUENCE: 6

atacttagac atgcat                                                     16


<210> SEQ ID NO 7
<211> LENGTH: 17
<212> TYPE: DNA
<213> ORGANISM: Artificial Sequence
<220> FEATURE:
<223> OTHER INFORMATION: Synthetic sequence
```

<400> SEQUENCE: 7
taagccattc aatcggt 17

<210> SEQ ID NO 8
<211> LENGTH: 34
<212> TYPE: DNA
<213> ORGANISM: Artificial Sequence
<220> FEATURE:
<223> OTHER INFORMATION: Synthetic sequence

<400> SEQUENCE: 8
ggtatctgat catcttccaa atcactccac caac 34

<210> SEQ ID NO 9
<211> LENGTH: 32
<212> TYPE: DNA
<213> ORGANISM: Artificial Sequence
<220> FEATURE:
<223> OTHER INFORMATION: Synthetic sequence

<400> SEQUENCE: 9
accactattt agtaggtaag aacggccatg ca 32

<210> SEQ ID NO 10
<211> LENGTH: 34
<212> TYPE: DNA
<213> ORGANISM: Artificial Sequence
<220> FEATURE:
<223> OTHER INFORMATION: Synthetic sequence

<400> SEQUENCE: 10
acgataactg atttaattct aataaataca tctc 34

<210> SEQ ID NO 11
<211> LENGTH: 34
<212> TYPE: DNA
<213> ORGANISM: Artificial Sequence
<220> FEATURE:
<223> OTHER INFORMATION: Synthetic sequence

<400> SEQUENCE: 11
ctggtggtgt agcgcgcgtg cggccccggc caag 34

<210> SEQ ID NO 12
<211> LENGTH: 34
<212> TYPE: DNA
<213> ORGANISM: Artificial Sequence
<220> FEATURE:
<223> OTHER INFORMATION: Synthetic sequence

<400> SEQUENCE: 12
ggcttaatct ttgagaccac aaggccatgc gatt 34

<210> SEQ ID NO 13
<211> LENGTH: 34
<212> TYPE: DNA
<213> ORGANISM: Artificial Sequence
<220> FEATURE:
<223> OTHER INFORMATION: Synthetic sequence

<400> SEQUENCE: 13
ccagtacacg aaaaaatttc ttgattaatg aaaa 34

<210> SEQ ID NO 14

<211> LENGTH: 16
<212> TYPE: DNA
<213> ORGANISM: Artificial Sequence
<220> FEATURE:
<223> OTHER INFORMATION: Synthetic sequence

<400> SEQUENCE: 14
gagccattcg cagttt 16

<210> SEQ ID NO 15
<211> LENGTH: 34
<212> TYPE: DNA
<213> ORGANISM: Artificial Sequence
<220> FEATURE:
<223> OTHER INFORMATION: Synthetic sequence

<400> SEQUENCE: 15
tcacagacct gttattgacg acggagtttc acaa 34

<210> SEQ ID NO 16
<211> LENGTH: 32
<212> TYPE: DNA
<213> ORGANISM: Artificial Sequence
<220> FEATURE:
<223> OTHER INFORMATION: Synthetic sequence

<400> SEQUENCE: 16
cgaccatact cccccccatt acgatggtcc ta 32

<210> SEQ ID NO 17
<211> LENGTH: 34
<212> TYPE: DNA
<213> ORGANISM: Artificial Sequence
<220> FEATURE:
<223> OTHER INFORMATION: Synthetic sequence

<400> SEQUENCE: 17
atgtggtagc cgtttctacc gcggctgctg gcac 34

<210> SEQ ID NO 18
<211> LENGTH: 34
<212> TYPE: DNA
<213> ORGANISM: Artificial Sequence
<220> FEATURE:
<223> OTHER INFORMATION: Synthetic sequence

<400> SEQUENCE: 18
ttgggtaatt tgcgcgcttg ttcctcgtta aggt 34

<210> SEQ ID NO 19
<211> LENGTH: 32
<212> TYPE: DNA
<213> ORGANISM: Artificial Sequence
<220> FEATURE:
<223> OTHER INFORMATION: Synthetic sequence

<400> SEQUENCE: 19
atattcgagc aatacgattt acattgtact ca 32

<210> SEQ ID NO 20
<211> LENGTH: 34
<212> TYPE: DNA
<213> ORGANISM: Artificial Sequence
<220> FEATURE:
<223> OTHER INFORMATION: Synthetic sequence

<400> SEQUENCE: 20
aatcgaaccc ttattccaca actttaatat acgc 34

<210> SEQ ID NO 21
<211> LENGTH: 17
<212> TYPE: DNA
<213> ORGANISM: Artificial Sequence
<220> FEATURE:
<223> OTHER INFORMATION: Synthetic sequence

<400> SEQUENCE: 21 gccccttct ctaagca 17

<210> SEQ ID NO 22
<211> LENGTH: 32
<212> TYPE: DNA
<213> ORGANISM: Artificial Sequence
<220> FEATURE:
<223> OTHER INFORMATION: Synthetic sequence

<400> SEQUENCE: 22
ttcacctacg gaaaccgatt accaagacct ct 32

<210> SEQ ID NO 23
<211> LENGTH: 16
<212> TYPE: DNA
<213> ORGANISM: Artificial Sequence
<220> FEATURE:
<223> OTHER INFORMATION: Synthetic sequence

<400> SEQUENCE: 23
aggaactatc aaataa 16

<210> SEQ ID NO 24
<211> LENGTH: 34
<212> TYPE: DNA
<213> ORGANISM: Artificial Sequence
<220> FEATURE:
<223> OTHER INFORMATION: Synthetic sequence

<400> SEQUENCE: 24
ccatggtagg ccactatgcc caaagttcaa ctac 34

<210> SEQ ID NO 25
<211> LENGTH: 34
<212> TYPE: DNA
<213> ORGANISM: Artificial Sequence
<220> FEATURE:
<223> OTHER INFORMATION: Synthetic sequence

<400> SEQUENCE: 25
aggttagcca gaaggaattt cgcagtagtt agtc 34

<210> SEQ ID NO 26
<211> LENGTH: 34
<212> TYPE: DNA
<213> ORGANISM: Artificial Sequence
<220> FEATURE:
<223> OTHER INFORMATION: Synthetic sequence

<400> SEQUENCE: 26
gcaggatcaa ccagatagat agggcagaaa tttg 34

<210> SEQ ID NO 27
<211> LENGTH: 32
<212> TYPE: DNA

<213> ORGANISM: Artificial Sequence
<220> FEATURE:
<223> OTHER INFORMATION: Synthetic sequence

<400> SEQUENCE: 27
aattttttca aagtaacaga cttgccctcc aa 32

<210> SEQ ID NO 28
<211> LENGTH: 32
<212> TYPE: DNA
<213> ORGANISM: Artificial Sequence
<220> FEATURE:
<223> OTHER INFORMATION: Synthetic sequence

<400> SEQUENCE: 28
ctgctgcctt ccttggagac attgattttt ta 32

<210> SEQ ID NO 29
<211> LENGTH: 17
<212> TYPE: DNA
<213> ORGANISM: Artificial Sequence
<220> FEATURE:
<223> OTHER INFORMATION: Synthetic sequence

<400> SEQUENCE: 29
ttgttacgac ttttagt 17

<210> SEQ ID NO 30
<211> LENGTH: 34
<212> TYPE: DNA
<213> ORGANISM: Artificial Sequence
<220> FEATURE:
<223> OTHER INFORMATION: Synthetic sequence

<400> SEQUENCE: 30
aagtcctggt tcgccaaatt tcacctctga caat 34

<210> SEQ ID NO 31
<211> LENGTH: 34
<212> TYPE: DNA
<213> ORGANISM: Artificial Sequence
<220> FEATURE:
<223> OTHER INFORMATION: Synthetic sequence

<400> SEQUENCE: 31
ctagtcggca tagtttacca ccacccacaa aatc 34

<210> SEQ ID NO 32
<211> LENGTH: 16
<212> TYPE: DNA
<213> ORGANISM: Artificial Sequence
<220> FEATURE:
<223> OTHER INFORMATION: Synthetic sequence

<400> SEQUENCE: 32
aagcatatga ctactg 16

<210> SEQ ID NO 33
<211> LENGTH: 34
<212> TYPE: DNA
<213> ORGANISM: Artificial Sequence
<220> FEATURE:
<223> OTHER INFORMATION: Synthetic sequence

<400> SEQUENCE: 33
atgtattagg ttatttattg tcactattcc aatt 34

<210> SEQ ID NO 34
<211> LENGTH: 32
<212> TYPE: DNA
<213> ORGANISM: Artificial Sequence
<220> FEATURE:
<223> OTHER INFORMATION: Synthetic sequence

<400> SEQUENCE: 34
cctccctgaa ttaggattcc aaagggtcga ga 32

<210> SEQ ID NO 35
<211> LENGTH: 32
<212> TYPE: DNA
<213> ORGANISM: Artificial Sequence
<220> FEATURE:
<223> OTHER INFORMATION: Synthetic sequence

<400> SEQUENCE: 35
cctcaaactt ccatcgtgtc tggacctggt ga 32

<210> SEQ ID NO 36
<211> LENGTH: 32
<212> TYPE: DNA
<213> ORGANISM: Artificial Sequence
<220> FEATURE:
<223> OTHER INFORMATION: Synthetic sequence

<400> SEQUENCE: 36
atttctcgta aggtgctgaa tactgatgcc cc 32

<210> SEQ ID NO 37
<211> LENGTH: 34
<212> TYPE: DNA
<213> ORGANISM: Artificial Sequence
<220> FEATURE:
<223> OTHER INFORMATION: Synthetic sequence

<400> SEQUENCE: 37
cgagtgggtc attaaaatct gtcaatcctt attg 34

<210> SEQ ID NO 38
<211> LENGTH: 32
<212> TYPE: DNA
<213> ORGANISM: Artificial Sequence
<220> FEATURE:
<223> OTHER INFORMATION: Synthetic sequence

<400> SEQUENCE: 38
tcctctaaat gaccaaatgc tctatcccca gc 32

<210> SEQ ID NO 39
<211> LENGTH: 32
<212> TYPE: DNA
<213> ORGANISM: Artificial Sequence
<220> FEATURE:
<223> OTHER INFORMATION: Synthetic sequence

<400> SEQUENCE: 39
tggttaagac tacgaccgtc cttggcaaat gc 32

<210> SEQ ID NO 40
<211> LENGTH: 32
<212> TYPE: DNA
<213> ORGANISM: Artificial Sequence
<220> FEATURE:

<223> OTHER INFORMATION: Synthetic sequence

<400> SEQUENCE: 40
gatcctgagg cctcacacgt aatcaacgca ag 32

<210> SEQ ID NO 41
<211> LENGTH: 34
<212> TYPE: DNA
<213> ORGANISM: Artificial Sequence
<220> FEATURE:
<223> OTHER INFORMATION: Synthetic sequence

<400> SEQUENCE: 41
ttaaggtctc gttcgttgtg tacaaagggc aggg 34

<210> SEQ ID NO 42
<211> LENGTH: 32
<212> TYPE: DNA
<213> ORGANISM: Artificial Sequence
<220> FEATURE:
<223> OTHER INFORMATION: Synthetic sequence

<400> SEQUENCE: 42
caggctccct ctccggcgaa aagttattat ga 32

<210> SEQ ID NO 43
<211> LENGTH: 25
<212> TYPE: DNA
<213> ORGANISM: Artificial Sequence
<220> FEATURE:
<223> OTHER INFORMATION: Synthetic sequence

<400> SEQUENCE: 43
gttataccat gtagtaattt taagc 25

<210> SEQ ID NO 44
<211> LENGTH: 32
<212> TYPE: DNA
<213> ORGANISM: Artificial Sequence
<220> FEATURE:
<223> OTHER INFORMATION: Synthetic sequence

<400> SEQUENCE: 44
gctctgagat ggagttctag gaattcctcg tt 32

<210> SEQ ID NO 45
<211> LENGTH: 34
<212> TYPE: DNA
<213> ORGANISM: Artificial Sequence
<220> FEATURE:
<223> OTHER INFORMATION: Synthetic sequence

<400> SEQUENCE: 45
cctgctttga acactctcga ccgtccctat taat 34

<210> SEQ ID NO 46
<211> LENGTH: 34
<212> TYPE: DNA
<213> ORGANISM: Artificial Sequence
<220> FEATURE:
<223> OTHER INFORMATION: Synthetic sequence

<400> SEQUENCE: 46
aaccagcaaa tgctagcctg atgacttgcg ctta 34

<210> SEQ ID NO 47
<211> LENGTH: 34
<212> TYPE: DNA
<213> ORGANISM: Artificial Sequence
<220> FEATURE:
<223> OTHER INFORMATION: Synthetic sequence

<400> SEQUENCE: 47
caaaatagat ttaagtttca gccttgctcc actc 34

<210> SEQ ID NO 48
<211> LENGTH: 32
<212> TYPE: DNA
<213> ORGANISM: Artificial Sequence
<220> FEATURE:
<223> OTHER INFORMATION: Synthetic sequence

<400> SEQUENCE: 48
cctctaagaa gtggataaga aagagctctc aa 32

<210> SEQ ID NO 49
<211> LENGTH: 32
<212> TYPE: DNA
<213> ORGANISM: Artificial Sequence
<220> FEATURE:
<223> OTHER INFORMATION: Synthetic sequence

<400> SEQUENCE: 49
agaacgtcta agggcacaaa ttaagccgca gg 32

<210> SEQ ID NO 50
<211> LENGTH: 32
<212> TYPE: DNA
<213> ORGANISM: Artificial Sequence
<220> FEATURE:
<223> OTHER INFORMATION: Synthetic sequence

<400> SEQUENCE: 50
aggccccgtt ggaaatgagc tttttaactg ca 32

<210> SEQ ID NO 51
<211> LENGTH: 34
<212> TYPE: DNA
<213> ORGANISM: Artificial Sequence
<220> FEATURE:
<223> OTHER INFORMATION: Synthetic sequence

<400> SEQUENCE: 51
agaacccaaa gactttggtt tccccgtgtt gagt 34

<210> SEQ ID NO 52
<211> LENGTH: 32
<212> TYPE: DNA
<213> ORGANISM: Artificial Sequence
<220> FEATURE:
<223> OTHER INFORMATION: Synthetic sequence

<400> SEQUENCE: 52
aaacaccacc cgatccttca ataaatccaa ga 32

<210> SEQ ID NO 53
<211> LENGTH: 34
<212> TYPE: DNA
<213> ORGANISM: Artificial Sequence
<220> FEATURE:
<223> OTHER INFORMATION: Synthetic sequence

<400> SEQUENCE: 53
cactgtataa attgcttatc atcaaagagt ccga 34

<210> SEQ ID NO 54
<211> LENGTH: 34
<212> TYPE: DNA
<213> ORGANISM: Artificial Sequence
<220> FEATURE:
<223> OTHER INFORMATION: Synthetic sequence

<400> SEQUENCE: 54
acaagaccct attattccat gctaatgaaa ccaa 34

<210> SEQ ID NO 55
<211> LENGTH: 26
<212> TYPE: DNA
<213> ORGANISM: Artificial Sequence
<220> FEATURE:
<223> OTHER INFORMATION: Synthetic sequence

<400> SEQUENCE: 55
gttagactca atgatccttc cgcagg 26

<210> SEQ ID NO 56
<211> LENGTH: 8
<212> TYPE: DNA
<213> ORGANISM: Artificial Sequence
<220> FEATURE:
<223> OTHER INFORMATION: Synthetic sequence

<400> SEQUENCE: 56 cgaaagtt 8

<210> SEQ ID NO 57
<211> LENGTH: 32
<212> TYPE: DNA
<213> ORGANISM: Artificial Sequence
<220> FEATURE:
<223> OTHER INFORMATION: Synthetic sequence

<400> SEQUENCE: 57
ttttttttaa ctttcgcgga ccggtttttt tt 32

<210> SEQ ID NO 58
<211> LENGTH: 32
<212> TYPE: DNA
<213> ORGANISM: Artificial Sequence
<220> FEATURE:
<223> OTHER INFORMATION: Synthetic sequence

<400> SEQUENCE: 58
ttttttttcg ggcggtatcg caattttttt tt 32

<210> SEQ ID NO 59
<211> LENGTH: 32
<212> TYPE: DNA
<213> ORGANISM: Artificial Sequence
<220> FEATURE:
<223> OTHER INFORMATION: Synthetic sequence

<400> SEQUENCE: 59
ttttttttcc aaccggccta ccattttttt tt 32

<210> SEQ ID NO 60
<211> LENGTH: 32

<212> TYPE: DNA
<213> ORGANISM: Artificial Sequence
<220> FEATURE:
<223> OTHER INFORMATION: Synthetic sequence

<400> SEQUENCE: 60
ttttttttta agcagagatc ccctttttt tt 32

<210> SEQ ID NO 61
<211> LENGTH: 33
<212> TYPE: DNA
<213> ORGANISM: Artificial Sequence
<220> FEATURE:
<223> OTHER INFORMATION: Synthetic sequence

<400> SEQUENCE: 61
taagccattc aatcggtact agcgattttt ttt 33

<210> SEQ ID NO 62
<211> LENGTH: 32
<212> TYPE: DNA
<213> ORGANISM: Artificial Sequence
<220> FEATURE:
<223> OTHER INFORMATION: Synthetic sequence

<400> SEQUENCE: 62
tttttttttc aattccacca aacgtttttt tt 32

<210> SEQ ID NO 63
<211> LENGTH: 32
<212> TYPE: DNA
<213> ORGANISM: Artificial Sequence
<220> FEATURE:
<223> OTHER INFORMATION: Synthetic sequence

<400> SEQUENCE: 63
ttttttttcc tgtatcctct agaatttttt tt 32

<210> SEQ ID NO 64
<211> LENGTH: 16
<212> TYPE: DNA
<213> ORGANISM: Artificial Sequence
<220> FEATURE:
<223> OTHER INFORMATION: Synthetic sequence

<400> SEQUENCE: 64
gctggctctt tttttt 16

<210> SEQ ID NO 65
<211> LENGTH: 32
<212> TYPE: DNA
<213> ORGANISM: Artificial Sequence
<220> FEATURE:
<223> OTHER INFORMATION: Synthetic sequence

<400> SEQUENCE: 65
ttttttttcg tcagtgccct tccgtttttt tt 32

<210> SEQ ID NO 66
<211> LENGTH: 16
<212> TYPE: DNA
<213> ORGANISM: Artificial Sequence
<220> FEATURE:
<223> OTHER INFORMATION: Synthetic sequence

<400> SEQUENCE: 66

```
tttttttttt accaca                                                   16


<210> SEQ ID NO 67
<211> LENGTH: 32
<212> TYPE: DNA
<213> ORGANISM: Artificial Sequence
<220> FEATURE:
<223> OTHER INFORMATION: Synthetic sequence

<400> SEQUENCE: 67

tttttttttc ctattcgaat gggctttttt tt                                 32


<210> SEQ ID NO 68
<211> LENGTH: 3396
<212> TYPE: RNA
<213> ORGANISM: Saccharomyces cerevisiae

<400> SEQUENCE: 68

guuugaccuc aaaucaggua ggaguacccg cugaacuuaa gcauaucaau aagcggagga     60

aaagaaacca accgggauug ccuuaguaac ggcgagugaa gcggcaaaag cucaaauuug    120

aaaucuggua ccuucggugc ccgaguugua auuuggagag ggcaacuuug gggccguucc    180

uugucuaugu uccuuggaac aggacgucau agagggugag aaucccgugu ggcgaggagu    240

gcgguucuuu guaaagugcc uucgaagagu cgaguuguuu gggaaugcag cucuaagugg    300

gugguaaauu ccaucuaaag cuaaauauug gcgagagacc gauagcgaac aaguacagug    360

auggaaagau gaaaagaacu uugaaaagag agugaaaaag uacgugaaau uguugaaagg    420

gaagggcauu ugaucagaca ugguguuuug ugcccucugc uccuuguggg uaggggaauc    480

ucgcauuuca cugggccagc aucaguuuug guggcaggau aaauccauag gaauguagcu    540

ugccucggua aguauuauag ccugugggaa uacugccagc ugggacugag gacugcgacg    600

uaagucaagg augcuggcau aaugguuaua ugccgcccgu cuugaaacac ggaccaagga    660

gucuaacguc uaugcgagug uuugggugua aaacccauac gcguaaugaa agugaacgua    720

gguuggggcc ucgcaagagg ugcacaaucg accgauccug augucuucgg auggauuuga    780

guaagagcau agcuguuggg acccgaaaga uggugaacua ugccugaaua gggugaagcc    840

agaggaaacu cugguggagg cucguagcgg uucugacgug caaaucgauc gucgaauuug    900

gguauagggg cgaaagacua aucgaaccau cuaguagcug guuccugccg aaguuucccu    960

caggauagca gaagcucgua ucaguuuuau gagguaaagc gaaugauuag agguuccggg   1020

gucgaaauga ccuugaccua uucucaaacu uuaaauaugu aagaaguccu uguuacuuaa   1080

uugaacgugg acauuugaau gaagagcuuu uagugggcca uuuuugguaa gcagaacugg   1140

cgaugcggga ugaaccgaac guagaguuaa ggugccggaa uacacgcuca ucagacacca   1200

caaaaggugu uaguucaucu agacagccgg acgguggcca uggaagucgg aauccgcuaa   1260

ggagugugua acaacucacc ggccgaauga acuagcccug aaaauggaug gcgcucaagc   1320

guguuaccua uacucuaccg ucaggguuga uaugaugccc ugacgaguag gcaggcgugg   1380

aggucaguga cgaagccuag accguaaggu cgggucgaac ggccucuagu gcagaucuug   1440

gugguaguag caaauauuca aaugagaacu uugaagacug aaguggggaa agguuccacg   1500

ucaacagcag uuggacgugg guuagucgau ccuaagagau ggggaagcuc cguuucaaag   1560

gccugauuuu augcaggcca ccaucgaaag ggaauccggu uaagauuccg gaaccuggau   1620

auggauucuu cacgguaacg uaacugaaug uggagacguc ggcgcgagcc cugggaggag   1680

uuaucuuuuc uucuuaacag cuuaucaccc cggaauuggu uuauccggag auggggucuu   1740
```

```
auggcuggaa gaggccagca ccuuugcugg cuccggugcg cuugugacgg cccgugaaaa   1800

uccacaggaa ggaauaguuu ucaugccagg ucguacugau aaccgcagca ggucuccaag   1860

gugaacagcc ucuaguugau agaauaaugu agauaaggga agucggcaaa auagauccgu   1920

aacuucggga uaaggauugg cucuaagggu cggguaguga gggccuuggu cagacgcagc   1980

gggcgugcuu guggacugcu ugguggggcu ugcucugcua ggcggacuac uugcgugccu   2040

uguuguagac ggccuuggua ggucucuugu agaccgucgc uugcuacaau uaacgaucaa   2100

cuuagaacug guacggacaa ggggaaucug acugucuaau uaaaacauag cauugcgaug   2160

gucagaaagu gauguugacg caaugugauu ucugcccagu gcucugaaug ucaaagugaa   2220

gaaauucaac caagcgcggg uaaacggcgg gaguaacuau gacucucuua agguagccaa   2280

augccucguc aucuaauuag ugacgcgcau gaauggauua acgagauucc cacugucccu   2340

aucuacuauc uagcgaaacc acagccaagg gaacgggcuu ggcagaauca gcggggaaag   2400

aagacccugu ugagcuugac ucuaguuuga cauugugaag agacauagag gguguagaau   2460

aagugggagc uucggcgcca gugaaauacc acuaccuuua uaguuucuuu acuuauucaa   2520

ugaagcggag cuggaauuca uuuuccacgu ucuagcauuc aaggucccau ucggggcuga   2580

uccggguuga agacauuguc agguggggag uuuggcuggg gcggcacauc uguuaaacga   2640

uaacgcagau guccuaaggg gggcucaugg agaacagaaa ucuccaguag aacaaaaggg   2700

uaaaagcccc cuugauuuug auuuucagug ugaauacaaa ccaugaaagu guggccuauc   2760

gauccuuuag ucccucggaa uuugaggcua gaggugccag aaaaguuacc acagggauaa   2820

cuggcuugug gcagucaagc guucauagcg acauugcuuu uugauucuuc gaugucggcu   2880

cuuccuauca uaccgaagca gaauucggua agcguuggau uguucaccca cuaauaggga   2940

acgugagcug gguuuagacc gucgugagac agguuaguuu uacccuacug augaauguua   3000

ccgcaauagu aauugaacuu aguacgagag gaacaguuca uucggauaau ugguuuuugc   3060

ggcugucuga ucaggcauug ccgcgaagcu accauccgcu ggauuauggc ugaacgccuc   3120

uaagucagaa uccaugcuag aacgcgguga uuucuuugcu ccacacaaua uagauggaua   3180

cgaauaaggc guccuugugg cgucgcugaa ccauagcagg cuagcaacgg ugcacuuggc   3240

ggaaaggccu ugggugcuug cuggcgaauu gcaaugucau uuugcguggg gauaaaucau   3300

uuguauacga cuuagaugua caacggggua uuguaagcag uagaguagcc uuguuguuac   3360

gaucugcuga gauuaagccu uuguugucug auuugu                             3396
```

<210> SEQ ID NO 69
<211> LENGTH: 26
<212> TYPE: DNA
<213> ORGANISM: Artificial Sequence
<220> FEATURE:
<223> OTHER INFORMATION: Synthetic sequence

<400> SEQUENCE: 69

```
gacggtctaa caaatcagac aacaaa                                          26
```

<210> SEQ ID NO 70
<211> LENGTH: 34
<212> TYPE: DNA
<213> ORGANISM: Artificial Sequence
<220> FEATURE:
<223> OTHER INFORMATION: Synthetic sequence

<400> SEQUENCE: 70
cgagggacta aaggatccat ggattctgac ttag 34

<210> SEQ ID NO 71
<211> LENGTH: 34
<212> TYPE: DNA
<213> ORGANISM: Artificial Sequence
<220> FEATURE:
<223> OTHER INFORMATION: Synthetic sequence

<400> SEQUENCE: 71
aaatttgagc ttttgccgct atcggtctct cgcc 34

<210> SEQ ID NO 72
<211> LENGTH: 34
<212> TYPE: DNA
<213> ORGANISM: Artificial Sequence
<220> FEATURE:
<223> OTHER INFORMATION: Synthetic sequence

<400> SEQUENCE: 72
gagtcaagct caacagggga tcagccccga atgg 34

<210> SEQ ID NO 73
<211> LENGTH: 16
<212> TYPE: DNA
<213> ORGANISM: Artificial Sequence
<220> FEATURE:
<223> OTHER INFORMATION: Synthetic sequence

<400> SEQUENCE: 73
gcttcactcg ccgtta 16

<210> SEQ ID NO 74
<211> LENGTH: 34
<212> TYPE: DNA
<213> ORGANISM: Artificial Sequence
<220> FEATURE:
<223> OTHER INFORMATION: Synthetic sequence

<400> SEQUENCE: 74
gattctgcca agcccgtgcc aaactcccca cctg 34

<210> SEQ ID NO 75
<211> LENGTH: 34
<212> TYPE: DNA
<213> ORGANISM: Artificial Sequence
<220> FEATURE:
<223> OTHER INFORMATION: Synthetic sequence

<400> SEQUENCE: 75
gacgaggcat ttggctatca agggggcttt tacc 34

<210> SEQ ID NO 76
<211> LENGTH: 32
<212> TYPE: DNA
<213> ORGANISM: Artificial Sequence
<220> FEATURE:
<223> OTHER INFORMATION: Synthetic sequence

<400> SEQUENCE: 76
aagctcttca ttcaaagttc actttcatta cg 32

<210> SEQ ID NO 77
<211> LENGTH: 34
<212> TYPE: DNA
<213> ORGANISM: Artificial Sequence
<220> FEATURE:
<223> OTHER INFORMATION: Synthetic sequence

<400> SEQUENCE: 77
gtattcccac aggctatccc aacagctatg ctct 34

<210> SEQ ID NO 78
<211> LENGTH: 34
<212> TYPE: DNA
<213> ORGANISM: Artificial Sequence
<220> FEATURE:
<223> OTHER INFORMATION: Synthetic sequence

<400> SEQUENCE: 78
tgtccacgtt caattaaagc gtgtattccg gcac 34

<210> SEQ ID NO 79
<211> LENGTH: 32
<212> TYPE: DNA
<213> ORGANISM: Artificial Sequence
<220> FEATURE:
<223> OTHER INFORMATION: Synthetic sequence

<400> SEQUENCE: 79
aatacttacc gaggcaatca ctgtacttgt tc 32

<210> SEQ ID NO 80
<211> LENGTH: 32
<212> TYPE: DNA
<213> ORGANISM: Artificial Sequence
<220> FEATURE:
<223> OTHER INFORMATION: Synthetic sequence

<400> SEQUENCE: 80
gggacagtgg gaatctacat tcagagcact gg 32

<210> SEQ ID NO 81
<211> LENGTH: 32
<212> TYPE: DNA
<213> ORGANISM: Artificial Sequence
<220> FEATURE:
<223> OTHER INFORMATION: Synthetic sequence

<400> SEQUENCE: 81
gagcttctgc tatcctgttt cctctggctt ca 32

<210> SEQ ID NO 82
<211> LENGTH: 16
<212> TYPE: DNA
<213> ORGANISM: Artificial Sequence
<220> FEATURE:
<223> OTHER INFORMATION: Synthetic sequence

<400> SEQUENCE: 82
tgttccaagg aacata 16

<210> SEQ ID NO 83
<211> LENGTH: 32
<212> TYPE: DNA
<213> ORGANISM: Artificial Sequence
<220> FEATURE:
<223> OTHER INFORMATION: Synthetic sequence

<400> SEQUENCE: 83
catttgaata tttgcttaca cactccttag cg 32

<210> SEQ ID NO 84
<211> LENGTH: 34
<212> TYPE: DNA
<213> ORGANISM: Artificial Sequence
<220> FEATURE:
<223> OTHER INFORMATION: Synthetic sequence

<400> SEQUENCE: 84
aacgcttgac tgccacatca gacagccgca aaaa 34

<210> SEQ ID NO 85
<211> LENGTH: 16
<212> TYPE: DNA
<213> ORGANISM: Artificial Sequence
<220> FEATURE:
<223> OTHER INFORMATION: Synthetic sequence

<400> SEQUENCE: 85
aagttgccct ctccaa 16

<210> SEQ ID NO 86
<211> LENGTH: 34
<212> TYPE: DNA
<213> ORGANISM: Artificial Sequence
<220> FEATURE:
<223> OTHER INFORMATION: Synthetic sequence

<400> SEQUENCE: 86
actaccacca agatctgtaa gaccccatct ccgg 34

<210> SEQ ID NO 87
<211> LENGTH: 34
<212> TYPE: DNA
<213> ORGANISM: Artificial Sequence
<220> FEATURE:
<223> OTHER INFORMATION: Synthetic sequence

<400> SEQUENCE: 87
gacttacgtc gcagtccaag acatcaggat cggt 34

<210> SEQ ID NO 88
<211> LENGTH: 32
<212> TYPE: DNA
<213> ORGANISM: Artificial Sequence
<220> FEATURE:
<223> OTHER INFORMATION: Synthetic sequence

<400> SEQUENCE: 88
aggcttcgtc actgacagag tataggtaac ac 32

<210> SEQ ID NO 89
<211> LENGTH: 32
<212> TYPE: DNA
<213> ORGANISM: Artificial Sequence
<220> FEATURE:
<223> OTHER INFORMATION: Synthetic sequence

<400> SEQUENCE: 89
gataggccac actttccttt tgttctactg ga 32

<210> SEQ ID NO 90
<211> LENGTH: 34
<212> TYPE: DNA
<213> ORGANISM: Artificial Sequence
<220> FEATURE:
<223> OTHER INFORMATION: Synthetic sequence

<400> SEQUENCE: 90
ccaactgctg ttgacgtccc agggctcgcg ccga 34

<210> SEQ ID NO 91
<211> LENGTH: 32
<212> TYPE: DNA
<213> ORGANISM: Artificial Sequence
<220> FEATURE:
<223> OTHER INFORMATION: Synthetic sequence

<400> SEQUENCE: 91
ttatgccagc atccttttag agctgcattc cc 32

<210> SEQ ID NO 92
<211> LENGTH: 34
<212> TYPE: DNA
<213> ORGANISM: Artificial Sequence
<220> FEATURE:
<223> OTHER INFORMATION: Synthetic sequence

<400> SEQUENCE: 92
aaccggattg caagtagtcc gcctagacct acca 34

<210> SEQ ID NO 93
<211> LENGTH: 32
<212> TYPE: DNA
<213> ORGANISM: Artificial Sequence
<220> FEATURE:
<223> OTHER INFORMATION: Synthetic sequence

<400> SEQUENCE: 93
ctaatcattc gctttatcac catctttcgg gt 32

<210> SEQ ID NO 94
<211> LENGTH: 34
<212> TYPE: DNA
<213> ORGANISM: Artificial Sequence
<220> FEATURE:
<223> OTHER INFORMATION: Synthetic sequence

<400> SEQUENCE: 94
cttccccatc tcttaggtac gttaccgtga agaa 34

<210> SEQ ID NO 95
<211> LENGTH: 34
<212> TYPE: DNA
<213> ORGANISM: Artificial Sequence
<220> FEATURE:
<223> OTHER INFORMATION: Synthetic sequence

<400> SEQUENCE: 95
cgcatcgcct ggcctgcata aaatcaggaa tctt 34

<210> SEQ ID NO 96
<211> LENGTH: 32
<212> TYPE: DNA
<213> ORGANISM: Artificial Sequence
<220> FEATURE:
<223> OTHER INFORMATION: Synthetic sequence

<400> SEQUENCE: 96
gaataggtca aggtcatact caaatccatc cg 32

<210> SEQ ID NO 97

<211> LENGTH: 32
<212> TYPE: DNA
<213> ORGANISM: Artificial Sequence
<220> FEATURE:
<223> OTHER INFORMATION: Synthetic sequence

<400> SEQUENCE: 97
cctttccgcc aagtgcaggc gttcagccat aa 32

<210> SEQ ID NO 98
<211> LENGTH: 34
<212> TYPE: DNA
<213> ORGANISM: Artificial Sequence
<220> FEATURE:
<223> OTHER INFORMATION: Synthetic sequence

<400> SEQUENCE: 98
ctccacgcct gcctactctg tggattttca cggg 34

<210> SEQ ID NO 99
<211> LENGTH: 34
<212> TYPE: DNA
<213> ORGANISM: Artificial Sequence
<220> FEATURE:
<223> OTHER INFORMATION: Synthetic sequence

<400> SEQUENCE: 99
tttcgacccc ggaacctgat tccgacttcc atgg 34

<210> SEQ ID NO 100
<211> LENGTH: 34
<212> TYPE: DNA
<213> ORGANISM: Artificial Sequence
<220> FEATURE:
<223> OTHER INFORMATION: Synthetic sequence

<400> SEQUENCE: 100
caaggccctc actacccaga ttccccttgt ccgt 34

<210> SEQ ID NO 101
<211> LENGTH: 34
<212> TYPE: DNA
<213> ORGANISM: Artificial Sequence
<220> FEATURE:
<223> OTHER INFORMATION: Synthetic sequence

<400> SEQUENCE: 101
acaccctcta tgtctctacg tggaaaatga attc 34

<210> SEQ ID NO 102
<211> LENGTH: 32
<212> TYPE: DNA
<213> ORGANISM: Artificial Sequence
<220> FEATURE:
<223> OTHER INFORMATION: Synthetic sequence

<400> SEQUENCE: 102
atgacattgc aattcgtcgc ggcaatgcct ga 32

<210> SEQ ID NO 103
<211> LENGTH: 17
<212> TYPE: DNA
<213> ORGANISM: Artificial Sequence
<220> FEATURE:
<223> OTHER INFORMATION: Synthetic sequence

<400> SEQUENCE: 103
atcgtaacaa caaggct 17

<210> SEQ ID NO 104
<211> LENGTH: 34
<212> TYPE: DNA
<213> ORGANISM: Artificial Sequence
<220> FEATURE:
<223> OTHER INFORMATION: Synthetic sequence

<400> SEQUENCE: 104
cctcataaaa ctgatacttc ggccggtgag ttgt 34

<210> SEQ ID NO 105
<211> LENGTH: 32
<212> TYPE: DNA
<213> ORGANISM: Artificial Sequence
<220> FEATURE:
<223> OTHER INFORMATION: Synthetic sequence

<400> SEQUENCE: 105
cctgctgcgg ttatcaccgt cacaagcgca cc 32

<210> SEQ ID NO 106
<211> LENGTH: 32
<212> TYPE: DNA
<213> ORGANISM: Artificial Sequence
<220> FEATURE:
<223> OTHER INFORMATION: Synthetic sequence

<400> SEQUENCE: 106
agctcccact tattctcgac ggtctacaag ag 32

<210> SEQ ID NO 107
<211> LENGTH: 17
<212> TYPE: DNA
<213> ORGANISM: Artificial Sequence
<220> FEATURE:
<223> OTHER INFORMATION: Synthetic sequence

<400> SEQUENCE: 107
atttatcccc acgcaaa 17

<210> SEQ ID NO 108
<211> LENGTH: 34
<212> TYPE: DNA
<213> ORGANISM: Artificial Sequence
<220> FEATURE:
<223> OTHER INFORMATION: Synthetic sequence

<400> SEQUENCE: 108
cgggcggcat ataaccagcg aggccccaac ctac 34

<210> SEQ ID NO 109
<211> LENGTH: 34
<212> TYPE: DNA
<213> ORGANISM: Artificial Sequence
<220> FEATURE:
<223> OTHER INFORMATION: Synthetic sequence

<400> SEQUENCE: 109
ggttcgatta gtctttcata tcaaccctga cggt 34

<210> SEQ ID NO 110
<211> LENGTH: 34
<212> TYPE: DNA

<213> ORGANISM: Artificial Sequence
<220> FEATURE:
<223> OTHER INFORMATION: Synthetic sequence

<400> SEQUENCE: 110
tcgctagata gtagatatct gcgttatcgt ttaa 34

<210> SEQ ID NO 111
<211> LENGTH: 32
<212> TYPE: DNA
<213> ORGANISM: Artificial Sequence
<220> FEATURE:
<223> OTHER INFORMATION: Synthetic sequence

<400> SEQUENCE: 111
ggtccgtgtt tcaagagaag gcactttaca aa 32

<210> SEQ ID NO 112
<211> LENGTH: 34
<212> TYPE: DNA
<213> ORGANISM: Artificial Sequence
<220> FEATURE:
<223> OTHER INFORMATION: Synthetic sequence

<400> SEQUENCE: 112
gctgttcacc ttggagatga atttcttcac tttg 34

<210> SEQ ID NO 113
<211> LENGTH: 34
<212> TYPE: DNA
<213> ORGANISM: Artificial Sequence
<220> FEATURE:
<223> OTHER INFORMATION: Synthetic sequence

<400> SEQUENCE: 113
tcagtcttca aagttctgtg ataagctgtt aaga 34

<210> SEQ ID NO 114
<211> LENGTH: 34
<212> TYPE: DNA
<213> ORGANISM: Artificial Sequence
<220> FEATURE:
<223> OTHER INFORMATION: Synthetic sequence

<400> SEQUENCE: 114
gacatcgaag aatcaaaact gttcctctcg tact 34

<210> SEQ ID NO 115
<211> LENGTH: 32
<212> TYPE: DNA
<213> ORGANISM: Artificial Sequence
<220> FEATURE:
<223> OTHER INFORMATION: Synthetic sequence

<400> SEQUENCE: 115
gaaccagcta ctagattgca cgtcagaacc gc 32

<210> SEQ ID NO 116
<211> LENGTH: 32
<212> TYPE: DNA
<213> ORGANISM: Artificial Sequence
<220> FEATURE:
<223> OTHER INFORMATION: Synthetic sequence

<400> SEQUENCE: 116
ggatctattt tgccgaataa accaattccg gg 32

<210> SEQ ID NO 117
<211> LENGTH: 32
<212> TYPE: DNA
<213> ORGANISM: Artificial Sequence
<220> FEATURE:
<223> OTHER INFORMATION: Synthetic sequence

<400> SEQUENCE: 117
atggttcagc gacgccaatc accgcgttct ag 32

<210> SEQ ID NO 118
<211> LENGTH: 34
<212> TYPE: DNA
<213> ORGANISM: Artificial Sequence
<220> FEATURE:
<223> OTHER INFORMATION: Synthetic sequence

<400> SEQUENCE: 118
ggtaactttt ctggcactcc agcggatggt agct 34

<210> SEQ ID NO 119
<211> LENGTH: 32
<212> TYPE: DNA
<213> ORGANISM: Artificial Sequence
<220> FEATURE:
<223> OTHER INFORMATION: Synthetic sequence

<400> SEQUENCE: 119
ggaacctttc cccactccac cgtccggctg tc 32

<210> SEQ ID NO 120
<211> LENGTH: 34
<212> TYPE: DNA
<213> ORGANISM: Artificial Sequence
<220> FEATURE:
<223> OTHER INFORMATION: Synthetic sequence

<400> SEQUENCE: 120
atggtttgta ttcacacatt gtgtggagca aaga 34

<210> SEQ ID NO 121
<211> LENGTH: 32
<212> TYPE: DNA
<213> ORGANISM: Artificial Sequence
<220> FEATURE:
<223> OTHER INFORMATION: Synthetic sequence

<400> SEQUENCE: 121
cactagaggc cgttcgtttc agggctagtt ca 32

<210> SEQ ID NO 122
<211> LENGTH: 32
<212> TYPE: DNA
<213> ORGANISM: Artificial Sequence
<220> FEATURE:
<223> OTHER INFORMATION: Synthetic sequence

<400> SEQUENCE: 122
gcgtcactaa ttagatttta cccgcgcttg gt 32

<210> SEQ ID NO 123
<211> LENGTH: 32
<212> TYPE: DNA
<213> ORGANISM: Artificial Sequence
<220> FEATURE:

<223> OTHER INFORMATION: Synthetic sequence

<400> SEQUENCE: 123
tatgatagga agagccgacc ttgaatgcta ga 32

<210> SEQ ID NO 124
<211> LENGTH: 32
<212> TYPE: DNA
<213> ORGANISM: Artificial Sequence
<220> FEATURE:
<223> OTHER INFORMATION: Synthetic sequence

<400> SEQUENCE: 124
ggcctttgaa acggagctta actctacgtt cg 32

<210> SEQ ID NO 125
<211> LENGTH: 34
<212> TYPE: DNA
<213> ORGANISM: Artificial Sequence
<220> FEATURE:
<223> OTHER INFORMATION: Synthetic sequence

<400> SEQUENCE: 125
tacctgattt gaggtcacac catgtctgat caaa 34

<210> SEQ ID NO 126
<211> LENGTH: 34
<212> TYPE: DNA
<213> ORGANISM: Artificial Sequence
<220> FEATURE:
<223> OTHER INFORMATION: Synthetic sequence

<400> SEQUENCE: 126
cttcccttat ctacattgca gaaatcacat tgcg 34

<210> SEQ ID NO 127
<211> LENGTH: 17
<212> TYPE: DNA
<213> ORGANISM: Artificial Sequence
<220> FEATURE:
<223> OTHER INFORMATION: Synthetic sequence

<400> SEQUENCE: 127
ccagcaagca cccaagg 17

<210> SEQ ID NO 128
<211> LENGTH: 17
<212> TYPE: DNA
<213> ORGANISM: Artificial Sequence
<220> FEATURE:
<223> OTHER INFORMATION: Synthetic sequence

<400> SEQUENCE: 128
taccccgttg tacatct 17

<210> SEQ ID NO 129
<211> LENGTH: 34
<212> TYPE: DNA
<213> ORGANISM: Artificial Sequence
<220> FEATURE:
<223> OTHER INFORMATION: Synthetic sequence

<400> SEQUENCE: 129
ccttatcccg aagttacacc atcgcaatgc tatg 34

<210> SEQ ID NO 130
<211> LENGTH: 32
<212> TYPE: DNA
<213> ORGANISM: Artificial Sequence
<220> FEATURE:
<223> OTHER INFORMATION: Synthetic sequence

<400> SEQUENCE: 130
tcccttggct gtggtttcaa catcactttc tg 32

<210> SEQ ID NO 131
<211> LENGTH: 34
<212> TYPE: DNA
<213> ORGANISM: Artificial Sequence
<220> FEATURE:
<223> OTHER INFORMATION: Synthetic sequence

<400> SEQUENCE: 131
cctacccaca aggagcaaaa ttcgacgatc gatt 34

<210> SEQ ID NO 132
<211> LENGTH: 34
<212> TYPE: DNA
<213> ORGANISM: Artificial Sequence
<220> FEATURE:
<223> OTHER INFORMATION: Synthetic sequence

<400> SEQUENCE: 132
aagcagtcca caagcactcg ttaattgtag caag 34

<210> SEQ ID NO 133
<211> LENGTH: 32
<212> TYPE: DNA
<213> ORGANISM: Artificial Sequence
<220> FEATURE:
<223> OTHER INFORMATION: Synthetic sequence

<400> SEQUENCE: 133
agccagttat ccctgtcaga tgtgccgccc ca 32

<210> SEQ ID NO 134
<211> LENGTH: 34
<212> TYPE: DNA
<213> ORGANISM: Artificial Sequence
<220> FEATURE:
<223> OTHER INFORMATION: Synthetic sequence

<400> SEQUENCE: 134
aactgatgct ggcccagtac gagcctccac caga 34

<210> SEQ ID NO 135
<211> LENGTH: 32
<212> TYPE: DNA
<213> ORGANISM: Artificial Sequence
<220> FEATURE:
<223> OTHER INFORMATION: Synthetic sequence

<400> SEQUENCE: 135
gtaacaagga cttcttcgat tgtgcacctc tt 32

<210> SEQ ID NO 136
<211> LENGTH: 34
<212> TYPE: DNA
<213> ORGANISM: Artificial Sequence
<220> FEATURE:
<223> OTHER INFORMATION: Synthetic sequence

<400> SEQUENCE: 136
accgaattct gcttcgggcg gtaacattca tcag 34

<210> SEQ ID NO 137
<211> LENGTH: 34
<212> TYPE: DNA
<213> ORGANISM: Artificial Sequence
<220> FEATURE:
<223> OTHER INFORMATION: Synthetic sequence

<400> SEQUENCE: 137
ttttacaccc aaaaatggcc cactaagttc atcc 34

<210> SEQ ID NO 138
<211> LENGTH: 34
<212> TYPE: DNA
<213> ORGANISM: Artificial Sequence
<220> FEATURE:
<223> OTHER INFORMATION: Synthetic sequence

<400> SEQUENCE: 138
aagaaactag ttccctatta gtgggttgtc tcac 34

<210> SEQ ID NO 139
<211> LENGTH: 34
<212> TYPE: DNA
<213> ORGANISM: Artificial Sequence
<220> FEATURE:
<223> OTHER INFORMATION: Synthetic sequence

<400> SEQUENCE: 139
aggccgtctt atttcactgg cgccgaaata agta 34

<210> SEQ ID NO 140
<211> LENGTH: 34
<212> TYPE: DNA
<213> ORGANISM: Artificial Sequence
<220> FEATURE:
<223> OTHER INFORMATION: Synthetic sequence

<400> SEQUENCE: 140
attacaactc gggcacctgg aatttaccac ccac 34

<210> SEQ ID NO 141
<211> LENGTH: 32
<212> TYPE: DNA
<213> ORGANISM: Artificial Sequence
<220> FEATURE:
<223> OTHER INFORMATION: Synthetic sequence

<400> SEQUENCE: 141
gtcttctttc cccgcttttt aattagacag tc 32

<210> SEQ ID NO 142
<211> LENGTH: 32
<212> TYPE: DNA
<213> ORGANISM: Artificial Sequence
<220> FEATURE:
<223> OTHER INFORMATION: Synthetic sequence

<400> SEQUENCE: 142
cagagcaagc cccacctcca tatccaggtt cc 32

<210> SEQ ID NO 143
<211> LENGTH: 32

<212> TYPE: DNA
<213> ORGANISM: Artificial Sequence
<220> FEATURE:
<223> OTHER INFORMATION: Synthetic sequence

<400> SEQUENCE: 143
gaacaatcca acgcttcagc tccgcttcat tg 32

<210> SEQ ID NO 144
<211> LENGTH: 34
<212> TYPE: DNA
<213> ORGANISM: Artificial Sequence
<220> FEATURE:
<223> OTHER INFORMATION: Synthetic sequence

<400> SEQUENCE: 144
gtacgacctg gcatgaacat agttactccc gccg 34

<210> SEQ ID NO 145
<211> LENGTH: 32
<212> TYPE: DNA
<213> ORGANISM: Artificial Sequence
<220> FEATURE:
<223> OTHER INFORMATION: Synthetic sequence

<400> SEQUENCE: 145
aagtcgtata caaatgccaa ttatccgaat ga 32

<210> SEQ ID NO 146
<211> LENGTH: 32
<212> TYPE: DNA
<213> ORGANISM: Artificial Sequence
<220> FEATURE:
<223> OTHER INFORMATION: Synthetic sequence

<400> SEQUENCE: 146
attctatcaa ctagagtggc ctcttccagc ca 32

<210> SEQ ID NO 147
<211> LENGTH: 32
<212> TYPE: DNA
<213> ORGANISM: Artificial Sequence
<220> FEATURE:
<223> OTHER INFORMATION: Synthetic sequence

<400> SEQUENCE: 147
gcccgctgcg tctgaccgtc tccacattca gt 32

<210> SEQ ID NO 148
<211> LENGTH: 32
<212> TYPE: DNA
<213> ORGANISM: Artificial Sequence
<220> FEATURE:
<223> OTHER INFORMATION: Synthetic sequence

<400> SEQUENCE: 148
actctactgc ttacaaaagt tcaattacta tt 32

<210> SEQ ID NO 149
<211> LENGTH: 34
<212> TYPE: DNA
<213> ORGANISM: Artificial Sequence
<220> FEATURE:
<223> OTHER INFORMATION: Synthetic sequence

<400> SEQUENCE: 149
ctaaggcaat cccggttgtt cttttcatct ttcc 34

<210> SEQ ID NO 150
<211> LENGTH: 16
<212> TYPE: DNA
<213> ORGANISM: Artificial Sequence
<220> FEATURE:
<223> OTHER INFORMATION: Synthetic sequence

<400> SEQUENCE: 150
ggtttctttt cctccg 16

<210> SEQ ID NO 151
<211> LENGTH: 32
<212> TYPE: DNA
<213> ORGANISM: Artificial Sequence
<220> FEATURE:
<223> OTHER INFORMATION: Synthetic sequence

<400> SEQUENCE: 151
tcacaatgtc aaactaacca gttctaagtt ga 32

<210> SEQ ID NO 152
<211> LENGTH: 32
<212> TYPE: DNA
<213> ORGANISM: Artificial Sequence
<220> FEATURE:
<223> OTHER INFORMATION: Synthetic sequence

<400> SEQUENCE: 152
aagcaatgtc gctatgacaa tgtcttcaac cc 32

<210> SEQ ID NO 153
<211> LENGTH: 32
<212> TYPE: DNA
<213> ORGANISM: Artificial Sequence
<220> FEATURE:
<223> OTHER INFORMATION: Synthetic sequence

<400> SEQUENCE: 153
tcagtcccag ctggcaaata tttagcttta ga 32

<210> SEQ ID NO 154
<211> LENGTH: 34
<212> TYPE: DNA
<213> ORGANISM: Artificial Sequence
<220> FEATURE:
<223> OTHER INFORMATION: Synthetic sequence

<400> SEQUENCE: 154
agctacattc ctatggaccc tattcaggca tagt 34

<210> SEQ ID NO 155
<211> LENGTH: 34
<212> TYPE: DNA
<213> ORGANISM: Artificial Sequence
<220> FEATURE:
<223> OTHER INFORMATION: Synthetic sequence

<400> SEQUENCE: 155
acatatttaa agtttgatag atgaactaac acct 34

<210> SEQ ID NO 156
<211> LENGTH: 16
<212> TYPE: DNA
<213> ORGANISM: Artificial Sequence
<220> FEATURE:
<223> OTHER INFORMATION: Synthetic sequence

<400> SEQUENCE: 156
gttcagcggg tactcc 16

<210> SEQ ID NO 157
<211> LENGTH: 17
<212> TYPE: DNA
<213> ORGANISM: Artificial Sequence
<220> FEATURE:
<223> OTHER INFORMATION: Synthetic sequence

<400> SEQUENCE: 157
accgttgcta gcctgct 17

<210> SEQ ID NO 158
<211> LENGTH: 32
<212> TYPE: DNA
<213> ORGANISM: Artificial Sequence
<220> FEATURE:
<223> OTHER INFORMATION: Synthetic sequence

<400> SEQUENCE: 158
ctctagcctc aaattcagcc ccccttagga ca 32

<210> SEQ ID NO 159
<211> LENGTH: 34
<212> TYPE: DNA
<213> ORGANISM: Artificial Sequence
<220> FEATURE:
<223> OTHER INFORMATION: Synthetic sequence

<400> SEQUENCE: 159
acccgacctt acggtctgga gccagcaaag gtgc 34

<210> SEQ ID NO 160
<211> LENGTH: 32
<212> TYPE: DNA
<213> ORGANISM: Artificial Sequence
<220> FEATURE:
<223> OTHER INFORMATION: Synthetic sequence

<400> SEQUENCE: 160
gacccttaga gccaatagaa aagataactc ct 32

<210> SEQ ID NO 161
<211> LENGTH: 34
<212> TYPE: DNA
<213> ORGANISM: Artificial Sequence
<220> FEATURE:
<223> OTHER INFORMATION: Synthetic sequence

<400> SEQUENCE: 161
gagggaaact tcggcaggct tgagcgccat ccat 34

<210> SEQ ID NO 162
<211> LENGTH: 34
<212> TYPE: DNA
<213> ORGANISM: Artificial Sequence
<220> FEATURE:
<223> OTHER INFORMATION: Synthetic sequence

<400> SEQUENCE: 162
gacaaggaac ggccccaaaa caactcgact cttc 34

<210> SEQ ID NO 163
<211> LENGTH: 32
<212> TYPE: DNA
<213> ORGANISM: Artificial Sequence
<220> FEATURE:
<223> OTHER INFORMATION: Synthetic sequence

<400> SEQUENCE: 163
tgaaatgcga gattcctgcc cttccctttc aa 32

<210> SEQ ID NO 164
<211> LENGTH: 32
<212> TYPE: DNA
<213> ORGANISM: Artificial Sequence
<220> FEATURE:
<223> OTHER INFORMATION: Synthetic sequence

<400> SEQUENCE: 164
tttatcctgc caccaatcac tctcttttca aa 32

<210> SEQ ID NO 165
<211> LENGTH: 32
<212> TYPE: DNA
<213> ORGANISM: Artificial Sequence
<220> FEATURE:
<223> OTHER INFORMATION: Synthetic sequence

<400> SEQUENCE: 165
ggcttaatct cagcagtagg gtaaaactaa cc 32

<210> SEQ ID NO 166
<211> LENGTH: 34
<212> TYPE: DNA
<213> ORGANISM: Artificial Sequence
<220> FEATURE:
<223> OTHER INFORMATION: Synthetic sequence

<400> SEQUENCE: 166
cttattgata tgcttaacaa tttcacgtac tttt 34

<210> SEQ ID NO 167
<211> LENGTH: 34
<212> TYPE: DNA
<213> ORGANISM: Artificial Sequence
<220> FEATURE:
<223> OTHER INFORMATION: Synthetic sequence

<400> SEQUENCE: 167
cgttaatcca ttcatgcgat ttctgttctc catg 34

<210> SEQ ID NO 168
<211> LENGTH: 16
<212> TYPE: DNA
<213> ORGANISM: Artificial Sequence
<220> FEATURE:
<223> OTHER INFORMATION: Synthetic sequence

<400> SEQUENCE: 168
gaaggtacca gatttc 16

<210> SEQ ID NO 169
<211> LENGTH: 34
<212> TYPE: DNA
<213> ORGANISM: Artificial Sequence
<220> FEATURE:
<223> OTHER INFORMATION: Synthetic sequence

<400> SEQUENCE: 169
ctcctcgcct agacgttaga ctccttcgta tggg 34

<210> SEQ ID NO 170
<211> LENGTH: 32
<212> TYPE: DNA
<213> ORGANISM: Artificial Sequence
<220> FEATURE:
<223> OTHER INFORMATION: Synthetic sequence

<400> SEQUENCE: 170
atcgactaac ccacgttttg tggtgtctga tg 32

<210> SEQ ID NO 171
<211> LENGTH: 24
<212> TYPE: DNA
<213> ORGANISM: Artificial Sequence
<220> FEATURE:
<223> OTHER INFORMATION: Synthetic sequence

<400> SEQUENCE: 171 tttttcgat ggagttcttt tttt 24

<210> SEQ ID NO 172
<211> LENGTH: 24
<212> TYPE: DNA
<213> ORGANISM: Artificial Sequence
<220> FEATURE:
<223> OTHER INFORMATION: Synthetic sequence

<400> SEQUENCE: 172
ttttttgaga gtaactattt tttt 24

<210> SEQ ID NO 173
<211> LENGTH: 24
<212> TYPE: DNA
<213> ORGANISM: Artificial Sequence
<220> FEATURE:
<223> OTHER INFORMATION: Synthetic sequence

<400> SEQUENCE: 173
ttttttgctc actaaaggtt tttt 24

<210> SEQ ID NO 174
<211> LENGTH: 24
<212> TYPE: DNA
<213> ORGANISM: Artificial Sequence
<220> FEATURE:
<223> OTHER INFORMATION: Synthetic sequence

<400> SEQUENCE: 174
ttttttctcg caacacggtt tttt 24

<210> SEQ ID NO 175
<211> LENGTH: 24
<212> TYPE: DNA
<213> ORGANISM: Artificial Sequence
<220> FEATURE:
<223> OTHER INFORMATION: Synthetic sequence

<400> SEQUENCE: 175
ttttttatct attgaaaatt tttt 24

<210> SEQ ID NO 176

<211> LENGTH: 24
<212> TYPE: DNA
<213> ORGANISM: Artificial Sequence
<220> FEATURE:
<223> OTHER INFORMATION: Synthetic sequence

<400> SEQUENCE: 176
tttttttcct tccgtcagtt tttt 24

<210> SEQ ID NO 177
<211> LENGTH: 24
<212> TYPE: DNA
<213> ORGANISM: Artificial Sequence
<220> FEATURE:
<223> OTHER INFORMATION: Synthetic sequence

<400> SEQUENCE: 177 ttttttagt ggacaacatt tttt 24

<210> SEQ ID NO 178
<211> LENGTH: 24
<212> TYPE: DNA
<213> ORGANISM: Artificial Sequence
<220> FEATURE:
<223> OTHER INFORMATION: Synthetic sequence

<400> SEQUENCE: 178
ttttttatac ccgagggctt tttt 24

<210> SEQ ID NO 179
<211> LENGTH: 24
<212> TYPE: DNA
<213> ORGANISM: Artificial Sequence
<220> FEATURE:
<223> OTHER INFORMATION: Synthetic sequence

<400> SEQUENCE: 179
ttttttaggc acccctttt tttt 24

<210> SEQ ID NO 180
<211> LENGTH: 37
<212> TYPE: DNA
<213> ORGANISM: Artificial Sequence
<220> FEATURE:
<223> OTHER INFORMATION: Synthetic sequence

<400> SEQUENCE: 180
ttttttgatt ctcaccctct atgacgtccg aaccgca 37

<210> SEQ ID NO 181
<211> LENGTH: 24
<212> TYPE: DNA
<213> ORGANISM: Artificial Sequence
<220> FEATURE:
<223> OTHER INFORMATION: Synthetic sequence

<400> SEQUENCE: 181
ttttttgctt accaaacatt tttt 24

<210> SEQ ID NO 182
<211> LENGTH: 24
<212> TYPE: DNA
<213> ORGANISM: Artificial Sequence
<220> FEATURE:
<223> OTHER INFORMATION: Synthetic sequence

<400> SEQUENCE: 182 tttttggca tcgcccctt tttt 24

<210> SEQ ID NO 183
<211> LENGTH: 24
<212> TYPE: DNA
<213> ORGANISM: Artificial Sequence
<220> FEATURE:
<223> OTHER INFORMATION: Synthetic sequence

<400> SEQUENCE: 183
tttttttcaa aaccttaatt tttt 24

<210> SEQ ID NO 184
<211> LENGTH: 29
<212> TYPE: DNA
<213> ORGANISM: Artificial Sequence
<220> FEATURE:
<223> OTHER INFORMATION: Synthetic sequence

<400> SEQUENCE: 184
acaaggacgc cttattcgta tcctttttt 29

<210> SEQ ID NO 185
<211> LENGTH: 12
<212> TYPE: DNA
<213> ORGANISM: Artificial Sequence
<220> FEATURE:
<223> OTHER INFORMATION: Synthetic sequence

<400> SEQUENCE: 185
aacccatttt tt 12

<210> SEQ ID NO 186
<211> LENGTH: 41
<212> TYPE: DNA
<213> ORGANISM: Artificial Sequence
<220> FEATURE:
<223> OTHER INFORMATION: Synthetic sequence

<400> SEQUENCE: 186
acaaaaaact tttttttcc tattcgaatg ggcttttttt t 41

<210> SEQ ID NO 187
<211> LENGTH: 32
<212> TYPE: DNA
<213> ORGANISM: Artificial Sequence
<220> FEATURE:
<223> OTHER INFORMATION: Synthetic sequence

<400> SEQUENCE: 187
acaggctata atacttgatg ctggcccagt ga 32

<210> SEQ ID NO 188
<211> LENGTH: 32
<212> TYPE: DNA
<213> ORGANISM: Artificial Sequence
<220> FEATURE:
<223> OTHER INFORMATION: Synthetic sequence

<400> SEQUENCE: 188
ttcaattaag taacaagacc ccggaacctc ta 32

<210> SEQ ID NO 189
<211> LENGTH: 32
<212> TYPE: DNA

<213> ORGANISM: Artificial Sequence
<220> FEATURE:
<223> OTHER INFORMATION: Synthetic sequence

<400> SEQUENCE: 189
gctccgtcag tgtagcccct tccgtcaatt cc 32

<210> SEQ ID NO 190
<211> LENGTH: 34
<212> TYPE: DNA
<213> ORGANISM: Artificial Sequence
<220> FEATURE:
<223> OTHER INFORMATION: Synthetic sequence

<400> SEQUENCE: 190
tacccgttga aaccatgagg actcaaggtt agcc 34

<210> SEQ ID NO 191
<211> LENGTH: 32
<212> TYPE: DNA
<213> ORGANISM: Artificial Sequence
<220> FEATURE:
<223> OTHER INFORMATION: Synthetic sequence

<400> SEQUENCE: 191
acaaggacgc cttatttcag acagccgcaa aa 32

<210> SEQ ID NO 192
<211> LENGTH: 34
<212> TYPE: DNA
<213> ORGANISM: Artificial Sequence
<220> FEATURE:
<223> OTHER INFORMATION: Synthetic sequence

<400> SEQUENCE: 192
acatcacttt ctgaccacca gctccgcttc attg 34

<210> SEQ ID NO 193
<211> LENGTH: 32
<212> TYPE: DNA
<213> ORGANISM: Artificial Sequence
<220> FEATURE:
<223> OTHER INFORMATION: Synthetic sequence

<400> SEQUENCE: 193
caattgaata ctgatgagaa ggaaaggccc cg 32

<210> SEQ ID NO 194
<211> LENGTH: 32
<212> TYPE: DNA
<213> ORGANISM: Artificial Sequence
<220> FEATURE:
<223> OTHER INFORMATION: Synthetic sequence

<400> SEQUENCE: 194
gacgaggcat ttggctcctt atctacatta tt 32

<210> SEQ ID NO 195
<211> LENGTH: 32
<212> TYPE: DNA
<213> ORGANISM: Artificial Sequence
<220> FEATURE:
<223> OTHER INFORMATION: Synthetic sequence

<400> SEQUENCE: 195
cttcgatccc ctaactatat acgctattgg ag 32

<210> SEQ ID NO 196
<211> LENGTH: 34
<212> TYPE: DNA
<213> ORGANISM: Artificial Sequence
<220> FEATURE:
<223> OTHER INFORMATION: Synthetic sequence

<400> SEQUENCE: 196
tcacaagcgc accggagcta tcaactagag gctg 34

<210> SEQ ID NO 197
<211> LENGTH: 34
<212> TYPE: DNA
<213> ORGANISM: Artificial Sequence
<220> FEATURE:
<223> OTHER INFORMATION: Synthetic sequence

<400> SEQUENCE: 197
accgaggcaa gctacattag gtcaaggtca tttc 34

<210> SEQ ID NO 198
<211> LENGTH: 34
<212> TYPE: DNA
<213> ORGANISM: Artificial Sequence
<220> FEATURE:
<223> OTHER INFORMATION: Synthetic sequence

<400> SEQUENCE: 198
aactctacgt tcggttcttg aatatttgct acta 34

<210> SEQ ID NO 199
<211> LENGTH: 34
<212> TYPE: DNA
<213> ORGANISM: Artificial Sequence
<220> FEATURE:
<223> OTHER INFORMATION: Synthetic sequence

<400> SEQUENCE: 199
aagaatttca cctctgagtt tccccgtgtt gagt 34

<210> SEQ ID NO 200
<211> LENGTH: 34
<212> TYPE: DNA
<213> ORGANISM: Artificial Sequence
<220> FEATURE:
<223> OTHER INFORMATION: Synthetic sequence

<400> SEQUENCE: 200
tttcgatggt ggcctgcgcg acggtctaca agag 34

<210> SEQ ID NO 201
<211> LENGTH: 32
<212> TYPE: DNA
<213> ORGANISM: Artificial Sequence
<220> FEATURE:
<223> OTHER INFORMATION: Synthetic sequence

<400> SEQUENCE: 201
tttatggtta agactagctg gcaccagact tg 32

<210> SEQ ID NO 202
<211> LENGTH: 34
<212> TYPE: DNA
<213> ORGANISM: Artificial Sequence
<220> FEATURE:

<223> OTHER INFORMATION: Synthetic sequence

<400> SEQUENCE: 202
gggccctgta tcgttatctg gaattaccgc ggct 34

<210> SEQ ID NO 203
<211> LENGTH: 34
<212> TYPE: DNA
<213> ORGANISM: Artificial Sequence
<220> FEATURE:
<223> OTHER INFORMATION: Synthetic sequence

<400> SEQUENCE: 203
taagtcgtat acaaatggag ccattcgcag tttc 34

<210> SEQ ID NO 204
<211> LENGTH: 32
<212> TYPE: DNA
<213> ORGANISM: Artificial Sequence
<220> FEATURE:
<223> OTHER INFORMATION: Synthetic sequence

<400> SEQUENCE: 204
aacgcttgac tgccacctgc caagcccgtt cc 32

<210> SEQ ID NO 205
<211> LENGTH: 32
<212> TYPE: DNA
<213> ORGANISM: Artificial Sequence
<220> FEATURE:
<223> OTHER INFORMATION: Synthetic sequence

<400> SEQUENCE: 205
cgttatcgtt taacagggat cagccccgaa tg 32

<210> SEQ ID NO 206
<211> LENGTH: 34
<212> TYPE: DNA
<213> ORGANISM: Artificial Sequence
<220> FEATURE:
<223> OTHER INFORMATION: Synthetic sequence

<400> SEQUENCE: 206
gggtactcct acctgatatc ctgccaccaa aact 34

<210> SEQ ID NO 207
<211> LENGTH: 32
<212> TYPE: DNA
<213> ORGANISM: Artificial Sequence
<220> FEATURE:
<223> OTHER INFORMATION: Synthetic sequence

<400> SEQUENCE: 207
tttcttcact ttgacagccc tcactacccg ac 32

<210> SEQ ID NO 208
<211> LENGTH: 34
<212> TYPE: DNA
<213> ORGANISM: Artificial Sequence
<220> FEATURE:
<223> OTHER INFORMATION: Synthetic sequence

<400> SEQUENCE: 208
ccgtccggct gtctagactt cgtcactgac ctcc 34

<210> SEQ ID NO 209
<211> LENGTH: 34
<212> TYPE: DNA
<213> ORGANISM: Artificial Sequence
<220> FEATURE:
<223> OTHER INFORMATION: Synthetic sequence

<400> SEQUENCE: 209
aaccatcgcc agcacaagca atacgcctgc tttg 34

<210> SEQ ID NO 210
<211> LENGTH: 32
<212> TYPE: DNA
<213> ORGANISM: Artificial Sequence
<220> FEATURE:
<223> OTHER INFORMATION: Synthetic sequence

<400> SEQUENCE: 210
gggggctttt acccttaata agtaaagaaa ct 32

<210> SEQ ID NO 211
<211> LENGTH: 32
<212> TYPE: DNA
<213> ORGANISM: Artificial Sequence
<220> FEATURE:
<223> OTHER INFORMATION: Synthetic sequence

<400> SEQUENCE: 211
ccagcaaagg tgctggacgc ctgcctactc gt 32

<210> SEQ ID NO 212
<211> LENGTH: 34
<212> TYPE: DNA
<213> ORGANISM: Artificial Sequence
<220> FEATURE:
<223> OTHER INFORMATION: Synthetic sequence

<400> SEQUENCE: 212
cgcgtcacta attagatttc tttccccgct gatt 34

<210> SEQ ID NO 213
<211> LENGTH: 34
<212> TYPE: DNA
<213> ORGANISM: Artificial Sequence
<220> FEATURE:
<223> OTHER INFORMATION: Synthetic sequence

<400> SEQUENCE: 213
ggacttctta catatttctt tgaaacggag cttc 34

<210> SEQ ID NO 214
<211> LENGTH: 34
<212> TYPE: DNA
<213> ORGANISM: Artificial Sequence
<220> FEATURE:
<223> OTHER INFORMATION: Synthetic sequence

<400> SEQUENCE: 214
aaacaacttc aaatccatcc gaagactttc gggt 34

<210> SEQ ID NO 215
<211> LENGTH: 32
<212> TYPE: DNA
<213> ORGANISM: Artificial Sequence
<220> FEATURE:
<223> OTHER INFORMATION: Synthetic sequence

<400> SEQUENCE: 215
accaagacct ctcggccgac catactcccc cc 32

<210> SEQ ID NO 216
<211> LENGTH: 34
<212> TYPE: DNA
<213> ORGANISM: Artificial Sequence
<220> FEATURE:
<223> OTHER INFORMATION: Synthetic sequence

<400> SEQUENCE: 216
agcatccttg acttacgctt ctgctatcct gagg 34

<210> SEQ ID NO 217
<211> LENGTH: 34
<212> TYPE: DNA
<213> ORGANISM: Artificial Sequence
<220> FEATURE:
<223> OTHER INFORMATION: Synthetic sequence

<400> SEQUENCE: 217
taattagaca gtcagatgga ccttgaatgc taga 34

<210> SEQ ID NO 218
<211> LENGTH: 32
<212> TYPE: DNA
<213> ORGANISM: Artificial Sequence
<220> FEATURE:
<223> OTHER INFORMATION: Synthetic sequence

<400> SEQUENCE: 218
ggattttcac gggccgcctg acggtagagt at 32

<210> SEQ ID NO 219
<211> LENGTH: 34
<212> TYPE: DNA
<213> ORGANISM: Artificial Sequence
<220> FEATURE:
<223> OTHER INFORMATION: Synthetic sequence

<400> SEQUENCE: 219
ttcagagcac tgggcagata aaggtagtgg tatt 34

<210> SEQ ID NO 220
<211> LENGTH: 32
<212> TYPE: DNA
<213> ORGANISM: Artificial Sequence
<220> FEATURE:
<223> OTHER INFORMATION: Synthetic sequence

<400> SEQUENCE: 220
aaaacgtcct tggcaatcaa ctacgagctt tt 32

<210> SEQ ID NO 221
<211> LENGTH: 24
<212> TYPE: DNA
<213> ORGANISM: Artificial Sequence
<220> FEATURE:
<223> OTHER INFORMATION: Synthetic sequence

<400> SEQUENCE: 221
taatttgcgc gcctgccgat aact 24

<210> SEQ ID NO 222
<211> LENGTH: 34

<212> TYPE: DNA
<213> ORGANISM: Artificial Sequence
<220> FEATURE:
<223> OTHER INFORMATION: Synthetic sequence

<400> SEQUENCE: 222
cagctggcag tattcccatc attcgcttta cctc 34

<210> SEQ ID NO 223
<211> LENGTH: 24
<212> TYPE: DNA
<213> ORGANISM: Artificial Sequence
<220> FEATURE:
<223> OTHER INFORMATION: Synthetic sequence

<400> SEQUENCE: 223
aacccttatt ccccgtttta agca 24

<210> SEQ ID NO 224
<211> LENGTH: 34
<212> TYPE: DNA
<213> ORGANISM: Artificial Sequence
<220> FEATURE:
<223> OTHER INFORMATION: Synthetic sequence

<400> SEQUENCE: 224
tgccttcctt ggatgtgcca accgggccca aagt 34

<210> SEQ ID NO 225
<211> LENGTH: 34
<212> TYPE: DNA
<213> ORGANISM: Artificial Sequence
<220> FEATURE:
<223> OTHER INFORMATION: Synthetic sequence

<400> SEQUENCE: 225
cccccgaccg tccctattct gtcaatcctt attg 34

<210> SEQ ID NO 226
<211> LENGTH: 32
<212> TYPE: DNA
<213> ORGANISM: Artificial Sequence
<220> FEATURE:
<223> OTHER INFORMATION: Synthetic sequence

<400> SEQUENCE: 226
gccggtgagt tgttacaggc atagttcacc at 32

<210> SEQ ID NO 227
<211> LENGTH: 32
<212> TYPE: DNA
<213> ORGANISM: Artificial Sequence
<220> FEATURE:
<223> OTHER INFORMATION: Synthetic sequence

<400> SEQUENCE: 227
ggtaactttt ctggcacaag ctcaacaggg tc 32

<210> SEQ ID NO 228
<211> LENGTH: 32
<212> TYPE: DNA
<213> ORGANISM: Artificial Sequence
<220> FEATURE:
<223> OTHER INFORMATION: Synthetic sequence

<400> SEQUENCE: 228
gttactcccg ccgtttatcc cgaagttacg ga 32

<210> SEQ ID NO 229
<211> LENGTH: 32
<212> TYPE: DNA
<213> ORGANISM: Artificial Sequence
<220> FEATURE:
<223> OTHER INFORMATION: Synthetic sequence

<400> SEQUENCE: 229
taagaagtgg ataaccaaga aagagctctc aa 32

<210> SEQ ID NO 230
<211> LENGTH: 32
<212> TYPE: DNA
<213> ORGANISM: Artificial Sequence
<220> FEATURE:
<223> OTHER INFORMATION: Synthetic sequence

<400> SEQUENCE: 230
atggtttgta ttcacatcac tggcgccgaa gc 32

<210> SEQ ID NO 231
<211> LENGTH: 34
<212> TYPE: DNA
<213> ORGANISM: Artificial Sequence
<220> FEATURE:
<223> OTHER INFORMATION: Synthetic sequence

<400> SEQUENCE: 231
caccgcgttc tagcatgcga aaagttatta tgaa 34

<210> SEQ ID NO 232
<211> LENGTH: 32
<212> TYPE: DNA
<213> ORGANISM: Artificial Sequence
<220> FEATURE:
<223> OTHER INFORMATION: Synthetic sequence

<400> SEQUENCE: 232
tcttaaccgg attcccccca tctcttagga tc 32

<210> SEQ ID NO 233
<211> LENGTH: 32
<212> TYPE: DNA
<213> ORGANISM: Artificial Sequence
<220> FEATURE:
<223> OTHER INFORMATION: Synthetic sequence

<400> SEQUENCE: 233
tctgttctcc atgagcacgt ggaaaatgaa tt 32

<210> SEQ ID NO 234
<211> LENGTH: 34
<212> TYPE: DNA
<213> ORGANISM: Artificial Sequence
<220> FEATURE:
<223> OTHER INFORMATION: Synthetic sequence

<400> SEQUENCE: 234
aatgacattg caattcgagg aactatcaaa taaa 34

<210> SEQ ID NO 235
<211> LENGTH: 34
<212> TYPE: DNA
<213> ORGANISM: Artificial Sequence
<220> FEATURE:
<223> OTHER INFORMATION: Synthetic sequence

<400> SEQUENCE: 235
tactctactg cttacaaata cttagacatg catg 34

<210> SEQ ID NO 236
<211> LENGTH: 34
<212> TYPE: DNA
<213> ORGANISM: Artificial Sequence
<220> FEATURE:
<223> OTHER INFORMATION: Synthetic sequence

<400> SEQUENCE: 236
ttgtgcacct cttgcgactg gcttcaccct attc 34

<210> SEQ ID NO 237
<211> LENGTH: 34
<212> TYPE: DNA
<213> ORGANISM: Artificial Sequence
<220> FEATURE:
<223> OTHER INFORMATION: Synthetic sequence

<400> SEQUENCE: 237
tcattcaaat gtccacggac taacccacgt ccaa 34

<210> SEQ ID NO 238
<211> LENGTH: 34
<212> TYPE: DNA
<213> ORGANISM: Artificial Sequence
<220> FEATURE:
<223> OTHER INFORMATION: Synthetic sequence

<400> SEQUENCE: 238 ccccttagg acatctgttc gcggcaatgc ctga 34

<210> SEQ ID NO 239
<211> LENGTH: 32
<212> TYPE: DNA
<213> ORGANISM: Artificial Sequence
<220> FEATURE:
<223> OTHER INFORMATION: Synthetic sequence

<400> SEQUENCE: 239
gtaggccact atcctactaa taaatacatc tc 32

<210> SEQ ID NO 240
<211> LENGTH: 34
<212> TYPE: DNA
<213> ORGANISM: Artificial Sequence
<220> FEATURE:
<223> OTHER INFORMATION: Synthetic sequence

<400> SEQUENCE: 240
acactcctta gcggattcag ggcatcatat caac 34

<210> SEQ ID NO 241
<211> LENGTH: 32
<212> TYPE: DNA
<213> ORGANISM: Artificial Sequence
<220> FEATURE:
<223> OTHER INFORMATION: Synthetic sequence

<400> SEQUENCE: 241
tagaaccaaa cgtcctaaca ctctaatttt tt 32

<210> SEQ ID NO 242
<211> LENGTH: 34
<212> TYPE: DNA
<213> ORGANISM: Artificial Sequence
<220> FEATURE:
<223> OTHER INFORMATION: Synthetic sequence

<400> SEQUENCE: 242
acccgcgctt ggttgaatcc cacttattct acac 34

<210> SEQ ID NO 243
<211> LENGTH: 34
<212> TYPE: DNA
<213> ORGANISM: Artificial Sequence
<220> FEATURE:
<223> OTHER INFORMATION: Synthetic sequence

<400> SEQUENCE: 243
gtttcaagac gggcggccca gctactagat ggtt 34

<210> SEQ ID NO 244
<211> LENGTH: 34
<212> TYPE: DNA
<213> ORGANISM: Artificial Sequence
<220> FEATURE:
<223> OTHER INFORMATION: Synthetic sequence

<400> SEQUENCE: 244
ctgaaaatca aaatcaataa gttcaattac tatt 34

<210> SEQ ID NO 245
<211> LENGTH: 32
<212> TYPE: DNA
<213> ORGANISM: Artificial Sequence
<220> FEATURE:
<223> OTHER INFORMATION: Synthetic sequence

<400> SEQUENCE: 245
atataaccat tatgccctga tcaaatgccc tt 32

<210> SEQ ID NO 246
<211> LENGTH: 32
<212> TYPE: DNA
<213> ORGANISM: Artificial Sequence
<220> FEATURE:
<223> OTHER INFORMATION: Synthetic sequence

<400> SEQUENCE: 246
tcgcagtcct cagtccccca caaggagcag ag 32

<210> SEQ ID NO 247
<211> LENGTH: 34
<212> TYPE: DNA
<213> ORGANISM: Artificial Sequence
<220> FEATURE:
<223> OTHER INFORMATION: Synthetic sequence

<400> SEQUENCE: 247
tgttcctcat ccctagtcgg catagcgagt gggt 34

<210> SEQ ID NO 248
<211> LENGTH: 34
<212> TYPE: DNA
<213> ORGANISM: Artificial Sequence
<220> FEATURE:
<223> OTHER INFORMATION: Synthetic sequence

<400> SEQUENCE: 248
gcctttccgc caagtgcctc tagaattacc acag 34

<210> SEQ ID NO 249
<211> LENGTH: 32
<212> TYPE: DNA
<213> ORGANISM: Artificial Sequence
<220> FEATURE:
<223> OTHER INFORMATION: Synthetic sequence

<400> SEQUENCE: 249
agactccttg gtccgtcgta ctttttcact ct 32

<210> SEQ ID NO 250
<211> LENGTH: 32
<212> TYPE: DNA
<213> ORGANISM: Artificial Sequence
<220> FEATURE:
<223> OTHER INFORMATION: Synthetic sequence

<400> SEQUENCE: 250
agtcttcaat aaatccgaaa aaatcggacc gg 32

<210> SEQ ID NO 251
<211> LENGTH: 32
<212> TYPE: DNA
<213> ORGANISM: Artificial Sequence
<220> FEATURE:
<223> OTHER INFORMATION: Synthetic sequence

<400> SEQUENCE: 251
gggctcgcgc cgacgttctt caaagttctc at 32

<210> SEQ ID NO 252
<211> LENGTH: 34
<212> TYPE: DNA
<213> ORGANISM: Artificial Sequence
<220> FEATURE:
<223> OTHER INFORMATION: Synthetic sequence

<400> SEQUENCE: 252
actactggac attgtactca ttccaccctc caat 34

<210> SEQ ID NO 253
<211> LENGTH: 34
<212> TYPE: DNA
<213> ORGANISM: Artificial Sequence
<220> FEATURE:
<223> OTHER INFORMATION: Synthetic sequence

<400> SEQUENCE: 253
acactcgcat agacgttcct atacccaaat tcga 34

<210> SEQ ID NO 254
<211> LENGTH: 34
<212> TYPE: DNA
<213> ORGANISM: Artificial Sequence
<220> FEATURE:
<223> OTHER INFORMATION: Synthetic sequence

<400> SEQUENCE: 254
cactttcatt acgcgtacag aaccgctacg agcc 34

<210> SEQ ID NO 255

<211> LENGTH: 34
<212> TYPE: DNA
<213> ORGANISM: Artificial Sequence
<220> FEATURE:
<223> OTHER INFORMATION: Synthetic sequence

<400> SEQUENCE: 255
tatggttcag cgacgccttc caaagggtcg agat 34

<210> SEQ ID NO 256
<211> LENGTH: 34
<212> TYPE: DNA
<213> ORGANISM: Artificial Sequence
<220> FEATURE:
<223> OTHER INFORMATION: Synthetic sequence

<400> SEQUENCE: 256
tctgcttacc aaaaatgacc tttccccact tcag 34

<210> SEQ ID NO 257
<211> LENGTH: 32
<212> TYPE: DNA
<213> ORGANISM: Artificial Sequence
<220> FEATURE:
<223> OTHER INFORMATION: Synthetic sequence

<400> SEQUENCE: 257
taatcattac gatggtttcg ccaagagcca ca 32

<210> SEQ ID NO 258
<211> LENGTH: 34
<212> TYPE: DNA
<213> ORGANISM: Artificial Sequence
<220> FEATURE:
<223> OTHER INFORMATION: Synthetic sequence

<400> SEQUENCE: 258
cctcttccag ccataagtct attttgccga cttc 34

<210> SEQ ID NO 259
<211> LENGTH: 24
<212> TYPE: DNA
<213> ORGANISM: Artificial Sequence
<220> FEATURE:
<223> OTHER INFORMATION: Synthetic sequence

<400> SEQUENCE: 259
attacaagac ccgaatgctt aatc 24

<210> SEQ ID NO 260
<211> LENGTH: 34
<212> TYPE: DNA
<213> ORGANISM: Artificial Sequence
<220> FEATURE:
<223> OTHER INFORMATION: Synthetic sequence

<400> SEQUENCE: 260
ctccacattc agttacgagc aagccccacc aagc 34

<210> SEQ ID NO 261
<211> LENGTH: 34
<212> TYPE: DNA
<213> ORGANISM: Artificial Sequence
<220> FEATURE:
<223> OTHER INFORMATION: Synthetic sequence

<400> SEQUENCE: 261
ggtttcgcaa agcaatgtcg ctatggatag gaag 34

<210> SEQ ID NO 262
<211> LENGTH: 34
<212> TYPE: DNA
<213> ORGANISM: Artificial Sequence
<220> FEATURE:
<223> OTHER INFORMATION: Synthetic sequence

<400> SEQUENCE: 262
atgtgccgcc ccagccagag gcgttcagcc ataa 34

<210> SEQ ID NO 263
<211> LENGTH: 32
<212> TYPE: DNA
<213> ORGANISM: Artificial Sequence
<220> FEATURE:
<223> OTHER INFORMATION: Synthetic sequence

<400> SEQUENCE: 263
aaacttccat cggctttgtc tggacctggt ga 32

<210> SEQ ID NO 264
<211> LENGTH: 34
<212> TYPE: DNA
<213> ORGANISM: Artificial Sequence
<220> FEATURE:
<223> OTHER INFORMATION: Synthetic sequence

<400> SEQUENCE: 264
cgtatccatc tatattgaga cattgatttt ttat 34

<210> SEQ ID NO 265
<211> LENGTH: 32
<212> TYPE: DNA
<213> ORGANISM: Artificial Sequence
<220> FEATURE:
<223> OTHER INFORMATION: Synthetic sequence

<400> SEQUENCE: 265
taagctgtta agaagaccac caagatctgc ac 32

<210> SEQ ID NO 266
<211> LENGTH: 34
<212> TYPE: DNA
<213> ORGANISM: Artificial Sequence
<220> FEATURE:
<223> OTHER INFORMATION: Synthetic sequence

<400> SEQUENCE: 266
agttctaagt tgatcgtgac aatgtcttca accc 34

<210> SEQ ID NO 267
<211> LENGTH: 34
<212> TYPE: DNA
<213> ORGANISM: Artificial Sequence
<220> FEATURE:
<223> OTHER INFORMATION: Synthetic sequence

<400> SEQUENCE: 267
accttaagag agtcatacaa tgtcaaacta gagt 34

<210> SEQ ID NO 268
<211> LENGTH: 32
<212> TYPE: DNA

<213> ORGANISM: Artificial Sequence
<220> FEATURE:
<223> OTHER INFORMATION: Synthetic sequence

<400> SEQUENCE: 268
gcccactaaa agctctataa aactgatacg ag 32

<210> SEQ ID NO 269
<211> LENGTH: 34
<212> TYPE: DNA
<213> ORGANISM: Artificial Sequence
<220> FEATURE:
<223> OTHER INFORMATION: Synthetic sequence

<400> SEQUENCE: 269
atcagtacag ggacagtggg aatctcttgg ctgt 34

<210> SEQ ID NO 270
<211> LENGTH: 34
<212> TYPE: DNA
<213> ORGANISM: Artificial Sequence
<220> FEATURE:
<223> OTHER INFORMATION: Synthetic sequence

<400> SEQUENCE: 270
ttcgttcttg attaatgttt aagtttcagc cttg 34

<210> SEQ ID NO 271
<211> LENGTH: 34
<212> TYPE: DNA
<213> ORGANISM: Artificial Sequence
<220> FEATURE:
<223> OTHER INFORMATION: Synthetic sequence

<400> SEQUENCE: 271
cctgaattag gattgggtaa ctgcaacaac ttta 34

<210> SEQ ID NO 272
<211> LENGTH: 34
<212> TYPE: DNA
<213> ORGANISM: Artificial Sequence
<220> FEATURE:
<223> OTHER INFORMATION: Synthetic sequence

<400> SEQUENCE: 272
gcttgagcaa actattcctt cctgtgctgc ggtt 34

<210> SEQ ID NO 273
<211> LENGTH: 34
<212> TYPE: DNA
<213> ORGANISM: Artificial Sequence
<220> FEATURE:
<223> OTHER INFORMATION: Synthetic sequence

<400> SEQUENCE: 273
aaagataact cctcccacgc tgcgtctgac caag 34

<210> SEQ ID NO 274
<211> LENGTH: 32
<212> TYPE: DNA
<213> ORGANISM: Artificial Sequence
<220> FEATURE:
<223> OTHER INFORMATION: Synthetic sequence

<400> SEQUENCE: 274
cgttaatcca ttcatgttca ccttggagac ct 32

<210> SEQ ID NO 275
<211> LENGTH: 32
<212> TYPE: DNA
<213> ORGANISM: Artificial Sequence
<220> FEATURE:
<223> OTHER INFORMATION: Synthetic sequence

<400> SEQUENCE: 275
cgagggacta aaggatcctc tatgtctctt ca 32

<210> SEQ ID NO 276
<211> LENGTH: 32
<212> TYPE: DNA
<213> ORGANISM: Artificial Sequence
<220> FEATURE:
<223> OTHER INFORMATION: Synthetic sequence

<400> SEQUENCE: 276
atcccgcatc gccagtgaaa cttcggcagg aa 32

<210> SEQ ID NO 277
<211> LENGTH: 32
<212> TYPE: DNA
<213> ORGANISM: Artificial Sequence
<220> FEATURE:
<223> OTHER INFORMATION: Synthetic sequence

<400> SEQUENCE: 277
ttaccgtgaa gaatccctgc tgttgacgtg ga 32

<210> SEQ ID NO 278
<211> LENGTH: 34
<212> TYPE: DNA
<213> ORGANISM: Artificial Sequence
<220> FEATURE:
<223> OTHER INFORMATION: Synthetic sequence

<400> SEQUENCE: 278
atgctttcgc agtagttctc cactcctggt ggtg 34

<210> SEQ ID NO 279
<211> LENGTH: 34
<212> TYPE: DNA
<213> ORGANISM: Artificial Sequence
<220> FEATURE:
<223> OTHER INFORMATION: Synthetic sequence

<400> SEQUENCE: 279
ttgttctact ggagattacc aattatccga atga 34

<210> SEQ ID NO 280
<211> LENGTH: 32
<212> TYPE: DNA
<213> ORGANISM: Artificial Sequence
<220> FEATURE:
<223> OTHER INFORMATION: Synthetic sequence

<400> SEQUENCE: 280
tgggttttac acccaacatc tttccatcac tg 32

<210> SEQ ID NO 281
<211> LENGTH: 34
<212> TYPE: DNA
<213> ORGANISM: Artificial Sequence
<220> FEATURE:

<223> OTHER INFORMATION: Synthetic sequence

<400> SEQUENCE: 281
cctagaaacc aacaaaacca ccacccacaa aatc 34

<210> SEQ ID NO 282
<211> LENGTH: 34
<212> TYPE: DNA
<213> ORGANISM: Artificial Sequence
<220> FEATURE:
<223> OTHER INFORMATION: Synthetic sequence

<400> SEQUENCE: 282
ccatcgaaag ttgatagcaa agtaaaagtc ctgg 34

<210> SEQ ID NO 283
<211> LENGTH: 34
<212> TYPE: DNA
<213> ORGANISM: Artificial Sequence
<220> FEATURE:
<223> OTHER INFORMATION: Synthetic sequence

<400> SEQUENCE: 283
aagccagtta tccctgtcaa tccaacgctt accg 34

<210> SEQ ID NO 284
<211> LENGTH: 34
<212> TYPE: DNA
<213> ORGANISM: Artificial Sequence
<220> FEATURE:
<223> OTHER INFORMATION: Synthetic sequence

<400> SEQUENCE: 284
ctccctctcc ggaatcgttg gaaatccagt acac 34

<210> SEQ ID NO 285
<211> LENGTH: 32
<212> TYPE: DNA
<213> ORGANISM: Artificial Sequence
<220> FEATURE:
<223> OTHER INFORMATION: Synthetic sequence

<400> SEQUENCE: 285
aaatcacatt gcgtcaagtc cacaagcacg cc 32

<210> SEQ ID NO 286
<211> LENGTH: 34
<212> TYPE: DNA
<213> ORGANISM: Artificial Sequence
<220> FEATURE:
<223> OTHER INFORMATION: Synthetic sequence

<400> SEQUENCE: 286
aaccaattcc ggggtgacct tagagccaat cctt 34

<210> SEQ ID NO 287
<211> LENGTH: 32
<212> TYPE: DNA
<213> ORGANISM: Artificial Sequence
<220> FEATURE:
<223> OTHER INFORMATION: Synthetic sequence

<400> SEQUENCE: 287
cgtctaaggg catcaccaaa ttaagccgca gg 32

<210> SEQ ID NO 288
<211> LENGTH: 32
<212> TYPE: DNA
<213> ORGANISM: Artificial Sequence
<220> FEATURE:
<223> OTHER INFORMATION: Synthetic sequence

<400> SEQUENCE: 288
taccccgttg tacatcccta ttagtgggtg aa 32

<210> SEQ ID NO 289
<211> LENGTH: 32
<212> TYPE: DNA
<213> ORGANISM: Artificial Sequence
<220> FEATURE:
<223> OTHER INFORMATION: Synthetic sequence

<400> SEQUENCE: 289
catcaggatc ggtcgaacca cccacttaga gc 32

<210> SEQ ID NO 290
<211> LENGTH: 32
<212> TYPE: DNA
<213> ORGANISM: Artificial Sequence
<220> FEATURE:
<223> OTHER INFORMATION: Synthetic sequence

<400> SEQUENCE: 290
tgaactaaca ccttttcgat cgatttgcac gt 32

<210> SEQ ID NO 291
<211> LENGTH: 34
<212> TYPE: DNA
<213> ORGANISM: Artificial Sequence
<220> FEATURE:
<223> OTHER INFORMATION: Synthetic sequence

<400> SEQUENCE: 291
cgacggtatc tgatcataga acccaaagac tttg 34

<210> SEQ ID NO 292
<211> LENGTH: 34
<212> TYPE: DNA
<213> ORGANISM: Artificial Sequence
<220> FEATURE:
<223> OTHER INFORMATION: Synthetic sequence

<400> SEQUENCE: 292
atatccaggt tccggaatac aacaaggcac gcaa 34

<210> SEQ ID NO 293
<211> LENGTH: 34
<212> TYPE: DNA
<213> ORGANISM: Artificial Sequence
<220> FEATURE:
<223> OTHER INFORMATION: Synthetic sequence

<400> SEQUENCE: 293
attctattat tccatgccaa atcactccac caac 34

<210> SEQ ID NO 294
<211> LENGTH: 32
<212> TYPE: DNA
<213> ORGANISM: Artificial Sequence
<220> FEATURE:
<223> OTHER INFORMATION: Synthetic sequence

<400> SEQUENCE: 294
tccccttgtc cgtaccacct accaaggccg tc 32

<210> SEQ ID NO 295
<211> LENGTH: 32
<212> TYPE: DNA
<213> ORGANISM: Artificial Sequence
<220> FEATURE:
<223> OTHER INFORMATION: Synthetic sequence

<400> SEQUENCE: 295
ggccccaacc tacgtttctc tcgccaatat tt 32

<210> SEQ ID NO 296
<211> LENGTH: 32
<212> TYPE: DNA
<213> ORGANISM: Artificial Sequence
<220> FEATURE:
<223> OTHER INFORMATION: Synthetic sequence

<400> SEQUENCE: 296
ccagcaagca cccaaggcgg taacattcat ca 32

<210> SEQ ID NO 297
<211> LENGTH: 32
<212> TYPE: DNA
<213> ORGANISM: Artificial Sequence
<220> FEATURE:
<223> OTHER INFORMATION: Synthetic sequence

<400> SEQUENCE: 297
tctatcccca gcacgaattt ctcgtaaggt gc 32

<210> SEQ ID NO 298
<211> LENGTH: 34
<212> TYPE: DNA
<213> ORGANISM: Artificial Sequence
<220> FEATURE:
<223> OTHER INFORMATION: Synthetic sequence

<400> SEQUENCE: 298
gtggtgtctg atgagcgtag aggccgttcg accc 34

<210> SEQ ID NO 299
<211> LENGTH: 34
<212> TYPE: DNA
<213> ORGANISM: Artificial Sequence
<220> FEATURE:
<223> OTHER INFORMATION: Synthetic sequence

<400> SEQUENCE: 299
cctctagcct caaattcaaa cccagctcac gttc 34

<210> SEQ ID NO 300
<211> LENGTH: 34
<212> TYPE: DNA
<213> ORGANISM: Artificial Sequence
<220> FEATURE:
<223> OTHER INFORMATION: Synthetic sequence

<400> SEQUENCE: 300
cgataggcca cactttcgta gggtaaaact aacc 34

<210> SEQ ID NO 301
<211> LENGTH: 34

<212> TYPE: DNA
<213> ORGANISM: Artificial Sequence
<220> FEATURE:
<223> OTHER INFORMATION: Synthetic sequence

<400> SEQUENCE: 301
agccgacaag gcttaatctc agcagaagca tatg 34

<210> SEQ ID NO 302
<211> LENGTH: 32
<212> TYPE: DNA
<213> ORGANISM: Artificial Sequence
<220> FEATURE:
<223> OTHER INFORMATION: Synthetic sequence

<400> SEQUENCE: 302
accccatctc cggatagacc ttacggtcta gg 32

<210> SEQ ID NO 303
<211> LENGTH: 34
<212> TYPE: DNA
<213> ORGANISM: Artificial Sequence
<220> FEATURE:
<223> OTHER INFORMATION: Synthetic sequence

<400> SEQUENCE: 303
cccaacagca gggctagttc attcgaggta acac 34

<210> SEQ ID NO 304
<211> LENGTH: 24
<212> TYPE: DNA
<213> ORGANISM: Artificial Sequence
<220> FEATURE:
<223> OTHER INFORMATION: Synthetic sequence

<400> SEQUENCE: 304
ggcagaaatt tgaatgtcat caaa 24

<210> SEQ ID NO 305
<211> LENGTH: 40
<212> TYPE: DNA
<213> ORGANISM: Artificial Sequence
<220> FEATURE:
<223> OTHER INFORMATION: Synthetic sequence

<400> SEQUENCE: 305
gatttaatat ttatccccac gcaatgtctc acgacggtct 40

<210> SEQ ID NO 306
<211> LENGTH: 40
<212> TYPE: DNA
<213> ORGANISM: Artificial Sequence
<220> FEATURE:
<223> OTHER INFORMATION: Synthetic sequence

<400> SEQUENCE: 306
gagtccgatg tggagcaaag aaattccagc ggatggtagc 40

<210> SEQ ID NO 307
<211> LENGTH: 40
<212> TYPE: DNA
<213> ORGANISM: Artificial Sequence
<220> FEATURE:
<223> OTHER INFORMATION: Synthetic sequence

<400> SEQUENCE: 307
tgtattagac cgttgctagc ctgcactgtt cctctcgtac 40

<210> SEQ ID NO 308
<211> LENGTH: 40
<212> TYPE: DNA
<213> ORGANISM: Artificial Sequence
<220> FEATURE:
<223> OTHER INFORMATION: Synthetic sequence

<400> SEQUENCE: 308
tttgagacat cgtaacaaca aggcaattct gcttcggtat 40

<210> SEQ ID NO 309
<211> LENGTH: 32
<212> TYPE: DNA
<213> ORGANISM: Artificial Sequence
<220> FEATURE:
<223> OTHER INFORMATION: Synthetic sequence

<400> SEQUENCE: 309
tcgcaatgct atgtttgtag tccgcctagc ag 32

<210> SEQ ID NO 310
<211> LENGTH: 32
<212> TYPE: DNA
<213> ORGANISM: Artificial Sequence
<220> FEATURE:
<223> OTHER INFORMATION: Synthetic sequence

<400> SEQUENCE: 310
tgtattccgg caccttcgat tagtctttcg cc 32

<210> SEQ ID NO 311
<211> LENGTH: 32
<212> TYPE: DNA
<213> ORGANISM: Artificial Sequence
<220> FEATURE:
<223> OTHER INFORMATION: Synthetic sequence

<400> SEQUENCE: 311
ccgacttcca tggccatcca ccagagtttc ct 32

<210> SEQ ID NO 312
<211> LENGTH: 32
<212> TYPE: DNA
<213> ORGANISM: Artificial Sequence
<220> FEATURE:
<223> OTHER INFORMATION: Synthetic sequence

<400> SEQUENCE: 312
gtagccgttt ctcaggttat accatgtagt aa 32

<210> SEQ ID NO 313
<211> LENGTH: 32
<212> TYPE: DNA
<213> ORGANISM: Artificial Sequence
<220> FEATURE:
<223> OTHER INFORMATION: Synthetic sequence

<400> SEQUENCE: 313
ttattgtcac tacctcactg tataaattgc tt 32

<210> SEQ ID NO 314
<211> LENGTH: 24
<212> TYPE: DNA
<213> ORGANISM: Artificial Sequence
<220> FEATURE:
<223> OTHER INFORMATION: Synthetic sequence

<400> SEQUENCE: 314 tttttattc gaggccattt tttt 24

<210> SEQ ID NO 315
<211> LENGTH: 24
<212> TYPE: DNA
<213> ORGANISM: Artificial Sequence
<220> FEATURE:
<223> OTHER INFORMATION: Synthetic sequence

<400> SEQUENCE: 315 tttttagca gataatattt tttt 24

<210> SEQ ID NO 316
<211> LENGTH: 24
<212> TYPE: DNA
<213> ORGANISM: Artificial Sequence
<220> FEATURE:
<223> OTHER INFORMATION: Synthetic sequence

<400> SEQUENCE: 316
ttttttcatt ttctatgctt tttt 24

<210> SEQ ID NO 317
<211> LENGTH: 24
<212> TYPE: DNA
<213> ORGANISM: Artificial Sequence
<220> FEATURE:
<223> OTHER INFORMATION: Synthetic sequence

<400> SEQUENCE: 317
ttttttccac cttaattgtt tttt 24

<210> SEQ ID NO 318
<211> LENGTH: 29
<212> TYPE: DNA
<213> ORGANISM: Artificial Sequence
<220> FEATURE:
<223> OTHER INFORMATION: Synthetic sequence

<400> SEQUENCE: 318
ggtctcgttc gttatcgcaa ttatttttt 29

<210> SEQ ID NO 319
<211> LENGTH: 24
<212> TYPE: DNA
<213> ORGANISM: Artificial Sequence
<220> FEATURE:
<223> OTHER INFORMATION: Synthetic sequence

<400> SEQUENCE: 319
tttttttagc aaataaaatt tttt 24

<210> SEQ ID NO 320
<211> LENGTH: 24
<212> TYPE: DNA
<213> ORGANISM: Artificial Sequence
<220> FEATURE:
<223> OTHER INFORMATION: Synthetic sequence

<400> SEQUENCE: 320
ttttttgtag atgacctgtt tttt 24

<210> SEQ ID NO 321
<211> LENGTH: 24
<212> TYPE: DNA
<213> ORGANISM: Artificial Sequence
<220> FEATURE:
<223> OTHER INFORMATION: Synthetic sequence

<400> SEQUENCE: 321 ttttttgag aatcctattt tttt 24

<210> SEQ ID NO 322
<211> LENGTH: 24
<212> TYPE: DNA
<213> ORGANISM: Artificial Sequence
<220> FEATURE:
<223> OTHER INFORMATION: Synthetic sequence

<400> SEQUENCE: 322
ttttttaatc aatagatatt tttt 24

<210> SEQ ID NO 323
<211> LENGTH: 24
<212> TYPE: DNA
<213> ORGANISM: Artificial Sequence
<220> FEATURE:
<223> OTHER INFORMATION: Synthetic sequence

<400> SEQUENCE: 323
ttttttgact taaactcctt tttt 24

<210> SEQ ID NO 324
<211> LENGTH: 24
<212> TYPE: DNA
<213> ORGANISM: Artificial Sequence
<220> FEATURE:
<223> OTHER INFORMATION: Synthetic sequence

<400> SEQUENCE: 324
ttttttgcga ttgattcttt tttt 24

<210> SEQ ID NO 325
<211> LENGTH: 24
<212> TYPE: DNA
<213> ORGANISM: Artificial Sequence
<220> FEATURE:
<223> OTHER INFORMATION: Synthetic sequence

<400> SEQUENCE: 325
ttttttgcat gagccatctt tttt 24

<210> SEQ ID NO 326
<211> LENGTH: 54
<212> TYPE: DNA
<213> ORGANISM: Artificial Sequence
<220> FEATURE:
<223> OTHER INFORMATION: Synthetic sequence

<400> SEQUENCE: 326
cattaaaaag caataattac aatgcttgcg cttactagga attcctcgtt tttt 54

<210> SEQ ID NO 327
<211> LENGTH: 24
<212> TYPE: DNA
<213> ORGANISM: Artificial Sequence
<220> FEATURE:
<223> OTHER INFORMATION: Synthetic sequence

<400> SEQUENCE: 327
tttttttctt accgactctt tttt 24

<210> SEQ ID NO 328
<211> LENGTH: 24
<212> TYPE: DNA
<213> ORGANISM: Artificial Sequence
<220> FEATURE:
<223> OTHER INFORMATION: Synthetic sequence

<400> SEQUENCE: 328
ttttttttga agaaacactt tttt 24

<210> SEQ ID NO 329
<211> LENGTH: 24
<212> TYPE: DNA
<213> ORGANISM: Artificial Sequence
<220> FEATURE:
<223> OTHER INFORMATION: Synthetic sequence

<400> SEQUENCE: 329
tttttttcag gcaaagtttt tttt 24

<210> SEQ ID NO 330
<211> LENGTH: 24
<212> TYPE: DNA
<213> ORGANISM: Artificial Sequence
<220> FEATURE:
<223> OTHER INFORMATION: Synthetic sequence

<400> SEQUENCE: 330
ttttttcacc cggttaagtt tttt 24

<210> SEQ ID NO 331
<211> LENGTH: 38
<212> TYPE: DNA
<213> ORGANISM: Artificial Sequence
<220> FEATURE:
<223> OTHER INFORMATION: Synthetic sequence

<400> SEQUENCE: 331
ttttttttcg aaggcacttt acaaagaact gcattccc 38

<210> SEQ ID NO 332
<211> LENGTH: 24
<212> TYPE: DNA
<213> ORGANISM: Artificial Sequence
<220> FEATURE:
<223> OTHER INFORMATION: Synthetic sequence

<400> SEQUENCE: 332
ttttttggat ttttgaggtc aaac 24

<210> SEQ ID NO 333
<211> LENGTH: 44
<212> TYPE: DNA
<213> ORGANISM: Artificial Sequence
<220> FEATURE:
<223> OTHER INFORMATION: Synthetic sequence

<400> SEQUENCE: 333
gtatttcagg atcaaccaga taacaaatca gacaacaatc gaag 44

<210> SEQ ID NO 334

<211> LENGTH: 16
<212> TYPE: DNA
<213> ORGANISM: Artificial Sequence
<220> FEATURE:
<223> OTHER INFORMATION: Synthetic sequence

<400> SEQUENCE: 334
tatgcttaag ttcagc 16

<210> SEQ ID NO 335
<211> LENGTH: 16
<212> TYPE: DNA
<213> ORGANISM: Artificial Sequence
<220> FEATURE:
<223> OTHER INFORMATION: Synthetic sequence

<400> SEQUENCE: 335
cgggcggtgt gtacaa 16

<210> SEQ ID NO 336
<211> LENGTH: 16
<212> TYPE: DNA
<213> ORGANISM: Artificial Sequence
<220> FEATURE:
<223> OTHER INFORMATION: Synthetic sequence

<400> SEQUENCE: 336
atcccggttg gtttct 16

<210> SEQ ID NO 337
<211> LENGTH: 16
<212> TYPE: DNA
<213> ORGANISM: Artificial Sequence
<220> FEATURE:
<223> OTHER INFORMATION: Synthetic sequence

<400> SEQUENCE: 337
cggaaacctt gttacg 16

<210> SEQ ID NO 338
<211> LENGTH: 16
<212> TYPE: DNA
<213> ORGANISM: Artificial Sequence
<220> FEATURE:
<223> OTHER INFORMATION: Synthetic sequence

<400> SEQUENCE: 338
tcgggcaccg aaggta 16

<210> SEQ ID NO 339
<211> LENGTH: 16
<212> TYPE: DNA
<213> ORGANISM: Artificial Sequence
<220> FEATURE:
<223> OTHER INFORMATION: Synthetic sequence

<400> SEQUENCE: 339
aacgcaagct gatgac 16

<210> SEQ ID NO 340
<211> LENGTH: 16
<212> TYPE: DNA
<213> ORGANISM: Artificial Sequence
<220> FEATURE:
<223> OTHER INFORMATION: Synthetic sequence

<400> SEQUENCE: 340
atgacgtcct gttcca 16

<210> SEQ ID NO 341
<211> LENGTH: 16
<212> TYPE: DNA
<213> ORGANISM: Artificial Sequence
<220> FEATURE:
<223> OTHER INFORMATION: Synthetic sequence

<400> SEQUENCE: 341
gcttttgccg cttcac 16

<210> SEQ ID NO 342
<211> LENGTH: 16
<212> TYPE: DNA
<213> ORGANISM: Artificial Sequence
<220> FEATURE:
<223> OTHER INFORMATION: Synthetic sequence

<400> SEQUENCE: 342
acggccccaa agttgc 16

<210> SEQ ID NO 343
<211> LENGTH: 16
<212> TYPE: DNA
<213> ORGANISM: Artificial Sequence
<220> FEATURE:
<223> OTHER INFORMATION: Synthetic sequence

<400> SEQUENCE: 343
ggcctcacta agccat 16

<210> SEQ ID NO 344
<211> LENGTH: 16
<212> TYPE: DNA
<213> ORGANISM: Artificial Sequence
<220> FEATURE:
<223> OTHER INFORMATION: Synthetic sequence

<400> SEQUENCE: 344
atgaccaagt ttgtcc 16

<210> SEQ ID NO 345
<211> LENGTH: 16
<212> TYPE: DNA
<213> ORGANISM: Artificial Sequence
<220> FEATURE:
<223> OTHER INFORMATION: Synthetic sequence

<400> SEQUENCE: 345
atggagttgc cccctt 16

<210> SEQ ID NO 346
<211> LENGTH: 41
<212> TYPE: DNA
<213> ORGANISM: Artificial Sequence
<220> FEATURE:
<223> OTHER INFORMATION: Synthetic sequence

<400> SEQUENCE: 346
taatgatccc tatttagtag gttaataaga acggccatgc a 41

<210> SEQ ID NO 347
<211> LENGTH: 16
<212> TYPE: DNA

<213> ORGANISM: Artificial Sequence
<220> FEATURE:
<223> OTHER INFORMATION: Synthetic sequence

<400> SEQUENCE: 347
cgcactcctc gccaca 16

<210> SEQ ID NO 348
<211> LENGTH: 34
<212> TYPE: DNA
<213> ORGANISM: Artificial Sequence
<220> FEATURE:
<223> OTHER INFORMATION: Synthetic sequence

<400> SEQUENCE: 348
cggagtttca caagattagg gcagggacgt aatc 34

<210> SEQ ID NO 349
<211> LENGTH: 34
<212> TYPE: DNA
<213> ORGANISM: Artificial Sequence
<220> FEATURE:
<223> OTHER INFORMATION: Synthetic sequence

<400> SEQUENCE: 349
agcaaatgct agcaccattc cgcaggttca ccta 34

<210> SEQ ID NO 350
<211> LENGTH: 34
<212> TYPE: DNA
<213> ORGANISM: Artificial Sequence
<220> FEATURE:
<223> OTHER INFORMATION: Synthetic sequence

<400> SEQUENCE: 350
agacctgtta ttgcctcaaa ttctccgctc tgag 34

<210> SEQ ID NO 351
<211> LENGTH: 34
<212> TYPE: DNA
<213> ORGANISM: Artificial Sequence
<220> FEATURE:
<223> OTHER INFORMATION: Synthetic sequence

<400> SEQUENCE: 351
cgggattctc accctctagc tttagatgga attt 34

<210> SEQ ID NO 352
<211> LENGTH: 34
<212> TYPE: DNA
<213> ORGANISM: Artificial Sequence
<220> FEATURE:
<223> OTHER INFORMATION: Synthetic sequence

<400> SEQUENCE: 352
cctctccaaa ttacaacctt ttcaaagttc tttt 34

<210> SEQ ID NO 353
<211> LENGTH: 34
<212> TYPE: DNA
<213> ORGANISM: Artificial Sequence
<220> FEATURE:
<223> OTHER INFORMATION: Synthetic sequence

<400> SEQUENCE: 353
caaggttaga ctcgctgtca atcggtacta gcga 34

<210> SEQ ID NO 354
<211> LENGTH: 34
<212> TYPE: DNA
<213> ORGANISM: Artificial Sequence
<220> FEATURE:
<223> OTHER INFORMATION: Synthetic sequence

<400> SEQUENCE: 354
tttcctccgc ttattgaaat gcgagattcc ccta 34

<210> SEQ ID NO 355
<211> LENGTH: 34
<212> TYPE: DNA
<213> ORGANISM: Artificial Sequence
<220> FEATURE:
<223> OTHER INFORMATION: Synthetic sequence

<400> SEQUENCE: 355
ccagatttca aatttgaccc tttcaacaat ttca 34

<210> SEQ ID NO 356
<211> LENGTH: 34
<212> TYPE: DNA
<213> ORGANISM: Artificial Sequence
<220> FEATURE:
<223> OTHER INFORMATION: Synthetic sequence

<400> SEQUENCE: 356
aggaacatag acaaggatac ttgttcgcta tcgg 34

<210> SEQ ID NO 357
<211> LENGTH: 34
<212> TYPE: DNA
<213> ORGANISM: Artificial Sequence
<220> FEATURE:
<223> OTHER INFORMATION: Synthetic sequence

<400> SEQUENCE: 357
tcgccgttac taaggcaggc acaaaacacc atgt 34

<210> SEQ ID NO 358
<211> LENGTH: 34
<212> TYPE: DNA
<213> ORGANISM: Artificial Sequence
<220> FEATURE:
<223> OTHER INFORMATION: Synthetic sequence

<400> SEQUENCE: 358
gaaaccgata gtccctcact tttagttcct ctaa 34

<210> SEQ ID NO 359
<211> LENGTH: 34
<212> TYPE: DNA
<213> ORGANISM: Artificial Sequence
<220> FEATURE:
<223> OTHER INFORMATION: Synthetic sequence

<400> SEQUENCE: 359
gcgcgtgcgg cccagaactc taagcagatc ctga 34

<210> SEQ ID NO 360
<211> LENGTH: 44
<212> TYPE: DNA
<213> ORGANISM: Artificial Sequence
<220> FEATURE:

<223> OTHER INFORMATION: Synthetic sequence

<400> SEQUENCE: 360
caaaatgaca ttgcaattcg cctcaaacac aaatcagaca acaa 44

<210> SEQ ID NO 361
<211> LENGTH: 39
<212> TYPE: DNA
<213> ORGANISM: Artificial Sequence
<220> FEATURE:
<223> OTHER INFORMATION: Synthetic sequence

<400> SEQUENCE: 361
cttagaggcg tttttttca gccataatcc agcggatgg 39

<210> SEQ ID NO 362
<211> LENGTH: 51
<212> TYPE: DNA
<213> ORGANISM: Artificial Sequence
<220> FEATURE:
<223> OTHER INFORMATION: Synthetic sequence

<400> SEQUENCE: 362
atcagtaggg tttttttaaa actaacctcc tattagtggt tttttgtgaa c 51

<210> SEQ ID NO 363
<211> LENGTH: 55
<212> TYPE: DNA
<213> ORGANISM: Artificial Sequence
<220> FEATURE:
<223> OTHER INFORMATION: Synthetic sequence

<400> SEQUENCE: 363
aatccgaaga gccgactttt ttatcgaaga atcaaaaagc aatgtccctg tggta 55

<210> SEQ ID NO 364
<211> LENGTH: 39
<212> TYPE: DNA
<213> ORGANISM: Artificial Sequence
<220> FEATURE:
<223> OTHER INFORMATION: Synthetic sequence

<400> SEQUENCE: 364
acttttctgg ctttttttacc tctagcctca aattccgag 39

<210> SEQ ID NO 365
<211> LENGTH: 50
<212> TYPE: DNA
<213> ORGANISM: Artificial Sequence
<220> FEATURE:
<223> OTHER INFORMATION: Synthetic sequence

<400> SEQUENCE: 365
ttctccatga gtttttttccc cccttaggac atctgcgttc ccacctgaca 50

<210> SEQ ID NO 366
<211> LENGTH: 39
<212> TYPE: DNA
<213> ORGANISM: Artificial Sequence
<220> FEATURE:
<223> OTHER INFORMATION: Synthetic sequence

<400> SEQUENCE: 366
atgtcttcaa cttttttccg gatcagcccc gaatgggac 39

<210> SEQ ID NO 367
<211> LENGTH: 51
<212> TYPE: DNA
<213> ORGANISM: Artificial Sequence
<220> FEATURE:
<223> OTHER INFORMATION: Synthetic sequence

<400> SEQUENCE: 367
acttattcta ctttttttacc ctctatgtac agggtcttct tttttttcc c 51

<210> SEQ ID NO 368
<211> LENGTH: 55
<212> TYPE: DNA
<213> ORGANISM: Artificial Sequence
<220> FEATURE:
<223> OTHER INFORMATION: Synthetic sequence

<400> SEQUENCE: 368
cgctgtcgct agatagtttt tttagatagg gacagtggga atctacgagg cattt 55

<210> SEQ ID NO 369
<211> LENGTH: 39
<212> TYPE: DNA
<213> ORGANISM: Artificial Sequence
<220> FEATURE:
<223> OTHER INFORMATION: Synthetic sequence

<400> SEQUENCE: 369
ggctacctta attttttgag agtcatagtt actcccgcc 39

<210> SEQ ID NO 370
<211> LENGTH: 50
<212> TYPE: DNA
<213> ORGANISM: Artificial Sequence
<220> FEATURE:
<223> OTHER INFORMATION: Synthetic sequence

<400> SEQUENCE: 370
gacattcaga gttttttcac tgggcagaaa tcacattgct tttaattaga 50

<210> SEQ ID NO 371
<211> LENGTH: 39
<212> TYPE: DNA
<213> ORGANISM: Artificial Sequence
<220> FEATURE:
<223> OTHER INFORMATION: Synthetic sequence

<400> SEQUENCE: 371
cagtcagatt cttttttccc ttgtccgtac cagttctaa 39

<210> SEQ ID NO 372
<211> LENGTH: 51
<212> TYPE: DNA
<213> ORGANISM: Artificial Sequence
<220> FEATURE:
<223> OTHER INFORMATION: Synthetic sequence

<400> SEQUENCE: 372
aagagaccta cttttttcaa ggccgtctag caagccccat tttttccaag c 51

<210> SEQ ID NO 373
<211> LENGTH: 55
<212> TYPE: DNA
<213> ORGANISM: Artificial Sequence
<220> FEATURE:
<223> OTHER INFORMATION: Synthetic sequence

<400> SEQUENCE: 373
agtcctcact acccgatttt ttcccttaga gccaatcctt atcctctaca ttatt 55

<210> SEQ ID NO 374
<211> LENGTH: 39
<212> TYPE: DNA
<213> ORGANISM: Artificial Sequence
<220> FEATURE:
<223> OTHER INFORMATION: Synthetic sequence

<400> SEQUENCE: 374
ctatcaacta gtttttttagg ctgttcacct tggagacct 39

<210> SEQ ID NO 375
<211> LENGTH: 50
<212> TYPE: DNA
<213> ORGANISM: Artificial Sequence
<220> FEATURE:
<223> OTHER INFORMATION: Synthetic sequence

<400> SEQUENCE: 375
ttccagccat attttttaga ccccatctcc ggataaacct aactcctccc 50

<210> SEQ ID NO 376
<211> LENGTH: 39
<212> TYPE: DNA
<213> ORGANISM: Artificial Sequence
<220> FEATURE:
<223> OTHER INFORMATION: Synthetic sequence

<400> SEQUENCE: 376
agggctcgcg ctttttttcga cgtctccaca ttcagttac 39

<210> SEQ ID NO 377
<211> LENGTH: 51
<212> TYPE: DNA
<213> ORGANISM: Artificial Sequence
<220> FEATURE:
<223> OTHER INFORMATION: Synthetic sequence

<400> SEQUENCE: 377
atctcttagg attttttttcg actaaccccc acttcagtct tttttttcaa a 51

<210> SEQ ID NO 378
<211> LENGTH: 55
<212> TYPE: DNA
<213> ORGANISM: Artificial Sequence
<220> FEATURE:
<223> OTHER INFORMATION: Synthetic sequence

<400> SEQUENCE: 378
gttctgcact agaggctttt ttcgttcgac ccgaccttac ggtccgtcag ggcat 55

<210> SEQ ID NO 379
<211> LENGTH: 39
<212> TYPE: DNA
<213> ORGANISM: Artificial Sequence
<220> FEATURE:
<223> OTHER INFORMATION: Synthetic sequence

<400> SEQUENCE: 379
catatcaacc ctttttttga cggtagagta taggtaaca 39

<210> SEQ ID NO 380
<211> LENGTH: 50

<212> TYPE: DNA
<213> ORGANISM: Artificial Sequence
<220> FEATURE:
<223> OTHER INFORMATION: Synthetic sequence

<400> SEQUENCE: 380
ctagatgaac tttttttaac accttttgtg gtgtctgatg ttcatcccgc 50

<210> SEQ ID NO 381
<211> LENGTH: 39
<212> TYPE: DNA
<213> ORGANISM: Artificial Sequence
<220> FEATURE:
<223> OTHER INFORMATION: Synthetic sequence

<400> SEQUENCE: 381
atcgccagtt cttttttgc ttaccaaaaa tggcccact 39

<210> SEQ ID NO 382
<211> LENGTH: 51
<212> TYPE: DNA
<213> ORGANISM: Artificial Sequence
<220> FEATURE:
<223> OTHER INFORMATION: Synthetic sequence

<400> SEQUENCE: 382
ctctaatcat tttttttcgc tttacctcgg aaacttcggt tttttcagga a 51

<210> SEQ ID NO 383
<211> LENGTH: 55
<212> TYPE: DNA
<213> ORGANISM: Artificial Sequence
<220> FEATURE:
<223> OTHER INFORMATION: Synthetic sequence

<400> SEQUENCE: 383
ccagctaccc aaattctttt ttgacgatcg atttgcacgt cagattcacc ctatt 55

<210> SEQ ID NO 384
<211> LENGTH: 39
<212> TYPE: DNA
<213> ORGANISM: Artificial Sequence
<220> FEATURE:
<223> OTHER INFORMATION: Synthetic sequence

<400> SEQUENCE: 384
caggcatagt tttttttcac catctttcgg gtcccaaca 39

<210> SEQ ID NO 385
<211> LENGTH: 50
<212> TYPE: DNA
<213> ORGANISM: Artificial Sequence
<220> FEATURE:
<223> OTHER INFORMATION: Synthetic sequence

<400> SEQUENCE: 385
gttttacacc ctttttttaaa cactcgcata gacgttagaa accattatgc 50

<210> SEQ ID NO 386
<211> LENGTH: 56
<212> TYPE: DNA
<213> ORGANISM: Artificial Sequence
<220> FEATURE:
<223> OTHER INFORMATION: Synthetic sequence

<400> SEQUENCE: 386
cagcatcctt gttttttact tacgtcgcgg ctataatact ttttttacc gaggca 56

<210> SEQ ID NO 387
<211> LENGTH: 50
<212> TYPE: DNA
<213> ORGANISM: Artificial Sequence
<220> FEATURE:
<223> OTHER INFORMATION: Synthetic sequence

<400> SEQUENCE: 387
agctacattc ccccagtgaa atgcgagatt cccttttttc tacccacaag 50

<210> SEQ ID NO 388
<211> LENGTH: 51
<212> TYPE: DNA
<213> ORGANISM: Artificial Sequence
<220> FEATURE:
<223> OTHER INFORMATION: Synthetic sequence

<400> SEQUENCE: 388
ttgttcgcta tttttttcgg tctctcgcac ttagagctgt tttttcattc c 51

<210> SEQ ID NO 389
<211> LENGTH: 55
<212> TYPE: DNA
<213> ORGANISM: Artificial Sequence
<220> FEATURE:
<223> OTHER INFORMATION: Synthetic sequence

<400> SEQUENCE: 389
caaacccgca ctcctctttt ttgccacacg ggattctcac cctcacggcc ccaaa 55

<210> SEQ ID NO 390
<211> LENGTH: 39
<212> TYPE: DNA
<213> ORGANISM: Artificial Sequence
<220> FEATURE:
<223> OTHER INFORMATION: Synthetic sequence

<400> SEQUENCE: 390
gttgccctct cttttttcaa attacaactc gggcaccga 39

<210> SEQ ID NO 391
<211> LENGTH: 50
<212> TYPE: DNA
<213> ORGANISM: Artificial Sequence
<220> FEATURE:
<223> OTHER INFORMATION: Synthetic sequence

<400> SEQUENCE: 391
cgccacaagg attttttcgc cttattcgta tccatctata tggattctga 50

<210> SEQ ID NO 392
<211> LENGTH: 22
<212> TYPE: DNA
<213> ORGANISM: Artificial Sequence
<220> FEATURE:
<223> OTHER INFORMATION: Synthetic sequence

<400> SEQUENCE: 392
tagcttcgcg gcaatgcctg at 22

<210> SEQ ID NO 393
<211> LENGTH: 33
<212> TYPE: DNA
<213> ORGANISM: Artificial Sequence
<220> FEATURE:
<223> OTHER INFORMATION: Synthetic sequence

<400> SEQUENCE: 393
gtactaagtt caattactat tgcggtaaca ttc 33

<210> SEQ ID NO 394
<211> LENGTH: 22
<212> TYPE: DNA
<213> ORGANISM: Artificial Sequence
<220> FEATURE:
<223> OTHER INFORMATION: Synthetic sequence

<400> SEQUENCE: 394
ggactaaagg atcgataggc ca 22

<210> SEQ ID NO 395
<211> LENGTH: 33
<212> TYPE: DNA
<213> ORGANISM: Artificial Sequence
<220> FEATURE:
<223> OTHER INFORMATION: Synthetic sequence

<400> SEQUENCE: 395
gcttttaccc ttttgttcta ctggagattt ctg 33

<210> SEQ ID NO 396
<211> LENGTH: 22
<212> TYPE: DNA
<213> ORGANISM: Artificial Sequence
<220> FEATURE:
<223> OTHER INFORMATION: Synthetic sequence

<400> SEQUENCE: 396
cttgaatgct agaacgtgga aa 22

<210> SEQ ID NO 397
<211> LENGTH: 33
<212> TYPE: DNA
<213> ORGANISM: Artificial Sequence
<220> FEATURE:
<223> OTHER INFORMATION: Synthetic sequence

<400> SEQUENCE: 397
aggtagtggt atttcactgg cgccgaagct ccc 33

<210> SEQ ID NO 398
<211> LENGTH: 33
<212> TYPE: DNA
<213> ORGANISM: Artificial Sequence
<220> FEATURE:
<223> OTHER INFORMATION: Synthetic sequence

<400> SEQUENCE: 398
gtttacccgc gcttggttga atttcttcac ttt 33

<210> SEQ ID NO 399
<211> LENGTH: 33
<212> TYPE: DNA
<213> ORGANISM: Artificial Sequence
<220> FEATURE:
<223> OTHER INFORMATION: Synthetic sequence

<400> SEQUENCE: 399
gttgatcgtt aattgtagca agcgacggtc tac 33

<210> SEQ ID NO 400
<211> LENGTH: 22
<212> TYPE: DNA
<213> ORGANISM: Artificial Sequence
<220> FEATURE:
<223> OTHER INFORMATION: Synthetic sequence

<400> SEQUENCE: 400
gctgcggtta tcagtacgac ct 22

<210> SEQ ID NO 401
<211> LENGTH: 33
<212> TYPE: DNA
<213> ORGANISM: Artificial Sequence
<220> FEATURE:
<223> OTHER INFORMATION: Synthetic sequence

<400> SEQUENCE: 401
aagcgcaccg gagccagcaa aggtgctggc ctc 33

<210> SEQ ID NO 402
<211> LENGTH: 22
<212> TYPE: DNA
<213> ORGANISM: Artificial Sequence
<220> FEATURE:
<223> OTHER INFORMATION: Synthetic sequence

<400> SEQUENCE: 402
gttaccgtga agaatccata tc 22

<210> SEQ ID NO 403
<211> LENGTH: 33
<212> TYPE: DNA
<213> ORGANISM: Artificial Sequence
<220> FEATURE:
<223> OTHER INFORMATION: Synthetic sequence

<400> SEQUENCE: 403
cataaaatca ggcctttgaa acggagcttc ccc 33

<210> SEQ ID NO 404
<211> LENGTH: 22
<212> TYPE: DNA
<213> ORGANISM: Artificial Sequence
<220> FEATURE:
<223> OTHER INFORMATION: Synthetic sequence

<400> SEQUENCE: 404
cgcttgagcg ccatccattt tc 22

<210> SEQ ID NO 405
<211> LENGTH: 33
<212> TYPE: DNA
<213> ORGANISM: Artificial Sequence
<220> FEATURE:
<223> OTHER INFORMATION: Synthetic sequence

<400> SEQUENCE: 405
ggattccgac ttccatggcc accgtccggc tgt 33

<210> SEQ ID NO 406
<211> LENGTH: 22
<212> TYPE: DNA
<213> ORGANISM: Artificial Sequence
<220> FEATURE:
<223> OTHER INFORMATION: Synthetic sequence

<400> SEQUENCE: 406
aaaagctctt cattcaaatg tc 22

<210> SEQ ID NO 407
<211> LENGTH: 33
<212> TYPE: DNA
<213> ORGANISM: Artificial Sequence
<220> FEATURE:
<223> OTHER INFORMATION: Synthetic sequence

<400> SEQUENCE: 407
gagaataggt caaggtcatt tcgaccccgg aac 33

<210> SEQ ID NO 408
<211> LENGTH: 22
<212> TYPE: DNA
<213> ORGANISM: Artificial Sequence
<220> FEATURE:
<223> OTHER INFORMATION: Synthetic sequence

<400> SEQUENCE: 408
gctatgctct tactcaaatc ca 22

<210> SEQ ID NO 409
<211> LENGTH: 33
<212> TYPE: DNA
<213> ORGANISM: Artificial Sequence
<220> FEATURE:
<223> OTHER INFORMATION: Synthetic sequence

<400> SEQUENCE: 409
cccaacctac gttcactttc attacgcgta tgg 33

<210> SEQ ID NO 410
<211> LENGTH: 33
<212> TYPE: DNA
<213> ORGANISM: Artificial Sequence
<220> FEATURE:
<223> OTHER INFORMATION: Synthetic sequence

<400> SEQUENCE: 410
gagcagaggg cacaaaacac catgtctgat caa 33

<210> SEQ ID NO 411
<211> LENGTH: 33
<212> TYPE: DNA
<213> ORGANISM: Artificial Sequence
<220> FEATURE:
<223> OTHER INFORMATION: Synthetic sequence

<400> SEQUENCE: 411
ttcaaagttc ttttcatctt tccatcactg tac 33

<210> SEQ ID NO 412
<211> LENGTH: 22
<212> TYPE: DNA
<213> ORGANISM: Artificial Sequence
<220> FEATURE:
<223> OTHER INFORMATION: Synthetic sequence

<400> SEQUENCE: 412
aggtaccaga tttcaaattt ga 22

<210> SEQ ID NO 413

<211> LENGTH: 50
<212> TYPE: DNA
<213> ORGANISM: Artificial Sequence
<220> FEATURE:
<223> OTHER INFORMATION: Synthetic sequence

<400> SEQUENCE: 413
cagacagccg caaaaaccaa ttttttttat ccgaatgaac tgttcctctc 50

<210> SEQ ID NO 414
<211> LENGTH: 50
<212> TYPE: DNA
<213> ORGANISM: Artificial Sequence
<220> FEATURE:
<223> OTHER INFORMATION: Synthetic sequence

<400> SEQUENCE: 414
cactttcatg gtttgtattc actttttttac tgaaaatcaa aatcaagggg 50

<210> SEQ ID NO 415
<211> LENGTH: 50
<212> TYPE: DNA
<213> ORGANISM: Artificial Sequence
<220> FEATURE:
<223> OTHER INFORMATION: Synthetic sequence

<400> SEQUENCE: 415
atgaattcca gctccgcttc atttttttttg aataagtaaa gaaactataa 50

<210> SEQ ID NO 416
<211> LENGTH: 50
<212> TYPE: DNA
<213> ORGANISM: Artificial Sequence
<220> FEATURE:
<223> OTHER INFORMATION: Synthetic sequence

<400> SEQUENCE: 416
ggcatgaaaa ctattccttc cttttttttgt ggattttcac gggccgtcac 50

<210> SEQ ID NO 417
<211> LENGTH: 50
<212> TYPE: DNA
<213> ORGANISM: Artificial Sequence
<220> FEATURE:
<223> OTHER INFORMATION: Synthetic sequence

<400> SEQUENCE: 417
caggttccgg aatcttaacc ggttttttat tccctttcga tggtggcctg 50

<210> SEQ ID NO 418
<211> LENGTH: 50
<212> TYPE: DNA
<213> ORGANISM: Artificial Sequence
<220> FEATURE:
<223> OTHER INFORMATION: Synthetic sequence

<400> SEQUENCE: 418
agggctagtt cattcggccg gtttttttga gttgttacac actccttagc 50

<210> SEQ ID NO 419
<211> LENGTH: 50
<212> TYPE: DNA
<213> ORGANISM: Artificial Sequence
<220> FEATURE:
<223> OTHER INFORMATION: Synthetic sequence

<400> SEQUENCE: 419
cacgttcaat taagtaacaa ggttttttac ttcttacata tttaaagttt 50

<210> SEQ ID NO 420
<211> LENGTH: 50
<212> TYPE: DNA
<213> ORGANISM: Artificial Sequence
<220> FEATURE:
<223> OTHER INFORMATION: Synthetic sequence

<400> SEQUENCE: 420
tccgaagaca tcaggatcgg tctttttga ttgtgcacct cttgcgaggc 50

<210> SEQ ID NO 421
<211> LENGTH: 50
<212> TYPE: DNA
<213> ORGANISM: Artificial Sequence
<220> FEATURE:
<223> OTHER INFORMATION: Synthetic sequence

<400> SEQUENCE: 421
atgcccttcc ctttcaacaa tttttttttc acgtactttt tcactctctt 50

<210> SEQ ID NO 422
<211> LENGTH: 50
<212> TYPE: DNA
<213> ORGANISM: Artificial Sequence
<220> FEATURE:
<223> OTHER INFORMATION: Synthetic sequence

<400> SEQUENCE: 422
gcttttgccg cttcactcgc cgtttttttt actaaggcaa tcccggttgg 50

<210> SEQ ID NO 423
<211> LENGTH: 66
<212> TYPE: DNA
<213> ORGANISM: Artificial Sequence
<220> FEATURE:
<223> OTHER INFORMATION: Synthetic sequence

<400> SEQUENCE: 423
tccgccaagt gcactaagtt cagcgggtac tcctacctga tttgaggagc aagcacccaa 60
ggcctt 66

<210> SEQ ID NO 424
<211> LENGTH: 67
<212> TYPE: DNA
<213> ORGANISM: Artificial Sequence
<220> FEATURE:
<223> OTHER INFORMATION: Synthetic sequence

<400> SEQUENCE: 424
tttcttttcc tccgcttttt tttattgata tgctcgttgc tagccttttt ttgctatggt 60
tcagcga 67

<210> SEQ ID NO 425
<211> LENGTH: 66
<212> TYPE: DNA
<213> ORGANISM: Artificial Sequence
<220> FEATURE:
<223> OTHER INFORMATION: Synthetic sequence

<400> SEQUENCE: 425
gagcaaagaa acccagctca cgttcgtctc acgacggtct aaatcaccgc gttctagcat 60
tgtgtg 66

<210> SEQ ID NO 426
<211> LENGTH: 66
<212> TYPE: DNA
<213> ORGANISM: Artificial Sequence
<220> FEATURE:
<223> OTHER INFORMATION: Synthetic sequence

<400> SEQUENCE: 426
cctgttccat gcttcggtat gatagaacgc ttaccgaatt caggaacata gacaaggata 60
tgacgt 66

<210> SEQ ID NO 427
<211> LENGTH: 66
<212> TYPE: DNA
<213> ORGANISM: Artificial Sequence
<220> FEATURE:
<223> OTHER INFORMATION: Synthetic sequence

<400> SEQUENCE: 427
aacgcttgat cccttggctg tggttattct gccaagcccg tctgccacaa gccagttatc 60
gctatg 66

<210> SEQ ID NO 428
<211> LENGTH: 66
<212> TYPE: DNA
<213> ORGANISM: Artificial Sequence
<220> FEATURE:
<223> OTHER INFORMATION: Synthetic sequence

<400> SEQUENCE: 428
acaaagaaaa ctcgactctt cgaagcgtca ctaattagat gcgttaatcc attcatgcgg 60
cacttt 66

<210> SEQ ID NO 429
<211> LENGTH: 66
<212> TYPE: DNA
<213> ORGANISM: Artificial Sequence
<220> FEATURE:
<223> OTHER INFORMATION: Synthetic sequence

<400> SEQUENCE: 429
cggatctata ctaccaccaa gatctcattt gaatatttgc ttttgccgac ttcccttacg 60
aagtta 66

<210> SEQ ID NO 430
<211> LENGTH: 66
<212> TYPE: DNA
<213> ORGANISM: Artificial Sequence
<220> FEATURE:
<223> OTHER INFORMATION: Synthetic sequence

<400> SEQUENCE: 430
aacctttcca cgtccaactg ctgttctgtt aagaagaaaa gaaattccgg ggtgataagg 60
acgtgg 66

<210> SEQ ID NO 431
<211> LENGTH: 66
<212> TYPE: DNA
<213> ORGANISM: Artificial Sequence
<220> FEATURE:
<223> OTHER INFORMATION: Synthetic sequence

<400> SEQUENCE: 431
caagctcact cttcacaatg tcaaccgccc cagccaaact catcgtttaa cagatgtgac 60
tagagt 66

<210> SEQ ID NO 432
<211> LENGTH: 66
<212> TYPE: DNA
<213> ORGANISM: Artificial Sequence
<220> FEATURE:
<223> OTHER INFORMATION: Synthetic sequence

<400> SEQUENCE: 432
gcacgcaaca agacgggcgg catatctcct tggtccgtgt ttgtagtccg cctagcagac 60
aacaag 66

<210> SEQ ID NO 433
<211> LENGTH: 66
<212> TYPE: DNA
<213> ORGANISM: Artificial Sequence
<220> FEATURE:
<223> OTHER INFORMATION: Synthetic sequence

<400> SEQUENCE: 433
ttcccacaag tcctcagtcc cagcaccatc gcaatgctat ggtcaacatc actttctgtg 60
gcagta 66

<210> SEQ ID NO 434
<211> LENGTH: 66
<212> TYPE: DNA
<213> ORGANISM: Artificial Sequence
<220> FEATURE:
<223> OTHER INFORMATION: Synthetic sequence

<400> SEQUENCE: 434
agctttagac caaaactgat gctggtatgg atttatcctg ccatggaatt taccacccca 60
atattt 66

<210> SEQ ID NO 435
<211> LENGTH: 66
<212> TYPE: DNA
<213> ORGANISM: Artificial Sequence
<220> FEATURE:
<223> OTHER INFORMATION: Synthetic sequence

<400> SEQUENCE: 435
gagcctccac gtctgaccaa ggcccacaag cacgcccgct gccagagttt cctctggcac 60
cgctac 66

<210> SEQ ID NO 436
<211> LENGTH: 66
<212> TYPE: DNA
<213> ORGANISM: Artificial Sequence
<220> FEATURE:
<223> OTHER INFORMATION: Synthetic sequence

<400> SEQUENCE: 436
gtcactgact agtctttcgc ccctatacta gatggttcga tctccacgcc tgcctactta 60
ggcttc 66

<210> SEQ ID NO 437

<211> LENGTH: 66
<212> TYPE: DNA
<213> ORGANISM: Artificial Sequence
<220> FEATURE:
<223> OTHER INFORMATION: Synthetic sequence

<400> SEQUENCE: 437
attccggcac ttctgctatc ctgagataaa actgatacga gccttaactc tacgttcgga 60
gcgtgt 66

<210> SEQ ID NO 438
<211> LENGTH: 54
<212> TYPE: DNA
<213> ORGANISM: Artificial Sequence
<220> FEATURE:
<223> OTHER INFORMATION: Synthetic sequence

<400> SEQUENCE: 438
atcgccagtt ctttttgct taccaaacgc cacaaggatt tttcgcctta ttcg 54

<210> SEQ ID NO 439
<211> LENGTH: 22
<212> TYPE: DNA
<213> ORGANISM: Artificial Sequence
<220> FEATURE:
<223> OTHER INFORMATION: Synthetic sequence

<400> SEQUENCE: 439
tatccatcta tatggattct ga 22

<210> SEQ ID NO 440
<211> LENGTH: 49
<212> TYPE: DNA
<213> ORGANISM: Artificial Sequence
<220> FEATURE:
<223> OTHER INFORMATION: Synthetic sequence

<400> SEQUENCE: 440
cttagaggcg tttttttcag ccataatcca gcggatggcg tccggctgt 49

<210> SEQ ID NO 441
<211> LENGTH: 54
<212> TYPE: DNA
<213> ORGANISM: Artificial Sequence
<220> FEATURE:
<223> OTHER INFORMATION: Synthetic sequence

<400> SEQUENCE: 441
attcggccgg ttttttgagt tgttacaaaa aaccaatttt tttatccgaa tgaa 54

<210> SEQ ID NO 442
<211> LENGTH: 49
<212> TYPE: DNA
<213> ORGANISM: Artificial Sequence
<220> FEATURE:
<223> OTHER INFORMATION: Synthetic sequence

<400> SEQUENCE: 442
atcagtaggg ttttttaaaa ctaacctcct attagtggtt tttgtgaac 49

<210> SEQ ID NO 443
<211> LENGTH: 54
<212> TYPE: DNA
<213> ORGANISM: Artificial Sequence
<220> FEATURE:
<223> OTHER INFORMATION: Synthetic sequence

<400> SEQUENCE: 443
aatccgaaga gccgactttt tatcgaagaa tcaaaaagca atgtccctgt ggta 54

<210> SEQ ID NO 444
<211> LENGTH: 54
<212> TYPE: DNA
<213> ORGANISM: Artificial Sequence
<220> FEATURE:
<223> OTHER INFORMATION: Synthetic sequence

<400> SEQUENCE: 444
tttgtattca ctttttactg aaaatcaatc ttaaccggtt tttattccct ttcg 54

<210> SEQ ID NO 445
<211> LENGTH: 49
<212> TYPE: DNA
<213> ORGANISM: Artificial Sequence
<220> FEATURE:
<223> OTHER INFORMATION: Synthetic sequence

<400> SEQUENCE: 445
agggctcgcg ctttttcgac gtctccacat tcagttacgg agatttctg 49

<210> SEQ ID NO 446
<211> LENGTH: 49
<212> TYPE: DNA
<213> ORGANISM: Artificial Sequence
<220> FEATURE:
<223> OTHER INFORMATION: Synthetic sequence

<400> SEQUENCE: 446
ttctccatga gtttttcccc ccttaggaca tctgcgttcc cacctgaca 49

<210> SEQ ID NO 447
<211> LENGTH: 54
<212> TYPE: DNA
<213> ORGANISM: Artificial Sequence
<220> FEATURE:
<223> OTHER INFORMATION: Synthetic sequence

<400> SEQUENCE: 447
atgtcttcaa ctttttccgg atcagccttc cagccatatt tttagacccc atct 54

<210> SEQ ID NO 448
<211> LENGTH: 49
<212> TYPE: DNA
<213> ORGANISM: Artificial Sequence
<220> FEATURE:
<223> OTHER INFORMATION: Synthetic sequence

<400> SEQUENCE: 448
cgggccgtca catgaattcc agctccgctt cattttttg aataagtaa 49

<210> SEQ ID NO 449
<211> LENGTH: 49
<212> TYPE: DNA
<213> ORGANISM: Artificial Sequence
<220> FEATURE:
<223> OTHER INFORMATION: Synthetic sequence

<400> SEQUENCE: 449
acttattcta ctttttaccc tctatgtaca gggtcttctt ttttttccc 49

<210> SEQ ID NO 450

```
<211> LENGTH: 54
<212> TYPE: DNA
<213> ORGANISM: Artificial Sequence
<220> FEATURE:
<223> OTHER INFORMATION: Synthetic sequence

<400> SEQUENCE: 450

cgctgtcgct agatagtttt ttagataggg acagtgggaa tctacgaggc attt          54


<210> SEQ ID NO 451
<211> LENGTH: 49
<212> TYPE: DNA
<213> ORGANISM: Artificial Sequence
<220> FEATURE:
<223> OTHER INFORMATION: Synthetic sequence

<400> SEQUENCE: 451

gacattcaga gtttttcact gggcagaaat cacattgctt ttaattaga                49


<210> SEQ ID NO 452
<211> LENGTH: 54
<212> TYPE: DNA
<213> ORGANISM: Artificial Sequence
<220> FEATURE:
<223> OTHER INFORMATION: Synthetic sequence

<400> SEQUENCE: 452

cagtcagatt ctttttccct tgtccgttat tccttccttt tttgtggatt ttca          54


<210> SEQ ID NO 453
<211> LENGTH: 49
<212> TYPE: DNA
<213> ORGANISM: Artificial Sequence
<220> FEATURE:
<223> OTHER INFORMATION: Synthetic sequence

<400> SEQUENCE: 453

aagagaccta ctttttcaag gccgtctagc aagccccatt tttccaagc                49


<210> SEQ ID NO 454
<211> LENGTH: 54
<212> TYPE: DNA
<213> ORGANISM: Artificial Sequence
<220> FEATURE:
<223> OTHER INFORMATION: Synthetic sequence

<400> SEQUENCE: 454

agtcctcact acccgatttt tcccttagag ccaatcctta tcctctacat tatt          54


<210> SEQ ID NO 455
<211> LENGTH: 49
<212> TYPE: DNA
<213> ORGANISM: Artificial Sequence
<220> FEATURE:
<223> OTHER INFORMATION: Synthetic sequence

<400> SEQUENCE: 455

atctcttagg attttttcga ctaacccca cttcagtctt tttttcaaa                 49


<210> SEQ ID NO 456
<211> LENGTH: 54
<212> TYPE: DNA
<213> ORGANISM: Artificial Sequence
<220> FEATURE:
<223> OTHER INFORMATION: Synthetic sequence

<400> SEQUENCE: 456
```

gttctgcact agaggctttt tcgttcgacc cgaccttacg gtccgtcagg gcat 54

<210> SEQ ID NO 457
<211> LENGTH: 49
<212> TYPE: DNA
<213> ORGANISM: Artificial Sequence
<220> FEATURE:
<223> OTHER INFORMATION: Synthetic sequence

<400> SEQUENCE: 457
ctagatgaac ttttttaaca ccttttgtgg tgtctgatgt tcatcccgc 49

<210> SEQ ID NO 458
<211> LENGTH: 49
<212> TYPE: DNA
<213> ORGANISM: Artificial Sequence
<220> FEATURE:
<223> OTHER INFORMATION: Synthetic sequence

<400> SEQUENCE: 458
ttcactcgcc gtttttttac taaggcaatc ccggttggca cgttcaatt 49

<210> SEQ ID NO 459
<211> LENGTH: 27
<212> TYPE: DNA
<213> ORGANISM: Artificial Sequence
<220> FEATURE:
<223> OTHER INFORMATION: Synthetic sequence

<400> SEQUENCE: 459
aagtaacaag gtttttactt cttacat 27

<210> SEQ ID NO 460
<211> LENGTH: 49
<212> TYPE: DNA
<213> ORGANISM: Artificial Sequence
<220> FEATURE:
<223> OTHER INFORMATION: Synthetic sequence

<400> SEQUENCE: 460
ctctaatcat ttttttcgct ttacctcgga aacttcggtt tttcaggaa 49

<210> SEQ ID NO 461
<211> LENGTH: 54
<212> TYPE: DNA
<213> ORGANISM: Artificial Sequence
<220> FEATURE:
<223> OTHER INFORMATION: Synthetic sequence

<400> SEQUENCE: 461
ccagctaccc aaattctttt tgacgatcga tttgcacgtc agattcaccc tatt 54

<210> SEQ ID NO 462
<211> LENGTH: 54
<212> TYPE: DNA
<213> ORGANISM: Artificial Sequence
<220> FEATURE:
<223> OTHER INFORMATION: Synthetic sequence

<400> SEQUENCE: 462
caggatcggt ctttttgatt gtgcaccttt caacaatttt ttttcacgta cttt 54

<210> SEQ ID NO 463
<211> LENGTH: 49
<212> TYPE: DNA

<213> ORGANISM: Artificial Sequence
<220> FEATURE:
<223> OTHER INFORMATION: Synthetic sequence

<400> SEQUENCE: 463
gttttacacc ctttttaaac actcgcatag acgttagaaa ccattatgc 49

<210> SEQ ID NO 464
<211> LENGTH: 54
<212> TYPE: DNA
<213> ORGANISM: Artificial Sequence
<220> FEATURE:
<223> OTHER INFORMATION: Synthetic sequence

<400> SEQUENCE: 464
cagcatcctt gtttttactt acgtcgcggc tataatactt tttttaccga ggca 54

<210> SEQ ID NO 465
<211> LENGTH: 49
<212> TYPE: DNA
<213> ORGANISM: Artificial Sequence
<220> FEATURE:
<223> OTHER INFORMATION: Synthetic sequence

<400> SEQUENCE: 465
ttgttcgcta ttttttcggt ctctcgcact tagagctgtt tttcattcc 49

<210> SEQ ID NO 466
<211> LENGTH: 54
<212> TYPE: DNA
<213> ORGANISM: Artificial Sequence
<220> FEATURE:
<223> OTHER INFORMATION: Synthetic sequence

<400> SEQUENCE: 466
caaacccgca ctcctctttt tgccacacgg gattctcacc ctcacggccc caaa 54

<210> SEQ ID NO 467
<211> LENGTH: 22
<212> TYPE: DNA
<213> ORGANISM: Artificial Sequence
<220> FEATURE:
<223> OTHER INFORMATION: Synthetic sequence

<400> SEQUENCE: 467
attgatatgc tcgttgctag cc 22

<210> SEQ ID NO 468
<211> LENGTH: 44
<212> TYPE: DNA
<213> ORGANISM: Artificial Sequence
<220> FEATURE:
<223> OTHER INFORMATION: Synthetic sequence

<400> SEQUENCE: 468
caaaatgaca ttgcaattcg cctcaaacac aaatcagaca acaa 44

<210> SEQ ID NO 469
<211> LENGTH: 49
<212> TYPE: DNA
<213> ORGANISM: Artificial Sequence
<220> FEATURE:
<223> OTHER INFORMATION: Synthetic sequence

<400> SEQUENCE: 469
acttttctgg ctttttacct ctagcctcaa attccgagcg gtaacattc 49

<210> SEQ ID NO 470
<211> LENGTH: 49
<212> TYPE: DNA
<213> ORGANISM: Artificial Sequence
<220> FEATURE:
<223> OTHER INFORMATION: Synthetic sequence

<400> SEQUENCE: 470
ggctacctta atttttgaga gtcatagtta ctcccgcccc gaagctccc 49

<210> SEQ ID NO 471
<211> LENGTH: 49
<212> TYPE: DNA
<213> ORGANISM: Artificial Sequence
<220> FEATURE:
<223> OTHER INFORMATION: Synthetic sequence

<400> SEQUENCE: 471
ctatcaacta gtttttaggc tgttcacctt ggagacctcg acggtctac 49

<210> SEQ ID NO 472
<211> LENGTH: 49
<212> TYPE: DNA
<213> ORGANISM: Artificial Sequence
<220> FEATURE:
<223> OTHER INFORMATION: Synthetic sequence

<400> SEQUENCE: 472
catatcaacc ctttttgac ggtagagtat aggtaacagg agcttcccc 49

<210> SEQ ID NO 473
<211> LENGTH: 66
<212> TYPE: DNA
<213> ORGANISM: Artificial Sequence
<220> FEATURE:
<223> OTHER INFORMATION: Synthetic sequence

<400> SEQUENCE: 473
tgctatggtt cagcgaaatg gcccactaaa agctcttcat tcaaatgtct ttcttttcct 60
ccgctt 66

<210> SEQ ID NO 474
<211> LENGTH: 49
<212> TYPE: DNA
<213> ORGANISM: Artificial Sequence
<220> FEATURE:
<223> OTHER INFORMATION: Synthetic sequence

<400> SEQUENCE: 474
caggcatagt ttttttcacc atctttcggg tcccaacaga ccccggaac 49

<210> SEQ ID NO 475
<211> LENGTH: 71
<212> TYPE: DNA
<213> ORGANISM: Artificial Sequence
<220> FEATURE:
<223> OTHER INFORMATION: Synthetic sequence

<400> SEQUENCE: 475
agctacattc ccccagtgaa atgcgagatt cccttttttct acccacaagg agcagagggc 60
tacgcgtatg g 71

<210> SEQ ID NO 476

<211> LENGTH: 49
<212> TYPE: DNA
<213> ORGANISM: Artificial Sequence
<220> FEATURE:
<223> OTHER INFORMATION: Synthetic sequence

<400> SEQUENCE: 476
gttgccctct ctttttcaaa ttacaactcg ggcaccgaca tcactgtac 49

<210> SEQ ID NO 477
<211> LENGTH: 66
<212> TYPE: DNA
<213> ORGANISM: Artificial Sequence
<220> FEATURE:
<223> OTHER INFORMATION: Synthetic sequence

<400> SEQUENCE: 477
ccgacttcca tggccactag cttcgcggca atgcctgatc agacagccgc cactccttag 60
cggatt 66

<210> SEQ ID NO 478
<211> LENGTH: 66
<212> TYPE: DNA
<213> ORGANISM: Artificial Sequence
<220> FEATURE:
<223> OTHER INFORMATION: Synthetic sequence

<400> SEQUENCE: 478
aggccacact ttcatggctg ttcctctcgt actaagttca attactattg ggactaaagg 60
atcgat 66

<210> SEQ ID NO 479
<211> LENGTH: 66
<212> TYPE: DNA
<213> ORGANISM: Artificial Sequence
<220> FEATURE:
<223> OTHER INFORMATION: Synthetic sequence

<400> SEQUENCE: 479
catatccagg ttccggaaaa tcaaggggc ttttaccctt ttgttctact gttaccgtga 60
agaatc 66

<210> SEQ ID NO 480
<211> LENGTH: 66
<212> TYPE: DNA
<213> ORGANISM: Artificial Sequence
<220> FEATURE:
<223> OTHER INFORMATION: Synthetic sequence

<400> SEQUENCE: 480
atgctagaac gtggaaaaag cgcaccggag ccagcaaagg tgctggcctc ccgaatggga 60
ccttga 66

<210> SEQ ID NO 481
<211> LENGTH: 66
<212> TYPE: DNA
<213> ORGANISM: Artificial Sequence
<220> FEATURE:
<223> OTHER INFORMATION: Synthetic sequence

<400> SEQUENCE: 481
ttgaatttct tcactttaga aactataaag gtagtggtat ttcactggcg gtttacccgc 60
gcttgg 66

<210> SEQ ID NO 482
<211> LENGTH: 66
<212> TYPE: DNA
<213> ORGANISM: Artificial Sequence
<220> FEATURE:
<223> OTHER INFORMATION: Synthetic sequence

<400> SEQUENCE: 482
cgacctggca tgaaaacacc agttctaagt tgatcgttaa ttgtagcaag gctgcggtta 60
tcagta 66

<210> SEQ ID NO 483
<211> LENGTH: 66
<212> TYPE: DNA
<213> ORGANISM: Artificial Sequence
<220> FEATURE:
<223> OTHER INFORMATION: Synthetic sequence

<400> SEQUENCE: 483
attttcaggg ctagttcatg gtggcctgca taaaatcagg cctttgaaac cgcttgagcg 60
ccatcc 66

<210> SEQ ID NO 484
<211> LENGTH: 66
<212> TYPE: DNA
<213> ORGANISM: Artificial Sequence
<220> FEATURE:
<223> OTHER INFORMATION: Synthetic sequence

<400> SEQUENCE: 484
aatccatccg aagacatatt taaagtttga gaataggtca aggtcatttc gctatgctct 60
tactca 66

<210> SEQ ID NO 485
<211> LENGTH: 66
<212> TYPE: DNA
<213> ORGANISM: Artificial Sequence
<220> FEATURE:
<223> OTHER INFORMATION: Synthetic sequence

<400> SEQUENCE: 485
cctacgttca ctttcataca aaacaccatg tctgatcaaa tgcccttccc tcttgcgagg 60
ccccaa 66

<210> SEQ ID NO 486
<211> LENGTH: 66
<212> TYPE: DNA
<213> ORGANISM: Artificial Sequence
<220> FEATURE:
<223> OTHER INFORMATION: Synthetic sequence

<400> SEQUENCE: 486
atttgagctt ttgccgcttc actctctttt caaagttctt ttcatctttc aggtaccaga 60
tttcaa 66

<210> SEQ ID NO 487
<211> LENGTH: 66
<212> TYPE: DNA
<213> ORGANISM: Artificial Sequence
<220> FEATURE:
<223> OTHER INFORMATION: Synthetic sequence

<400> SEQUENCE: 487
tccgccaagt gcactaagtt cagcgggtac tcctacctga tttgaggagc aagcacccaa 60
ggcctt 66

<210> SEQ ID NO 488
<211> LENGTH: 66
<212> TYPE: DNA
<213> ORGANISM: Artificial Sequence
<220> FEATURE:
<223> OTHER INFORMATION: Synthetic sequence

<400> SEQUENCE: 488
gagcaaagaa acccagctca cgttcgtctc acgacggtct aaatcaccgc gttctagcat 60
tgtgtg 66

<210> SEQ ID NO 489
<211> LENGTH: 66
<212> TYPE: DNA
<213> ORGANISM: Artificial Sequence
<220> FEATURE:
<223> OTHER INFORMATION: Synthetic sequence

<400> SEQUENCE: 489
cctgttccat gcttcggtat gatagaacgc ttaccgaatt caggaacata gacaaggata 60
tgacgt 66

<210> SEQ ID NO 490
<211> LENGTH: 66
<212> TYPE: DNA
<213> ORGANISM: Artificial Sequence
<220> FEATURE:
<223> OTHER INFORMATION: Synthetic sequence

<400> SEQUENCE: 490
aacgcttgat cccttggctg tggttattct gccaagcccg tctgccacaa gccagttatc 60
gctatg 66

<210> SEQ ID NO 491
<211> LENGTH: 66
<212> TYPE: DNA
<213> ORGANISM: Artificial Sequence
<220> FEATURE:
<223> OTHER INFORMATION: Synthetic sequence

<400> SEQUENCE: 491
acaaagaaaa ctcgactctt cgaagcgtca ctaattagat gcgttaatcc attcatgcgg 60
cacttt 66

<210> SEQ ID NO 492
<211> LENGTH: 66
<212> TYPE: DNA
<213> ORGANISM: Artificial Sequence
<220> FEATURE:
<223> OTHER INFORMATION: Synthetic sequence

<400> SEQUENCE: 492
cggatctata ctaccaccaa gatctcattt gaatatttgc ttttgccgac ttcccttacg 60
aagtta 66

<210> SEQ ID NO 493
<211> LENGTH: 66

<212> TYPE: DNA
<213> ORGANISM: Artificial Sequence
<220> FEATURE:
<223> OTHER INFORMATION: Synthetic sequence

<400> SEQUENCE: 493
aacctttcca cgtccaactg ctgttctgtt aagaagaaaa gaaattccgg ggtgataagg 60
acgtgg 66

<210> SEQ ID NO 494
<211> LENGTH: 66
<212> TYPE: DNA
<213> ORGANISM: Artificial Sequence
<220> FEATURE:
<223> OTHER INFORMATION: Synthetic sequence

<400> SEQUENCE: 494
caagctcact cttcacaatg tcaaccgccc cagccaaact catcgtttaa cagatgtgac 60
tagagt 66

<210> SEQ ID NO 495
<211> LENGTH: 66
<212> TYPE: DNA
<213> ORGANISM: Artificial Sequence
<220> FEATURE:
<223> OTHER INFORMATION: Synthetic sequence

<400> SEQUENCE: 495
gcacgcaaca agacgggcgg catatctcct tggtccgtgt ttgtagtccg cctagcagac 60
aacaag 66

<210> SEQ ID NO 496
<211> LENGTH: 66
<212> TYPE: DNA
<213> ORGANISM: Artificial Sequence
<220> FEATURE:
<223> OTHER INFORMATION: Synthetic sequence

<400> SEQUENCE: 496
ttcccacaag tcctcagtcc cagcaccatc gcaatgctat ggtcaacatc actttctgtg 60
gcagta 66

<210> SEQ ID NO 497
<211> LENGTH: 66
<212> TYPE: DNA
<213> ORGANISM: Artificial Sequence
<220> FEATURE:
<223> OTHER INFORMATION: Synthetic sequence

<400> SEQUENCE: 497
agctttagac caaaactgat gctggtatgg atttatcctg ccatggaatt taccacccca 60
atattt 66

<210> SEQ ID NO 498
<211> LENGTH: 66
<212> TYPE: DNA
<213> ORGANISM: Artificial Sequence
<220> FEATURE:
<223> OTHER INFORMATION: Synthetic sequence

<400> SEQUENCE: 498
gagcctccac gtctgaccaa ggcccacaag cacgcccgct gccagagttt cctctggcac 60
cgctac 66

<210> SEQ ID NO 499
<211> LENGTH: 66
<212> TYPE: DNA
<213> ORGANISM: Artificial Sequence
<220> FEATURE:
<223> OTHER INFORMATION: Synthetic sequence

<400> SEQUENCE: 499
gtcactgact agtctttcgc ccctatacta gatggttcga tctccacgcc tgcctactta 60
ggcttc 66

<210> SEQ ID NO 500
<211> LENGTH: 66
<212> TYPE: DNA
<213> ORGANISM: Artificial Sequence
<220> FEATURE:
<223> OTHER INFORMATION: Synthetic sequence

<400> SEQUENCE: 500
attccggcac ttctgctatc ctgagataaa actgatacga gccttaactc tacgttcgga 60
gcgtgt 66

<210> SEQ ID NO 501
<211> LENGTH: 306
<212> TYPE: RNA
<213> ORGANISM: Artificial Sequence
<220> FEATURE:
<223> OTHER INFORMATION: Synthetic sequence

<400> SEQUENCE: 501
gggauggacu cgccugugcu cuggagcuug auccgaaagc uuccacagug aggacugcuc 60 cguggggua agagagcacc aggcacugag gccugggagu uccacagacc aacaccccug 120
cuccuggcgg cucccacccg gggcuuagac ccucaggucc cuaauauccc ggaggugcuc 180
ucaaucagaa agguccugcu ccgcuucgca guggaaugga acggauuuag aagccugcag 240
uaggggagug gggaguggag agagggagcc cagaguuaca gacggcggcg agaggaagga 300
ggggcg 306

<210> SEQ ID NO 502
<211> LENGTH: 36
<212> TYPE: RNA
<213> ORGANISM: Artificial Sequence
<220> FEATURE:
<223> OTHER INFORMATION: Synthetic sequence

<400> SEQUENCE: 502
ccucucgccg ccguugagag ccaggccaga gcacag 36

<210> SEQ ID NO 503
<211> LENGTH: 26
<212> TYPE: RNA
<213> ORGANISM: Artificial Sequence
<220> FEATURE:
<223> OTHER INFORMATION: Synthetic sequence

<400> SEQUENCE: 503
uuccacugcc acuccccacu ccccua 26

<210> SEQ ID NO 504
<211> LENGTH: 38

<212> TYPE: RNA
<213> ORGANISM: Artificial Sequence
<220> FEATURE:
<223> OTHER INFORMATION: Synthetic sequence

<400> SEQUENCE: 504
guuggucugg gagcaggacc uuucugaucu guaacucu 38

<210> SEQ ID NO 505
<211> LENGTH: 46
<212> TYPE: RNA
<213> ORGANISM: Artificial Sequence
<220> FEATURE:
<223> OTHER INFORMATION: Synthetic sequence

<400> SEQUENCE: 505
cccacggagc aguccucauc ccaggccuca gugccuaucc guucca 46

<210> SEQ ID NO 506
<211> LENGTH: 22
<212> TYPE: RNA
<213> ORGANISM: Artificial Sequence
<220> FEATURE:
<223> OTHER INFORMATION: Synthetic sequence

<400> SEQUENCE: 506
gcgaguccau cccaagcccc gg 22

<210> SEQ ID NO 507
<211> LENGTH: 36
<212> TYPE: RNA
<213> ORGANISM: Artificial Sequence
<220> FEATURE:
<223> OTHER INFORMATION: Synthetic sequence

<400> SEQUENCE: 507
gggcucccuc ucucgaagcu ggaaccugug gaagcu 36

<210> SEQ ID NO 508
<211> LENGTH: 17
<212> TYPE: RNA
<213> ORGANISM: Artificial Sequence
<220> FEATURE:
<223> OTHER INFORMATION: Synthetic sequence

<400> SEQUENCE: 508
guuuguccaa auucucc 17

<210> SEQ ID NO 509
<211> LENGTH: 34
<212> TYPE: RNA
<213> ORGANISM: Artificial Sequence
<220> FEATURE:
<223> OTHER INFORMATION: Synthetic sequence

<400> SEQUENCE: 509
gcuugaaacc gauagucgaa gagcaauaau uaca 34

<210> SEQ ID NO 510
<211> LENGTH: 32
<212> TYPE: RNA
<213> ORGANISM: Artificial Sequence
<220> FEATURE:
<223> OTHER INFORMATION: Synthetic sequence

<400> SEQUENCE: 510
ccguuacccg uugaaaaaug aaccaucgcc ag 32

<210> SEQ ID NO 511
<211> LENGTH: 32
<212> TYPE: RNA
<213> ORGANISM: Artificial Sequence
<220> FEATURE:
<223> OTHER INFORMATION: Synthetic sequence

<400> SEQUENCE: 511
gagccacaag gacucauauu ggagcuggaa uu 32

<210> SEQ ID NO 512
<211> LENGTH: 16
<212> TYPE: RNA
<213> ORGANISM: Artificial Sequence
<220> FEATURE:
<223> OTHER INFORMATION: Synthetic sequence

<400> SEQUENCE: 512
auacuuagac augcau 16

<210> SEQ ID NO 513
<211> LENGTH: 17
<212> TYPE: RNA
<213> ORGANISM: Artificial Sequence
<220> FEATURE:
<223> OTHER INFORMATION: Synthetic sequence

<400> SEQUENCE: 513
uaagccauuc aaucggu 17

<210> SEQ ID NO 514
<211> LENGTH: 34
<212> TYPE: RNA
<213> ORGANISM: Artificial Sequence
<220> FEATURE:
<223> OTHER INFORMATION: Synthetic sequence

<400> SEQUENCE: 514
gguaucugau caucuuccaa aucacuccac caac 34

<210> SEQ ID NO 515
<211> LENGTH: 32
<212> TYPE: RNA
<213> ORGANISM: Artificial Sequence
<220> FEATURE:
<223> OTHER INFORMATION: Synthetic sequence

<400> SEQUENCE: 515
accacuauuu aguagguaag aacggccaug ca 32

<210> SEQ ID NO 516
<211> LENGTH: 34
<212> TYPE: RNA
<213> ORGANISM: Artificial Sequence
<220> FEATURE:
<223> OTHER INFORMATION: Synthetic sequence

<400> SEQUENCE: 516
acgauaacug auuuaauucu aauaaauaca ucuc 34

<210> SEQ ID NO 517
<211> LENGTH: 34
<212> TYPE: RNA
<213> ORGANISM: Artificial Sequence
<220> FEATURE:
<223> OTHER INFORMATION: Synthetic sequence

<400> SEQUENCE: 517 cuggugugu agcgcgcgug cggccccggc caag 34

<210> SEQ ID NO 518
<211> LENGTH: 34
<212> TYPE: RNA
<213> ORGANISM: Artificial Sequence
<220> FEATURE:
<223> OTHER INFORMATION: Synthetic sequence

<400> SEQUENCE: 518
ggcuuaaucu uugagaccac aaggccaugc gauu 34

<210> SEQ ID NO 519
<211> LENGTH: 34
<212> TYPE: RNA
<213> ORGANISM: Artificial Sequence
<220> FEATURE:
<223> OTHER INFORMATION: Synthetic sequence

<400> SEQUENCE: 519
ccaguacacg aaaaaauuuc uugauuaaug aaaa 34

<210> SEQ ID NO 520
<211> LENGTH: 16
<212> TYPE: RNA
<213> ORGANISM: Artificial Sequence
<220> FEATURE:
<223> OTHER INFORMATION: Synthetic sequence

<400> SEQUENCE: 520
gagccauucg caguuu 16

<210> SEQ ID NO 521
<211> LENGTH: 34
<212> TYPE: RNA
<213> ORGANISM: Artificial Sequence
<220> FEATURE:
<223> OTHER INFORMATION: Synthetic sequence

<400> SEQUENCE: 521
ucacagaccu guuauugacg acggaguuuc acaa 34

<210> SEQ ID NO 522
<211> LENGTH: 32
<212> TYPE: RNA
<213> ORGANISM: Artificial Sequence
<220> FEATURE:
<223> OTHER INFORMATION: Synthetic sequence

<400> SEQUENCE: 522
cgaccauacu cccccccauu acgauggucc ua 32

<210> SEQ ID NO 523
<211> LENGTH: 34
<212> TYPE: RNA
<213> ORGANISM: Artificial Sequence
<220> FEATURE:
<223> OTHER INFORMATION: Synthetic sequence

<400> SEQUENCE: 523
augugguagc cguuucuacc gcggcugcug gcac 34

<210> SEQ ID NO 524
<211> LENGTH: 34
<212> TYPE: RNA
<213> ORGANISM: Artificial Sequence
<220> FEATURE:
<223> OTHER INFORMATION: Synthetic sequence

<400> SEQUENCE: 524
uuggguaauu ugcgcgcuug uuccucguua aggu 34

<210> SEQ ID NO 525
<211> LENGTH: 32
<212> TYPE: RNA
<213> ORGANISM: Artificial Sequence
<220> FEATURE:
<223> OTHER INFORMATION: Synthetic sequence

<400> SEQUENCE: 525
auauucgagc aauacgauuu acauuguacu ca 32

<210> SEQ ID NO 526
<211> LENGTH: 34
<212> TYPE: RNA
<213> ORGANISM: Artificial Sequence
<220> FEATURE:
<223> OTHER INFORMATION: Synthetic sequence

<400> SEQUENCE: 526
aaucgaaccc uuauuccaca acuuuaauau acgc 34

<210> SEQ ID NO 527
<211> LENGTH: 17
<212> TYPE: RNA
<213> ORGANISM: Artificial Sequence
<220> FEATURE:
<223> OTHER INFORMATION: Synthetic sequence

<400> SEQUENCE: 527
gcccccuucu cuaagca 17

<210> SEQ ID NO 528
<211> LENGTH: 32
<212> TYPE: RNA
<213> ORGANISM: Artificial Sequence
<220> FEATURE:
<223> OTHER INFORMATION: Synthetic sequence

<400> SEQUENCE: 528
uucaccuacg gaaaccgauu accaagaccu cu 32

<210> SEQ ID NO 529
<211> LENGTH: 16
<212> TYPE: RNA
<213> ORGANISM: Artificial Sequence
<220> FEATURE:
<223> OTHER INFORMATION: Synthetic sequence

<400> SEQUENCE: 529
aggaacuauc aaauaa 16

<210> SEQ ID NO 530
<211> LENGTH: 34
<212> TYPE: RNA
<213> ORGANISM: Artificial Sequence
<220> FEATURE:
<223> OTHER INFORMATION: Synthetic sequence

<400> SEQUENCE: 530
ccaugguagg ccacuaugcc caaaguucaa cuac 34

<210> SEQ ID NO 531
<211> LENGTH: 34
<212> TYPE: RNA
<213> ORGANISM: Artificial Sequence
<220> FEATURE:
<223> OTHER INFORMATION: Synthetic sequence

<400> SEQUENCE: 531
agguuagcca gaaggaauuu cgcaguaguu aguc 34

<210> SEQ ID NO 532
<211> LENGTH: 34
<212> TYPE: RNA
<213> ORGANISM: Artificial Sequence
<220> FEATURE:
<223> OTHER INFORMATION: Synthetic sequence

<400> SEQUENCE: 532
gcaggaucaa ccagauagau agggcagaaa uuug 34

<210> SEQ ID NO 533
<211> LENGTH: 32
<212> TYPE: RNA
<213> ORGANISM: Artificial Sequence
<220> FEATURE:
<223> OTHER INFORMATION: Synthetic sequence

<400> SEQUENCE: 533
aauuuuuuca aaguaacaga cuugcccucc aa 32

<210> SEQ ID NO 534
<211> LENGTH: 32
<212> TYPE: RNA
<213> ORGANISM: Artificial Sequence
<220> FEATURE:
<223> OTHER INFORMATION: Synthetic sequence

<400> SEQUENCE: 534
cugcugccuu ccuuggagac auugauuuuu ua 32

<210> SEQ ID NO 535
<211> LENGTH: 17
<212> TYPE: RNA
<213> ORGANISM: Artificial Sequence
<220> FEATURE:
<223> OTHER INFORMATION: Synthetic sequence

<400> SEQUENCE: 535
uuguuacgac uuuuagu 17

<210> SEQ ID NO 536
<211> LENGTH: 34
<212> TYPE: RNA
<213> ORGANISM: Artificial Sequence
<220> FEATURE:
<223> OTHER INFORMATION: Synthetic sequence

<400> SEQUENCE: 536
aaguccuggu ucgccaaauu ucaccucuga caau 34

<210> SEQ ID NO 537

<211> LENGTH: 34
<212> TYPE: RNA
<213> ORGANISM: Artificial Sequence
<220> FEATURE:
<223> OTHER INFORMATION: Synthetic sequence

<400> SEQUENCE: 537
cuagucggca uaguuuacca ccacccacaa aauc 34

<210> SEQ ID NO 538
<211> LENGTH: 16
<212> TYPE: RNA
<213> ORGANISM: Artificial Sequence
<220> FEATURE:
<223> OTHER INFORMATION: Synthetic sequence

<400> SEQUENCE: 538
aagcauauga cuacug 16

<210> SEQ ID NO 539
<211> LENGTH: 34
<212> TYPE: RNA
<213> ORGANISM: Artificial Sequence
<220> FEATURE:
<223> OTHER INFORMATION: Synthetic sequence

<400> SEQUENCE: 539
auguauuagg uuauuuauug ucacuauucc aauu 34

<210> SEQ ID NO 540
<211> LENGTH: 32
<212> TYPE: RNA
<213> ORGANISM: Artificial Sequence
<220> FEATURE:
<223> OTHER INFORMATION: Synthetic sequence

<400> SEQUENCE: 540
ccucccugaa uuaggauucc aaagggucga ga 32

<210> SEQ ID NO 541
<211> LENGTH: 32
<212> TYPE: RNA
<213> ORGANISM: Artificial Sequence
<220> FEATURE:
<223> OTHER INFORMATION: Synthetic sequence

<400> SEQUENCE: 541
ccucaaacuu ccaucguguc uggaccuggu ga 32

<210> SEQ ID NO 542
<211> LENGTH: 32
<212> TYPE: RNA
<213> ORGANISM: Artificial Sequence
<220> FEATURE:
<223> OTHER INFORMATION: Synthetic sequence

<400> SEQUENCE: 542
auuucucgua aggugcugaa uacugaugcc cc 32

<210> SEQ ID NO 543
<211> LENGTH: 34
<212> TYPE: RNA
<213> ORGANISM: Artificial Sequence
<220> FEATURE:
<223> OTHER INFORMATION: Synthetic sequence

<400> SEQUENCE: 543 cgagugggguc auuaaaaucu gucaauccuu auug 34

<210> SEQ ID NO 544
<211> LENGTH: 32
<212> TYPE: RNA
<213> ORGANISM: Artificial Sequence
<220> FEATURE:
<223> OTHER INFORMATION: Synthetic sequence

<400> SEQUENCE: 544
uccucuaaau gaccaaaugc ucuaucccca gc 32

<210> SEQ ID NO 545
<211> LENGTH: 32
<212> TYPE: RNA
<213> ORGANISM: Artificial Sequence
<220> FEATURE:
<223> OTHER INFORMATION: Synthetic sequence

<400> SEQUENCE: 545
ugguuaagac uacgaccguc cuuggcaaau gc 32

<210> SEQ ID NO 546
<211> LENGTH: 32
<212> TYPE: RNA
<213> ORGANISM: Artificial Sequence
<220> FEATURE:
<223> OTHER INFORMATION: Synthetic sequence

<400> SEQUENCE: 546
gauccugagg ccucacacgu aaucaacgca ag 32

<210> SEQ ID NO 547
<211> LENGTH: 34
<212> TYPE: RNA
<213> ORGANISM: Artificial Sequence
<220> FEATURE:
<223> OTHER INFORMATION: Synthetic sequence

<400> SEQUENCE: 547
uuaaggucuc guucguugug uacaaagggc aggg 34

<210> SEQ ID NO 548
<211> LENGTH: 32
<212> TYPE: RNA
<213> ORGANISM: Artificial Sequence
<220> FEATURE:
<223> OTHER INFORMATION: Synthetic sequence

<400> SEQUENCE: 548
caggcucccu cuccggcgaa aaguuauuau ga 32

<210> SEQ ID NO 549
<211> LENGTH: 25
<212> TYPE: RNA
<213> ORGANISM: Artificial Sequence
<220> FEATURE:
<223> OTHER INFORMATION: Synthetic sequence

<400> SEQUENCE: 549
guuauaccau guaguaauuu uaagc 25

<210> SEQ ID NO 550
<211> LENGTH: 32
<212> TYPE: RNA

<213> ORGANISM: Artificial Sequence
<220> FEATURE:
<223> OTHER INFORMATION: Synthetic sequence

<400> SEQUENCE: 550
gcucugagau ggaguucuag gaauuccucg uu 32

<210> SEQ ID NO 551
<211> LENGTH: 34
<212> TYPE: RNA
<213> ORGANISM: Artificial Sequence
<220> FEATURE:
<223> OTHER INFORMATION: Synthetic sequence

<400> SEQUENCE: 551
ccugcuuuga acacucucga ccgucccuau uaau 34

<210> SEQ ID NO 552
<211> LENGTH: 34
<212> TYPE: RNA
<213> ORGANISM: Artificial Sequence
<220> FEATURE:
<223> OTHER INFORMATION: Synthetic sequence

<400> SEQUENCE: 552
aaccagcaaa ugcuagccug augacuugcg cuua 34

<210> SEQ ID NO 553
<211> LENGTH: 34
<212> TYPE: RNA
<213> ORGANISM: Artificial Sequence
<220> FEATURE:
<223> OTHER INFORMATION: Synthetic sequence

<400> SEQUENCE: 553
caaaauagau uuaaguuuca gccuugcucc acuc 34

<210> SEQ ID NO 554
<211> LENGTH: 32
<212> TYPE: RNA
<213> ORGANISM: Artificial Sequence
<220> FEATURE:
<223> OTHER INFORMATION: Synthetic sequence

<400> SEQUENCE: 554
ccucuaagaa guggauaaga aagagcucuc aa 32

<210> SEQ ID NO 555
<211> LENGTH: 32
<212> TYPE: RNA
<213> ORGANISM: Artificial Sequence
<220> FEATURE:
<223> OTHER INFORMATION: Synthetic sequence

<400> SEQUENCE: 555
agaacgucua agggcacaaa uuaagccgca gg 32

<210> SEQ ID NO 556
<211> LENGTH: 32
<212> TYPE: RNA
<213> ORGANISM: Artificial Sequence
<220> FEATURE:
<223> OTHER INFORMATION: Synthetic sequence

<400> SEQUENCE: 556
aggccccguu ggaaaugagc uuuuuaacug ca 32

<210> SEQ ID NO 557
<211> LENGTH: 34
<212> TYPE: RNA
<213> ORGANISM: Artificial Sequence
<220> FEATURE:
<223> OTHER INFORMATION: Synthetic sequence

<400> SEQUENCE: 557
agaacccaaa gacuuugguu uccccguguu gagu 34

<210> SEQ ID NO 558
<211> LENGTH: 32
<212> TYPE: RNA
<213> ORGANISM: Artificial Sequence
<220> FEATURE:
<223> OTHER INFORMATION: Synthetic sequence

<400> SEQUENCE: 558
aaacaccacc cgauccuuca auaaauccaa ga 32

<210> SEQ ID NO 559
<211> LENGTH: 34
<212> TYPE: RNA
<213> ORGANISM: Artificial Sequence
<220> FEATURE:
<223> OTHER INFORMATION: Synthetic sequence

<400> SEQUENCE: 559
cacuguauaa auugcuuauc aucaaagagu ccga 34

<210> SEQ ID NO 560
<211> LENGTH: 34
<212> TYPE: RNA
<213> ORGANISM: Artificial Sequence
<220> FEATURE:
<223> OTHER INFORMATION: Synthetic sequence

<400> SEQUENCE: 560
acaagacccu auuauuccau gcuaaugaaa ccaa 34

<210> SEQ ID NO 561
<211> LENGTH: 26
<212> TYPE: RNA
<213> ORGANISM: Artificial Sequence
<220> FEATURE:
<223> OTHER INFORMATION: Synthetic sequence

<400> SEQUENCE: 561
guuagacuca augauccuuc cgcagg 26

<210> SEQ ID NO 562
<211> LENGTH: 8
<212> TYPE: RNA
<213> ORGANISM: Artificial Sequence
<220> FEATURE:
<223> OTHER INFORMATION: Synthetic sequence

<400> SEQUENCE: 562 cgaaaguu 8

<210> SEQ ID NO 563
<211> LENGTH: 32
<212> TYPE: RNA
<213> ORGANISM: Artificial Sequence
<220> FEATURE:

<223> OTHER INFORMATION: Synthetic sequence

<400> SEQUENCE: 563
uuuuuuuuaa cuuucgcgga ccgguuuuuu uu 32

<210> SEQ ID NO 564
<211> LENGTH: 32
<212> TYPE: RNA
<213> ORGANISM: Artificial Sequence
<220> FEATURE:
<223> OTHER INFORMATION: Synthetic sequence

<400> SEQUENCE: 564
uuuuuuuucg ggcgguaucg caauuuuuuu uu 32

<210> SEQ ID NO 565
<211> LENGTH: 32
<212> TYPE: RNA
<213> ORGANISM: Artificial Sequence
<220> FEATURE:
<223> OTHER INFORMATION: Synthetic sequence

<400> SEQUENCE: 565
uuuuuuuucc aaccggccua ccauuuuuuu uu 32

<210> SEQ ID NO 566
<211> LENGTH: 32
<212> TYPE: RNA
<213> ORGANISM: Artificial Sequence
<220> FEATURE:
<223> OTHER INFORMATION: Synthetic sequence

<400> SEQUENCE: 566
uuuuuuuuua agcagagauc cccuuuuuuu uu 32

<210> SEQ ID NO 567
<211> LENGTH: 33
<212> TYPE: RNA
<213> ORGANISM: Artificial Sequence
<220> FEATURE:
<223> OTHER INFORMATION: Synthetic sequence

<400> SEQUENCE: 567
uaagccauuc aaucgguacu agcgauuuuu uuu 33

<210> SEQ ID NO 568
<211> LENGTH: 32
<212> TYPE: RNA
<213> ORGANISM: Artificial Sequence
<220> FEATURE:
<223> OTHER INFORMATION: Synthetic sequence

<400> SEQUENCE: 568
uuuuuuuuuc aauuccacca aacguuuuuu uu 32

<210> SEQ ID NO 569
<211> LENGTH: 32
<212> TYPE: RNA
<213> ORGANISM: Artificial Sequence
<220> FEATURE:
<223> OTHER INFORMATION: Synthetic sequence

<400> SEQUENCE: 569
uuuuuuuucc uguauccucu agaauuuuuu uu 32

<210> SEQ ID NO 570
<211> LENGTH: 16
<212> TYPE: RNA
<213> ORGANISM: Artificial Sequence
<220> FEATURE:
<223> OTHER INFORMATION: Synthetic sequence

<400> SEQUENCE: 570
gcuggcucuu uuuuuu 16

<210> SEQ ID NO 571
<211> LENGTH: 32
<212> TYPE: RNA
<213> ORGANISM: Artificial Sequence
<220> FEATURE:
<223> OTHER INFORMATION: Synthetic sequence

<400> SEQUENCE: 571
uuuuuuuucg ucagugcccu uccguuuuuu uu 32

<210> SEQ ID NO 572
<211> LENGTH: 16
<212> TYPE: RNA
<213> ORGANISM: Artificial Sequence
<220> FEATURE:
<223> OTHER INFORMATION: Synthetic sequence

<400> SEQUENCE: 572
uuuuuuuuuu accaca 16

<210> SEQ ID NO 573
<211> LENGTH: 32
<212> TYPE: RNA
<213> ORGANISM: Artificial Sequence
<220> FEATURE:
<223> OTHER INFORMATION: Synthetic sequence

<400> SEQUENCE: 573
uuuuuuuuuc cuauucgaau gggcuuuuuu uu 32

<210> SEQ ID NO 574
<211> LENGTH: 1542
<212> TYPE: RNA
<213> ORGANISM: Escherichia coli

<400> SEQUENCE: 574
aaauugaaga guuugaucau ggcucagauu gaacgcuggc ggcaggccua acacaugcaa 60
gucgaacggu aacaggaaac agcuugcugc uucgcugacg aguggcggac gggugaguaa 120
ugucugggaa acugccugau ggagggggau aacuacugga aacgguagcu aauaccgcau 180
aacgucgcaa gaccaaagag ggggaccuua gggccucuug ccaucggaug ugcccagaug 240
ggauuagcua guaggugggg uaacggcuca ccuaggcgac gaucccuagc uggucugaga 300
ggaugaccag ccacacugga acugagacac gguccagacu ccuacgggag gcagcagugg 360
ggaauauugc acaaugggcg caagccugau gcagccaugc cgcguguaug aagaaggccu 420
ucggguugua aaguacuuuc agcggggagg aagggaguaa aguuaauacc uuugcucauu 480
gacguuaccc gcagaagaag caccggcuaa cuccgugcca gcagccgcgg uaauacggag 540
ggugcaagcg uuaaucggaa uuacugggcg uaaagcgcac gcaggcgguu uguuaaguca 600
gaugugaaau ccccgggcuc aaccugggaa cugcaucuga uacuggcaag cuugagucuc 660
guagaggggg guagaauucc agguguagcg gugaaaugcg uagagaucug gaggaauacc 720 ggugggcgaag gcggcccccu ggacgaagac ugacgcucag gugcgaaagc gugggggagca 780 aacaggauua gauacccugg uaguccacgc cguaaacgau gucgacuugg agguugugcc 840
cuugaggcgu ggcuuccgga gcuaacgcgu uaagucgacc gccuggggag uacggccgca 900
agguuaaaac ucaaaugaau ugacgggggc ccgcacaagc gguggagcau gugguuuaau 960
ucgaugcaac gcgaagaacc uuaccugguc uugacaucca cggaaguuuu cagagaugag 1020
aaugugccuu cgggaaccgu gagacaggug cugcauggcu gucgucagcu cguguuguga 1080
aauguugggu uaagucccgc aacgagcgca acccuuaucc uuuguugcca gcgguccggc 1140
cgggaacuca aaggagacug ccagugauaa acuggaggaa gguggggaug acgucaaguc 1200
aucauggccc uuacgaccag ggcuacacac gugcuacaau ggcgcauaca aagagaagcg 1260
accucgcgag agcaagcgga ccucauaaag ugcgucguag uccggauugg agucugcaac 1320
ucgacuccau gaagucggaa ucgcuaguaa ucguggauca gaaugccacg gugaauacgu 1380
ucccgggccu uguacacacc gcccgucaca ccaugggagu ggguugcaaa agaaguaggu 1440
agcuuaaccu ucgggagggc gcuuaccacu uugugauuca ugacuggggu gaagucguaa 1500
caagguaacc guaggggaac cugcgguugg aucaccuccu ua 1542

<210> SEQ ID NO 575
<211> LENGTH: 32
<212> TYPE: DNA
<213> ORGANISM: Artificial Sequence
<220> FEATURE:
<223> OTHER INFORMATION: Synthetic sequence

<400> SEQUENCE: 575
ctacctactt cttttgattc accgtggcat tc 32

<210> SEQ ID NO 576
<211> LENGTH: 32
<212> TYPE: DNA
<213> ORGANISM: Artificial Sequence
<220> FEATURE:
<223> OTHER INFORMATION: Synthetic sequence

<400> SEQUENCE: 576
ccctctacga gactcaggta ttaactttac tc 32

<210> SEQ ID NO 577
<211> LENGTH: 34
<212> TYPE: DNA
<213> ORGANISM: Artificial Sequence
<220> FEATURE:
<223> OTHER INFORMATION: Synthetic sequence

<400> SEQUENCE: 577
aagcagcaag ctgtttcggt ccccctcttt ggtc 34

<210> SEQ ID NO 578
<211> LENGTH: 34
<212> TYPE: DNA
<213> ORGANISM: Artificial Sequence
<220> FEATURE:
<223> OTHER INFORMATION: Synthetic sequence

<400> SEQUENCE: 578
gggcccccgt caattcactg tctcacggtt cccg 34

<210> SEQ ID NO 579
<211> LENGTH: 32

<212> TYPE: DNA
<213> ORGANISM: Artificial Sequence
<220> FEATURE:
<223> OTHER INFORMATION: Synthetic sequence

<400> SEQUENCE: 579
gcggtcgact taacgcttta cggcgtggac ta 32

<210> SEQ ID NO 580
<211> LENGTH: 32
<212> TYPE: DNA
<213> ORGANISM: Artificial Sequence
<220> FEATURE:
<223> OTHER INFORMATION: Synthetic sequence

<400> SEQUENCE: 580
cacaaagtgg taagcgcgat tccgacttca tg 32

<210> SEQ ID NO 581
<211> LENGTH: 34
<212> TYPE: DNA
<213> ORGANISM: Artificial Sequence
<220> FEATURE:
<223> OTHER INFORMATION: Synthetic sequence

<400> SEQUENCE: 581
atcgaattaa accacattct gaaaacttcc gtgg 34

<210> SEQ ID NO 582
<211> LENGTH: 34
<212> TYPE: DNA
<213> ORGANISM: Artificial Sequence
<220> FEATURE:
<223> OTHER INFORMATION: Synthetic sequence

<400> SEQUENCE: 582
gtgcaatatt ccccacttaa cgtcaatgag caaa 34

<210> SEQ ID NO 583
<211> LENGTH: 34
<212> TYPE: DNA
<213> ORGANISM: Artificial Sequence
<220> FEATURE:
<223> OTHER INFORMATION: Synthetic sequence

<400> SEQUENCE: 583
aagggccatg atgacttgag tcgagttgca gact 34

<210> SEQ ID NO 584
<211> LENGTH: 34
<212> TYPE: DNA
<213> ORGANISM: Artificial Sequence
<220> FEATURE:
<223> OTHER INFORMATION: Synthetic sequence

<400> SEQUENCE: 584
gcctgcgtgc gctttaccct ccaagtcgac atcg 34

<210> SEQ ID NO 585
<211> LENGTH: 34
<212> TYPE: DNA
<213> ORGANISM: Artificial Sequence
<220> FEATURE:
<223> OTHER INFORMATION: Synthetic sequence

<400> SEQUENCE: 585
gcggccgtac tccccagtca caacacgagc tgac 34

<210> SEQ ID NO 586
<211> LENGTH: 17
<212> TYPE: DNA
<213> ORGANISM: Artificial Sequence
<220> FEATURE:
<223> OTHER INFORMATION: Synthetic sequence

<400> SEQUENCE: 586
tcaccccagt catgaat 17

<210> SEQ ID NO 587
<211> LENGTH: 34
<212> TYPE: DNA
<213> ORGANISM: Artificial Sequence
<220> FEATURE:
<223> OTHER INFORMATION: Synthetic sequence

<400> SEQUENCE: 587
ttcccggccg gaccgctaca aggcccggga acgt 34

<210> SEQ ID NO 588
<211> LENGTH: 34
<212> TYPE: DNA
<213> ORGANISM: Artificial Sequence
<220> FEATURE:
<223> OTHER INFORMATION: Synthetic sequence

<400> SEQUENCE: 588
gtctggaccg tgtctcatgg cacggagtta gccg 34

<210> SEQ ID NO 589
<211> LENGTH: 34
<212> TYPE: DNA
<213> ORGANISM: Artificial Sequence
<220> FEATURE:
<223> OTHER INFORMATION: Synthetic sequence

<400> SEQUENCE: 589
tcatcctctc agaccagtaa cgcttgcacc ctcc 34

<210> SEQ ID NO 590
<211> LENGTH: 32
<212> TYPE: DNA
<213> ORGANISM: Artificial Sequence
<220> FEATURE:
<223> OTHER INFORMATION: Synthetic sequence

<400> SEQUENCE: 590
gacgtcatcc ccacctgaca gccatgcagc ac 32

<210> SEQ ID NO 591
<211> LENGTH: 34
<212> TYPE: DNA
<213> ORGANISM: Artificial Sequence
<220> FEATURE:
<223> OTHER INFORMATION: Synthetic sequence

<400> SEQUENCE: 591
agcccgggga tttcacacca gggtatctaa tcct 34

<210> SEQ ID NO 592
<211> LENGTH: 16
<212> TYPE: DNA
<213> ORGANISM: Artificial Sequence
<220> FEATURE:
<223> OTHER INFORMATION: Synthetic sequence

<400> SEQUENCE: 592
ctgttaccgt tcgact 16

<210> SEQ ID NO 593
<211> LENGTH: 32
<212> TYPE: DNA
<213> ORGANISM: Artificial Sequence
<220> FEATURE:
<223> OTHER INFORMATION: Synthetic sequence

<400> SEQUENCE: 593
tttgagtttt aaccttgttt gctccccacg ct 32

<210> SEQ ID NO 594
<211> LENGTH: 32
<212> TYPE: DNA
<213> ORGANISM: Artificial Sequence
<220> FEATURE:
<223> OTHER INFORMATION: Synthetic sequence

<400> SEQUENCE: 594
caggcttgcg cccattttgc gacgttatgc gg 32

<210> SEQ ID NO 595
<211> LENGTH: 32
<212> TYPE: DNA
<213> ORGANISM: Artificial Sequence
<220> FEATURE:
<223> OTHER INFORMATION: Synthetic sequence

<400> SEQUENCE: 595
tgcagttccc aggttggtgc ttcttctgcg gg 32

<210> SEQ ID NO 596
<211> LENGTH: 34
<212> TYPE: DNA
<213> ORGANISM: Artificial Sequence
<220> FEATURE:
<223> OTHER INFORMATION: Synthetic sequence

<400> SEQUENCE: 596
gttagctccg gaagccaggt tgcgctcgtt gcgg 34

<210> SEQ ID NO 597
<211> LENGTH: 34
<212> TYPE: DNA
<213> ORGANISM: Artificial Sequence
<220> FEATURE:
<223> OTHER INFORMATION: Synthetic sequence

<400> SEQUENCE: 597
acgcggcatg gctgcatcct tcctccccgc tgaa 34

<210> SEQ ID NO 598
<211> LENGTH: 34
<212> TYPE: DNA
<213> ORGANISM: Artificial Sequence
<220> FEATURE:
<223> OTHER INFORMATION: Synthetic sequence

<400> SEQUENCE: 598
cacctggaat tctacccccg ccttcgccac cggt 34

<210> SEQ ID NO 599
<211> LENGTH: 17
<212> TYPE: DNA
<213> ORGANISM: Artificial Sequence
<220> FEATURE:
<223> OTHER INFORMATION: Synthetic sequence

<400> SEQUENCE: 599
ccctcccgaa ggttaag 17

<210> SEQ ID NO 600
<211> LENGTH: 34
<212> TYPE: DNA
<213> ORGANISM: Artificial Sequence
<220> FEATURE:
<223> OTHER INFORMATION: Synthetic sequence

<400> SEQUENCE: 600
agacattact cacccgttat tagctaccgt ttcc 34

<210> SEQ ID NO 601
<211> LENGTH: 34
<212> TYPE: DNA
<213> ORGANISM: Artificial Sequence
<220> FEATURE:
<223> OTHER INFORMATION: Synthetic sequence

<400> SEQUENCE: 601
agcttgccag tatcagattc gcacctgagc gtca 34

<210> SEQ ID NO 602
<211> LENGTH: 32
<212> TYPE: DNA
<213> ORGANISM: Artificial Sequence
<220> FEATURE:
<223> OTHER INFORMATION: Synthetic sequence

<400> SEQUENCE: 602
gctccaccgc ttgtgcgtct tcgtccaggg gg 32

<210> SEQ ID NO 603
<211> LENGTH: 34
<212> TYPE: DNA
<213> ORGANISM: Artificial Sequence
<220> FEATURE:
<223> OTHER INFORMATION: Synthetic sequence

<400> SEQUENCE: 603
tgcatgtgtt aggcctgcat ctgggcacat ccga 34

<210> SEQ ID NO 604
<211> LENGTH: 32
<212> TYPE: DNA
<213> ORGANISM: Artificial Sequence
<220> FEATURE:
<223> OTHER INFORMATION: Synthetic sequence

<400> SEQUENCE: 604
gttccagtgt ggctggacct actagctaat cc 32

<210> SEQ ID NO 605
<211> LENGTH: 34
<212> TYPE: DNA
<213> ORGANISM: Artificial Sequence
<220> FEATURE:
<223> OTHER INFORMATION: Synthetic sequence

<400> SEQUENCE: 605
tgagccatga tcaaactagg tgagccgtta cccc 34

<210> SEQ ID NO 606
<211> LENGTH: 32
<212> TYPE: DNA
<213> ORGANISM: Artificial Sequence
<220> FEATURE:
<223> OTHER INFORMATION: Synthetic sequence

<400> SEQUENCE: 606
gtgtagccct ggtcgtaagg cacattctca tc 32

<210> SEQ ID NO 607
<211> LENGTH: 32
<212> TYPE: DNA
<213> ORGANISM: Artificial Sequence
<220> FEATURE:
<223> OTHER INFORMATION: Synthetic sequence

<400> SEQUENCE: 607
gctgcctccc gtaggatggc aagaggccct aa 32

<210> SEQ ID NO 608
<211> LENGTH: 32
<212> TYPE: DNA
<213> ORGANISM: Artificial Sequence
<220> FEATURE:
<223> OTHER INFORMATION: Synthetic sequence

<400> SEQUENCE: 608
ggcagtctcc tttgaggact taacccaaca tt 32

<210> SEQ ID NO 609
<211> LENGTH: 34
<212> TYPE: DNA
<213> ORGANISM: Artificial Sequence
<220> FEATURE:
<223> OTHER INFORMATION: Synthetic sequence

<400> SEQUENCE: 609
gcgccattgt agcacgtcgc actttatgag gtcc 34

<210> SEQ ID NO 610
<211> LENGTH: 34
<212> TYPE: DNA
<213> ORGANISM: Artificial Sequence
<220> FEATURE:
<223> OTHER INFORMATION: Synthetic sequence

<400> SEQUENCE: 610
tcctccagtt tatcacttga tccacgatta ctag 34

<210> SEQ ID NO 611
<211> LENGTH: 17
<212> TYPE: DNA
<213> ORGANISM: Artificial Sequence
<220> FEATURE:
<223> OTHER INFORMATION: Synthetic sequence

<400> SEQUENCE: 611
cgcaggttcc cctacgg 17

<210> SEQ ID NO 612

<211> LENGTH: 16
<212> TYPE: DNA
<213> ORGANISM: Artificial Sequence
<220> FEATURE:
<223> OTHER INFORMATION: Synthetic sequence

<400> SEQUENCE: 612
ccgccagcgt tcaatc 16

<210> SEQ ID NO 613
<211> LENGTH: 32
<212> TYPE: DNA
<213> ORGANISM: Artificial Sequence
<220> FEATURE:
<223> OTHER INFORMATION: Synthetic sequence

<400> SEQUENCE: 613
tctgacttaa caaaccgtat taccgcggct gc 32

<210> SEQ ID NO 614
<211> LENGTH: 32
<212> TYPE: DNA
<213> ORGANISM: Artificial Sequence
<220> FEATURE:
<223> OTHER INFORMATION: Synthetic sequence

<400> SEQUENCE: 614
ttaccttgtt acgactccaa tccggactac ga 32

<210> SEQ ID NO 615
<211> LENGTH: 16
<212> TYPE: DNA
<213> ORGANISM: Artificial Sequence
<220> FEATURE:
<223> OTHER INFORMATION: Synthetic sequence

<400> SEQUENCE: 615
ccgccactcg tcagcg 16

<210> SEQ ID NO 616
<211> LENGTH: 32
<212> TYPE: DNA
<213> ORGANISM: Artificial Sequence
<220> FEATURE:
<223> OTHER INFORMATION: Synthetic sequence

<400> SEQUENCE: 616
ttttttttcg gtgtgtggca acaatttttt tt 32

<210> SEQ ID NO 617
<211> LENGTH: 33
<212> TYPE: DNA
<213> ORGANISM: Artificial Sequence
<220> FEATURE:
<223> OTHER INFORMATION: Synthetic sequence

<400> SEQUENCE: 617
caacccactc ccatggtgtg acgggttttt ttt 33

<210> SEQ ID NO 618
<211> LENGTH: 48
<212> TYPE: DNA
<213> ORGANISM: Artificial Sequence
<220> FEATURE:
<223> OTHER INFORMATION: Synthetic sequence

<400> SEQUENCE: 618
tttttttttc gcttctcttt gtatatgtca agaccaggta tttttttt 48

<210> SEQ ID NO 619
<211> LENGTH: 32
<212> TYPE: DNA
<213> ORGANISM: Artificial Sequence
<220> FEATURE:
<223> OTHER INFORMATION: Synthetic sequence

<400> SEQUENCE: 619
ttttttttag gataagcgcc tcaatttttt tt 32

<210> SEQ ID NO 620
<211> LENGTH: 32
<212> TYPE: DNA
<213> ORGANISM: Artificial Sequence
<220> FEATURE:
<223> OTHER INFORMATION: Synthetic sequence

<400> SEQUENCE: 620
ttttttttgg gcacaagccc agtatttttt tt 32

<210> SEQ ID NO 621
<211> LENGTH: 48
<212> TYPE: DNA
<213> ORGANISM: Artificial Sequence
<220> FEATURE:
<223> OTHER INFORMATION: Synthetic sequence

<400> SEQUENCE: 621
ttttttttac gcatttcacc gctaagtact ttacaacccg tttttttt 48

<210> SEQ ID NO 622
<211> LENGTH: 48
<212> TYPE: DNA
<213> ORGANISM: Artificial Sequence
<220> FEATURE:
<223> OTHER INFORMATION: Synthetic sequence

<400> SEQUENCE: 622
ttttttttaa ggccttcttc atacagtagt tatccccctc tttttttt 48

<210> SEQ ID NO 623
<211> LENGTH: 48
<212> TYPE: DNA
<213> ORGANISM: Artificial Sequence
<220> FEATURE:
<223> OTHER INFORMATION: Synthetic sequence

<400> SEQUENCE: 623
ttttttttag gttcttcgcg ttgcattcct ccagatctct tttttttt 48

<210> SEQ ID NO 624
<211> LENGTH: 32
<212> TYPE: DNA
<213> ORGANISM: Artificial Sequence
<220> FEATURE:
<223> OTHER INFORMATION: Synthetic sequence

<400> SEQUENCE: 624
ttttttttcg tcgcctcttc aatttttttt tt 32

<210> SEQ ID NO 625
<211> LENGTH: 48
<212> TYPE: DNA

<213> ORGANISM: Artificial Sequence
<220> FEATURE:
<223> OTHER INFORMATION: Synthetic sequence

<400> SEQUENCE: 625 tttttttaa ggaggtgatc caacgcttgc tctcgcgagg tttttttt 48

<210> SEQ ID NO 626
<211> LENGTH: 32
<212> TYPE: DNA
<213> ORGANISM: Artificial Sequence
<220> FEATURE:
<223> OTHER INFORMATION: Synthetic sequence

<400> SEQUENCE: 626
ttttttttat tccgatctag ggattttttt tt 32

<210> SEQ ID NO 627
<211> LENGTH: 24
<212> TYPE: DNA
<213> ORGANISM: Artificial Sequence
<220> FEATURE:
<223> OTHER INFORMATION: Synthetic sequence

<400> SEQUENCE: 627
ttttttttca tcaggcagtt tccc 24

<210> SEQ ID NO 628
<211> LENGTH: 84
<212> TYPE: DNA
<213> ORGANISM: Artificial Sequence
<220> FEATURE:
<223> OTHER INFORMATION: Synthetic sequence

<400> SEQUENCE: 628
ccgccactcg tcagcgaagc agcaagctgt ttcggtcccc ctctttggtc gtgcaatatt 60
ccccacttaa cgtcaatgag caaa 84

<210> SEQ ID NO 629
<211> LENGTH: 80
<212> TYPE: DNA
<213> ORGANISM: Artificial Sequence
<220> FEATURE:
<223> OTHER INFORMATION: Synthetic sequence

<400> SEQUENCE: 629
ttaccttgtt acgactccaa tccggactac gagtgtagcc ctggtcgtaa ggcacattct 60
catcgctcca ccgcttgtgc 80

<210> SEQ ID NO 630
<211> LENGTH: 62
<212> TYPE: DNA
<213> ORGANISM: Artificial Sequence
<220> FEATURE:
<223> OTHER INFORMATION: Synthetic sequence

<400> SEQUENCE: 630
ttcccggccg gaccgctaca aggcccggga acgtcaaccc actcccatgg tgtgacgggt 60
tt 62

<210> SEQ ID NO 631
<211> LENGTH: 85
<212> TYPE: DNA
<213> ORGANISM: Artificial Sequence
<220> FEATURE:
<223> OTHER INFORMATION: Synthetic sequence

<400> SEQUENCE: 631
agcttgccag tatcagattc gcacctgagc gtcagggccc ccgtcaattc actgtctcac 60
ggttcccgaa gggccatgat gactt 85

<210> SEQ ID NO 632
<211> LENGTH: 64
<212> TYPE: DNA
<213> ORGANISM: Artificial Sequence
<220> FEATURE:
<223> OTHER INFORMATION: Synthetic sequence

<400> SEQUENCE: 632
tctgacttaa caaaccgtat taccgcggct gcgttccagt gtggctggac ctactagcta 60
atcc 64

<210> SEQ ID NO 633
<211> LENGTH: 64
<212> TYPE: DNA
<213> ORGANISM: Artificial Sequence
<220> FEATURE:
<223> OTHER INFORMATION: Synthetic sequence

<400> SEQUENCE: 633
ggcagtctcc tttgaggact taacccaaca ttgcggtcga cttaacgctt tacggcgtgg 60
acta 64

<210> SEQ ID NO 634
<211> LENGTH: 82
<212> TYPE: DNA
<213> ORGANISM: Artificial Sequence
<220> FEATURE:
<223> OTHER INFORMATION: Synthetic sequence

<400> SEQUENCE: 634
gctgcctccc gtaggatggc aagaggccct aactgttacc gttcgacttg catgtgttag 60
gcctgcatct gggcacatcc ga 82

<210> SEQ ID NO 635
<211> LENGTH: 80
<212> TYPE: DNA
<213> ORGANISM: Artificial Sequence
<220> FEATURE:
<223> OTHER INFORMATION: Synthetic sequence

<400> SEQUENCE: 635
gtcttcgtcc agggggccct ctacgagact caggtattaa ctttactcca ggcttgcgcc 60
cattttgcga cgttatgcgg 80

<210> SEQ ID NO 636
<211> LENGTH: 68
<212> TYPE: DNA
<213> ORGANISM: Artificial Sequence
<220> FEATURE:
<223> OTHER INFORMATION: Synthetic sequence

<400> SEQUENCE: 636
gcctgcgtgc gctttaccct ccaagtcgac atcggttagc tccggaagcc aggttgcgct 60
cgttgcgg 68

<210> SEQ ID NO 637
<211> LENGTH: 68
<212> TYPE: DNA
<213> ORGANISM: Artificial Sequence
<220> FEATURE:
<223> OTHER INFORMATION: Synthetic sequence

<400> SEQUENCE: 637
tctgaaaact tccgtgggcg ccattgtagc acgtcgcact ttatgaggtc ccgcaggttc 60
ccctacgg 68

<210> SEQ ID NO 638
<211> LENGTH: 84
<212> TYPE: DNA
<213> ORGANISM: Artificial Sequence
<220> FEATURE:
<223> OTHER INFORMATION: Synthetic sequence

<400> SEQUENCE: 638
ccgccagcgt tcaatctgag ccatgatcaa actaggtgag ccgttacccc tcatcctctc 60
agaccagtaa cgcttgcacc ctcc 84

<210> SEQ ID NO 639
<211> LENGTH: 70
<212> TYPE: DNA
<213> ORGANISM: Artificial Sequence
<220> FEATURE:
<223> OTHER INFORMATION: Synthetic sequence

<400> SEQUENCE: 639
tttcatcagg cagtttccca gacattactc acccgttatt agctaccgtt tccacgcggc 60
atggctgcat 70

<210> SEQ ID NO 640
<211> LENGTH: 80
<212> TYPE: DNA
<213> ORGANISM: Artificial Sequence
<220> FEATURE:
<223> OTHER INFORMATION: Synthetic sequence

<400> SEQUENCE: 640
gacagccatg cagcactttg agttttaacc ttgtttgctc cccacgcttg cagttcccag 60
gttggtgctt cttctgcggg 80

<210> SEQ ID NO 641
<211> LENGTH: 85
<212> TYPE: DNA
<213> ORGANISM: Artificial Sequence
<220> FEATURE:
<223> OTHER INFORMATION: Synthetic sequence

<400> SEQUENCE: 641
gtctggaccg tgtctcatgg cacggagtta gccgagcccg gggatttcac accagggtat 60
ctaatcctgc ggccgtactc cccag 85

<210> SEQ ID NO 642
<211> LENGTH: 68
<212> TYPE: DNA
<213> ORGANISM: Artificial Sequence
<220> FEATURE:
<223> OTHER INFORMATION: Synthetic sequence

<400> SEQUENCE: 642
ccttcctccc cgctgaacac ctggaattct acccccgcct tcgccaccgg tatcgaatta 60
aaccacat 68

<210> SEQ ID NO 643
<211> LENGTH: 82
<212> TYPE: DNA
<213> ORGANISM: Artificial Sequence
<220> FEATURE:
<223> OTHER INFORMATION: Synthetic sequence

<400> SEQUENCE: 643
gagtcgagtt gcagacttca ccccagtcat gaatcacaaa gtggtaagcg cgattccgac 60
ttcatggacg tcatccccac ct 82

<210> SEQ ID NO 644
<211> LENGTH: 100
<212> TYPE: DNA
<213> ORGANISM: Artificial Sequence
<220> FEATURE:
<223> OTHER INFORMATION: Synthetic sequence

<400> SEQUENCE: 644
tcacaacacg agctgactcc tccagtttat cacttgatcc acgattacta gccctcccga 60
aggttaagct acctacttct tttgattcac cgtggcattc 100

<210> SEQ ID NO 645
<211> LENGTH: 32
<212> TYPE: DNA
<213> ORGANISM: Artificial Sequence
<220> FEATURE:
<223> OTHER INFORMATION: Synthetic sequence

<400> SEQUENCE: 645
ttttttttat tccgatctag ggattttttt tt 32

<210> SEQ ID NO 646
<211> LENGTH: 32
<212> TYPE: DNA
<213> ORGANISM: Artificial Sequence
<220> FEATURE:
<223> OTHER INFORMATION: Synthetic sequence

<400> SEQUENCE: 646
ttttttttcg gtgtgtggca acaatttttt tt 32

<210> SEQ ID NO 647
<211> LENGTH: 48
<212> TYPE: DNA
<213> ORGANISM: Artificial Sequence
<220> FEATURE:
<223> OTHER INFORMATION: Synthetic sequence

<400> SEQUENCE: 647
ttttttttaa ggccttcttc atacagtagt tatccccctc tttttttt 48

<210> SEQ ID NO 648
<211> LENGTH: 48
<212> TYPE: DNA
<213> ORGANISM: Artificial Sequence
<220> FEATURE:
<223> OTHER INFORMATION: Synthetic sequence

<400> SEQUENCE: 648
tttttttttc gcttctcttt gtatatgtca agaccaggta tttttttt 48

<210> SEQ ID NO 649
<211> LENGTH: 32
<212> TYPE: DNA
<213> ORGANISM: Artificial Sequence
<220> FEATURE:
<223> OTHER INFORMATION: Synthetic sequence

<400> SEQUENCE: 649
ttttttttgg gcacaagccc agtatttttt tt 32

<210> SEQ ID NO 650
<211> LENGTH: 48
<212> TYPE: DNA
<213> ORGANISM: Artificial Sequence
<220> FEATURE:
<223> OTHER INFORMATION: Synthetic sequence

<400> SEQUENCE: 650
ttttttttaa ggaggtgatc caacgcttgc tctcgcgagg tttttttt 48

<210> SEQ ID NO 651
<211> LENGTH: 48
<212> TYPE: DNA
<213> ORGANISM: Artificial Sequence
<220> FEATURE:
<223> OTHER INFORMATION: Synthetic sequence

<400> SEQUENCE: 651
ttttttttag gttcttcgcg ttgcattcct ccagatctct tttttttt 48

<210> SEQ ID NO 652
<211> LENGTH: 32
<212> TYPE: DNA
<213> ORGANISM: Artificial Sequence
<220> FEATURE:
<223> OTHER INFORMATION: Synthetic sequence

<400> SEQUENCE: 652
ttttttttcg tcgcctcttc aatttttttt tt 32

<210> SEQ ID NO 653
<211> LENGTH: 32
<212> TYPE: DNA
<213> ORGANISM: Artificial Sequence
<220> FEATURE:
<223> OTHER INFORMATION: Synthetic sequence

<400> SEQUENCE: 653
ttttttttag gataagcgcc tcaatttttt tt 32

<210> SEQ ID NO 654
<211> LENGTH: 48
<212> TYPE: DNA
<213> ORGANISM: Artificial Sequence
<220> FEATURE:
<223> OTHER INFORMATION: Synthetic sequence

<400> SEQUENCE: 654
ttttttttac gcatttcacc gctaagtact ttacaacccg tttttttt 48

<210> SEQ ID NO 655
<211> LENGTH: 62
<212> TYPE: RNA
<213> ORGANISM: Artificial Sequence
<220> FEATURE:
<223> OTHER INFORMATION: Synthetic sequence

<400> SEQUENCE: 655
cgcggcuggu uucucaggcu cccucuuauu augaaucauc aaaguugcuu auacuuagac 60
au 62

<210> SEQ ID NO 656
<211> LENGTH: 64
<212> TYPE: RNA
<213> ORGANISM: Artificial Sequence
<220> FEATURE:
<223> OTHER INFORMATION: Synthetic sequence

<400> SEQUENCE: 656
uuaaaaaaac accacccgau ccaagaauuu caccuccgcc aagagccaca aggacuggaa 60
uuac 64

<210> SEQ ID NO 657
<211> LENGTH: 64
<212> TYPE: RNA
<213> ORGANISM: Artificial Sequence
<220> FEATURE:
<223> OTHER INFORMATION: Synthetic sequence

<400> SEQUENCE: 657
ugaggccuca aucaacgcaa gcugaugaag caccacuauu uaguagacgg ccaugcacca 60
ccac 64

<210> SEQ ID NO 658
<211> LENGTH: 62
<212> TYPE: RNA
<213> ORGANISM: Artificial Sequence
<220> FEATURE:
<223> OTHER INFORMATION: Synthetic sequence

<400> SEQUENCE: 658
uccaucggcu ugaaaccgaa uuacaaugcu cuauccugac caaguuuguc caaauucucc 60
gc 62

<210> SEQ ID NO 659
<211> LENGTH: 64
<212> TYPE: RNA
<213> ORGANISM: Artificial Sequence
<220> FEATURE:
<223> OTHER INFORMATION: Synthetic sequence

<400> SEQUENCE: 659
aagacuuuga uuucucgugc ccccgaccgu cccuaugaac acucuaauuu uuucuccaau 60
uguu 64

<210> SEQ ID NO 660
<211> LENGTH: 62
<212> TYPE: RNA
<213> ORGANISM: Artificial Sequence
<220> FEATURE:
<223> OTHER INFORMATION: Synthetic sequence

<400> SEQUENCE: 660
aacaacuuuc cccguuaccc guugaaacca ucgccagcac aagggacaag cauaugacua 60
cu 62

<210> SEQ ID NO 661
<211> LENGTH: 62
<212> TYPE: RNA
<213> ORGANISM: Artificial Sequence
<220> FEATURE:
<223> OTHER INFORMATION: Synthetic sequence

<400> SEQUENCE: 661
ggauaaccag caaaugcucu ugcgcuuacu aggaauaguu gcccccuucu cuaagcagau 60
cc 62

<210> SEQ ID NO 662
<211> LENGTH: 62
<212> TYPE: RNA
<213> ORGANISM: Artificial Sequence
<220> FEATURE:
<223> OTHER INFORMATION: Synthetic sequence

<400> SEQUENCE: 662
ccucguuauu ugcgcgccug cugccuuuuu aucuaauaaa uacaugauuu aaugagccau 60
uc 62

<210> SEQ ID NO 663
<211> LENGTH: 64
<212> TYPE: RNA
<213> ORGANISM: Artificial Sequence
<220> FEATURE:
<223> OTHER INFORMATION: Synthetic sequence

<400> SEQUENCE: 663
uuccucuaaa ccagcacgac ggaguuuccu guuauugccu caaacuggug aguuuccccg 60
uguu 64

<210> SEQ ID NO 664
<211> LENGTH: 64
<212> TYPE: RNA
<213> ORGANISM: Artificial Sequence
<220> FEATURE:
<223> OTHER INFORMATION: Synthetic sequence

<400> SEQUENCE: 664
ucugagaugg uccucguuga agagcaauau agucccucua agaagugcuc ucaaucuguc 60
aauc 64

<210> SEQ ID NO 665
<211> LENGTH: 64
<212> TYPE: RNA
<213> ORGANISM: Artificial Sequence
<220> FEATURE:
<223> OTHER INFORMATION: Synthetic sequence

<400> SEQUENCE: 665
uuaugguuaa gacuacgauu ggcaaaugcu uucgcagaaa ggccccguug gaaauuuuaa 60
cugc 64

<210> SEQ ID NO 666
<211> LENGTH: 62
<212> TYPE: RNA
<213> ORGANISM: Artificial Sequence
<220> FEATURE:
<223> OTHER INFORMATION: Synthetic sequence

<400> SEQUENCE: 666
acaagaccuu auugucacua ccuccccgauu uuaagcaugu auuaaccaug uaguaaagga 60
ac 62

<210> SEQ ID NO 667
<211> LENGTH: 62
<212> TYPE: RNA
<213> ORGANISM: Artificial Sequence
<220> FEATURE:
<223> OTHER INFORMATION: Synthetic sequence

<400> SEQUENCE: 667
ucuaagggca ucacagacac aagauuacca agaccuuacg gaaaccuugu uacgacuuuu 60
ag 62

<210> SEQ ID NO 668
<211> LENGTH: 67
<212> TYPE: RNA
<213> ORGANISM: Artificial Sequence
<220> FEATURE:
<223> OTHER INFORMATION: Synthetic sequence

<400> SEQUENCE: 668
cucaagguua gccagaaggu aguuagucuu caauaaaucc cuagucggca uaguccacaa 60
aaucaag 67

<210> SEQ ID NO 669
<211> LENGTH: 67
<212> TYPE: RNA
<213> ORGANISM: Artificial Sequence
<220> FEATURE:
<223> OTHER INFORMATION: Synthetic sequence

<400> SEQUENCE: 669
gagcaauacg ccugcuuuua aucauuacga ugguccuacu ccccccagaa cccagaguca 60
aauuaag 67

<210> SEQ ID NO 670
<211> LENGTH: 67
<212> TYPE: RNA
<213> ORGANISM: Artificial Sequence
<220> FEATURE:
<223> OTHER INFORMATION: Synthetic sequence

<400> SEQUENCE: 670
gcaguuucac uguauaaaag uccgaagaca uugauuuccu uggauguggu agcccuggca 60
ccagacu 67

<210> SEQ ID NO 671
<211> LENGTH: 67
<212> TYPE: RNA
<213> ORGANISM: Artificial Sequence
<220> FEATURE:
<223> OTHER INFORMATION: Synthetic sequence

<400> SEQUENCE: 671
aaaguaaaag uccugguuug acaauugaau acugauaagg ugccgagugg gucacuuauu 60
gugucug 67

<210> SEQ ID NO 672
<211> LENGTH: 67
<212> TYPE: RNA

<213> ORGANISM: Artificial Sequence
<220> FEATURE:
<223> OTHER INFORMATION: Synthetic sequence

<400> SEQUENCE: 672
ggcaggauca accagauagg gcagaaauuu gaaugaacca ugguaggcca cuauaaaguu 60
caacuac 67

<210> SEQ ID NO 673
<211> LENGTH: 67
<212> TYPE: RNA
<213> ORGANISM: Artificial Sequence
<220> FEATURE:
<223> OTHER INFORMATION: Synthetic sequence

<400> SEQUENCE: 673
gcauggcuua aucuuugacc augcgauucg aaaaguccgg aaucgaaccc uuauuaauau 60
acgcuau 67

<210> SEQ ID NO 674
<211> LENGTH: 67
<212> TYPE: RNA
<213> ORGANISM: Artificial Sequence
<220> FEATURE:
<223> OTHER INFORMATION: Synthetic sequence

<400> SEQUENCE: 674
uaucaaauaa acgauaacuc ucuuccaaag ggucgaugaa uuaggauugg guaaagguau 60
uuacauu 67

<210> SEQ ID NO 675
<211> LENGTH: 67
<212> TYPE: RNA
<213> ORGANISM: Artificial Sequence
<220> FEATURE:
<223> OTHER INFORMATION: Synthetic sequence

<400> SEQUENCE: 675
uccaguacac gaaaaaauug auuaaugaaa acgucccggu aucugaucau cuucucacuc 60
caccaac 67

<210> SEQ ID NO 676
<211> LENGTH: 32
<212> TYPE: RNA
<213> ORGANISM: Artificial Sequence
<220> FEATURE:
<223> OTHER INFORMATION: Synthetic sequence

<400> SEQUENCE: 676
uaaugauccu uccgcagguu cacccucggc ca 32

<210> SEQ ID NO 677
<211> LENGTH: 27
<212> TYPE: RNA
<213> ORGANISM: Artificial Sequence
<220> FEATURE:
<223> OTHER INFORMATION: Synthetic sequence

<400> SEQUENCE: 677
guuaaggucu cguucguuac aaagggc 27

<210> SEQ ID NO 678
<211> LENGTH: 19

<212> TYPE: RNA
<213> ORGANISM: Artificial Sequence
<220> FEATURE:
<223> OTHER INFORMATION: Synthetic sequence

<400> SEQUENCE: 678
agguuagacu cgcgugcgg 19

<210> SEQ ID NO 679
<211> LENGTH: 19
<212> TYPE: RNA
<213> ORGANISM: Artificial Sequence
<220> FEATURE:
<223> OTHER INFORMATION: Synthetic sequence

<400> SEQUENCE: 679
aauauauucc auuccaauu 19

<210> SEQ ID NO 680
<211> LENGTH: 19
<212> TYPE: RNA
<213> ORGANISM: Artificial Sequence
<220> FEATURE:
<223> OTHER INFORMATION: Synthetic sequence

<400> SEQUENCE: 680
ucaaucggua cuagcgacg 19

<210> SEQ ID NO 681
<211> LENGTH: 18
<212> TYPE: RNA
<213> ORGANISM: Artificial Sequence
<220> FEATURE:
<223> OTHER INFORMATION: Synthetic sequence

<400> SEQUENCE: 681
cccagaacgg gcuccacu 18

<210> SEQ ID NO 682
<211> LENGTH: 18
<212> TYPE: RNA
<213> ORGANISM: Artificial Sequence
<220> FEATURE:
<223> OTHER INFORMATION: Synthetic sequence

<400> SEQUENCE: 682
acaaaauagu uccaugcu 18

<210> SEQ ID NO 683
<211> LENGTH: 18
<212> TYPE: RNA
<213> ORGANISM: Artificial Sequence
<220> FEATURE:
<223> OTHER INFORMATION: Synthetic sequence

<400> SEQUENCE: 683
uugcgaccau agaaacca 18

<210> SEQ ID NO 684
<211> LENGTH: 18
<212> TYPE: RNA
<213> ORGANISM: Artificial Sequence
<220> FEATURE:
<223> OTHER INFORMATION: Synthetic sequence

<400> SEQUENCE: 684
agggacguac uaagccau 18

<210> SEQ ID NO 685
<211> LENGTH: 18
<212> TYPE: RNA
<213> ORGANISM: Artificial Sequence
<220> FEATURE:
<223> OTHER INFORMATION: Synthetic sequence

<400> SEQUENCE: 685
ccugguggug uuucagcc 18

<210> SEQ ID NO 686
<211> LENGTH: 30
<212> TYPE: RNA
<213> ORGANISM: Artificial Sequence
<220> FEATURE:
<223> OTHER INFORMATION: Synthetic sequence

<400> SEQUENCE: 686
uuuuaauucc uuuaagcccu uccgucuuuu 30

<210> SEQ ID NO 687
<211> LENGTH: 30
<212> TYPE: RNA
<213> ORGANISM: Artificial Sequence
<220> FEATURE:
<223> OTHER INFORMATION: Synthetic sequence

<400> SEQUENCE: 687
uuuuuguauc guuaucgaau gggcccuuuu 30

<210> SEQ ID NO 688
<211> LENGTH: 30
<212> TYPE: RNA
<213> ORGANISM: Artificial Sequence
<220> FEATURE:
<223> OTHER INFORMATION: Synthetic sequence

<400> SEQUENCE: 688
uuuuucagug uagcgcgcug gcuccguuuu 30

<210> SEQ ID NO 689
<211> LENGTH: 28
<212> TYPE: RNA
<213> ORGANISM: Artificial Sequence
<220> FEATURE:
<223> OTHER INFORMATION: Synthetic sequence

<400> SEQUENCE: 689
uuuuggcggu guguaucgca auuauuuu 28

<210> SEQ ID NO 690
<211> LENGTH: 28
<212> TYPE: RNA
<213> ORGANISM: Artificial Sequence
<220> FEATURE:
<223> OTHER INFORMATION: Synthetic sequence

<400> SEQUENCE: 690
uuuuaaccgg gcccccuacc aucguuuu 28

<210> SEQ ID NO 691
<211> LENGTH: 28
<212> TYPE: RNA
<213> ORGANISM: Artificial Sequence
<220> FEATURE:
<223> OTHER INFORMATION: Synthetic sequence

<400> SEQUENCE: 691
uuuucuuucg uucucggacc ggccuuuu 28

<210> SEQ ID NO 692
<211> LENGTH: 30
<212> TYPE: RNA
<213> ORGANISM: Artificial Sequence
<220> FEATURE:
<223> OTHER INFORMATION: Synthetic sequence

<400> SEQUENCE: 692
uuuuaccaca guuaugcucu agaauuuuuu 30

<210> SEQ ID NO 693
<211> LENGTH: 30
<212> TYPE: RNA
<213> ORGANISM: Artificial Sequence
<220> FEATURE:
<223> OTHER INFORMATION: Synthetic sequence

<400> SEQUENCE: 693
uuuucuauuc uauuaaacca aacgucuuuu 30

<210> SEQ ID NO 694
<211> LENGTH: 10
<212> TYPE: RNA
<213> ORGANISM: Artificial Sequence
<220> FEATURE:
<223> OTHER INFORMATION: Synthetic sequence

<400> SEQUENCE: 694
aaaguugaua 10

<210> SEQ ID NO 695
<211> LENGTH: 28
<212> TYPE: RNA
<213> ORGANISM: Artificial Sequence
<220> FEATURE:
<223> OTHER INFORMATION: Synthetic sequence

<400> SEQUENCE: 695
uuuuagcaga caaagauccc cuaauuuu 28

<210> SEQ ID NO 696
<211> LENGTH: 38
<212> TYPE: RNA
<213> ORGANISM: Artificial Sequence
<220> FEATURE:
<223> OTHER INFORMATION: Synthetic Sequence

<400> SEQUENCE: 696
gugggagccg caccuccggg auauuagcgc cccuccuu 38

<210> SEQ ID NO 697
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 697
uucggaucaa gcuagcaggg gu 22